US007126044B2

(12) United States Patent
Gmitter, Jr. et al.

(10) Patent No.: US 7,126,044 B2
(45) Date of Patent: Oct. 24, 2006

(54) **PLANT GENES CONFERRING RESISTANCE TO *CITRUS TRISTEZA* VIRUS**

(75) Inventors: Frederick G. Gmitter, Jr., Lakeland, FL (US); Zhanao Deng, Bradenton, FL (US); Hongbin Zhang, College Station, TX (US)

(73) Assignee: University of Florida Research Foundation, Gainesville, FL (US)

( * ) Notice: Subject to any disclaimer, the term of this patent is extended or adjusted under 35 U.S.C. 154(b) by 571 days.

(21) Appl. No.: 10/298,122

(22) Filed: Nov. 15, 2002

(65) Prior Publication Data

US 2003/0221214 A1 Nov. 27, 2003

Related U.S. Application Data

(60) Provisional application No. 60/336,549, filed on Nov. 15, 2001.

(51) Int. Cl.
*A01H 5/00* (2006.01)
*C12N 15/82* (2006.01)
*C12N 15/29* (2006.01)

(52) U.S. Cl. ...................... 800/301; 800/279; 800/316; 800/294; 800/293; 536/23.6; 435/320.1; 435/419

(58) Field of Classification Search ..................... None
See application file for complete search history.

(56) References Cited

U.S. PATENT DOCUMENTS 6,127,607 A * 10/2000 Ausubel et al. ............. 800/301

OTHER PUBLICATIONS

Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
Deng et al., "Fine genetic mapping and BAC contig development for the *Citrus tristeza* virus resistance gene locus in *Poncirus trifoliata* (Raf.)," Mol. Genet Genomics, 265: 739-747, 2001.
Deng et al., "Cloning and characterization of NBS-LRR class resistance-gene candidate sequences in citrus," Theor Appl Genet, 101: 814-822, 2000.
Deng et al., "Construction of a bacterial artificial chromosome (BAC) library for citrus and identification of BAC contigs containing resistance gene candidates," Theor Appl Genet, 102: 1177-1184, 2001.
Yu et al., "Factors affecting Agrobacterium-mediated transformation and regeneration of sweet orange and citrange," Plant Cell, Tissue and Organ Culture, 71: 147-155, 2002.
Yang et al., "Sequence Analysis of a 282-Kilobase Region Surrounding the *Citrus tristeza* Virus Resistance Gene (Ctv) Locus in *Poncirus trifoliata L.*Raf.," Plant Physiol. 131, 1-11, 2003.
Yang et al., Construction of a 1.2-Mb contig including the *Citrus tristeza* virus resistance gene locus using a bacterial artificial chromosome library of *Poncirus trifoliata* (L.) Raf., Genome, 44, 382-393, 2001.
Baker et al., "Signaling in Plant-Microbe Interactions," Science, 276: 726-733, 1997.
Wang et al., "Xa21D Encodes a Receptor-like Molecule with a Leucine-Rich Repeat Domain That Determines Race-Specific Recognition and is Subject to Adaptive Evolution," The plant Cell, 10: 765-779, 1998.
Staskawicz et al., "Molecular Genetics of Plant Disease Resistance," Science, 268: 661-667, 1995.

* cited by examiner

*Primary Examiner*—Anne Kubelik
(74) *Attorney, Agent, or Firm*—Akerman Senterfitt

(57) ABSTRACT

Nucleic acids and polypeptides were identified and isolated from *Poncirus trifoliata*, a sexually compatible close relative of *Citrus*. These sequences, when present in a plant genome, result in the expression of resistance to CTV infection. Several methods of transforming citrus plants to produce citrus plants that are resistant to the broad genetic diversity of CTV strains are described. Transformed CTV-resistant germplasm and breeding lines can be used in conventional breeding programs to create new cultivars that carry and express the resistance genes.

26 Claims, 1 Drawing Sheet

SEQUENCE LISTING

<160> NUMBER OF SEQ ID NOS: 19

<210> SEQ ID NO 1
<211> LENGTH: 99116
<212> TYPE: DNA
<213> ORGANISM: artificial
<220> FEATURE:
<223> OTHER INFORMATION: Poncirus trifoliata and Citrus grandis hybrid
<220> FEATURE:
<221> NAME/KEY: misc_feature
<222> LOCATION: (62342)..(62362)
<223> OTHER INFORMATION: N denotes unsequenced nucleotides
<220> FEATURE:
<221> NAME/KEY: misc_feature
<222> LOCATION: (1795)..(1795)
<223> OTHER INFORMATION: N denotes unsequenced nucleotide

<400> SEQUENCE: 1
taagtaaaat aaaagattat ttttcctttt atcgaagaaa ccaaagacaa gaaattgata 60
tagttaaagc ctgttccatt taccaaaacc gaattaataa tctaattaat tcgaaacaaa 120
atgatttaac ctttctccaa aaagatttga gtttacaaag aattgaaaat gatttacaaa 180
gagatttcat taaaagaaaa atttctgatt tcaaaaccct aattgaaaaa gaaatttgtg 240
ctgatctgcc ttctgctttt tggaatagaa aacaacatat ggtagatttg ccttatgaaa 300
attcttttga tgaaaaacag atacccacta aagctcgacc aattcaaatg aatatggatt 360
tagaacgaca ttgtaaagaa gaaattaatg atcttgtaaa aaaaggactt attgtaaaat 420
caaggtcacc ttggtcatgt gccgcttttt atgttaataa aaattctgaa attgagagag 480
gcacaccaag acttgtcata aattacaagc ctttaaataa agctttaaaa tggattaggt 540
acccgatacc taataaaaag gatttgttac aaaaactgca ttctgctttc atattttcaa 600
aatttgacat gaaatcagta ttttggcaaa tccaaatcca tccaaaagaa cgttataaaa 660
ccgcttttac tgttccattt ggacagtatg agtggactgt catgcctttt ggtttaaaaa 720
atgcaccttc agaatttcaa agaattatga atgacattta taatccttat tctgattttt 780
gtattgttta tattgatgac gtgttgattt tttcaaattc aattgatcaa catttcaaac 840
atttaaagac cttttatttt gccaccagaa aggctggatt ggcaatttca aattccaaag 900
tctccttatt tcaaacaaaa atccggttct taggtcatca tatttcaaaa ggaaccatta 960
ctccaattga gcgatcactc gcttttgctg ataaatttcc tgacaaaatt ttggataaaa 1020
cccaactaca aagattttta ggcagcttaa attatgttct tgatttctgt ccaaatatta 1080
gtaggttatc taaacctttg catgataggc taaaaaagaa acctgctgca tgaactgatg 1140
agcatacaaa gactgttaga ttaataaaga attttgttaa gagcattcca tgtttatatc 1200
ttgcaaatcc tgcattgcct aagatagttg aaactgatgc atctgattta ggttatggag 1260
gtattttaaa gcaaaaggaa aatgataaag aacaaattat tcaatatgtt tctgcacatt 1320
ggaatgattg tcaaaagaac tattctacta ttaaaaaaga aattctttcc attgttttgt 1380
gcatatcaaa attccaaagt gatttattaa atcaaaaatt tttacttaga atagattgca 1440
aagctgcaaa acatgtttta gaaaaagatg ttcaaaacat tgcatcaaaa caaatttttg 1500
cacgatggca agccatttta agtgtttttg attttgatat tgaatttatt aaaggcgata 1560
aaaattctgt tccagatttt ctaactcgag aatttcttca aaacagataa tgccgccaaa 1620
gcgtcgagac aaaggaaaag gcatagccaa agacactgat tccctaaagc cctccaaaga 1680
atcccaatca actcctttta aagaaaaatt actatcctca gccatgccaa tcaaatcctg 1740

-continued

```
gattgaaatg gtcgaagatg aagaacaaaa agccctttct aaatccatct cctcngacca   1800
acaagtcaaa gaatggatgg aatccattac aaagtcccct gagcttatgt ttgccttaca   1860
aggcatttca aaatctaaag ccctttctca gatcggttgt tctgtggaag attagcattg   1920
aagataatta atccagtgca tgtgctcacg aagacggttg cggtgacaag gtttcaggag   1980
taatatctat ctcattttta aaagtattat aacacatcat tttactacta ttgcataaat   2040
ttacaaaatt tattattttg ttatattcta ttaacaccat taattgacta attagttaat   2100
taataatcac caatttcatc ggttcataat ttttgttgtc agcaagaata aaagtattac   2160
aatattagaa attaaaaata taaactagct agaataatca atatgagcat atggatttaa   2220
tcattagaaa aattgaattt aggccctttt tataaatacc tataaatcat ccattaatta   2280
agactatttc cataaatttc taaaaaagaa ttagtatttt actatgcacc aattagataa   2340
aggagtgtga ttcaatgaga agtccaatga aacaacaaaa caaataaaat aaaatgaaat   2400
ttgtggtaat accaaaaccg taatagagaa taagagcaaa agcttaaagc ctgtaatcat   2460
tggagaaggg gaagccacac agagatggga atttcaagaa ggaagcccct ctctctcagg   2520
gacactctca agaaaccttc ctctccaaag gtttcgcagg tgcctttttt ttttctcttt   2580
ctttttggtg tagggttttt ttttggttaa attgtgttta gatattgtta aatgatgatg   2640
tggtactatg aaaattagag tttgatgagt tctgtcgact caaaatttga ttttttcttt   2700
ttgcacgtgg gtattgatca caaaaacttg atcgaaaaat aagaactttt ccatgaaaga   2760
aacagaaccc atgttgtgat tttgtttttg gagtgtttct ttgctcatat gaccgagtat   2820
tttgtacttt attttattta tatagggtcc ttcagtaaat tagttacttt ttggcgttta   2880
aatgctgtga gtgttgcaat tttgaccaaa aaagcatatt taatgctttg aatttttgtt   2940
gataaagttg ttgagctaaa ctataaatat ttattaggaa acacaggtaa aaaactgtaa   3000
actttgttat gataattgct tggtttatag tattcttgct atatgttgaa tgaaattatg   3060
acatgatact ccacaaatga tttactagtt tgctaagaga cttcagagtt cttcggatta   3120
catgggccat tcataaggag attatcatga aataagatct tcgatattgt ttgaggcaaa   3180
gaactatggt tttggcggcc cctgcccgta ggcctgcctt cacttggcaa agatgcggta   3240
catttggtcc aatttaaacc gttacagaat ttctactagt ttactttaga aggttatgag   3300
ataaaatgaa tcagcgcacc atacagatgg aggattttct gatgaatatc tagccgatca   3360
acttttgcat ggccagttac taactaatta ttcttttaca tagattggta acattgaaga   3420
tgcatgttcc tttttctggc aaagagagat tacgcgaact catgaaaatt actgcaaggt   3480
ttgaggcaaa gaattatgct attgctatga gtgaggtact ttatgttgtt gcattctata   3540
aatttcataa aatatataca tatacaacaa aattgaaaat tatgcacctt tatttttcct   3600
ttccaaaatt cttacttaga ttcacccttc cccttcccct ccccccgccc cccaacattg   3660
ttttcttctt ctgtggtttt gacaaacatg acatggagta ttaggagatc taaagttcta   3720
aatttatctc aaatttcagt cagattatcg gcagagaata tctcttaaga tgcatcagtt   3780
ggattcacgg tctcaaaatg caatgcctta gctctctgcc atgcacccac tgccggtagt   3840
ggcagcagat tcctgttcca ggtaataacc atggaatttg aatatttgct tttatccaat   3900
gcagttgttg aagcttcacg tagaagcttc actcgcaaat taacccatat taacaacatt   3960
atgctttttg actagtagaa ttattacctt tatttacgct cttaacataa atgcaagaca   4020
tgggatgcta gacattgcaa cttcttaaat ccttgcatta ggggaatgtc tatgttggcg   4080
```

-continued

```
tattttgtaa aattaaaatc atttggaatc ccttcacttg tatgaactat ttattaatac   4140
attcttatgt acttttcttt gtttgcagca tgaaatttct gccgcaatga gcaaagtcag   4200
aacagctttt agctggaaaa gcttacatga gttacaaagc ttaggacaat tgatagatat   4260
tgtaactaag tttgatggtg agaaatttga aaatgtatat cgaagattgt atggattgga   4320
aaagtataat cttatacttc ttattaatgt gtgttccaga gtgtagtaaa ttgtcattta   4380
atgaatggat tctgaaaaat atatgttaat ggtgtgtttg gaagtgctta agcatgattt   4440
tgttacctta attacaatgt ttaaattcat aagaaaagaa tttgggtgca ttttaggtat   4500
actcatatca cttttggtac aaattcttag atggttgaag cttttaatgc ttatcttaat   4560
ttagaatatg tctttcaact agctgtgaat gcttttggta gttagtcttt agtgaatgat   4620
atttctcatt tttatccaaa ctttaaaaaa gtattgaata aaataacaca cgtgacatga   4680
tatggtattt ctttgatgtt aatgtcttgt gaattcaaga atacgcattg tagaaggtct   4740
atttaaaaaa tttgtatatt gttgtataac tttgatttta tttcgaacct aaattttaaa   4800
tatttattag tatgaacttg accacgactc tgaatataac atgcataact gataaataaa   4860
tttttgaata tgttattttt catatgcgca atggaccaac acataaattt aacaaataaa   4920
actcactttg ggagggtatg gcaaacttgt tgacttaatt agtaattatt atagttcttg   4980
ttttatattt aaaaatgggc ttcctcagga aaaaaattaa taaaataggg caacttaagt   5040
atcttaagat tagccggttg cttattaaaa ataaaaataa aatagattag ccggttgggt   5100
tgttgttaga tacagtatca actcatactt cttgtctgat ttgacttgtt ttgtaatttc   5160
gtcgatttaa cataatacaa tcaatgaagt atcacttcta gtagtatttc aattttaatt   5220
tcaaacgggc attatatata ttttgttata aattttttta ataatcagtt aaattttgtt   5280
aatattactt gaaatttcta atttcttttt tcagaagtcc taatctaaat aatagtcctt   5340
atagacgata agtttgagga aaaaaagaga tggattataa aaatagtaaa tgatttaaaa   5400
tcataaggag taatgattgc caattatcaa actaaccaac aacaaaaagt actttgcctt   5460
aaaaaagatg aatttctgta atttcccagg actaataata atctcatggc ccttgtacaa   5520
ttatgggatt tccatataaa gataatttta attagaataa gtatctaaaa agagatcaag   5580
tttatttatc ttctttattg tttaagaaat tattaaaata aacacctacc aatcctctac   5640
catactccta tgcaaaaaga ttgaaattct aaactttttg caccattaaa actttatcat   5700
atccatccca ctaaaatttt tttagaagat atgttatgcc ctatttaata tgaaattata   5760
catttgactt gttgaattaa ttatttcatt aacttaagtg taaatttttt tttaaatatc   5820
tcatgtattt atatttttag ttcaattgta aaatttaaat taagcccaaa tgcccaattg   5880
aataaaataa aataaatatt taaaatcata ttttaacttt ttcacgattt tggctctttg   5940
tgccttcctt taaaggccaa aagtcttgat ttctatctaa aacttttgat actgacatat   6000
tttaactttt gaatggcagt agaggagaac aaaaaaataaa attttagaaa cccagaacac   6060
tggcaattgt aaaatgtatc aaatattgat atataattct tatagttaat atttttaata   6120
tttttatatg ttttattcct tacattttat actagtaaaa attttaacct gcatgaattt   6180
aattttgttg ctataccact gtatccttcc aacacccact acatacaaat tttattaatt   6240
tctcaattca ttaataattt cttagaaaat tctaaaagtt atcttgaata atttttcaaa   6300
aaccgttaga aactttccct taaaaaattc tgatatatat taatctaact ttcataaata   6360
ttaaggaaat tttattttt attttcagta aaatgaattc gaaatcacaa aatttcaaac   6420
ggaatattgt ggtatgagtc acgacaatac gtggcaatcg tatattaaaa gaattgaaaa   6480
```

-continued

```
ttagaagaaa aacttgaaat taaaacaact aagcttaatc acatttagat ccctgaactt   6540
taatattatt tcctacacga agagaaagtg tgttgattgt acaatacata ttaattttta   6600
tattttatga aaacacaaat aataatttta tttcaacaac aaatatagta ataagagatt   6660
caacgttagg atagatttaa gcgcacatca ttacaattca ttaatggttg tatttatttt   6720
attacactaa caaatatgag gatacaatcc gctgtttata atatattata attatattag   6780
aatatctttt ttaattttta ctatttatct tttattaata tatttaactc ttcaactaat   6840
acaataaaat ttttaaagta tgaaatattt aattattaca taacaaaaaa taaagaaaat   6900
tattaaatcc accgaacatc ttgatgtaac tgaattaact gaaagttctt tcagtgttaa   6960
ccgatggtta aaattcaaca ttactataag ctaatcttat ttctatcatt ttaatttggc   7020
cggtttgata taaaacaaac attattccat tatttgagaa aacatgaaaa atagggacat   7080
atatgttatt atccagaccc agtacacacg tatggacatg cgattataag tggaggaatt   7140
atccatttaa gcttccttat tcttcatttc ggtccaattc gacacctgac cctttctttc   7200
tctttttcgg agaaagcaaa caaaccaacc aacaaaactt atcggctgca atcaatccct   7260
caaggttctt cttctccttc catttcatta aatttgttta tatataaatt tttttgactt   7320
attttgacaa gtgattaaga gttaaggaca acatccaccg attgttgtaa gattcttgat   7380
tttggttttt ttttcggatt cttttactga aatgggttga ataatataat ataatcatac   7440
tttgagtcaa ttgcagctga aattagttct tttttaaaag aaaaaaataa aaagttgaaa   7500
tggttttaaa tcagtcaatc gtgcatggat cctaatagag atttggtgag ttattttgaa   7560
tcagaattct tcatctgttt gtgaatttga ccaaattttt gtgccagaac gttttccttt   7620
gaattccttt ttttctttta gttattcatt tgtctctttg gatgtttcgt gtttgtgggt   7680
gtgtgcaaac tggttaaaga ttcgattttt tcacggaaaa acgaaatttt cctgtgaaac   7740
tacggaaccc atcttctgtt tttttttttc tttaaaaaat gattctagaa tattttgttt   7800
acccaaaaca aaagcaaccc agaaaagctt tactgtggaa ataaaagtac aggttgttca   7860
tatggattct taagtaaatt tcaagttttc tgtggtttag atgctgtcca tgttgtaatt   7920
ttgatctaaa gggatttggt cgccttggat ttccaatggg aaatgcagtg aagctgggga   7980
attttaagtg atactctgtt gaagtatgga tggccgaaaa gtcaaagagt tgtctatata   8040
aggaaactaa tgctactgca aaagccagct gactgtatat ttgtctagag caacatgtgt   8100
atagtgagac tgtagtttga tgattgcttc catcatacat gctagctgaa caaaattatc   8160
ttttgtcgta ttatggttgt ggcgcttttg gctagaaggc attgaatttc attagattat   8220
gtgttgcgcc cgtaatggtg tattatttaa tggaatatca ggtgtttgtt atgcactttt   8280
ttaagagtgt catgatatat tttttcccc aattaaacca aacaaggaaa attagtggta   8340
gaaacaagaa gtatttattt gagatcaact ataaggttgc tctatgttcg caaatagaaa   8400
atgacgaaca ctgaaattat tggtgctaaa agctataagg ttgtgaattc ctcttaagat   8460
caaagagtca tataacattt ttatatgtag attgactttt tgtattcata agttatgtgt   8520
ttggaaataa tggtttttta taaagaaata cgtcgttaca tggagaacgt tcaagttttt   8580
tcaaatccta atagtaaatt tcgatgttaa aatgacatat aatttgaatc gattgtcatt   8640
gacttctttc ctcaccctct tagtttagaa tctgatggat accaataatt ggaggcctac   8700
tcctccagtt ggagagtcca acctggacac aggtgactgg agaacacagt tgcagcccga   8760
ttcgcgtcaa agaattgtga acaagatgta agtgtgcaag cttctttctt tctcctttta   8820
```

-continued

```
tgatcagccg catccgtcgc ttataggtac tatgaatttt tttgtgtcct ttgtaaggta   8880
taacccttttt aagcatttgt ggcgatttaa atgatatata gctcaggtta ctatgaaaac   8940
gacaaaagga atatcaaaga cagttataag tactgttatc tgtcatatgt gagaaacact   9000
atcctcaaaa ctagttattt gttgttcaca aatagcttaa gagttgaatc atgaacctgc   9060
ttgcagatag tggcttatcg cctatatatc ggcactgaat gcaaaacttg aacacaaaat   9120
ttaattggtt aggattgtcc tatttatcac tctgtattgt ttggccaact tcctcaattt   9180
gattaaggca catgatcaaa tgaatattgt tttgtgactg agaatgggct ttggagtgcc   9240
aacatagtga ctcattaatt tattgatttt gtttagaatg gatacattaa agagacatct   9300
tcctttttct ggccaagacg gattaaatga actcaagaaa attgctggaa ggtttgagga   9360
aaagatctat actgctgcct caagtcaggt aattccaatt tgacttcctt gaattttcaa   9420
tatttcatat atttgtttat gtaaagttta tgtgcactat atcttgcacg tggaggtaca   9480
gacacatgca tatttggtgc taaatagact tgtaaaggaa gtgtcaacaa aaggactgaa   9540
aaatgaaaaa agaaatagaa agaaataaaa atgatattgg ctgtagatgg tctttagttt   9600
cttagtatct gttacagatg ctgtcattta aaatgcactt tgaaaaaagg aaagaggaga   9660
gagaataaga aagttggaag gggaaaaagg gctgctgtgg ttacaaatct cctaaaatat   9720
gaaagcgaaa ataaaatcct tttttcctct ttgaccttgc cgcataggat ggtagtggtt   9780
gtaaggaaga ctttctgagc ataatgagcc cctgggcatt ttctatttgc tgtttatgtc   9840
atgtcttatc gttttcttta gtcatggcat gaccattagc ttctgtttct tctgttttcc   9900
attttttttt cttttgtgat tctggcaact tggagtgcta aattattttg tactggtatc   9960
gaatttttca gtcggattat ctgcggaaga tatctctgaa gatgctttca atggagtcaa  10020
agtctcagaa tgcaatgcct aattcattgc aatccaacaa tcctggcagt agcaacagac  10080
cccctgatcc aggtagtgac atggaatatt aaatgcagtt tcgcagcttc gctttcaatc  10140
tgacaacaaa ctgctgtttg gaaagtagag ctggttatca ttattcagac acatgttagt  10200
aatgcatgaa tgttcatttt gattatatat ttcgataaaa aacacggtta tatatgtgtg  10260
aattagtttt gttggacatt ccaagccgta agtttatgct gccaagtgga gccagttgta  10320
gtatttgtag ccatataaga tttgaactta aaaacaatgt ggcctgttat gtgtgtgttg  10380
tcaactgtaa ctgtgtttat tttcttgtag aaaaccatag tctttgtgtt aattttgata  10440
atagcattat tggcgagctc aggggcggac gccatgtaag actaaagggt gccatggccc  10500
cccctggatt ttaaaatatt ttgaaatttt tgaataaaat atgaataatt tacacactga  10560
tccctgtaca attatgtttg gcccccccctt aaatttataa gtttaaattt ggcccccctt  10620
aaatttcctc ctgagatccg cccctgggcg agcttcatgg caattatcta atatatgctt  10680
atattgctac tatgttttag gaatatcaaa gtgaatcatt tattaactat aaattttaat  10740
tggacatggt taggtattta ttcatgtcat ctagtgttag atacgccttt tttaatctaa  10800
gaaccatatt gcagaaatga gtggatttgg ttgtcctgtc ctatacattc atattaatta  10860
ctgtttatca tcaatacata tatcgtggag ggttgcaaag gaaaggcaat tgatacatgt  10920
gtccaaatat aatttgttat tgtttttcat tcttatttcc agatacattt tgatgcttgg  10980
tgaattatga attgattgct ctgaattaac tccgcaattg gtgtttaaat gattctttta  11040
gtttaaatgt tagtcgttca agggctttaa tggctatgtt tttgggatgg tagttcctct  11100
aagttggtgt ttttgttgat ttttttactt tacatagggt ctatgcaaaa ccaagttcac  11160
aatcaagggc aatcacttcc tattccattg tcagctaatc agtcccaagt acggcaacag  11220
```

-continued

```
ctattatcgc agaacattca gaataacatg tcgtcagcag gagttcaagg ttcttctgga  11280
ctatcatctg ctcttccttc tgtctctggt ttatcccagt ctcctatccc tagtgttgta  11340
ggccaaactg tcaacatgca aaatatgtct gggatttcac aaaactcagg agggaattca  11400
atggggcagg gggtgccctc caatcttttc gccaattccc agaggcaaat tcaaggaagg  11460
caacaggtcc tcccccaaca gcaacaacag caatcccaga attcacagca gtttttatat  11520
cacccgcagt atccacaaca gcttctgaac aagaagctgc aacagggagg tctctcacac  11580
acactaatgc aacctcagat ccagcagcag ccacaacagc agccaaacct attgcagcct  11640
aatcagttgc aatcttctca gcaatctggt atgcaaacat catctgttat gcctaacatg  11700
atgcaatcag cctctctccc tggtcttcaa cagaaccagc agtcttcagt tcagcaatca  11760
acacaaccca tgatgcagca gcatccacaa tcagtcctta ggccgcagca acaacagcaa  11820
caaactgtgg gtattcatca acagcaaaca ccaatgccac agcagtcagt aatgccacca  11880
cagcaacagc aacagcagca gctaatggga caacaaccaa acactgtaaa catgcagcag  11940
agtcagttga ttggccaaca aaacaatgtt ggagacatgc agcagcagca gaggttgctt  12000
ggccagcaga gtaatcttcc aaacttgcag cagcaaccac agcagcaaca gcaacagcaa  12060
cagcagcagc agcagcagtt aatggctcag caaaacctct caagtatgca tcatcaacag  12120
ttgggcccac aaagtaatgt ttcaggatta cagcagcagc cgcagcaaca gctgcttgga  12180
actcagtctg ggaactctag catgcagact aatcaacacc ctgcacatat gttacagcaa  12240
cccaaggttc cactgcagca acaaatgcag cagagtgctc ctaatttgtt accgaatcaa  12300
ggccagcaac agcaatcaca accacaacag cagcagatga tgtcacaaat tcaatcacag  12360
cctactcagc tgcaacagca gttgggttta cagcaacagc ctaatccatt acaacgagat  12420
atgcagcaaa gacttcaggc atcaggtcaa gcatctgctt ccttgcttca accgcagaat  12480
gtaatggatc agcaaaagca gttatatcaa ccacaaagag cccttccaga gacatcgtca  12540
agtatgttgt ttcatatatg cggttaatta gtcttgttat ggctgtgcct ttgctgtttt  12600
attccatttt attagtaaga tttattccct tttaacctca catatatcaa tttttttataa  12660
tagtatctaa atcttttgcc ttataaaagt gcattatggt ccatgagatt ttatctcatt  12720
ggtcattgca ataatggatt cacaagtaat gcttcaattt gtatttcgta tattttttca  12780
tttactaagt taatgccatg ttttatcttg atcaaatctg taagctcatt gtaaagacgc  12840
cagttcccaa tttgtctctc tgtcccacca ctactccttt gcgcacatac actgaaactt  12900
attgcttctc aacatcactt ctattgatgc tactgaaggc tcctctttct tgcagagcaa  12960
ctaagaattt taaatgcatg gttgattgtg gacaggagtg aagtttgttt tccatatctt  13020
ttttgcttga agagtttatg agtgccatct cttaattgtt ttgcttgtgg gagaaattga  13080
ttcttgtttt cttgtccgcc taaattgctt cagatagtta tgatgaagtc atcttgcttt  13140
gctttgttcc accgtatgaa ttacatattt gcttgtgatt tgcttctttg tgatgctgtt  13200
gatcccacca tcaaaacctg cacaacatga tcccaatttt ttccttttgc cactggaatt  13260
tcaggttacc ttaaattcta ttgaaatatc cgtgactgct ccactgcatg gcatgtgtat  13320
agtataattt tctgtgttat ttattacgaa tcaaacatat gcctttccat taacttacac  13380
gtgcctttat tataatggta gcatctcttg actccacaca ccagacagga caagcaaatg  13440
gggttgattg gcaagaggag gtgtatcaaa aggtaatttt tcatgtcctt taataaagtc  13500
tacttataat tctcgtaaga aaatattcaa ggtgatgatc tgggtctgat agtggtgaaa  13560
```

-continued

```
tttggattgg gaaaacctag ggtctattaa gaatgttcaa cttgaaatca cttagaaact  13620
gtattgatat ccttgtgata gtaactcaac acctttttag gataaagaga tccattaatc  13680
ttagaagact tgtcaaagca taaatgaaat tttttgtgac ttaggtggcg tttgtttttt  13740
tagtctgaaa tctgagtaga cctgaattag tctgaattct taatggatct gaatgtctga  13800
atctgaataa tatgtttgtt ttttcgtctg aacctcagaa aataagtatt aagttgtttg  13860
ttttttttcaa cttaaaaacc tgaaaatata tacttttaca tttgtatcct tattaaattt  13920
aaatgtcaaa taaataatat attaaatacc acaatatttt aacatttata agtaaaacta  13980
tattcaagtg aatacataat tattttagaa ttttaatata taaaatacca taaatttcaa  14040
attttatcgt atataatata agaaagaaaa aataaggata tttttatgtg gggtaaatgt  14100
ctatgggtga attttgggat agacatgaaa aataaattat aaaatatgga tatttttgac  14160
attagcaagt aattgactta attcagattt ctccattaag taaaaagcca aaaaaattag  14220
cttattttat taagtcaaaa ttatgtaaaa agtctcatta agttataaaa acaaacacct  14280
ctaattaatt taattaatta aattaagtca ctttaagtca ttaagttaaa aaacaaacgc  14340
caccttaatc tattatttct ttgtttgatc ttacagcaaa aattccctta agcgttcatt  14400
acaccaagaa aatgaggatg agtgattcag gtcaccctgt gaaaattaag tttcttgatt  14460
aggactgagg tagtcatact agatattaga tgatataaag tgacgatgat aaaaaatttg  14520
gggcaaagaa agctaaaccg tggcgagaga ggttactgct ttcttgagtt atcttctgta  14580
tacctgtatt tttgttttgc attctctaat cagggtaggg atctatgatt ttttgagaca  14640
actacaaatc tatcattgag agtttattta tcaaaaagaa catttttcca tcgttttatc  14700
aaaatttagg ctcgtttcct tattcatttt cactcccgcc ccaatatatg tatgcttaaa  14760
ttccacagtt gtgtaaaatc ttatgatttg tcgatctgct tttcatgatc ccctctcgag  14820
gaaccatcca ttattcaaaa tgcaaatccc atgaacagtc tttcttttac cctcgttcat  14880
ggccatactt ccaatgcata ggcatggttt atgtaggatg caaataaggt gtaatttgac  14940
tgtttaagta cacaggaacc ctgactattg gcatggttca cctatgaact cttaagactt  15000
tctgtgaaat tgtgatctga gatttttctg attttgaaaa atgatggaga aaaccatctg  15060
ttatgtcaat gttttgctta ttatgcttta tagtgaatta agttttgaat taagtttacc  15120
tttgttcctc tttaatggat agcgtattta atgtacttgg ttttctttct ccttgtattc  15180
atttcactaa tgttactgta acttgtgaat caccgaactg atggtttggt tcgtacttat  15240
tttttcattt ttgatgagaa gtttgaagct gaaatatgtt ttcatgtcta aaatgataat  15300
tcatcctttc actcatacat atctgcgttt atgaattttt ttcactttaa tctgaccttt  15360
tctgttaaga aaaaattatg actgatggag aaacaatccg ttatgtcatg ttttgctgat  15420
tatgctctat agtgaattag gtttagcttt gttcctcttt aatggatagc atatttaatg  15480
tacttggttt tctttctcct tgtattcctt tcactaacat ttctgttaag aaaaaattat  15540
gactgatata ctaaccatct gtgctgttaa atattctata tgcaacaact atctgttcta  15600
ccctgtggaa cgtgaagtag cgaataattt aataattttg ttttgcaaat tttactttgc  15660
agattaaaag catgaaggag atgtatttac ccgaattaaa tgaaatgtat cagaaaattg  15720
ctgctaaatt gcagcaggta agcgatccct ttatcctcaa ccatattgat taactagcgt  15780
ttccatctga tctctggctg taatggaata ttccttcaag ttcatctgct tatcaattct  15840
tagggcgtgt tctgtcagga agccttttca gatattctct aagccttcca cttctcttgc  15900
ctcctataga gaacaaaaat tatatcgcca acatgttgtc tgcatcgttg ttatcgtgtt  15960
```

-continued

```
attttttact gtaataggct gtttcttatt atgtatattt tgtttctgct tgtcagcatg  16020
attctcttcc acaacaaccg aaatcagatc agcttgaaaa gctgaaaata tttaagacca  16080
tgttggagcg cattatatca tttttacagg tttcgaaaag caatatttta cctagtttta  16140
aggagaagct gggttcttat gagaagcaaa tagttaattt catcagtaca aacaggccaa  16200
ggaagcctgt ttcttcaatg caacagcaag gacagctacc cccaacacat atgcattcca  16260
tgcagcagca acagtctcaa attagtcaag ggcagcctca tgacaatcaa atgaactcac  16320
agattcaatc aatgaactta gcaggttcaa tggttactat gcaaccaaac aatgtgacaa  16380
atgtacagca taattcagta ccttctgtct caggggtttc aacttcacaa cagaatatgt  16440
taaattcagt gctgccaggt cccaatatgg attcaggaca aggaacttca ttaagctcaa  16500
tgcatcaagt taatgctgga tctctgcaac aaaattcagt gagtgctccc caacaagcaa  16560
gcattaacaa tttagcatca caaagtggag tgaacatgct gcagtcaaat attaatcctc  16620
tccagtcgaa ttcaaatatg atgcaacacc agcatttgaa gcaacatcag gagcagcaaa  16680
ttttacagtc acaacagcta aaacaaatgc aacagcagcg ccaaatgcag tttcagaaac  16740
agcagcttat gcaacaacag cagcagcaac aacatcaaca gcaacagcat cagcagcaac  16800
agcatcagca gcaacagcat cagcaacaac atcagcaagc aaaacagcaa ctgccagcac  16860
agctgccgac acaccaaatg ccacagctga atcagatgaa tgatgtaaat gacttgaaaa  16920
ttaggcaggg gatggctgtt aagcctggtg tttttcagca acatctgaca tcgggccagc  16980
gctcagctta ttcccatcaa ccattgaaac caggggctca gtttcctatt tcttcacccc  17040
agctccttca gactgcatcc cctcaaatac cacaacattc ttctcctcag gttgaccagc  17100
agaatctgct tcaatcaatc acaaaaagtg gaaccccatt gcagtccgtg aactctcctt  17160
ttgttgttcc atctccttca acacccatgg ctccatcgcc tatgccaggg gattctgaga  17220
aacccatatc tggtatttct tcactttcaa atgctggaaa tattggacat caacaaacca  17280
ccagtgctca agcagcagca ccatcccttg caattggcac tcctgggata tcagcctcac  17340
ctttgcttgc tgagtttact ggtccagatg gtgctcatgg taatgctttg acagctattt  17400
ctatcaaggc aagtgttaca gagcagcctc ttgagcgctt aattaaagcg gtaaatatat  17460
cttggtacac cgagtttttg tggtatttag tgatgtttcc ccatataaaa gggataatta  17520
tattgttttc ttaaaattta tatctgtttt gaatatattg tttgtttatt tttcaggtga  17580
aatcaatgtc acctaaagca ttgagtgcat ctgtcagtga cattgggtca gttgtgagta  17640
tgattgatag gatagcagga tcagcgccag gtaatgggtc tagagctgct gttggtgagg  17700
atttggttgc catgaccaag tgtcgtctgc aggctagaaa tttcatcaca caggatggat  17760
cgagtggacc gaggaaaatg aggcgttata caagtgcaat gcccttgagt gttgtatcat  17820
cagccggtag catgaatgat agttttaagc aattgactgg ttcagagacc tctgacctgg  17880
agtcaactgc aacatctagt atcaagaggc caagaatgga ggtattgtac ttagtttcta  17940
acttgtataa caacagtagg ttcatgttaa tggactaatt gcagttggat ttatgataca  18000
aaactttgct tgacaccttt tgctgtagtt actgggactg catctatgaa atgttctttt  18060
tttgagttac taaatgattg actatctagt tttacaaaga caaaatattc tctttacaat  18120
tttgcacttg gcaaataact taccttttct tcataagtcc tatttcaagg acatttatta  18180
attctttgaa attccagttt ttgtaacctt tgatttatgt aatgcataag ttggatcata  18240
tcaaatgcaa agaggcgcta cttattttgc ttctgtattc tatagaacta ttagggccat  18300
```

-continued

```
ctttatgtta atcactctta ggtataacaa aaatatttgg tacctgttac aggctaatca  18360
cgcccttttg gaagaaataa gggaaataaa tcaacggctt atagacacag tggttgatat  18420
cagtgatgaa gatgctgatc caactgcagc tggttctgct ggtgaagggg gtgaagggac  18480
tgttgttaaa tgctctttta gtgctgttgc tctcagtcca aatttgaaat cacagtatgc  18540
ttcagcacaa atggtgaggt tttttgcctt ccaaaaagga ataaaatcct tactttctag  18600
tgctttcctc tgtatttatt cgtgtttcca tgaattgcag tcacctattc agcccttgcg  18660
tttgcttgtt cctacaaatt acccaaattg ctctccaata ctattagaca agttccctgt  18720
ggaaattagg taagggaatg ctacatttct acttttctat tttattttcc agaagttggt  18780
attacttgta gcagcatgtt gtgttatttt cattaactca ctgaaactgc tctccaatac  18840
tttccatagt tcctttttc cactcatccc gcctaatcgt atcttttgat tgaaaatttg  18900
ttgaatgagc caaaatcatc taaacttact ttccttgtgt ccaacttaaa tgacataatc  18960
aattttctag accaagtctg acaaactcgt gaaaccacga aacacacttt gtttttgaca  19020
gtaaggaata cgaagatctt tcggtgaagg caaagtccag gtttagcatc tctctacgaa  19080
gcctttcaca acccatgtca ctcggggaga tagccaggac ttgggatgtt tgtgcaagaa  19140
cagttatttc tgagtatgcc cagcaaagtg gtggaggcag tttcagctca aaatacggaa  19200
cctgggaaaa ctgcctgagc gccgcatgat catgccttca gactcgctgc aaatctgtca  19260
aacggttatt ccagttagcc atgctgaaga atttactaca aatgcttcag ccatggtgat  19320
gactgaacca ctcaagcact ttgccagatg ggcaccgtca acacaggcac tgtgttttgg  19380
ggaagttttg tcttaccttg tagctctcat ggggttaggg tgtataaaag ttctcttggg  19440
gtaaaagcac agcaatagca tccatatagc attgaccatg tgtatttata atgtaaaaga  19500
tgtctgtaat tatggtgcaa ttctgtaatg tgagaaggta tcctgttttg atttggttgt  19560
tttcagttga aagatgagag aaagtgagaa actttttttct ctcttaatgt tctagaaatt  19620
ttattgcaag gaatgaaggt tttatttagt aaatgttgat ttttctttta atacgagttc  19680
aaatgagcat tgaaagataa ttatggggat cgttaactaa ataatttcaa tgggttgctt  19740
tggttacaat ttgatcaaag atcaatttta atctgagata tttaagagat tctaatctac  19800
tgttggagaa aaagactttt agcccagaac gtttttcctt ctgtgctgga aatggggtat  19860
tgatgccctg tactctactg cacacaactc gtggcataca gctaagacat tgttgactac  19920
ttgttttctc cgacatcagt gtgagtaatg atatttacac gtaaaatttg aaaaaaatta  19980
ttaacacata agaaatattt cactaaaaaa ataaatttat tcaccttgtt attttattta  20040
ttttttaaa taaatgttct ccttctattt gttttgtata attttatatg taattttgca  20100
tgtaaatcat ttgccgtcaa ttattagtcg ttgcgtgaaa gctcactgct ttaattttgg  20160
ggaccttgat atttaaatca tttaatttat tttccgtcaa ttcccatttc actctattct  20220
tgtggtgtcg tgatggtttg gtaatcacat ccaaacgggc tctagactaa agttcttcca  20280
tcagactctt gtttttcttt atcgaaatct catacaaaat atgggtaatg ttattggaat  20340
ccagttctca tgtgatgcca ttttgtctca cggcctaaat tgtactctcg gcaaagcagc  20400
atgcataagc cagctcgaag ataatcttgt tgatttgcag actaaattgg aaaaattaat  20460
tgaagcaaag aatgacgtga tgatgagggt tgtaattgct gaaagacaac aaatgagatg  20520
cttgaaccaa gtgcaagggt ggctttcaag ggtgcagtct gtggagaccg aagctggtca  20580
actgataaga gatggctctc aagaaattga gaaattatgt cttggtggct actgttccaa  20640
gaactgcaag tccagctaca actttgggaa agaggtggct caaaaggtgc aacttgtgga  20700
```

-continued

```
gactctaatg ggagaaaaag attttgcagt ggtggctcag aggtctcaag aatctgtagc  20760
agatgaaaga cctactgagc caattgtagt aggcctgcaa tctcagcttg aacaagtttg  20820
gagatgcctc gtagaagaac cagctggaat tgttggccta tatggcatgg gtggtgttgg  20880
taagactacg cttttaactc atatcaacaa caagtttctt caagtgccaa acgattttga  20940
ttgtgtgatt tgggttgttg tgtccaaaga ctggcgtctt gaaaatattc aagagattat  21000
tgggggggaaa ataggtttga tgaatgagtc atggaagagt aaaagcctcc aggagaaatc  21060
actagacatc ttcaagattt taagggagaa gaagtttgtt ttgttgctag atgacttatg  21120
gcagcgggtt gatttaacaa aagtgggcgt ccctcttccc agcccacaaa gtagtgcatc  21180
taaagtcgta tttacaaccc gttctgaaga aatttgtggt ttgatggaag cccaaaaaaa  21240
gttcaaagtg gcttgcttat cagataaaga tgcatgggaa ttgttttgtc acaaagttgg  21300
agaagaaact ctgaacaatc atcctgatat tcctgagctg gcacagacag ttgccaaaga  21360
gtgtgggggt atgccacttg cacttattac cattggccga gctatgtctt gcaagaggac  21420
gctgcaagaa tggagacacg caattcaagt gttaagaaca acagcttccg agtttccagg  21480
tttgggaaat taggtgtatc ctcttttaaa attcagctat gaaagtctgc ccaatgatat  21540
tgttagatct tgtctcttgt actgtagttt atatccagag gattatcgaa tttctaaaga  21600
gaatttgata gattgttgga ttggtgagag ttttctgaat gaaagggtaa aatttgaagt  21660
acaaaatcaa ggatactata ttttgggcat tcttgttcat gcatgtttac tagaagaggt  21720
gggagaagat gaagtaaaaa tgcatgacgt gattcgggac atggctttgt ggatagcatg  21780
cgacagtgag aagaagggga agaaattttt agtatgtgca ggtgctggat tgactgagga  21840
cccaggtgtt aggggatggg aaaatgtgag tagattgtca ctgatgcaaa atcgcattaa  21900
gaatctgtca gagattccta agtgccctca tctccttact ttatttctta acagtaatga  21960
gttaaagata atcactaatg acttctttca gtttatgcct tctctcaaag ttttaagcct  22020
atcacgcaac agacgactaa ccaacttaca gttagggatt tcaaagttgg tttcactcca  22080
acatcttgat ctttcactta caaacataga aaagttgtca ggagagttaa aggccttggt  22140
aaatctcaaa tgtttgaatt tggaatacac atggagttta gtgacaattc cacagcaact  22200
aatagctagt ttttcgaggt tacatgtgtt gagaatgttt ggtgttggtg atgatgcatt  22260
tgaagtagca tcagaagaca gcgtttttatt tgatgggggt gaatttttag tggaggaatt  22320
gcttggtttg aatcatttag aggttttgag cttgaccttg agaagtcctt atgctctcca  22380
gagctttttg acctcgcata agttacaatg ttgtactcaa gctctattcc ttcaatactt  22440
caaagattca acatcgcttg ttgtttcatc tttggcaaac ctgaagcgcc tcaacgtatt  22500
acggattgca gactgtgaaa aattggaaga attgaagatt gattatacaa gggaaataca  22560
acattttggt ttccgcagcc tttgtaaggt tgaaatagcc aggtgccaaa aattgaagga  22620
cctgacattc cttgtttttg ctccaaacct cgagtctatt gaagtaaaaa gttgccttgc  22680
attggaagaa attgtaactg atgttccgaa ggcaatggga aatctaaacc tatttgcaaa  22740
actccaatat cttgaattgc ttggtctgcc aaatttgaag agcatttact ggaagcccct  22800
gtccttccca cgtctgaaag aaatgacaat aatcacttgt aataagctta aaaagcttcc  22860
agttgattcc aacagtgcaa aggagcgtaa aattgttatt cgtggagaca gagaatggtc  22920
gcgacagctt caatgggagg atgaagccac tcaaaatgtt tttcttccct gtttcaaatc  22980
tctactggag attactgagc aaagattgta atggaattct ggtgagtgct atttcttaca  23040
```

-continued

```
ttaattcttc ttgttaattt cctccatgta acaaaatact ctgtttcttt ccttcccatt  23100
tgttgtatgt tgtgacacag cttgatcaaa gcagccttgt tgattgttac aagatatttg  23160
cagaattatg aggtttcata tgacaatttt cctattttca gaactgaaca agaaaatatt  23220
tatcaaaaaa gtctaatgca ttcctctgta tttaatatgt gtatttagat gagttgcagt  23280
cacctgttaa gcccttgtgt ttgcttgttc ctacaaatga ccctaattgc tctccaatgc  23340
agttagagaa gttttcagtt gaaatcaggt aagggaatgc tacatttcat tttgagtttt  23400
ctttttgat tttggaagtt cgtgtgttac ttatagcgca ccagctcctc gtgttaatta  23460
ttttaataaa ctcactaaaa ttttgctcca gtactttcat ttttgtttat tttgaaatta  23520
atctccaata gtttttttcc gatggtgaca cctaatcatg aggagacgtg gtgagccttg  23580
tagtaataaa ttgtaaattg attctacatg atgtatattt tgaacttgtt attctacttt  23640
tatatgtgtt tgattgaatg atatttcagt gtgttatcaa agagtaataa aatattatta  23700
caacttaggt taaaacttag gcctatttga tattaaggta ctataatttt caagcacaac  23760
tgatgtttaa aaaaaaaact ataattataa aacaaaaact gatagcgttt agtaaatatg  23820
attttaagta attttttgac aaaaaataat aaagatatta tagatttttc atcgtataag  23880
tgtgaaatga aatcaattta actttgtagc cccaataaca agtatttatc aaacactcaa  23940
gtggtgatac aactaatcaa tctcaatagc aatcagggct ttagtattct ttagatttta  24000
taagttgatg ggcctagaaa tttaattaca attactgcca atgagaggaa agtactcttt  24060
gtttatgaaa tatgggatgt accgaacaca acttgtggca agctaagatg aatcgttcat  24120
attcgtatat tccctgccac tcgttcattg catatgattt tcatatttga gagcacactt  24180
tattttgaaa ttgggggcca tgtttaatac attttgtgtc ttgccaaaca atgcattaca  24240
cttattatgt atatgaattt catgcctata caaggtacat ttttcaagta tatatcctct  24300
ttaactgttg gggtgttccc aattttcatt ttgtttattt atttattttt aactactatt  24360
agccttcgga cagctcccct gtactctctt gctttcttag tattaaaaac atgcattgat  24420
ataagaaaga catgcaaaat aaaatttacc ttctctaggt cttcacatca ccaatgtaaa  24480
ttggatatac atcaatttca agtccatgaa gatttgctta cctctgcgca gttcacaaat  24540
gcttttccct ctagctgact gattgaaaca aacaatttga aattcaaacg gtgcttatat  24600
aactaaagag gagatttgat tacaaggcat attatgtttc aacatactga taagattaga  24660
gaagttttat ttacatctct atacctatca tggcaattgt tgatataatc atgttacaac  24720
agataataaa ttaatttcag ttaattgctt tgtgcattgc aagacattta attaattata  24780
tatgaatata taatacaatg taatttgact ttcaaaaggg ctttcaaaaa acattttgag  24840
ttttgttgca tggtatgact agattgagaa gcaaagctga tattgaattg gtggtggcca  24900
ctttttggac gtggagtgca agaaaccatt tcttatttaa aggaaagagg gagaatccta  24960
ggttgctgat agctaagaca gaagctgtgg ttgatgcatg caaaagaact caattaccag  25020
catctgcatc tgttggaaat cattaggctt tgtttcagca gacatgaagt cccctccaac  25080
gaggctattt caaggtaaat gtagatgcag ccaccaactc aggaaagcaa accccagggc  25140
tgggagctgt tattcgagat gaatctggaa tgtaattgca gctgccatta agccttcaaa  25200
gtttttttgg agatgtatcc tttgtggtgg caaaagcgat ggaatggggc gtgcagattg  25260
cagggcgtgc aggcttgacg ttattggttg ttgaatcaga ctctcaagag gtggttaatt  25320
ttgtaaacaa caggcagcac agcagatccc agatcttctg ggttatctta gaaattcaga  25380
acctattgaa gggctttgat catgttagta tccagtatgc tcagatactg cccactcttt  25440
```

-continued

```
agttaaacta gctttagaga gatgtatgaa tgggttcata cccttcacaa ctgatgcatt  25500
tattttcttc aatgaatcga aagtggtttt tatgctttaa aaataacaaa gaaataaata  25560
aaaaatacgg acaccaactt tgacttttaa aggggtttga catccgttag ctataccaag  25620
gaaaattctt tccattatac tcattttttt attcaatccc attttgtcga aatcttatag  25680
aaaaatatgg ggaacgctat cggaatccaa ttctcatgtg atgccatttt atctctctgc  25740
ctagattgta ctctcaagag agcagcatat gtaagccggc ttgaagataa tcttgatgat  25800
ttgcagactc aactgaataa attaattgaa gcaaagaata atgaattgat gagaatgaag  25860
tgatattgag gcttgtaatt gctgaaagac aacaaatgag acgcttgaat caagtgcaag  25920
gttggatttc aagggtggaa gctgtgaaaa ctgaagttgg tgaattgaca agaaatagct  25980
ctcaagaaat tgagaaataa tgtcttggag gctactgttc caagagctgt aagtcgagct  26040
ataagtttgg gaaacaagtg gctaaaacgc tacaagatgt gaagaattta atgggcgaag  26100
gagcttttga ggttgtggct aagagagctc caaaatccgt agcggatgaa aggcctaccg  26160
agccaaacgt tgtaggtttg caatctcaac ttgaacaagt ttggagatgt cttgtagaag  26220
aaccagctgg aattgttggt ctatatggca tgggtggtgt cggtaaaact actctattaa  26280
cccatatcaa caacaaattt cttgtgagtt caactgattc tgattgtgtg atatggattg  26340
tagtttcgaa agacctaaaa cttgaaaaaa ttcaagaaat tatcgggaag aaggtaggct  26400
tgttggatgg tgattcatcg aagaataaaa attctgaaga gaaagctcta gaaatcttca  26460
ggtttttgag taaaaagaag tttgtattgt tgctagatga tatatgggag cgagttcatc  26520
taacaaaggc gggcgtccct cttcctggcc ttaaaaacaa tgcatctaaa gtcgtattta  26580
aaaccaggct tgtttgtctg gggcctcatg gaagctaaca agaagtttaa agtggaatgc  26640
ttatcagata acgatgcttg ggaactgttt cgacagaaag ttgggttaga aacacttgac  26700
agccatcatg atatcctaga gcttgcccaa acagtggcca agaagtgtgt tggtttgccg  26760
cttgcactta tcaccattgg tcgagctata gcttccaaac agacacctag agaatggagg  26820
tatgcaattc aattgttaag aacatcagct tctgagtttt caggtttagg aaaagaggta  26880
aaccctcttt taaaattcag ttatgattgg ttgcccaatg atacaattag atcttgtctc  26940
ttatattgta gtttttatcc agaggattat ttgatttcta aagagatttt aatatattgt  27000
tggattggtg agggattttt aagggtacta cattttgggc attcttcttc atgcttgttt  27060
attggaagag ggaggagaca atgaagtaaa aatgcatgat gtgattcgcg acatggcttt  27120
gtgtatatga attttttact ttaatctgcc ctttttttatt aagaaaaaat tatgactgat  27180
ataccaacca tctgtgttgt ttaacattct agcaagtaga ggacaaagaa ttcttagttg  27240
ttccttcttt ttgatttagc cacttttagc aagtgtttat atgcaaacaa tttaatcaag  27300
tgttcatctg ttgtaccccg cggaacctga agaagtgaat aatttaacaa ttctgtcttg  27360
gggaagtttt gtcttgcctt gcagctctca tggggtgata tgtatgaagg ttcttttggg  27420
gtaaaagcac aggaataaca tccacacagc attgagcaga tgtagttatt atgtaaaaga  27480
tgtctgtaac tattctgcaa tactgcaatg tgagtttgta gaatggtatc ttgttttgat  27540
ctggttgttt tctagaaatt gtattgcaag gaatgaaggt tttgcttagt gaatgttgat  27600
tttcttttaa tacgagttca aatgagcttt gaaagtaata ttacatggct agccaatttt  27660
ccttgaggga tttcaatgct ggtttgaata caacatcttg atcttccata cacaagcatc  27720
taagagttgc tgaaagagct aaaggccttg gtaaatcttg aatgttcgaa tttagattgt  27780
```

-continued

```
gccaacgagt taattgatat cccacggcaa ctgaagtcta atttttgaaa gttgcgagtg  27840
ttgagaattt tggtgccggc tttttggctt tttatcaagc accagacaac agcattttac  27900
ttggtgaggg tgaagttttt agcagaggaa ttgcttggtt tggaacattt agattttaga  27960
ggtattggaa ttcactttgg cgagttttca cgctcttcaa attattttga gctcagaaaa  28020
cttgtgaggt tgtaccattt gagtaaaaca ggccacactt aaaatcatgg gcgaagctct  28080
ttgtgggcta acttgggctt atcccaacta gattttagga aaaactttta gttttattta  28140
taaagttgcc attgcgtcaa ttttacgaaa gagtaataat gtaattataa attttttttat  28200
aaatttattt tatataaatt aatatattat gattaaatta attaaattaa atatttataa  28260
aactgctact gctgtaattt tattaaattg ccacttcaat atttataaac agcactccag  28320
taatttctct aaattgccac cgcagtattt acaaaactcc actccaacgt ctttttattt  28380
tttattttt atttttaaa atagctcctg tcatcatttt cccagatttc ttcttcctta  28440
ccccgtctta ttttgaaaat ttccattgct ttctctaaca aagttgcgaa gacaaagaat  28500
ttaacacttt gaaactttgt aagacgcagc ttcaacagta tctaattata tttgagtttc  28560
ttttttgact taattataca actttgatgt actaactaaa ctttctttaa gcttttgttt  28620
gtttttttaga taaattccat gcttaaaatt tacttgaaaa aaatttagtt tagtccagtg  28680
tataaaagat tcctaggttc gcccctgcac ataatatata tttatatcta attaaatttt  28740
tttaaaagtc aatattatat tttttatgtc attaaatgaa gtcttgttat tttatcgaat  28800
tatattcaac ttgaaaatag ttttagcttt tagatataag ttatgtaagt acaagttcaa  28860
agtatattag tattaaatta ctaatattaa atcatttata atctgatgtt gaaaaaaaaa  28920
tgtcattcaa tcatatgcat ttaactaaat tcaaatataa tctaaattca aataccttaa  28980
aattattagg gaaaaaaaaa ccacaactct atactattta ttgagtaaac ctaagttaat  29040
tctatcatta acaaccattt atttatttaa attattgccc cttttggtta cttaattaaa  29100
taagggttaa ataatcattt cttgaattga caaacacttc tcttcacaga cggtcaagaa  29160
cctaaatata aataatttga acaagaagaa tttatatgct aaactatttt gaagttgttc  29220
taaaataaaa ccccaaccat aattacataa ttaaaattat attatatatt ttattattta  29280
ttattttgta aatacagtcg tgatttatgt tttatcttaa aataatttta agataactat  29340
cgccacatat atatatatat atatatatat atatattttt tttttttttt taagaggcca  29400
tttatataaa tttagctgag aatatcagcg atcacaatgt taataatctt taacttaaaa  29460
atacacgtgg cagttattga tttgagagca aactaaaatt tatttatttg tattctctgg  29520
ccacgaaact acaaaagctt caagcttgtt aaagaattga atcaattgat accattactg  29580
caatcaaacg cagagatggg aatttcaaga ggaaatcctc tgtcgaccca ggtgctattt  29640
ttgagtgtgt gtttatatat tgttaattaa atgatcttat gctgccatga atttaagtgc  29700
ttgatgaatt ttttagaccc aagattttgt cttagcatca gatttttgta tgaagatgct  29760
tccttttgtt tttatctgtt gtgattacta ttttttgtta tgtgggcatt caccaacttg  29820
atcaaaaata gaaactttgc catgaaacaa acagaagtac agaacccatg ttgtgacttt  29880
gtttttgttt tttttttttg actgtttatt tgctttaatg aaaagcccat atgagctcaa  29940
agaggaagaa attagtgagc gttgtggggc atatatacta ttgagcgtta ttatgtattg  30000
ctttgcaatt ttgttgagaa agatgatgag ccatctataa ttatttcatg atattcagaa  30060
agacagtcgt taaactgcat ctttgttatg acaattgatt tgatcaaaac attctgctta  30120
aatgaaataa tgacatgatt gactccacga tacggttttg tattgtggct tttttggcta  30180
```

-continued

```
acagacttgt gagttcttca ggttgtgtgt gtcatatata aggaattatg atgggttaga  30240
cttttgatgt tgttttatga acttaatttg gctaatatgg tgaatatttg ggagtgtaat  30300
gccatagaaa atattgattt tctcgaccaa aaattacaaa ccaaaagtac ttggatacta  30360
gtatgtatat gagagaatag atcaagcgat atgctgatgt catcaacagc caggaaatgg  30420
gtgctgattt ttaaagaatc tttctgctgt aatgaagtgt ttaaaatgtt tactttgtat  30480
gcttgatatc aagtatgaga gaaaaaagaa aaagaaattc aattttgcag taacggttgt  30540
gaattagtga aaagttggta caattaactt ttcttctttt cccttctccc ttctccctct  30600
gcttttgatg tgctcttgat gtaaaatttc tattatgctt ctgtatgata ttatgaatgt  30660
gatattaatt tttacctgct taagttaaat gttcttttcg ttctttgcag gttttttta  30720
atattacatt tagttttgtt ctaagatatg catttttttt cattggctta gaatatgatg  30780
acttctcgtc agaagggggt agctatgctg gacccaagtg actggagaaa tccgttatcg  30840
catgattccc gacaaagaat tgtcaacaaa atgtacgtgt cttttctcct cctcccagcc  30900
ataattcatc tactcgagaa ccactatata gtttgtgggc tatcttttac agttttagct  30960
cgtattagta ttaagtggca gtgatttgag tggcaatacc atttccatag aagaatagaa  31020
attgttactg ggtatggctc ccatcaaaac tagttatttg cttctcagaa tttatttttc  31080
tattctctta ttgtggatat attcatggga ataaaagcgc aggcattgct caccaaatac  31140
aaaatttgag tgtgaaatcc tatctgagat atggctacat cctagggtga ctatgtcatg  31200
ctgtatcaat cgaccaaatg atatgtatca ttattgtgct tatatagagc attgatgcaa  31260
ataaagaatt tgcagaatga aacattccct tatcaaactt tcctgccctt tcttgattcc  31320
ttttcaaaac tattaaattc agttcaccat tataggtaaa gtatatgccc attctgtttc  31380
ttgtgacatt tcagctccta gtgatatcat tagaaaacgt gtagagatct agcaccatta  31440
tttcattttt tgtgatacgt tacttttcac attttgtgtt atgtactggg ttctatagtg  31500
atacactttt tgggtaactt attgcaattc attttatctg attctggcct tgcttgaatt  31560
ggttcccttt aaagcctatt gcccagaaaa ttgtacaata gttggcacac aaaattagat  31620
attttggtgt tggctgtccg catgccaaaa tgaatggaac tgtatcatta attatattgg  31680
tcttccagct atcagttcat ggactatagc tgtcaaggct gaatggctgc ttgatttcca  31740
aataagactt gctgaaataa tagtctgttt ctactctttc ctgctcaaga gttaaattta  31800
acaaagttcc ctgattcttt cagataagaa gggtaactgc cagagagtac tgtgctttct  31860
ttacatatag atattatgta ctttgtattt tcatcatatt atgatcttgg gcttgagaat  31920
tcaaatactt catattgtat actgattgag tgttctctga gaaaccgaac aatgtgcata  31980
gtgactcatt aatatattgt tttttaatag aatggataca ttgaagagac atcttccatt  32040
ttctggccca gagggattaa atgaactcaa gagaattgcc gatcggtttg aagaaaagat  32100
atttacttct gccacaagtc aggtaattcc agtttgaggc tttttttgtt atgattaata  32160
tgtaaatact ctttcctttt atatgtgctt tgatgcaggg ctgttccttt gtgtttcttt  32220
tcctttttaaa gattccttat atttatttgt gtaaatctat gtgtgaactg tgcacatgga  32280
cgcacagaca tgtatatgcg gtgcaaaata gccacgtact tgggaaattg ggaaagaaaa  32340
gtctccaaag agggagagtg gaaaatcgag gagggaaatg gggtaaatac gtatcaaatg  32400
atattggctc ttgatagtca ttaatttgtg atgacgatga agcagatgat gtcattgttg  32460
aattttttttt tataaaaaaa agagagaata atgaagttgg aagagaaaaa agttgcaaat  32520
```

-continued

```
cttctaacct gttaaactga aggaagaaaa aaaagaaagg aactcaaaga agattttctg  32580
aacataatag tctagcattt tttattttct gttgaaacca tattttacta ttttagttta  32640
tttatattca ttgcacaaca attaggtcat gttttctttt gttttctgtt ttatattctt  32700
tgatcatttt ggcaacatgg agtactatga ttaatcagtt tgtaccggtc tcaaatttca  32760
gtcagattat ctgcggaaaa tatctctgaa gatgctttca atggagtcca ggtctcagaa  32820
tgctagcggg agcaacgaac cccctcatcc aggtagtgac atggaatagt aaatgcggct  32880
tcactttcaa tttgtctccg aaacccttcc ctacaatcaa tcctagcatt cttatgtgtt  32940
ctttactttt gcagcttgaa tatttcttcc ccgacaatcg aagtcataac agtttgattg  33000
gctggattag ctttcctcca gacctctcac tatagttata aataattccc atatttgata  33060
tcatgatctg tggatttcag atctcagaaa atattatttg taaccatatg tgtctgatca  33120
tgagaagttt gaaaatatac atcaaaaact gtatggattg gaaaaatata atcttattat  33180
aatgtgtttg agagtgctct taaattgtca tttgatgaac ggatttggga tacattataa  33240
tatgatgtca ttattaatta gggtgtgtta ttggaagtgc ttaactatga ttgatttacc  33300
ttacttatat ttgtttaatg cattttttctt tcatcactta tgaaaagaat tcctaaatat  33360
ttaaatattt caatgtttat atcttaactt caaatataat aaaataaaat aaaataattg  33420
ttctccaata tgaggctacg aactaagggt ctacgtcaat aacatgacat gataattttt  33480
gtaaattttt cttaaattca aaataatttt tgttactaat tcaaatgttt aatataatgt  33540
gacagcttaa tgcaattgcc acatcagttg agattcaagt tacgactcaa accctgaaat  33600
tcctacaggt ccctaacatt aatattttat aaagtcaata ttgaagttga actatggggt  33660
tcgttggcta tttctcacta acagatgaat cattttatct tctacaaagg attcagtttt  33720
cttgcattgt acgatatgaa ttaaaattat catatgttgt tctgaattaa tttttcttc  33780
tctcgtgcaa atcagaaaga aatgttgtat atggaaagta taagatatta ggagttttac  33840
agtatctttt tttgacaaac agagaaattc agtcttaaat atgagaacaa actaaaagct  33900
acgaaataca ttggcctttt tgagaagtag gaaaaaaata tttttttttt tgaaaaaaaa  33960
aggatttggc acctcaatgc tttaataacc taatgttatt cctctttaca atctatatgt  34020
aacttttggt ttgattttc tatgtactct cttccaatgg ccaatttagg ctatgtttgg  34080
tgttgagata ttataactca aaaattttaa gatttatcac ttaaaagata gagtagcggt  34140
ggggaaaaag agagagagag ctgaaattat gaaataaaaa ttattaatat attgtaaata  34200
agatgtttaa ataaaaaaat tgacaaaaat agtaaaaatg caataccaaa caagaattta  34260
tttaggatac cgattacaag tatgtgaaga tttgtttttc tgctttgcag ttattttctt  34320
ctagctgact aatgaattat tgtgaaattg ctatgaaaat tactaaggaa attatcagcc  34380
atataccctt aaatggcacc cgtatcaaat atgctacaac atttttcaag tatatcactc  34440
gtataccta agttgacaaa acacttatgt cgtccaacaa tctattaact tcctttagtt  34500
aacaattaaa atatggcaga aatattttgt caacttaaaa tatacgagtg atatacttaa  34560
aaggtgttgt aggacgtttg atactgatat catttaaagg tatatggttg ataatttccc  34620
aaattactac tataacttat ggcaaattgg caattaaaaa tcataaaagt ctttcctctt  34680
gaatgagaaa gggggttatt ttcgtttact ctatatatat agtgtcacaa tcaagattag  34740
caaaggtttg ttcacaaacc accatctatg aaactatgat gacaaatatt atttgctatt  34800
atcatgtcac tgcattactc taatgccatt atttgcctaa ttaaatattc atgtcggttt  34860
taagatgaat ttcaagacat ttaactaacc atatctattg tattttataa tggtgctcta  34920
```

-continued

```
gctagctggt taccagcttt gactttcaat ggggtttgat taattactct gcatatagac  34980
cattatatac taggacggcc aatggttaat gtaatataaa cacaataaat tttaatcaaa  35040
tatgaatttt ctgaatgaat gtttctttat tttatgaatt ttatttaaac gatatcccaa  35100
ttttaaaaaa aaaaagaaaa aaagaaagaa aatcagcgcg tttgtctcct ccccattgtc  35160
atgatcaacc ttgttggaaa cgttggtgag aaaagtaata ctatacgtta attgctttta  35220
atattttaat cgttggtggc acgaccgcac aagaaagtaa aagttgttat atatatattt  35280
taaataaaag tttggctttc aataattcaa ctttgaaaaa ggtacaaaat atgtgtagga  35340
cattcgttga accacattat tgattctagc aaagcttacc ttataaataa tgtaacaaac  35400
aaccaataaa tataggtcat tgattttaat attttttaaa tctaatggat aaaaataatt  35460
ttaacctaaa atgaagtaca tgtgtaattg ttatttatag aaaatttcat ttctaatcat  35520
atatttactt atttttaaa taagtcctca ttaatttttt ataattaacg gttttctcat  35580
ccatctcttt tataattatt tttaaaattt tataaagttt ttactatatt tttataaaga  35640
tttaaattag tattattata ttcataaaaa taacaaattc tcaataaatt ttttgtacct  35700
acatttataa tttattttct ctcttgagac atagactagg tttttcttct aacaaacaca  35760
taaacacaca cacacattca atctattttt catcctaaat acatactatt agtgatgtcg  35820
catagatttt ttaatctaaa tttagtatct tgaattataa gagatattat atgtgttttt  35880
tcaatacgag ataggtgttt tttcaatccg cagtctgcct gtgtagtttt ttcaattcga  35940
gaagcaggaa aaatatttgt tttcttctag ctgactgatg aattattaag aaattgctga  36000
gaaaattact actataactt atggcaattg gcaattaaag gggggctatt ttcgtttatt  36060
atatagggtg tcacaatcaa gattagcaga agtttgtttg caaaccactc tctatgacac  36120
aagattagca gaagattgtt cgatagttga aaaaaaaagt gaaacaaaac cagtggtaat  36180
agatctgcaa acagaggcag tttgataaaa ttgttactga ttaattaata agttggtctc  36240
tctcatttag ggttggcaat ttaagggcct gggccgggct ttgccaagcc caggaccagg  36300
cccatataat gttaaataag tccaggccct ctcaaagccc atccaagttg agcgggcttg  36360
gggcgggccg ggccttgacg ggcttgggcc gggcctcggg ccaagcccgg gcttttacga  36420
aattttaaat ttaaaaaaaa aaaaaattat aaattttcaa aaaataatta accaatacat  36480
aatactacaa taggctaaaa acttaaatat aattatctaa tacatgatta gcaacacaaa  36540
atataaaaat actaacaata caagtaccgt acacaacgta caaatcaacc actaatataa  36600
aaaaaaaact aatagagatt taccgattta ggaattttga cattttgtga caaaaccttt  36660
gccctttccc tttgcccgat ttttttatta ttttgtttaa ttattttttc aattttataa  36720
tatattatac attttttatt atatatatgg cttctaagtc agaagaggct atagaagttt  36780
ggtcatcttg ttctaatact ccaatcttgc tagattgagg agtatcagga gctatttgaa  36840
ctttattaga agaggacgaa gcagattcaa tcctaatttt caaatgcgtt taccacactg  36900
tttgatgtat tcctattggg attaccagca ggcttggttc aatacctttt ttatacaaaa  36960
ccctaaaagg tctcattcat ggttattttt ctttaattct aaaataaccg tacaaagcct  37020
tccaaactgg ttccaacaat ggtggaatta ttttggttca agttagggaa aagtgtttta  37080
ttgtttagag tcttcgtttt taaagtcttg tgttttattt tgaagttttg tttttgtggt  37140
gaatttttac tggtcgtaag tcccgtttta ggataagaat tccgctgagg gctgtaatcc  37200
catacctgta gccattctga ccaaaccaaa aataagccat aaggctttga ctatggattc  37260
```

-continued

```
tctcctccat agaacatcat ccttttctag ctcttcttcc gggaagacta gtgatttaaa  37320
gcatgttgtg agttcaaaag aattcgttat tgagaacttt gataaagcaa ttgattgttg  37380
ggaacttcca tagatttcaa aagaaaaaat ttacaaaaca aaaatgcttg acgttttaaa  37440
aaatgattat attataaaga ctgaagaacg tgacataact ctttcagagc cttttgaaac  37500
aattcatttg ttttcagaaa agtctttaaa gaaattaata gaaaagaatt tcaagtatat  37560
acacattggt ctcatctaag taggaataaa gcctttaacg aaagaaggtc tagatacctc  37620
tatactggcc gtcctaagag atgggcgatt catctctttt gatgattctt tgctaagtag  37680
catcgaatct agtctgtgta aaggtccaat tccttttgac tgttatccaa atataacaat  37740
ttctcttaaa gacaaaaatg ttttaaaaag catgattttg gagaacaaaa cccataatta  37800
caaaatgatt aaagggtcaa ttccagtagc cttaattttt aaaatttcat ataaggctat  37860
ggtttctgca tttagtacac aacatagatt ccagtcaaag agggatgaaa cacttctctt  37920
gcagactgac ctgtctagag caaacactgt cattccaaag ccaatccaat ggaaagatat  37980
caatcttcca gaggaatgga tcttagaggg agctgctccc ccaacgatcc caaaacaact  38040
tgagccaaat acagagttgc aaaatgtgac tcagtattcc gatggtaaag ttaaactatt  38100
attcagaagg tctatgtcat ccagattttc taataaagag tcgtgctcaa gtatccctac  38160
tttagaaagg aaatttacaa aaatcccctc tgtcataaat ctcccatacc aatctacaaa  38220
gagtcaaccg aggttttcca cctcagatat acctagttct tctatacatt ctgttgacta  38280
tactacaaat gttccacacc ctatctacac tagtagtcaa catgtacaaa gtcaggaaga  38340
gaaggaacct tctcttccaa catctcctac attttctgct gtcacagaaa atgtcattaa  38400
tatcatagag aaagaatttg aattagataa aacattactg cataatgatt tttattctga  38460
tttaaacaaa gaaaaaaaaa tttggttttt caaacaattt ttaaatcaaa gaaaagaaat  38520
ccaacaaatt tattatgaat ttgtgaattt tcataaagtt catatattgt tttttgattg  38580
gttcgaaata tattcttctg agaacaacat aacctatcct ttcaaagagt caaaccccat  38640
tactattaga aaaaagatcc ctgagtggaa actttctgat agtgataaaa ccatcgaatc  38700
tgagcatcca cctcttcgga gtctaaccat tgatcatggc gaacctccta tccaaattag  38760
agcctcacct tacaaaatcc caaaaccaaa tgattctgat tcaaatttaa gtagtattat  38820
ccaacagaat aatttctgta atactaactt aaatacaatt ggaaagcagt tgactaggat  38880
agaaaaccaa ttccagaagt caaccatcac tgtttcatcc acttctccta ttccatcaaa  38940
atcggattat gacaaaaagc ttaaggaagc tattttcaaa cctttccagg tttcgaaaac  39000
tagccaaaag cttgttcaag agtcaaaatc agattttgct aaagccatta gagaacaatt  39060
agataggatt gaatctgctt cgtcctcttc taataaagtt caaatagctc ctaatactcc  39120
tcaatctagc aagattggag tattagaaca agatgaccaa acttctatag cctcttctga  39180
cttagaagcc ttcaaagatg aagcacctac tcctagagcc aacaaaatcc attgggaact  39240
tgcccctcct acagtcaaat cccctcctga tttggctata gacaacaggc ctagtgcatt  39300
aaatcaatct cgatataatg cattctctgt ctatgaatga aatattgatg gcatgtccga  39360
atacaatatc ttaggagtct tgcaacaaat gaccatggca gctaatgcct ataaaactca  39420
atccggaacc tctgacatgg ctattgcaga gattcttatc gccggtttta ctggtcaatt  39480
aaaaggttgg tgggatcatc ttctcactag gcagcaacaa atggatattc ttaatgctat  39540
ccaaattgat gaaaatagga tacctattct cgatcaattc aacaatccta tccaggatgc  39600
tgttgctacc ttaatcctta ccatttccct ccattttata ggtgaccctt ctcacctcag  39660
```

-continued agacaaaaat gctgagttac tacataattt aagatgtagg aaacttagtg atttccaatt 39720
atacaaaacc accttcttca ccagactctt tcttagagat gatgcgaatc atactacttg 39780
gaaagagaaa ttcttagcag gtctacctac ccttttaggt gaaaaggtta gaaattccat 39840
caaagccctt tatgacaata gaattcctta tgatgagctc acctatggtc aacttgtcag 39900
tttcgttaat aaggaaggtt taaagatttg tcaagatttg aagttacaga aacgactaaa 39960
acaagagctt aggcagtcta agcgagaact tggtagtttc tgtaaacaat tcaattatga 40020
tccttttaaa gcttccactt ccaaagattg taatggtaag tgctcttcga gatcttacaa 40080
aaaacattac aagtcaaaaa gccataggaa accctttctt ggacataggg aaaattttta 40140
taagaaacct actaggcctt ataaaaagtc cagattccct agaaagaaag attttaaagc 40200
cacaccaaaa actcctttca atttcaagga agccatttgt catcgatgtg gtataaaagg 40260
ccatactgca aaatattaca aaatgaacag aaagcttcat gaacttggtc ttgatgacga 40320
catcctttcc aaaattgccc ccccttatga ttgagtcttc gaattctgaa tcctctatgt 40380
caggggatag tgattcttta caaattgatg agttaattga ttcagatact tctgtatcta 40440
acagtagtga ttctgaatca gagtcttatt taaagaaaat taatattttg actaaagacc 40500
aagagacttt tcttgaactt gtaaagcata tttctgatcc aaatctccaa aaagaatatc 40560
ttgaaaagct tttaaaaaca atggatttca acaaagctga gacttccaaa gttccaatcg 40620
taaaaaagaa ttcttatgat cttactgaaa ttttagataa aaagaaaacc aaaaaatcgg 40680
tccctaatat ccaagacctc caaaaagaga ttaaggatat taagtccgaa attaaagatt 40740
tgaaagaaaa acaaaaaagt gattctgaaa ccatccaact tcttttacaa aaacatttac 40800
aggatgattc agataacgag tctactcata gtgaaaatca tattgagcaa aatgttgata 40860
acattgagtc tgtcccacat gattttctct tcgttttaaa gcaagttacc actcgaaaat 40920
atttgattaa agccacctta atcttttcaa atgattttgc aattgatgcc attgcccttt 40980
ttgatactgg tgcagattta aattgcataa gacaagatat tgttccaaaa cgatttcatg 41040
aaaagacaaa agaaaggctt tctgccgcca acaattcaaa attaaaagtt gattctaaag 41100
tcgaagcctc tattcataac aatggtttcg aatttaaaac ctcttttatt cttacaaatg 41160
atattcatca tgctgtaatt ttaggaactc cttttataaa tcttataact ccgtatactg 41220
ttaattatga cagtatatct ttcaaagtaa aaaataaaaa gattattttt ccttttatcg 41280
aaaaaccaaa gacaagaaat ttgaatattg ttaaagcctg ttccatttac caaaaccgaa 41340
ttaataatct aattaattcg aaacaaaatg atttaacctt tctccaaaaa gatttgagtt 41400
tacaaagaat tgaaaatgat ttacaaagag atttcattaa aagaaaaatt tctgatttca 41460
aaaccctaat tgaaaaagaa atttgtgctg atctgccttc tgctttttgg aatagaaaac 41520
aacatatggt agatttgcct tatgaaaatt cttttgatga aaaacagata cccactaaag 41580
ctcgaccaat tcaaatgaat atggatttag aacgacattg taaagaagaa attaatgatc 41640
ttgtaaaaaa aggacttatt gtaaaatcaa ggtcaccttg gtcatgtgcc gctttttatg 41700
ttaataaaaa ttctgaaatt gagagaggca caccaagact tgtcataaat tacaagcctt 41760
taaataaagc tttaaaatgg attaggtacc cgatacctaa taaaaaggat ttgttacaaa 41820
aactgcattc tgctttcata ttttcaaaat ttgacatgaa atcaggattt tggcaaatcc 41880
aaatccatcc aaaagaccgt tataaaactg cttttactgt tccatttgga cagtatgagt 41940
ggactgtcat gccttttggt ttaaaaaatg caccttcaga atttcaaaga attatgaatg 42000

-continued

```
acatttataa tccttattct gatttttgta ttgtttatat tgatgacgtg ttgatttttt  42060
caaattcaat tgatcaacat ttcaaacatt taaagacctt ttattttgcc accagaaagg  42120
ctggattggc aatttcaaat tccaaagtct ccttatttca aacaaaaatc cggttcttag  42180
gtcatcatat ttcaaaagga accattactc caattgagcg atcactcgct tttgctgata  42240
aatttcctga caaaattttg gataaaaccc aactacaaag atttttaggc agcttaaatt  42300
atgttcttga tttctgtcca aatattagta ggttatctaa acctttgcat gataggctaa  42360
aaaagaaacc tgctgcatgg actgatgagc atacaaagac tgttagatta ataaagaatt  42420
ctgttaagag cattccatgt ttatatcttg caaatcctgc attgcctaag atagttgaaa  42480
ctgatgcatc tgatttaggt tatggaggta ttttaaagca aaaggaaaat gataaagaac  42540
aaattattca atatgtttct gcacattgga atgattgtca aaagaactat tctactatta  42600
aaaaagaaat tctttccatt gttttgtgca tatcaaaatt ccaaagtgat ttattaaatc  42660
aaaaattttt acttagaata gattgcaaag ctgcaaaaca tgttttagaa aaagatgttc  42720
aaaacattgc atcaaaacaa atttttgcac gatggcaagc cattttaagt gtttttgatt  42780
ttgatattga atttattaaa ggcgataaaa attctgttcc agattttcta actcgagaat  42840
ttcttcaaaa cagataatgc cgccaaagcg tcgagacaaa ggaaaaggca tagccaaaga  42900
cactgattcc ctaaagccct ccaaagaatc ccaatcaact ccttctaaag aaaaattact  42960
atcctcagcc atgccaatca aatcctggat tgaaatggtc gaagatgaag aacaaaaagc  43020
cctttctaaa tccatctcct ctgaccaaca agtcaaagaa tggatggaat ccattacaaa  43080
gtcccctgag cttatgcttg ccttacaagg catttcaaaa tctaaagccc tttctcagat  43140
ccctgaggaa gaaaaaccca tttctaaaga aattacaaaa ctatcttccc aaagccaaaa  43200
tgttgtcatt tctggtgaaa gctcatcttc tcagattgtt ctttcccagc caacaccttc  43260
aaagaaaacc tccgattggt ttgataaatc ccattttcaa aatgttttaa ctatggaaca  43320
tgggttttac cattctgatc cttttcaagc aatttcaaag ttttttcctc aaagctggtt  43380
tttcaaccca tgggatttaa caaaacccca gtcatattat caaagcatcc ttgaagccac  43440
tgagtctgta aaattcaaac acttctttct cagtgaaacc cattctgagc cggcctactc  43500
cacggccacg attttaaaag ttttgagtcc aaatcagtgg ggcgaccaac tccataaata  43560
caaatctttc cctccaaatt ttcaaatgcg tttaccacac tgtttggtgt attcctattg  43620
ggattaccag caggcttggt tcaatacctt ttttatacaa aaccctaaaa gatctcattc  43680
atggttattt ttctttaatt ctaaaataac cgtacaaagc cttccaaact ggttccaaca  43740
atggtggaat tattttggtt caacaccaca aatcttaact cccaatgcca cccattgtct  43800
aaaccttttt aaagcccatt ataccccatc tgactcagag aaaagatttt ctccatttct  43860
ctgtttctgt acaaatttct tcctcccatg ggtatggatg tggaacttcc ggtatcatac  43920
ccaagaaaaa caactactta tccaaagaac cttcaaagtc aaatggtggt caaaatttga  43980
tgaacaaacc aagctcaccg aaacccttgt ccaaaattgg cttggttcaa aaggtttcct  44040
accgccaacc attaaagaat caaaagccca acaaattttc cttacccaaa aatcaaaagc  44100
ccaatctctc ttgggcagtg ccaaaactga agcagaatac ttcaaagtca tgcaacaact  44160
tcttgctaca cgatcagaga catcagttgc aagttcctcc tccagcacct cggcagatga  44220
agaacccttt atctctctgg gtgatgagaa tgaagatgac tgcttcggca ttttctctcc  44280
aataaagcat taaagctata ttacgataga atcttggttt tacctacttc tatgtatgta  44340
catttttgta cttaaaaaaa aaatgatgac aaaaacattt ctttcgggtg gtccactgga  44400
```

-continued

```
cacaagtgag agcgcacatg tctcttcacc cgtatttctg tatgtatttt gtactttgta  44460
ttttgtaact tcttgtacaa agcctactat tcaaagatac catccaaaga ttactgtgca  44520
cttgaagctc cgctacagtg aacagtgcca aagactactg tgcacttaca gttcgtttgt  44580
ataaaaaccg ggaggaagac ttagactcct caggttttca ttttccaatt tcagagcttc  44640
tctctcttct tctcctcctt ctctctacat ctctctctct aggaatctga aattcaaaga  44700
cactaaggaa attttcctcc gggttagttc cttgtctgcg aattaatttc ctttcttttc  44760
ttttcaaaga atcagaaaac caaatgtaag catttaattt tattttattt tttcaaagca  44820
ttgtaatttt attttaacgc acttaaagca tgcacgttta aatttctgca atttaaattt  44880
tcgcaatttt aatttcagca atttaattta aagcaattta aatttccgtg tgcacgttta  44940
aattctgcat gcatcggaga ctgatcttta tcagatctcc catacaaatt ctacgttcct  45000
cagaggcata gagaccggat ctctcccctc tgttgtaatt ctcttctccc cccttcttca  45060
gagcaccact tccgggatcc ggatttggta ctgtgtttgt agctcagcca aaatcaacct  45120
aatttatatt tggtaatgca cctaaaattt gactaacctc gttccaaagc atatctcaat  45180
aaataataaa taacttaaag ctggatcaaa attattttga gtatatcggc tggaatacct  45240
aagggttgcg ggctactggc ccaaaggaag tttaaatagc ttggcggaaa catatccatt  45300
gccaaggacc tcgtccctta tacaacgcca cgtactcaaa atattaacaa tttgacaaag  45360
ccgaataaaa tttgattatt ttattatcca aagcaatcat catttgcaat ccaatcatta  45420
gcaatccaaa gcaagtgcat ttcaaagcaa tcttaattaa atttggtaaa gatagtcttt  45480
aaaaagaatc aaccactata caatttgttt tattaatcaa tcaataaaga cttctttttg  45540
taaacacacc ctgttttcgg tcttatttcc ttctggtatc agagccaagt tagggaaaag  45600
tgttttattg tttagagtct tcgtttttaa agtcttgtgt tttattttga agttttgttt  45660
ttgtggtgaa tttttactgg tcgtaagtcc cgttttagga taagaattcc gctgagggct  45720
gtaatctcat acctgtagcc attctgacca aaccaaaaat aagccataag gctttgacta  45780
tggattctct cctccataga acatcatcct tttctagctc ttcttccggg aagactagtg  45840
atttaaagca tgttgtgagt tcagaagaat tcgttattga gaactttgat aaagcaattg  45900
attgttggga acttccaaag atttcaaaag aaaaaattta caaaacaaaa atgcttgacg  45960
ttttaaaaaa tgattatatt ataaagactg aagaacgtga cataactctt tcagagcctt  46020
ttgaaacaat tcatttgttt tcagaaaagt ctttaaagaa attaatagaa aagaatttca  46080
agtatataca cattggtctc atccaagtag gaataaagac tttaacgaaa gaaggtctag  46140
atacctctat actggtcgtc ctaagagatg ggcgattcat ctcttttgat gattctttgc  46200
taagtagcat cgaatctagt ctgtgtaaag gtccaatttc ttttgactgt tatccaaata  46260
taacaatttc tcttaaagac aaaaatgttt taaaaagtat gattttgcag atcaaaaccc  46320
ataattacaa aatgattaaa gggtcaattc cagtagcctt aatttttaaa atttcatata  46380
aggctatggt ttctgcattt agtacacaac atagattcca gtcaaagagg gatgaaacac  46440
ttctcttgca gactgacctg tctaaagcaa acactgtcat tccaaagcca atccaatgga  46500
aagatatcaa tcttccagag gaatggatct tagagggagc tgctccccca acgttcccaa  46560
aacaacttga gccaaataca gagttgcaaa atgtgactca gtattccgat ggtaaagtta  46620
aactatcatt cagaaggtct atgtcatcca gattttctga taaagagtcg tactcaagta  46680
tccctacttt agaaaggaaa tttacaaaaa tcccctctgt cataaatctc tcataccaat  46740
```

-continued ctacaaagag tcaaccgagg ttttccacct cagatatacc tagttcttct atacattctg 46800
ttgactatac tacaaatgtt ccacacccta tctacactag tagttaacat gtacaaagtc 46860
aggaagagaa ggaaccttct cttccaacat cttctacatt ttctgctgtc acagaaaatg 46920
tcattaatgt catagagaaa gaatttgaat tagataaaac attactgcat aatgattttt 46980
attctgattt aaacaaagaa aaaagaattt ggtttttcaa acaatttttt aattaaagaa 47040
aagaaagcca acaaatggat attcttaatg ctatccaaat tgatgaaaat aggatactta 47100
ttctcgatca attcaacaat cctatctagg atgctgttgc taccttaatc cttaccattt 47160
ccctccattt tataggtgac ccttctcacc tcagagacaa aaatgctgag ttactacata 47220
atttaagatg taggaaactt agtgatttcc aattatacaa aaccaccttc ttcaccagac 47280
tctttcttag agatgatgcg aatcatacta cttggaaaga gaaattctta gcatgtctac 47340
ctaccctttt aggtgaaaag gttagaaatt tcatcaaagc cctttatgac aatcgaattc 47400
cttatgatga gctcacctat ggtgaacttg tcagtttcgt taataaggaa ggtttaaaga 47460
tttgtcaaga tttgaagtta cagaaacgac taaaataaga gattaggcag tctaagcgag 47520
aacttggtag tttctgtaaa caattcaatt atgatccttt taaagcttcc acttccaaag 47580
attgtaatgg taagtgctct tcgagacctt acaaaaaaca ttacaagtca aaaagccata 47640
ggaaactctt tcttggacat agggaaaatt tttataagaa acctactagg ccttataaaa 47700
agtccagatt ccctagaaag aaagatttta aagccacacc aaaaactcct ttcaatttca 47760
aggaagccat ttgtcatcga tgtggtataa aaggccatac tgcaaaatat tgcaaaatga 47820
acagaaagct tcatgaactt ggtcttgatg acgacatcct ttccaaaatt gcccccctta 47880
tgattgagtc ttcgaattct gaatcctcta tgtcagggga tagtgattct ttacaaattg 47940
atgagttaat tgattcagat acttctgtat ctaacagtag tgattctgaa tcagagtctt 48000
atttaaagaa aattaatgtt ttgactaaag accaagagac ttttcttgaa cttgtaaagc 48060
atatttctga tccaaatctc caaaaagaat atcttgaaaa gcttttaaaa acaatggatt 48120
tcaacaaagc tgagacttcc aaagttccaa tcgtaaaaaa gaattcttat gatcttactg 48180
aaattttaga taaaaagaaa accaaaaaat cggtccctaa tatccaagac ctccaaaaag 48240
agattaagga tattaagtcc gaaattaaag atttgaaaga aaaacaaaaa agtgattctg 48300
aaaccatcca acttctttta caaaaacatt tacaggatga ttcagataac gagtctactc 48360
atagtgaaaa tcatattgag caaaatgttg ataacattga gtctgtccca catgattttc 48420
tcttcgtttt aaagcaagtt accactcgaa aatatttgat taaagccacc ttaatctttt 48480
caaatgattt tgcaattgat gccattgccc tttttgatac tggtgcagat ttaaattgca 48540
taagacaaga tattgttcca aaacgatttc atgaaaagac aaaagaaagg ctttctgccg 48600
ccaacaattc aaaaattaaa gttgattcta aagtcgaagc ctctattcat aacaatggtt 48660
tcgaatttaa aacctctttt attcttacaa atgatattca tcatgttgta attttaggaa 48720
ctccttttat aaatcttata actccgtata ctgttaatta tgacagtata tctttcaaag 48780
taaaaaataa aaagattatt tttcctttta tcgaaaaacc aaagacaaga aatttgaata 48840
ttgttaaagc ctgttccatt taccaaaacc gaattaataa tctaattaat tcgaaacaaa 48900
atgatttaac ctttctccaa aaagatttga gtttacaaag aattgaaaat gatttacaaa 48960
gagatttcat taaaagaaaa atttctgatt tcaaaaccct aattgaaaaa gaaatttgtg 49020
ctgatctgcc ttctgctttt tgaaatagaa aacaacatat ggtagatttg ccttatgaaa 49080
attcttttga tgaaaaacag atacccacta aagctcgacc aattcaaatg aatatggatt 49140

-continued

```
tagaacgaca ttgtaaagaa gaaattaatg atcttgtaaa aaaaggactt attgtaaaat  49200
caaggtcacc ttggttatgt gccgcttttt atgttaataa aaattctgaa attgagagag  49260
gcacaccaag acttgtcata aattacaagc ctttaaataa agctttaaaa tggattaggt  49320
acccgatacc taataaaaag gatttgttac aaaaactgca ttctgctttc atattttcaa  49380
aatttgacat gaaatcagta ttttggcaaa tccaaatcca tccaaaagac cgttataaaa  49440
ccgcttttac tgttccattt ggacagtatg agtggactgt catgcctttt ggtttaaaaa  49500
atgcaccttc agaatttcaa agaattatga atgacattta taatccttat tctgattttt  49560
gtattgttta tattgatgac gtgttgattt tttcaaattc aattgatcaa catttcaaac  49620
atttaaagac cttttatttt gccaccagaa aggctggatt ggcaatttca aattccaaag  49680
tctccttatt tcaaacaaaa atccggttct taggtcatca tatttcaaaa ggaaccatta  49740
ctccaattga gcgatcactc acttttgctg ataaatttcc tgacaaaatt ttggataaaa  49800
cccaactaca aagattttta ggcagcttaa attatgttct tgatttctgt ccaaatatta  49860
gtaggttatc taaaccttta catgataggc taaaaaagaa acctgctgca tgaactgatg  49920
agcatacaaa gactgttaga ttaataaaga attttgttaa gagcattcca tgtttatatc  49980
ttgcaaatcc tgcattgcct aagatagttg aaactgatgc atctgattta ggttatggag  50040
gtaaaccctt tctcagatcc ctgaggaaga aaaactcatt tctaaagaaa ttacaaaact  50100
atcttcccaa agccaaaatg ttgtcatttc tggtgaaagc tcatcttctc agattgttct  50160
ttcccagcca acaccttcaa agaaaacctc cgattggttt gataaatccc attttcaaaa  50220
tgttttaact atggaacatg ggttttacca ttctgatcct tttcaagcaa tttcaaagtt  50280
tttttctcaa agctggtttt tcaaaccatg ggatttaaca aaaccccagt catattatca  50340
aagcatcctt gaagccactg agtatgtaaa attcaaacac ttctttctca gtgaaaccca  50400
ttctgagccg gcctactcca cggccacgat tttaaaagtt ttgagtccaa atcagtgggg  50460
cgaccaactc cataaataca aatctttccc tccaaatttt caaatgcgtt taccacactg  50520
tttggtgtat tcctattggg attaccagca ggcttggttc aataccttttt ttatacaaaa  50580
ccctaaaagg tctcattcat ggttattttt ctttaattct aaaataaccg tacaaagcct  50640
tccaaactgg ttccaacaat ggtggaatta ttttggttca acaccacaaa tcttaactac  50700
caatgccacc cattgtctaa accttttttaa agcccattat accccatctg actcagagaa  50760
aagattttct ccatttctct gtttctgtac aaatttcttc ctcccatggg tatggatgtg  50820
gaacttccgg tatcataccc aagaaaagca actacttatc caaagaacct tcaaagtcaa  50880
atggtggtca aaatttgatg aacaaaccaa gctcaccgaa acccttgtcc aaaattggct  50940
tggttcaaaa ggtttcctac cgccaaccat taaagaatca aaagcccaac aaattttcct  51000
tacccaaaaa tcaaaagccc aatctctctt ggccagtgcc aaaactgaag cagaatactt  51060
caaagtcatg caacagcttc tcgctacacg atcagagaca tcagttgcaa gttcctcctc  51120
cagcacctcg gcagatgaag aaccctttat ctctctgggt gatgagaatg aagatgactg  51180
cttcggcatt ttctctccaa taaagcatta aagctatatt acgatagaat cttggtttta  51240
cctacttcta tgtatgtaca gttttgtact taaaaaaaaa tgatgacaaa aacatttctt  51300
tcgggtggtc cactggacac aagtgagagc gcacatgtct cttcacccgt atttctgtat  51360
gtattttgta ctttatattt tgtaacttct tgtacaaagc ctactattca aagatatcat  51420
ccaaagatta ctgtgcactt gaagctccgc tacagtgaac agtgccaaag actactgtgc  51480
```

-continued

```
acttacagtt cgtttgtata aaaaccggga ggaagactta gactcctcag gttttcattt  51540
tccaatttta gagcttctct ctcttcttct cctccttctc tctacatctc tctctctagg  51600
aatctgaaat tcaaagacac taaggaaatt ttcctccggg ttagttcctt gtttgcgaat  51660
taatttcctt tcttttcttt tcaaagaatc agaaaaccaa atgtaagcat ttaattttat  51720
tttatttttt caaagcattg taattttatt ttaacgcaat taaagcatgc acgtttaaat  51780
ttctgcaatt taaattttcg caattttaat ttcagcaatt taatttaaag caatttaaat  51840
ttccgtatgc acgtttaaat tctgcatgca tcggagacta atctttatca gatctcccat  51900
acaaattcta cgttcctcag aggcatagag accggatctc tcccctctgt tgtaattctc  51960
ttctcccccc ttcttcagag caccacttcc gggatccgga tttggtactg tgtttgtagc  52020
tcagccaaaa tcaacctaat ttatatttgg taatgcacct aaaatttgac taacctcgtt  52080
ccaaagcata tctcaataaa taataaataa tttaaagctg gatcaaaatt attttgagta  52140
tatcggctgg aatacctaag ggttgcgggc tactggccca aaggaagttt aaatagcttg  52200
gcggaaacat atccattggc aaggacctcg tcccttatac aacgccacgt actcaaaata  52260
ttaacaattt gacaaagccg aataaaattt gattatttta ttatccaaag caatcatcat  52320
ttgcaatcca atcattagca atccaaagca agtgcatttc aaagcaatct taattaaatt  52380
tagtaaagat agtctttaaa aagaatcaac cacgatacaa tttgttttat taatcaatca  52440
ataaagactt ctttttgtaa acacaccctg ttttcggtct tatttccttg ggtatcgggg  52500
tacctaatcc attttaaagt tttatttaaa agcttgtaat ttatgacaag tcttggtgtg  52560
cctctctcaa tttcagaatt tttattaaca taaaaagcgg cacatgacca aggtgacctt  52620
gattttacaa taagtcattt ttttacaaga tcattaattt cttctttaca atgtcgttct  52680
aaatccatat tcatttgaat tggtcgagct ttagtgggta tctgtttttc atcaaaagaa  52740
ttttcataag gcaaatctac catatgttgt tttctattcc aaaaagcaga aggcagatca  52800
gcacaaattt ctttttcaat tagggttttg aaatcagaaa tttttctttt aatgaaatct  52860
ctttgtaaat cattttcaat tccttgtaaa ctcaaatctt tttggagaag tgttaaatca  52920
ttttgtttcg aattaattag attattaatt cggttttggt aaatggaaca ggctttaaca  52980
atattcaaat ttcttgtctt tggtttttcg ataaaaggaa aaataatctt tttatttttt  53040
actttgaaag atatactgtc ataattaaca gtatacggag ttataagatt tataaaagga  53100
gttcctaaaa ttacagcatg atgaatatca tttgtaagaa taaaagaggt tttaaattcg  53160
aaaccattgt tatgaataga ggcttcgact ttagaatcaa cttttaattt tgaattgttg  53220
gcggcagaaa gcctttcttt tgtcttttca tgaaatcgtt ttggaacaat atcttgtctt  53280
atgtaattta aatctgcacc agtatcaaaa atggcaatgg catcaattgc aaaatcattt  53340
gaaaagatta aggtggattt aatcaaatat ttccttctgg tatcagagcc aagttaggga  53400
aaagtgtttt attgtttaga gtcttcgttt ttaaagtctt gtgttttatt ttgaagtttt  53460
gtttttgtgg tgaattttta ctggtcgtaa gtcccgtttt aggataagaa ttccgctgag  53520
ggctgtaatc ccatacctgt agccattctg accaaaccaa aaataagcca taaggctttg  53580
actatggatt ctctcctcca tagaacatca tccttttcta gctcttcttc cgggaagact  53640
agtgatttaa agcatgttgt gagttcagaa gaattcgtta ttgagaactt tgataaagca  53700
attgattgtt gggaacttcc aaagatttca aaagaaaaaa tttacaaaac aaaaatgctt  53760
gacgttttaa aaaatgatta tattataaag actgaagaac gtgacataac tctttcagag  53820
ccttttgaaa caattcattt gttttcagaa aagtctttaa agaaattaat agaaaagaat  53880
```

-continued ttcaagtata tacacattgg tctcatccaa gtaggaataa agcctttaac gaaagaaggt 53940
ctagatacct ctatactggt cgtcctaaga gatgggcgat tcatctcttt tgatgattct 54000
ttgctaagta gcatcgaatc tagtctgtgt aaaggtccaa tttcttttga ctgttatcca 54060
aatataacaa tttctcttaa agacaaaaat gttttaaaaa gcatgatttt gcagatcaaa 54120
acccataatt acaaaatgat taaagggtca attccagtag ccttaatttt taaaatttca 54180
tataaggcta tggtttctgc atttagtaca caacatagat tccagtcaaa gagggatgaa 54240
acacttctct tgcagactga cctgtctaga gcaaacactg tcattccaaa gccaatccaa 54300
tggaaagata tcaatcttcc agaggaatgg atcttagagg gagctgctcc cccaacgatc 54360
ccaaaacaac ttgagccaaa tacagagttg caaaatgtga ctcagtattc cgatggtaaa 54420
gttaaactat cattcagaag gtctatgtca tccagatttt ctgataaaga gtcgtgctca 54480
agtatcccta ctttagaaag gaaatttaca aaaatcccct ctgtcataaa tctcccatac 54540
caatctacaa agagtcaacc gaggttttcc acctcagata tacctagttc ttctatacat 54600
tctgttgact atactacaaa tgttccacac cctatctaca ctagtagtca acatgtacaa 54660
agtcaggaag agaaggaacc ttctcttcca acatctccta cattttctgc tgtcacagaa 54720
aatgtcatta atgtcataga gaaagaattt gaattagata aaacattact gcataatgat 54780
ttttattctg atttaaacaa agaaaaaaaa atttggtttt tcaaacaatt tttaaatcaa 54840
agaaaagaaa tccaacaaat ttattatgaa tttgtgaatt ttcataaagt tcatatattg 54900
ttttttgatt ggttcaaaat atattcttct gagaacaaca taacctatcc tttcaaagag 54960
tcaaacccca ttactattag aaaaaagatc cctgagtgga aactttctga tagtgataaa 55020
accatcgaat ctgagcatcc acctcttcgg agtctaacca ttgatcatgg cgaacctcct 55080
atccaaatta gagcctcacc ttacaaaatc ccaaaaccaa atgattctga ttcaaattta 55140
agtagtatta tccaacagaa taatttctgt aatactaact taaatacaat tggaaagcag 55200
ttgactagga tagaaaacca attccagaag tcaaccatca ctgtttcatc cacttctcct 55260
attccatcaa aatcggatta tgacaaaaag tttaaggaac ctattttcaa acatttccag 55320
gtttcgaaaa ctagccaaaa gcttgttcaa gagtcaaaat cagattttgc taaagccatt 55380
agagaacaat tagataggat tgaatctgct tcgtcctctt ctaataaagt tcaaatagct 55440
cctgatactc ctcaatctag caagattgga gtattagaac aagatgacta aacttctata 55500
gcctcttctg acttagaagc cttcaaagat gaagcaccta ctcctagagc caacaaaatc 55560
cattaggaac ttgcccctcc tacagtcaaa tcccctcctg atttggctat agacaacagg 55620
cctagtgcat taaatcaatc tcgatataat gcatcctctg tctatgaatg gaatattgat 55680
ggcatgtccg aatacaatat cttaggagtc ttgcaacaaa tgaccatggc agctaatgcc 55740
tataaaactc aatccggaac ctctgacatg gctattgcag agattcttat cgccggtttt 55800
actggtcaat taaaaggttg gtgggatcat cttctcacta ggcagcaaca aatggatatt 55860
cttaatgtta tccaaattga tgaaaataag atacctattc tcgatcaatt caacaatcct 55920
atccaggatg ctgttgctac cttaatcctt accatttccc tccattttat aggtgaccct 55980
tctcacctca gagacaaaaa tgctgagtta ctacataatt taagatgtag gaaacttagt 56040
gatttccaat tatacaaaac caccttcttc accagactct ttcttagaga tgatgcgaat 56100
catactactt ggaaagagaa attcttagca ggtctaccta cccttttagg tgaaaaggtt 56160
agaaattcca tcaaagccct ttatgacaat cgaattcctt atgatgagct cacctatggt 56220

-continued gaacttgtca gtttcgttaa taaggaaggt ttaaagattt gtcaagattt gaagttacag 56280
aaacgactaa aacaagagct taggcagtct aagcgagaac ttggtagttt ctgtaaacaa 56340
ttcaattatg atccttttaa aacttccact tccaaagatt gtaatggtaa gtgctcttcg 56400
agaccttaca aaaaacatta caagtcaaaa agccatagga aaccctttat tggacatagg 56460
gaaaattttt ataagaaact tactaggcct tataaaaagt ccagattccc taaaaagaaa 56520
gattttaaag ccacaccaaa aactcctttc aatttcaagg aagccatttg tcatcgatgt 56580
ggtataaaag gtcatactgc aaaatattgc aaaatgaaca gaaagcttca tgaacttggt 56640
cttgatgacg acatcctttc caaaattgcc cctcttatga ttgagtcttc gaattctgaa 56700
tcctctatgt caggggatag tgattcttta caaattgatg agttaattga ttcagatact 56760
tctgtatcta acagtagtga ttctgaatca gagtcttatt taaagaaaat taatgttttg 56820
actaaagacc aagagacttt tcttgaactt gtaaagcata tttctgatcc aaatctccaa 56880
aaagaatatc ttgaaaagct tttaaaaaca atggatttca acaaacctga gacttccaaa 56940
gttccaatcg taaaaaagaa ttcttatgat cttactgaaa ttttagataa aaagaaaacc 57000
aaaaaatcgg tccctaatat ccaagacctc caaaaagaga ttaaggatat taagtccgaa 57060
attaaagatt tgaaagaaaa acaaaaaagt gattctgaaa ccatccaact tcttttacaa 57120
aaacatttac aggatgattc agataatata gatattatac atatatatat atcttataat 57180
acatatattt attttgtaaa gcaattaatt tttttcaatt ttataatata ttatacattt 57240
tttaatatat atatatatat attatacata catatatata tatatatata tatatatata 57300
tatatatata tatattataa tacatatatt tattttgtaa agcaattaat ttttttttaat 57360 tttataatat attatacatt ttttaatata tatataaagc cattatccat aatatattat 57420
atatatatat aaaatttatt atttattata aagtccgagc ttttcattta ggctcttgac 57480
tgagtccata tgttatgggc tttactaact ttgagccctt acccataatt tcaaatcacg 57540
ggccggactt aaagcccgcg gacctggacc gggacttttc ttccaaccct actctcatta 57600
cattcaaata atgaaaaccg ctgagtactc tcttcaaatt agatgacgtt gctttgataa 57660
cttctcctcc taatttagag ataaggtggg gatttcgttt tcttttttta ttaatatttt 57720
aatataactg tggggccggc aaatgcagag aaaatggtaa gtgaatgaaa acaattgttt 57780
ctgtcttcat tttgttgttc agctatcatt ttccatattt aattacaaat ggaacaacaa 57840
aaagcaaggt cataatgaca acaagaagaa ttcttttatt aaattacaag ctgaggataa 57900
atgttaaatt aattacaaaa gcaaaaggct aatttattca aggcaagtaa agcagtcagg 57960
aatggtacat gcctaatcct ttctaaattt acaaaacaca aaattttttc aatccgcagc 58020
agcttgtgtt aaaattatct tggtttctcg tagttgattt ctattatcca aaaaaaatgg 58080
gtaacatttt gcaaatcgca atcgattgtg ctattttcaa tcgttgcctg gattgctttc 58140
ttggaaaagc agcatatata agaaacctgc aagacaatgt tgtagccttg gagactgaat 58200
tgggaaaact aatcgaagca aagaacgatg tgatggcgag agtcgtcaac gctgaaaggc 58260
aaccaatgat gacaaggctg aacaaagttc atggctggct gtcgagggtg gacgctgtta 58320
aagctgaagc tgatgaattg ataagacaag gctctcaaga aattgagaaa ctatgtcttg 58380
gaggctactg ttccaagaac tgccattcaa gctacaagtt tggcaaaaaa gtgaccaaaa 58440
agctaagata tgtcgggact ttaatggccg aaggagcctt tgaagtggta gctgagagag 58500
ctccagaatc agtagcgaat gaaaggccta tcgagccaac agtaataggc ttgcaatcac 58560
aactcgagca agtttggaga tgtcttgtag aagaacgagc tggaattgtc ggcctatacg 58620

-continued

```
gcatgggcgg tgtcggtaaa actacactat tgacccatat caacaacaaa tttcttgaga  58680
gtacaactaa ttttaatagg aaatgtgata tgggttgtag tgtcaaaaga cttgcgactt  58740
gaaaacattc aagacactat cggggagaag attggtttgc tgaatgatgc atggaagaaa  58800
agaagtgttg aacagaaagc tctagacatc ttcaggattt tgaaggagaa gaagtttgtt  58860
ttgttgctag atgacttatg gcagcgagtt gatttagtaa aagtgggtgt ccctctccct  58920
ggcccacaaa gtagtacatc caaagtggta ttcacaaccc gttccgagga agtttgtggt  58980
ttaatggaag ctcacaagaa gtttaaagtg gcatgcttat cagatatcaa tgcttgggaa  59040
ttgtttcgac agaaagttgg ggaagaagtt ctacagagtc atactgatat tcttgggctg  59100
gcacatacag ttgctaagga gtgtggtggt ttgccactgg cacttattac cattggccga  59160
gctatggctt gcaagaagac acctgaagag tggagatacg caatccaagt gttaagaaca  59220
tcaagttctc agtttgcagg tttgggaaac gaggtttacc ctcttctaaa attcagttat  59280
gataatttgc ccaatgacac aattagatca tgtctcttat attgtagttt atatccagaa  59340
gattattgca tttctaaaga gaatttgata gattgttgga tcggcgaggg atttttgact  59400
gaaagggacc ggtttggaga acaaaaccaa ggataccata ttctgggcat tcttcttcat  59460
gcctgcttac tggaagaggg aggagacggt gaagtaaaga tgcacgacgt gattcgagat  59520
atggcattat ggatagcatg cgacattgaa aatgagaagg ggaacgtttt ggtttatgca  59580
ggtgttggat tgacagaagc gccagaggtc aaaggttggg aaaatgtgag gagaatttca  59640
ttgatggaca atcaaattac gaatctgtct gaggttgcta catgccctca tctccttact  59700
ttgtttctta acgaaaataa gctacggatg atcggtttga agaaaagata tttacttctg  59760
ccacaagtca ggtaattcca gtttgaggct ttttttgtta tgattaatat gtaaatactc  59820
tttcctttta tatgtgcttt gatgcagggc tgttcctttg tgtttctttt ccttttaaag  59880
attccttata tttatttgtg taaatctatg tgtgaactgt gcacatggac gcacagacat  59940
gtatatgcgg tgcaaaatag ccacgtactt gggaaattgg gaaagaaaag tctccaaaga  60000
gggagagtgg aaaatcgagg agggaaatgg ggtaaatacg tatcaaatga tattggctct  60060
tgatagtcat taatttgtga tgacgatgaa gcagatgatg tcattgttga attttttttt  60120
ataaaaaaaa gagagaataa tgaagttgga agagaaaaaa gttgcaaatc ttctaacctg  60180
ttaaactgaa ggaagaaaaa aaagaaagga actcaaagaa gattttctga acataatagt  60240
ctagcatttt ttattttctg ttgaaaccat attttactat tttagtttat ttatattcat  60300
tgcacaacaa ttaggtcatg ttttcttttg ttttctgttt tatattcttt gatcagatgg  60360
gatacaatgt ttcagaactt gaaacccaca tgaaaggtca aattttttct tttcaatatg  60420
tcgttctgaa tttgatttta gattgtaatg gtgagagatg ggtttttggg gttcttccac  60480
cagattttta ttttttattt aatttttttac ttaatttata ggggtgtgtt aaagaagaag  60540
atcattgaat ttcccataca aattctacgt tcctcagagg catagagacc ggatcttctc  60600
caatttcatt tggaattatc ataattgcag atcggcgagg gatttttgac tgaaagggac  60660
cggtttggag aacaaaacca aggataccat attctgggca ttcttcttca tgcctgctta  60720
ctggaagagg gaggagacgg tgaagtaaag atgcacgacg tgattcgaga tatggcatta  60780
tggatagcat gcgacattga aaatgagaag gggaacgttt tggtttatgc aggtgttgga  60840
ttgacagaag cgccagaggt caaaggttgg gaaaatgtga ggagaatttc attgatggac  60900
aatcaaatta cgaatctgtc tgaggttgct acatgccctc atctccttac tttgtttctt  60960
```

-continued

```
aacgaaaata agctacggat gatccacaat gacttcttcc aatttatgcc ctctctcaaa  61020
gttttaaatt tgtcgcacgc cgaactaacc gaactacccg tagggattgc agagctggtt  61080
tcactgcaac atcttgatct ttctgaatca gatatatcag agttgccaga agagttaaag  61140
gcattggtaa atcttaagtg tttgaatttg gaatggacaa ggtatttaat ttcaattcca  61200
cgtcaactaa tctctaatct ttcaaggtta catgtgttgc gaatgttcgg tgctcgtcat  61260
aatgcttttg acaaagcatc agaagacaac gttttattgg gcgggggtga actcgttgta  61320
gaggaactgc ttggtttgaa atatttggag gtgattagct tcaacttgag aagttcccgt  61380
gctctccaaa gtttttgag ctcgcataag ttacgaagtt gtactcaagc tctgttactc  61440
caacacttca aagatacgac attccttgaa atttcagctt tggccgatct gaagcaactc  61500
aaccgattgc ggatttctga atgtaaaaag ttggaagaat taaagatgga ttatccagga  61560
gtagttcaac aatttgtttt ccacggtctt aagaaggttg aaattgtcaa ttgcaataaa  61620
ttgaaggact tgacattcct tgctttcgct ccaaacctca agtctattga agtattaggt  61680
tgcgttgcta tggaagaaat ggtaagtgtg ggaaaatttg ccgcagttcc agaggtgacg  61740
gcaaatctaa acccatttgc aaagcttcaa tatcttgatt tagttggtgc aataaatttg  61800
aagagcattt actggatgcc cctgtccttc ccacttctga aatatttgag ggcaatgaat  61860
tgccataagc ttaaaaagct tccattcgat tccaatagtg caagagagcg taacattgtt  61920
attaggggat acacaaaatg gtgggatcag cttgaatggg tggacgaagc cactcgaaat  61980
gcttttcttc cctgtttcaa aactttggac tgagatcaca tttgattaat ttctggtgcg  62040
tgctttctct tacattagtt cttctcatta atttccttca tgcagacatc tgcacctaat  62100
aacttactct acttacacaa tatgttatta atttttatta gttcctcttg ttaatctcct  62160
tcattgtaat ctatgtaact tggtctgatc gtttgaaggt actctctcag agatccagat  62220
tcaggtttta tcgtcatcaa gtgccgcttc atctctctct tattgcaaga ctcttggaga  62280
cgctccaatc aaaaatttgc tcagtgccat tcttttgtat ttttgtctct tttatgtttg  62340
cnnnnnnnnn nnnnnnnnnn nnttccattc ggtttctac ctttttcttt tttttaatct  62400
gttttaatgc ttgtattctt ctttgcactg tacaaaatat acaaggagaa aggctcatca  62460
cttcccttct tttgtttgtt tattttggtc tataaaacta taatttaacc caaggtttga  62520
ttttgatctt ttttaaaatc aaaccattag atctaatgtt caacgctacg atgtatctaa  62580
ttacttgttt attaatcttg ccagtatggg ttcaaaatta aaaacataaa gttgataaag  62640
ttggtataat tacacaacgt tgggaaaagg atcacaaata ctcttcaggc tcacaatgaa  62700
tttctctagt attagtcaat gaaatcaaca gatcggttaa aaatcattta tactccaggt  62760
tttatcaaca agcagcgata acaatatatg tcataagaga cactggaagt taaaaaattc  62820
attattgatt aaataattaa aaacctctca gccgtttttg tcgcctaatt attgattttt  62880
attttatttt atttttttgc aacaattcat ggataacaaa accggcagca agggatgtca  62940
tttctatagc tcccttgttt ttacaaaaac gtaagagggg tcaaatatta ctattagaag  63000
attcaattcc ctccaattac ttattaagat aaaattttca actatttatt tatactaaat  63060
tctcctattt taaaaacaaa cttttaagag tactctcatt gttgatcaaa gttagcgaat  63120
atccattaca ttaatattag taaatttgta gtgtgaaatt ttttaagaaa acacacacac  63180
acaagtacta agaaggtcgg ttaatttcgt tttattaatt acacgccaca accaagatta  63240
gcaagacttg attaaatatc agtgtctgtg ataacaatta tttgacatta ttatgtgact  63300
acgttaatct aataagatta tttgcctaat taaacattca agctggtttt caactgaatt  63360
```

-continued gcaagacatt taattatcta ttatagatgt ataaactaca gaagtacata tattatggta 63420
cagttggtta cccaacattt actcgtaagg gggtttgatg actctctctc tctctctcac 63480
tctctctctg tctctctata tatatagaaa caattattac ctcccactta tctttccctt 63540
atatgtcgaa atctcatacg aaaaatgggt aacagtttcg gaatccaatt cacttatgat 63600
gcaattgtac tctcaacaaa gcagcatacg gatgcaagct tgaacagaat cttgttgatt 63660
tgcagactaa attgaaaaag ttaattgaat caaagaatta tgtgatgata agggttgtaa 63720
ttgctctatg actgcaaatg agacccttgt aattcatagt gtggggttca agggtggaag 63780
caatagatgg attgctgtgg tgtatatttt taacttgtta ttgtactatt atttgtgttt 63840
agttgattga agtttcattt tattttcaaa aagcaagaaa atgttatttt aacttaggcc 63900
acttacagtt cttaagattt tatacttaag ttgatggccc ttagaaattt aattgcaagt 63960
gccaatgaga gtaaagtggc atgcacaaca gatgagagaa gacttttagc ttaaggtcct 64020
tttctttact agtaaaatag gggatgtact acacacaact tgtggccgtc tacaataaga 64080
taaatgttga tgacaaattg gtcgttgcat ttacttttca tatatctgaa agcacagtat 64140
ttaatttgaa attaggggcc acttttaata tatttttggc tctaacgtaa caagaacaat 64200
aacaacaata ataaagatta cgaggtttgt ttgcatctca ctatctatca tagcaattat 64260
ttgacataaa taatcatgtt accacaaata aaaaagttaa tttatttgtg catagatagg 64320
cacgcaccca gtagctattg aatgaacaat tattactcac taagaatcaa tctttccctc 64380
atactcaaat actttttctt caatcccaat tagtagaaat ctcaaagaaa ttatgggtaa 64440
cgtttttgga gtccaaatac catggagcaa cattttccct cgttgcctag attggattct 64500
caacgaagca aaatatataa gccagcttga ggataatctt gatgatttgc agactaaatt 64560
ggaacaatta attgaagcca aagacgatgt gatgaatagg gttgaaattg ctgaaaggca 64620
acaaatgagc cgcctgaatc aagtgcaagg gtgggtttca agggtggaag ctgttaaagc 64680
tgaggctgat caactgataa gagttggctc tcaagaaatt gagagattat gtctttgggg 64740
ctactgttcc aagaactgca agtcaagcta cgactttgga aaaaaggtga ctaaaaagct 64800
gcaacttgtg gagactttaa tgggcgaagg aatttttgag gtggttgctg agaaagtacc 64860
aggagctgct gcaactgaga gacctactga gccaacagta ataggcttgc aatcacaact 64920
tgagcaagtt tggagatgtc ttgtagaaga accagctgga attgtcggcc tatacggcat 64980
gggcggtgtc ggtaaaacta cactattgac ccatatcaac aacaaatttc ttgagagtac 65040
aactaatttt aattatgtga tatgggttgt agtgtcaaaa gacttgcgac ttgaaaacat 65100
tcaagaaact atcggggaga agattggttt gttgaatgat acatggaaga atagaagaat 65160
tgaacagaaa gctctagaca tcttcaagat tttgaaggag aagaaatttg tgctgttgct 65220
agatgactta tggcagcggg ttgatttagt agaagtgggt gtccctctcc ctggcccaca 65280
aagtagtaca tccaaagtgg tattcacatc ccgttccgaa gaagtttgtg gtttgatgga 65340
agctcacaag aagtttaaag tggcgtgctt atcagatatc gatgcttggg aactgtttca 65400
acagaaagtt ggagaagaaa ctctgaagag tcccgatatt cgtcaactag cccaaacagc 65460
agccaaggag tgtggtggtt tgccactagc tcttatcacc attggccgag ctatggcttg 65520
caagaagaca cctgaagaat ggacttatgc aattgaggtg ttaagaacgt caagctctca 65580
atttccaggt ttgggaaatg aggtttaccc tcttttaaaa ttcagttacg atagcttgcc 65640
cagtgacaca attagatcat gtctcttata ttgctgttta tatccagaag attattgcat 65700

-continued

```
ttctaaagag attttgatag attgttggat cggcgaggga tttttgacag agagggacag  65760
gtttggagaa caaaaccaag gataccatat tctgggtatt cttcttcatg cctgtttact  65820
ggaagaggga ggcgatggtg aagtaaaaat gcatgatgtg gttcgagata tggcattgtg  65880
gatagcatgc gccattgaaa aggagaaaga taattttttg gtttatgcag gggttggatt  65940
aattgaagca cccgatgtca gcggatggga aaaagcaagg agattgtcat tgatgcacaa  66000
tcaaattacg aatctatcag aggttgctac atgccctcat ctccttactt tgtttctgaa  66060
cgaaaatgag ctacagatga tccacaatga cttcttccga tttatgccct ctctcaaagt  66120
tctaaatctg gcagacagca gtctaaccaa cttaccagag gggatttcaa agttggtttc  66180
actgcaacat cttgacctgt caaaatccag catagaagag ttgccactag agttaaaggc  66240
attggtaaat ctcaagtgtt tgaatttgga atatacatgg agtttaacta caatcccgcg  66300
tcaactaata tctaatcttt caaggttaca tgtcctgaga atgtttgctg ctagtcatag  66360
tgccttcgat agagcatcag aagacagcat tttatttggt gggggtgaac tcatagtaga  66420
ggaactgctt ggtttgaaat atttagaggt gattagcttc accttgagaa gttctcatgg  66480
tctccaaagc tttttgagct cgcataagtt acgaagttgt actcgagcgc tcttactcca  66540
atgcttcaac gattcgacat cgcttgaagt ttcagccttg gcagatctga agcaacttaa  66600
cagattatgg attacagagt gtaaaaagtt ggaggagtta aagatggatt atacaaggga  66660
agttcaacaa tttgttttcc acagtcttaa gaaggttgaa atattggctt gctctaagtt  66720
gaaggacttg acattccttg tcttcgctcc aaacctcgag tctattgaac taatgggttg  66780
ccctgctatg gaagaaatgg taagtatggg aaagtttgca gaagttccag aggtggtggc  66840
aaatctaaac ccatttgcaa aactccaaaa tcttaaatta tttggtgcta caaatttgaa  66900
gagcatttac tggaagcccc tgcccttccc acatctgaaa tcgatgagtt tctcgcattg  66960
ctataagctc aaaaagcttc cacttgattc caatagtgca agagagcgta acattgttat  67020
tagtggaacc agaagatggt gggaacagct cgaatgggtg gatgaagcta ctcgaaatgc  67080
ttttcttccc tgtttcgact cttgagcaga gatcacattt gattgatttc tggtgcgtac  67140
ttcttctcgc attaatcttt tataataatt tccttcatgc agaagtctgc acctaataac  67200
ttgttacttc aatgtgttct taattgtttg aaggtactct gagaggtgca gattcaattt  67260
tttatcaagt ggcgaatcat ttagctattg cgggactcga tttcactcct gttgcaagac  67320
tcttggagag actcaaatca taaatttgat cagtgatttt gctcctatat gtgtgctcag  67380
cggatgtgtt catgcattca attaggtttt ctacctcttt tttttttttt ctttaacttt  67440
tgggctttta tatttgtatt cttcttcgta ccatgcatcc aaaagttgca gaagttgttc  67500
caaggtagtg atgtatttaa ttatttaata caaatttcga attgtctcaa actttttata  67560
attaatcctg ctatcaaaaa atcttgtatc ttcagacttg gtgttctaaa gattcatctc  67620
tggtagtctt ttatcggttc aatttatttt gattcactct aatgaacggc tcgattcttg  67680
attttcagtt tttttttttt aatttttaaa taaatgtaaa taaagccaat ttccctacgt  67740
tgaagaaaat ctttttgtta tggtataatg caatgcaaga ggcgaaatat tagacggttt  67800
gtgaatgtta tgacatgcat tatatattaa attttttttt catatgaatg attctgaaat  67860
tttattaaga aaaaagagga gaaaatatta taaaatcact gatttgaagt gatatttgga  67920
gaagacctca agcatcctca agtagatctg aagcgcagtt gtgcaaacaa gtaaaatgcg  67980
taccacgaat taagctcaag caactgaacc atctgaagcg cagttaccat ggcggcttga  68040
agctggagct catgagacaa gttgaagctg gctgctgaag atgagtcaca ctctctgacc  68100
```

-continued

```
aaatacaatc ccgtcccttc ggagctgcaa actcaataac ctgaacaatc gaatacatct  68160
caacataaaa catgtttgat ggccaagagg cattgcaaaa ttgcctcgaa agcgccattg  68220
aaactacgaa acacagcact acaacaagct gcaagtcatg gattacccca tgtcaaatca  68280
tttgtgttga ttttgatcca agtagctctt ggaaagacgc cggatataag ccattaatga  68340
cagaagaagg acggcctgcc acatgacaaa ttcaaggttg aaaagatagg caaagatgtg  68400
gcaccatttc gcggacgaac agatccaaga aagctaaggt ggctggctag ctataagttg  68460
gtttatatat atatggaaag tgcaatgtac atggcttttc actattgaat ttggagaagt  68520
taattaccag taaaaggcaa aaattttcct ctaaagttga tgaaatcgaa atttgatgaa  68580
gttggaatga ttaattgttt atgcagtaaa aagcacaatt tacacaacgt tgtcaaaacg  68640
acaaatacct tgcagctcag ggctcacaat gaatttgtca agtgttagtc aatgaaatcc  68700
ttttgttttt tttttttttt tgtcaccgtt tctgccgtac agcatatgat tattaccgcc  68760
tgtagataaa acctagactc tgttacttac ggatccagct ttagccaact cccattactt  68820
gcatttgtat gaatttttc tctctcctca ggacatgtgt gctcttccca ttgggtgtgt  68880
atgttacaga ttctgtaaca tagcaacctc tcaaaaaaaa aaaaaaaaaa acaaaggggc  68940
acctctctta tcatttttgc cgctcactta ttgatttttt taatctcttt tcacaatata  69000
tggacaacaa aaacggcagc agggttgtag tttttatcac tctcgtgtct ctgaagcaat  69060
atctggtctc actgctgatt caggtccctc ttattgtctg ttaagatgaa tttgtcaaca  69120
atttacctgc agtaaatctt cccattttga aaacaaattt tttttagagt actctcattg  69180
ttgatcaaag tcagtgaatt ttctccataa tatagtaaat ttgtagtgta aaaattaaaa  69240
aaaaaaggta ctaacagaca tattacataa ttcaataata gtaattgata agaatttttt  69300
atgatgatgt atgatcttct tacataatgg gattggtcta gactcttaag atttagatat  69360
tttaatctat atcattagtt taattaagtg gataaataat tagttaatta ataagagtaa  69420
ccttaaaatt aagttgatga attcaaatta aatagaaata cttatggatt caacgcgaat  69480
aaagagaggt ggtgattcat ataactcttt ttctttcctt attttaattt ataaaaaact  69540
ttttttaagc attttttttta aatattaaca atatttctaa acaatctata tctttttatt  69600
tctacaaata tgttaaattg ttgatcaaaa tcttaaaatg ttcatttatt atattattga  69660
ctctgtaaaa aaaaatgcag cattatagag agatccaact agtaaatatt aatgagttta  69720
atcgatgtaa ttataattct caaaagataa tgagaaaaaa aataatttat tgtgagacca  69780
aaaagaaaaa aaatgaaaaa taataaacca accccagaca ccatatcttc aatttgtagc  69840
tgctggccac caattcacca gtggccggca cgtaatcgcg agacgttttg agaatctgta  69900
ccgtttctat tttatttaac gtaaaatcca aatcaatgac agccccatgt tcaaatcggc  69960
ccataaacca tccaacacct ggcgccaagt gtcctgtttt tttttcccac ccttcttttg  70020
ctttcaatac aatgtgccgt gtcatgttac cgtagaaact tccaaaattc tatgaaactc  70080
gccgtcacgt ttatcgttag gaaagccgtt gtatctgcaa attaaaaata attaataaat  70140
taaataaaag ccgttggccc aacgtcgaag aaatggatct gttaaaaagg gccccatttt  70200
ggagataatt acggaagtgg cccagctaca tgaagggtct gtcctcgtgt ggccctcgct  70260
aatcatcggt cgtggcccgt gggtagacta ttttcatttt gaggtggcgt tattgtgtcg  70320
ccaccattat gcttactttt cataattacc ttttgaaaaa aataacaata ataataataa  70380
tacctgtttc tcgattttct tgttcttttc ttcttctatt ttcttttaat tatttgggtg  70440
```

-continued

```
tgacattact gtgagcttat gaaaaaaaat aaaaatattt tgagaaacgt gaaatgattg 70500
gtgattaaat tagagagatt tatttacttc ttttatgcaa aattgatttc attttagtta 70560
gaattttaat ttacatgtca gattataagt ttgatatttt gtacgtaacc tcttattagc 70620
tcctattagg ctacatttat tggcacttcc tcttggttgc tttttgttta tgtacatgta 70680
atattattaa ctgagttata ttaaaagtct agtatgttta tgttctattt cacatttaaa 70740
ttttaaaaac aactttatct attcaaatcc atattataat cattctcaat aacggaaaat 70800
caaatctgta cttcaaataa aaatgatgag attggaggcc ttatcatttc aaaattgaaa 70860
aataaatttc attagtagtt gttacaacca aaaatttgat agtgacattc gaattagaga 70920
taaatctgga gggtaaatca gtcaaaagca ccgaactgta gttcacttgt tcttaccagc 70980
caagatctga taatgacaaa aagaattaaa gacacaaatc tcaagggtaa ttttgtcaaa 71040
ttaaatcagt aatcacacag gagaagtacc tgcagattct gacagttgac cagacgacgc 71100
cagacttgtc tatgctagtt tcaaactgga ccagacccag agatccaact gttaagttac 71160
tttacacgtg gcgctctatt ccgcattcca gcaaatatct cttgaccaac aggcgccgat 71220
ttgagcgccc tcccgctttc cgaaaaagcc taaaccggac ggggtccact catactggac 71280
ccctttacct tgttctacaa ggaaacgata ttattgtaac atcatggcgc gtgggacaca 71340
gttaattaca attgaagagt attttgtttc gaattgtaaa attaaaaaaa aattctttta 71400
taaaatagga gtttaatact aagagcctgt ttggtatggc ttatttaaga gatataagtg 71460
gttatttaat tgtataagaa ctttttaaaa ttttttatgg tgtttggtta ttttttttagt 71520
agagtttttt tagtttaaat aagttaattt acctctacta ggaaaagctt aaaatttgag 71580
cttttgggaa tagaggttat aaaatttttc taaaaatata taatataaaa aatattacac 71640
agtttaatgg ttcaaaagta cttttttttat tgacaaccaa acacccaatg actttttgtc 71700
caaaaactgt attggtataa actctacttc tataagctct actgttataa actctattta 71760
ataaactgta ccaaacggag cctaagtcta cacatgctca cattaagtta aatattttta 71820
tgttagatac gccttttact tgccaaatgt ttgagataaa gccaattata acaataaata 71880
ataaacatat tacaacatat catggaaatg caattgtggt gaatcattga gtctctcaca 71940
acaattatta ttgacaaatt aagtatttat ttactataag agttattcat aaattacaaa 72000
atgtaaatta tttacttttt gatttaacat actgtttaat taataataaa gagaatacta 72060
taaattttta cattgtgttt ataataaaag ttatactagc tagtatttaa tataatgaaa 72120
agttgtagtg ttaagttatt acgtgaaaat caactatcca agttataagg ttgggtgact 72180
tttaagggga ataactccat ttgcttttga aggattagca actataaata aaaaatgaca 72240
aaaggaaaaa tctatctttc attataaaga atgagacgaa aatttacatt atttcatctt 72300
atatatttta cttgaaccca ttgagtgcta atatgcttga gttattttct ttttaattaa 72360
ttatccaata tcctccaaat ctaatttagg catctgagat ttctcaccgg aatttccatt 72420
gacaaatccc aataattttt ttttttagtt ttcaagttaa aaatttcaag tttagattga 72480
tgttgaagtt cggtttatat cgatttttca ctaaaaacat attctatata ttgaggtcat 72540
ttttccggct tcaacagcaa tccttacaaa aatgattatc catagttcta aggtacaaaa 72600
tttattttga aaaaaatgta gcaacgattg caatttttat taaattaaaa tcctccgtgt 72660
tttacaccct atcattagcg cgtgaaaagt gagtcgcggt agcccctagt ttttcttttc 72720
caaacacgaa agtgaaatcc gaacccgcga gccgctacta gtttatccgc ataaccaacg 72780
gcaaccctca cacaaaaacg ccactcaaat cctacaaaat tgcaatccgc ccactctcct 72840
```

-continued

```
tcccccacct ataaataccc tcctttcgta gcacttaggt ttgcccaaat aacgccccaa  72900
aacggcgctc taaaagaata ttttctgtta gaaataaaaa atctctccaa ttttcttcct  72960
tctgataatc acaatgccaa tatcatcctc accaagaaac aaatccaacg gttcagatct  73020
agccacgttt cgcagaaact cactctcctc ctctttcgcc tcttctacct cttccagttt  73080
ctcctcctcc actttcttcg cacgtgccac ctctcccaca cgtgccaatc cgtaccacgg  73140
ccaccacaat gaccgcgccc acagtcacaa ccgatcctcg ccgtctgtcc ggttctcaat  73200
cgacaaccgc ccgatctccc ccggccgttc gatctcgtac acgcgacaga taagtaaaag  73260
caacaatgcg gcatcgttca acgcccccaa gaggacctgc gcgtgttcgc cgactacgca  73320
tcctggctcc ttccggtgcg cactgcataa gaggacgaac agctacagca gtcataaaac  73380
ggcgtcgtct tcgcattact caagtagtag gctgaattat aggagatcag cgatgacgaa  73440
ttcgctcgtg agaatcggag gagtggaagg agaattggtc aaacgtgcat tgactgccct  73500
gattaggcct tcttctcacc agcaacgccg ccgagccgct tttgagccga ggccgagccg  73560
gctctctatt atgtctaaag cggatgattt gtgaattgtg gctgttttat cgggacttgt  73620
tttgagtgag ttggcgagtt gactcagtga tttggtggac aagagtgact caggctttcg  73680
gcctttttat tttcttgggt tgtcttgtga cagaaagttt tgggagaagt ggtggaaacg  73740
atgtagttgt aaaagagtta aggaaatgaa tctgggaaat ttagcaataa tccagaagtt  73800
gtaattattt agtaaattca agagagagtt ttagtggcct tgaaaaacta aatcatgatc  73860
gaataaaagt taaagtaagc aaattagtga aaacaagtaa attaaattat cttctgaaac  73920
taattaaaaa ttattgtttt ggacttaaaa tatatataat ataaaattat ggtcctaccg  73980
tagtatcata cctcaattaa attcggccgt tggattcagt ctcagtctac agtgattacc  74040
acagctgaat tcagctattg gattcaacct ttggggtcac cggttaattt ttaaatttgt  74100
tctaattttt aaaaactttc tgagttttag atttgttgca tggtgaaaat ttatttattt  74160
gtaaaaaaaa ttttaccgtt agttactttt aacattaatc gttagttgat tatataaaga  74220
taatattact tttaacaata atttactgtt attttatcct ctttaaatta ttaatatttt  74280
tttaaaattt tttaaaaaaa taaaattaaa aaattatctt taaattattg atattttttt  74340
aaaactgcta caagaaagat aaaattaaaa acttgaaaat aaaatagtca taatttttac  74400
ttatgatatt gtaaatattt agaattgaga aggataaaat tatcaaaaaa taaggattgt  74460
acttttcgcg ccaataattt ttttttttta gttatgtcag tgtacaaact gttgttaagg  74520
gcaatattat ctttgcacag tcaactaacg gtcaatatta aaattaactg acggtaggga  74580
gtgttttaca aataaataaa ttctcgtcat ttatttgtaa caaacccaaa cctcagggga  74640
gatttttaaa aattacccgt caccagaact agatttgtct acagtggtta cctcagctga  74700
attcagctat tagattcagc cttctccaga attaaatttt aattatgtta ttgtattact  74760
atagtactat aatttgatat atatatatat atatatatta ttaagatttt tattatgagt  74820
gtttttattt tttatacaaa aatattattg aatcttatta tttaataata tgtttatatt  74880
aaggagatga ttattttttta taattgattt aattttaatt aattcaatta ttaagtttat  74940
ttttttaatt taatatttaa ttaatattat taaaattata ttttaaaata tttttaatta  75000
attaattaat tttaattatt atctaaataa aatttaataa ttaatattat tacttatttt  75060
tataattttt gataatatag taatagaata ataatatttt tttaaaatta acattattta  75120
tcttcacaat tttttataat tttatgaata tttttcattt tgaaacatcg taaagattct  75180
```

-continued atttaattgg acaagattat aataaaatat tattttattt aagttcttta gatgttatta 75240
ttaatttaat atttataatt tataaagacg taaatataaa agtattaatt ttttaaatta 75300
aaaaattaat ctttatttta ataatttaga taaaaaatat catttaaatt tagatattta 75360
attttattta taaatttata tcaattaagg tctaatttta aatttaaaaa aaaaactcca 75420
cctaaatttt ttaaatttat aacttattaa gatatccata taatatatat aatttttttt 75480
aattatgttt taataaatat attattaaat tatatagttt aataattcct tcaacttaaa 75540
aaaaaaagtg tctgcccttg tgaatttata gtgattgcac gcgtggcatg taataattga 75600
gatccttggg ccgtggaccc agggagcaca ttcgatcatc accgtgttgc atattattga 75660
aaaagaattt ataattcaaa acaattagga aaaatactaa agaaatgaca aaataataat 75720
agaatgtact aaaacgtggt atgatgtcat agtattatct gattatttga tctattttgt 75780
aaaaaatata tatataattt tatagttaat tatatatttc tgtttaaata tcagtatcca 75840
agcaataatt gtattttttt tcatatcgaa tattttataa acaaaataat tcctattttg 75900
tacttatttt tgtaggcatg gatgatggac attccccaac cacgagtttt gccaaagaag 75960
ttcttcagat taaagaaaat ttacacatta ttgcattttg atgtcaaagt caaagagctt 76020
acaaattgtt tttttttggg tacaaaaaaa ttgacagggt agaagattgt gattctatta 76080
aggtttcctt cgtaagacag tttttttttgt gaatttacat ttaatttagt taatttttga 76140
tatcaaacta cgtctattga catccaacga tggtatgcaa ctgtgacatc gtgccactgt 76200
tataccacag atttccctaa cttttgacaa atatttagct aaaatgaagt gaaaaacagc 76260
ttggattcca caaatgacaa aatttgatta aataatttcc caaaattgac cctttgaatc 76320
aaattttttg cattttgaat aaaaaaaaaa tttgcaacaa gtggttcctt tgctgcgttg 76380
gatggtttgg gttggagccg tcgatgcttt atgggctcga tgaaggactc tttggattgc 76440
ataaaatttg ttattttatg cgtccgatgt cgtcgtactc gcgagatttt taatctaaat 76500
ttgtgcatat atatatatat ttgccttttt tcaatgattt taaatgttaa aaattttcac 76560
aaatctactt atgataaatc caaaacgttt taccaaaacg ttttacttta gctctgttat 76620
atagtacaat ttggatattt ggacaaaagt aggtattttg cgccatttgg accaatttga 76680
ttcgaatgct agttctagtt ttggtttaga aaattttgaa tcgataaatg aatgaaaatt 76740
aaaataaaga aagtgatgaa ccaatccaaa ttgatttggt tcagttcttc gagtaaagat 76800
taattatcct aataagttaa gtttatttaa aaattaccca tcctatataa gggactcgaa 76860
cgaaatatat ttcaaaatat taaaaaaata aaacaaatgt taaatgtata taagaaactt 76920
gttttgttac attagataat agaatgagta atttaccatt taattattgg ctgatttatt 76980
gatcggatta aggctttttt tattgaggtg gacacagaag tttgccacaa taatatagaa 77040
ttaaatttaa aaaaaaaacc accaattatg ggaaggcaca ggcgacgtgt gcaccgatgt 77100
ttggggatag gagacaaatc aatggcttca gcacattttg gcaatctcaa tccatgacat 77160
cttgggtagc attatcattt actgacagcc tgacatgttc ttgaagaatc tacaatttct 77220
taataagaaa atcatcacta atttaaaaat tttccagaat tttttaatac cccatgtctg 77280
cacattcatt gacatcagac aattgaaaat tcatgcccaa ttgagaccat tagaaattcg 77340
gaatctgaat tattgatggg tgcaaaaagt atgttatgct tgtggcagtc catccatgaa 77400
tgtggtcatg tcgattattg actgccaaaa ctttgctaca tcctttgcat actacatata 77460
tacgacagtg catgaattta gaaagaaaat gagatacaaa aattttgaaa acttacattg 77520
cttttttttt tatctattaa aggatttgta ccggtctatt tttatgtaca taataaagat 77580

-continued ataaaaggaa taaatatttt cttcacacta gctgtagcgg cctaatgctg tggctggatt 77640
ctttcctatt tgttggcaat aatcttgcca acggaaagcc tctcgctaaa gctgtacaag 77700
atgctaaatt ggtctcaaat ttatggattg tatgttgcgg cagtttaggt tgacattccc 77760
cccctcaagc atggcagtgt cgtacactgc acccgtagtt tgtctagtaa gaagatgaac 77820
tgtcgtttgg ccaaaggttt ggtgaaggaa taggcaaaca tgccgttttg tggaaacatg 77880
gcaagtgtga agaaatccta gaacaacttt ctcatgaaca aagtgcacat caagtccttt 77940
atgcgttgta cgtctatgaa aaactgggtc ttttgttaat cgcattgaac tcttactatc 78000
acagagcagt gtaggtgatt tctcgaattg taaaccaatc tcttgtaaga tgtgcctaat 78060
ccaagtgagt tctatagcag ttgtggcaat aaagcgcctt tcagtgctcg atcaagatac 78120
aatgtgttgt ttccttggaa ctttatgaaa tgcaattgcc actaagatag acataatatc 78180
caattgtgct tcttctagta gttgaacaac ctgcccaatc aaagtcagaa aaagcataaa 78240
gattgaaagc actttgagaa gtttaccgga gttcgtaatt tataattcct ttgaggtatc 78300
gaaggagata cttgactgcc ctgaaatcag ctttggcgga ccttgaaagc tttgagaagt 78360
tgatgccaca ttagtgtgtg gcatcaactg gttcggcatc gtctagcaaa gggcgagatt 78420
taatggccat gggggtcttg atagaagagc acctaagcat gtgccttggt gatgaggtca 78480
cgtgtgtacg tggcttagga taggaaaaat gccgttagta tattccgtta tttcaatgcc 78540
aaggaagtac ttcaaattac taaggtcttt taatgtgaac ttggaactga atgtgtgaat 78600
gatgtatcga atcttgccag tgcatccaca taaaattagt ataagaatta atactgagtt 78660
gcagcaaaaa ataaataaag atgagtcggc tttgttgcca agatcaatga gggctgttga 78720
aaggcattca aaataagccc taggtaccta aggccataaa agggcttttg caaacttgca 78780
aacatataaa gggtaagtgg catcttagaa gccaggaggt tgttccattt atgctatttc 78840
attcaatttg caatgtaaaa aggcattgct gacatgtact aactgcaatt gccaaaatta 78900
gacgaatggt ggtggcttta accacaagac tgaaggtctc atcgaagtca atgccatata 78960
tttgagtaaa tcctttcgcg accagtcatg cattgtaata gtaaacattg tcattctctt 79020
tatacggtag acatacttcg atcctatgac acttttgttt catggtcgtg tgtctaagga 79080
ccatgaatga tttttctgga gacctaggat tttgttttgc atggcttgca tccattctgg 79140
actcttaatc gcggttttga aggctatatg ttcaggttgt gagactcggc tggtttgaag 79200
tgcaagatta gaatttaatc ttagttttgg agagtgatca tactgttacg ggcaactcaa 79260
atttggcttc aatggaggct aattctgtgt gcacaggtat gcttagtaaa agtccgccta 79320
aaaccggagt gcgcttaaaa tttggcatca agatacactt agaaaggggc cgccaacaca 79380
actagccagc cgtgattagc ttagcaatca tccaagcctg gcccaaattc aagaggtttc 79440
tataattgta aatattctag agttttctag aattaagcat ttaagtccaa aagatatttg 79500
tgcaacttgc tatgaaattt caagaactag cacccaatac ctataaatat ggatgagttt 79560
cttatttgct caacaaccac accacacaac aaactcacca gaacacacaa actctgaagc 79620
tcttgtaaaa agctatctta taatttttct ttagtgtgta ataaaatcat attttggtca 79680
tattgctctc gcttctctct agtattgtca caagtttctt cgcttggtta gtttgagaag 79740
tattataggc ttatttagaa acttgtgtgt taaaagtcac ctaagtgcag catggacttg 79800
ctatgcaaaa ctctcatcct atgacaatag ggtcagcatt aagggtttga gaggtgttgt 79860
ctaaagaaga gatatttacc aaagatatcg gtaattcgat agtttagtga tgaggggagg 79920

-continued

```
tatatgtagt gcttgagaaa ttcaaacttt ttgtatgtga aactgtgtga ccgaatttga  79980
aggttgatga ttgattctgc aagattgcat gagtatcacc agcttccaag tttatttgtg  80040
ggattgtaga aggaggattt tactggtcat gaaatatcgt aaagggggca gaggatgtag  80100
caagattaac attatttcgt aatgtccgtt gggtagagtt tacattatgt ccaaaatctc  80160
ctttgaaaca aggaagttgg attaacgtga ttttgggatt taaatggggc tgaactcacg  80220
tcatggccaa attccttgtt gtttttctaa tttttgaata accattcatt gcgggaaaga  80280
aagcttgtaa acttcacatg tctttgcaca aagtaaaatt tactttacct tttagcatgt  80340
tgtatagctt tagcaagagg ctttctgtta gcaagattat tgttaggaat agcaaaaaag  80400
tctaagccgg cccaaaccta aatcaggcct tctaattttt tttaaaaaaa taaatttata  80460
aattataata attaaattaa atttggaaaa taatggaaaa ataaaagaaa taagtttgaa  80520
ttcttaattt atatatcaat aatgaatcaa aaacttaaaa ttataatact aaactctctt  80580
ttaagtgtta attagttaaa agagtacttg aattagagaa cctagtacta acaaaattaa  80640
atttcttaat ttttatttac tttattttct ttatttatta ttttatttta ttcattatta  80700
attataataa tttgatcatt attaacttat ttcaagttta catcaattta aaaaaaattt  80760
aaaaataagt aaaagctcaa atccatccca ggcccacagt gggctcgacc caagccccta  80820
atttgtcaac cctaattatt gcaaacaaat gaatcttgta actgtagccc aagtacaatt  80880
tgaggaaaaa cctttagtga attaaaaaaa atctccatat taaatttttt tttaaacgta  80940
acaaattgta aactaactgc gactcaacat tggcaattat ctacgctaat gactccataa  81000
attggatttg tcgatggagg atgacgatcg atggttaggt gaggtgaggg tcgactttcg  81060
agtcttaatg tgagggtggc accaacttga gttcctcggt ttagaaaaaa aacaggggtt  81120
gcctatttta caaatttggg ggagatgatg agaagaagaa attatttgat ttttgacttt  81180
tgagaaatag gtatttcatt ttaaaatttt aatgagagag aagggaatgc aaagggagac  81240
gacgatgaat aggtttttgt tgcttttttt tttttaatgt tatagtgcaa agtcataggg  81300
tttgtttttg ttataattta tttttgggta aaagctcatt tagtccctat agtttaagct  81360
tagtatccat ttggtcccta tatttttaaa aatgcctcaa aacatcccta ccgttaaagt  81420
attgataccc ctaccgttat ctttcattta ttttggttta tttttacaat attacccttt  81480
tataataatt tttttagata ttaataaaaa ataataatta aattaccaat ttaaccctaa  81540
aaaatttaaa aaattatatt aatttttttt ttttgcaaac accatttgca cacttgatag  81600
tttgcataca attttggaca attaaatttc aaattttcaa cacaagattg agtttttcat  81660
cattcaaact tctcatgtct aaactttatt tattgaggtg ctaaaagata aatatattgg  81720
caattgataa ataaagtcaa tgataagttt gatacaacca ttgattaaat atcattaaaa  81780
aaaaagtacc tacaattaga agttaaaaaa aaaatgtcac catcggtaaa ctatcaataa  81840
tgctacaacc agcacaaaat aaaagagacc aataaacgaa gacaggtgga ttatgtttgg  81900
ctttatagtt ttggaatact tccagtcaaa cttgaaatac ttccagtcaa actgctcccc  81960
agaagcaaat aaacaatcgt tgatcaaagc tgcatcacca ttgctgctgt tttaagtaaa  82020
taagttcaat taatattgtg tgtatttcgc aaggaattta agatataaca taccttttat  82080
ttacttctat aatgttgttc acatttaggt ttgagagggt tgtgttagag aaacccttat  82140
ttttcctttt tgcttttgtc tcataggatt tggttgactt tgtatatatc ttgttgaaat  82200
tgttgctgaa ataatagaaa aaataaataa aaggatgagc atattgttat actagtaaat  82260
ctaaaaataa aaatgaaaat agtttaaaga cctgcttgtt tggctatgcc aggggatgaa  82320
```

-continued

```
ccgacattgg tttttttgatg tttttgtctc ttagcattcg gttgacttcc actaggtcca  82380
gattggattt cacctccact caattacctt gctgaagtta aaaaaagtta tattaaattt  82440
tattttattt attaatttgt ttcatacatt aattttattt tcatctgtta aaaattacgt  82500
acaaaaaacat gtacaacaac atatacctaa aactttcaac ctccaaatta aaataaccta  82560
atcaaaacta ctaactacta aataaacatt taaaagatta attaaatcat aatgacctga  82620
tggataggtt gtgctggaag atgaattagt aattgtattc tgcatcaaaa tgaaaatata  82680
atgttagcaa cccatgtccc aacatttatt gacctgaatc aatatgagaa cacattttaa  82740
atcatattaa gtacctcttt attcaatgga caacttctct tattgtgtcc aagtttattg  82800
cactggctgc atgtcaaagt gtaccttttc ttgcgagctg gtccttcatt tctttctctt  82860
ttcctgttat gcttaggcct gccaatttta acatatttta ctggaggcaa taggataggc  82920
ttgtcaactg aaggccaatt acattggtcc ggtattgggc atatggtctc agagtaagtc  82980
cttaaataag catctttttt cagactctca tcaataaagt cgattggttc aagactatta  83040
cgtgaaatgc atgccattgc atgcttgcaa ggcatgccac taatttgcca ggccccacaa  83100
tcacattcaa atttcttcaa atcaaccaca taatgtctct cttcatcatc tataaattcc  83160
aacacctcat actgagcttt actggctttc acaacaatca atttccttaa agccttcgat  83220
atttttgtca attttctatg cactcttgga ggcaaatcag aatatcacaa cgctgccttt  83280
tctcttcttc gaatgagcct tttcataatc ttcaatctta taaattcaag caattgaagg  83340
attggttttt tcctgtactc attgagtaga gaattccaac tctctgacat attattagta  83400
acatgatcaa tcttgaaaaa gggatcaaaa gtatgacatg cccaagtttc tggttcatta  83460
tgcatcaacc attcataagc ctctttcttg aattctttaa ttttttttcat ttccttctca  83520
aaatccactt tgtttgttgc tctcacagcc ttccaaaaca ttcctcttaa ctcctcagca  83580
gagtgttcct tcctgaaatt cgcataaata tatcttgcac aatgtcttgt ggtacaccca  83640
ggcaaaactt catcaattgc ctgaattaaa cccttttgtc tgtcggacat tatagtaaga  83700
gccatctcat tcactatacc aagatgttcc ttcaacaatt caagaaacca tttccaactg  83760
tccttgcact caacctcaca aatgcaaact gccaatggga atatgccatt attggcatca  83820
agtgtaacgg ctgtcagcaa gataccacca aatgatgtct taaggtggca gccatcaact  83880
ccaatgaacc ttctacatcc acgtataaat ccattttgta gtgcgtcaaa acttatgaat  83940
atcctcttga agtacgtctc tacaccttgt gtttcatatt gaattttcac cattgccctt  84000
ttattcttta taagaagaac gttggcatag tcatgtaact ttgcataaga ttttgtgtag  84060
tcactatcag caatttttag aaccctttttt ttggccatat acaacctttt ctttgtagtt  84120
gaacaagaaa acctcttcct caattcatct gacatggatt cacaaccgat atcaggatta  84180
aaactaataa aaccatacaa tttctgagct atccatctac tagttacttc aggattctta  84240
aacagctctt tgcacttatg ttcaccacct tttaaagttt taatctggaa tgtaactttg  84300
tcaaccaata aagatgcatg ggttctccat ggacattcct ttccttcttt gtccttccca  84360
gcacacacgg ctgtaactct acatttgtca ttctttttcc ttttcaaaac tcttgactct  84420
tgaatatcat aatccttcaa tacattctta aactcttgag cacaactaaa agtttgccca  84480
acttccaaaa caatatcatc atcaccatcg ggtttcttga accttttttt tcttaaatcc  84540
cttgtcatct tcaatattac agcgtcatct tcttcatcac ttgcaataga tacatcttca  84600
ttatcactct cacaatctga catgccatca tccccatcaa attcattaat atcaaaccct  84660
```

-continued

```
aaatcaactt caggttcact atcagactta acaatatcac caatatcttc atcagaccag  84720
tcaatagact caacactgat tgcatcatca ctttcaccat ctaaaatatc aacattaact  84780
gcatttgagg caaaatgatt atcttcaggg caagtttgag ctaaaacggg tgacaagctg  84840
gccaaggata acgcatccat ctccaaatta atagaattaa gacccttggc ttgaattaag  84900
ttaaccaaat tctggaagtc tttatcattg ttcaattcaa tcccttcatt ggaccatggg  84960
acaatgccag taagcttaaa gctctcatca taatgcttgt gccttccaaa gacattattc  85020
aagacatcgt tgatgaggga tacaagactc aagcaatcag gatcataagc atcctccaca  85080
tctttgccta aaaatcgaac taaaatgctg atttgactca tttgaatcta ccaacataaa  85140
gatgaacaaa aaattatcag aaacttaaaa ctattacata cgaattcata aaatacaaaa  85200
tcgacattat agaactttat atgattatga tttttttttt tacaaaaaaa tactcaatca  85260
agtgaagtta aaataatttc ttttcaatta caaatccatt ccactaccaa tattaagcta  85320
cgaaacaacc atgaaagggt taaaaaaaaa gaaagaaaat aaaacctgtt caacttttag  85380
tttactgtaa aacaaaaatc gttcaactgt tagtctactt cttatggaat tttagtcttg  85440
ggaagaaata cccattcaag tgaaaagaaa aataatttct tttcactgaa cacatggaag  85500
attaaaaaaa taaataaata aacaagacca acgtgagacg taccagaata ggccaatttc  85560
cttcgttgtc ggttttgaca tctgctgcaa gactacgttt ccaatagaaa aaattttata  85620
gcaagaaaat tgttatgagt tttaaaaaag caagtcactt aagttcttaa agcgagggtt  85680
ttaaagaata ttagggttaa aatacgtttt tgccactatg gatctaggtt atcgtaataa  85740
ttttttaaaa ttttaaattt tactaagaaa aatacatttt taccctcatg aatctagaat  85800
taacagtaac ggaggtgatg ccgagggtgt tttgaggcat ttttaaaaat acagggacta  85860
aacggacact aatcttaaaa tatagggact aaatgggctt ttaccctta tttttttagtg  85920
taaagtcaaa aattccttac actttaacca tgaactgtag ccaaaaaatt ttcagctcac  85980
cctaaaaaat gtgccagctt caccattgat tgtaatgtac ttaaaccttg aacgagtgga  86040
gatacaaacc ttaaaagctt attacattat ctaaaacgat attgctagtt aaaccaacta  86100
atattcatga tctatatgaa aaacagtgat caaagttgta ttttatatta taattttgtt  86160
ttatcatgca aattcagagc gcacttattg agaaatataa aactctttta tcaatccaga  86220
agggaaaagg cccaattgag atcaaattta aattttgagt agtaaacatg gccttggcaa  86280
ttaggggctt cagctagaaa aattgaccca tacaaactgt aataaggttt gggatgagcc  86340
catgttacac ttatatatga ttttttttta aaattgattt attatgtcac ttgatctggt  86400
gtgaacgcgt agatcccaca acacacttta ctaatcacta atataaattt gatatgctta  86460
gagcatctcc aaaagtcttt ataaatttta ctcttcaaat acctatttgc ttatttatgt  86520
ggtaaataga aaggtaaaaa aatataatat tctccaaaag actcttcaaa tagaaataaa  86580
ttaatattat tttaatcaaa taattatttt ttaaagaaaa agtcaataac aattaaaaca  86640
cttctctctc tttctttaat aaaaagtaat aaaatacaaa ttgaaaagag agaaattatc  86700
tctccaaatt tgaagagaga gaatcaattc ttatttgaaa aattttaatt gaagtgtctt  86760
ttggagattt aaatattaat gtgactcttc aaataagtaa taaaatctta tttgaatagg  86820
cttttggtga tgctcttagt tgtacactta tttatgattt ttatttattt tttaataatc  86880
ttcagaattt ttattaaaaa agaagaagga ggttgaagga acataactaa ttaggtccgg  86940
ttacgatgga gacttggagt tgctccacct tagaatttgt ttaataacta caccatactg  87000
tgaataattt atttattttt attatttatc actctaatta tgtggttatt aaatagtaat  87060
```

-continued ttatgatgga acaacctcac cataatcact gcctaaaaaa atccttaatt ttacttgtac 87120
aaatttcttt tccatcactc ctattactcc atcagttcat cttactatgt caaacccaaa 87180
caattaaatt aaatatttat gaaaattgtt tctcaataaa tatgaaaacg atttcttcca 87240
caaaaaagaa aaaagaaaaa caatagaaca gcttcataaa ttattcaaaa gttacggctc 87300
ttttaatctt aaaattgcga caagaagaga aattggattt gattacattc atgttctcaa 87360
tcacataacg tgacctaacc ttatctcatt tacgtgtata aacaatgtgg cttgctgcca 87420
agacattgac gtataaacat caactacctt tcaatttcga caaaacaggg gggaaaaaaa 87480
aattagagga caaaagacaa aacacgaata gttggcttta tatatatttt ttaactttct 87540
taaaattaaa aaaaaaaaat gtttcagaac ttttatgtgc ttttgaaaat tgtctatgta 87600
acaaaaaaaa aattatttcg aacaatttga attttgaaag ttgtatgagc atgtaaaatt 87660
atgggggcta ttaatttgct ctgttcaata gctatttaaa acacccacat aaacacactg 87720
ataagcttca taaatttgga ggtacaagcc tatacatacg gtaggttaat aaatgtgctt 87780
ttttcaagtt gtttaatctt actttttaac acttcttttc tttctaatta attacaaaat 87840
taagacaaaa tacgttgaag ggtagatcta ataattgttt atttaccctt ctgtaaatac 87900
gtgctggtgt ggatggaatg aacccaccta agcattcaga gtgattggta tatatacgtg 87960
aagcatgtct ccaataattc ttcaaattta tttgaggaca tatggttcca cattgctcaa 88020
ttatcattaa ttttgagtgt gtcatgctca aatcaatcat tttcacttga aaagagactt 88080
tattctcatt atttttcttt ttcgtgctct aagcagccac gtgataagaa caaatgataa 88140
cctatataca tgatggcagc agttgccctg aaaaaccctt ttggcacact attcagtctc 88200
cgtaaatgaa aaattgatac gtgttttagt gcgtaccatg acgggtgtaa tgacacgtat 88260
ctgatgaaaa cccctttcta attacttttt gttgttttac ttttaaattc caatccaatt 88320
ttggtataaa gaggaatcac ttatttattc aacaagttat tcctcatgat tctctctaga 88380
gtttgtttgt ggtagctaag ttgtgaaaat gaagtggcac tattgatttt cgccaacaca 88440
acaatgtttg acatgtccaa tctttgtcca gaaatgccta aaaatctaac tagaaatcaa 88500
agtaaatatc gaaatgaaga ctcgagaaat ttggactgtg tatgctaatg acacgatcgc 88560
acgctaatta atttgtttca tccatttaat attttccact ttgagggaga aaaacaaatc 88620
aacacacgtc ttaagcattt gagatgaata aaaatatccc cgttgggaat gttggtgcat 88680
tgtaaggctc ttttatttca actttatagg tacattattc ttaacaaaaa tataaatttt 88740
cccgggaatt tgttaaaaaa atgttgtttt gcatcacatt gactgatgtt atttcacaat 88800
taattaatag aataaagaca aaagacgcag cacgcaaaac tgggatattc attttcaatc 88860
tggttctagt gtttttacag tttagttgtt ggtcaaatca tttagacatt tgctaatttc 88920
catttacaac acgtgcgagc tgagcgccag gcctccagtc tttaaggctc caacctttca 88980
ggtttcagct catcaaatcc ttcatcattc ttcggctact tgcattcttg tcccaaaaca 89040
atgctaaaag tctgaacttt tagcaaaaga aagcagaaag tttgaaactt tgaggaccca 89100
gaatgcgaaa catagcgctc aaggcaggga gcaggccacc atgggtgggc ttggcagcag 89160
ctgtgtgggt ggagatagca gctgggaatg cttacaactt ccctttgtac tcgcccgcat 89220
taaaatcagt tatgggttat aatcagcaac agctcacaat attgggtgtc gccaatgata 89280
ttggagagag tgtgggactg ctacctggta ttgcttgcaa caagttcccc ccttgggctg 89340
tgcttcttgt cggtgttgtg ctttgtttct tgggttatgg tgttatttgg cttactgtta 89400

-continued

```
gccagactat cactggcctg ccttattggg tggtaagtat tctctcttct ttattgattg  89460
ctttttggaa tagattgcat tgagagaata tatcagcaaa ctcagatggg gatttgattt  89520
tatgggagtt tttgcttgaa gggtgagtat aattgtttct ctgactagat tgtttgagta  89580
ctcacttgag ggttgattcc atggaactaa taggggtaag taagatggat ggatttgaaa  89640
gcaaattggg tttgcctagg ttggtgctac atggtgttga gtttttattt tctcttcatt  89700
attattataa gtctgatttt ctgagagttt atggatgttt tgtcgactga attgtgaagt  89760
tgattggctg gaactatgcc acgaggttca atggaagata tcatttcatc ttggtggact  89820
tcttttcatg gccattagag gatttgatca tttggaatta ctacttcatg ggtattgata  89880
acttttggat tttgatggct ttgttactga ttcaaatttt tgggatgatc aggtggagct  89940
atatgttgat agttagtctt tctgttttag tgaaaatatt gaatctctgg ctacctactc  90000
aaggattttg attctccgtg ggctgtgagt tagattcatc ttgatctgat tgggaattgc  90060
aaattttgtg tgtctgtatc ttcgtgttct aagtttgagt gtcataaaat ttatatgaac  90120
ttatctttat attttctggt caaccagaat tttacaaatg cttgatcatg gcatttttttg  90180
cggttgcaag atcttactag ttttctgcaa atttgacttt cttagtttct acaacagtca  90240
aatacaagca actagagctt gatattaaat tagtgagcta atgtgagaaa attgtttgtg  90300
atttggaatt gctacttgct tacgtatgta taaagatgct ttaaaagaaa aataccgcat  90360
tgatgtgctc atccacaaag gataaatctg ttgaatttaa atttttattg aaagcctttt  90420
ctcattcctt tgcctttagc gtgtagtagc aagttccggg gagtctttgt aaatacaagt  90480
tgaaaatgaa catatcgtac cttttgatga aatatcccca atttctgaat tttgaggttt  90540
ggtccttgtt aataatggtc catccaatga aaggtaaaag gtctgtgaat gttggaataa  90600
catatgtgca gtaacatgct tgttctcgac atattttgtg tgaggggctt atttaagtgt  90660
ctctaactgg agttttgtca aagccttttc tttatatcac tgtacctggc ctggtaatat  90720
tggaatgtgc agttgaattt tccttgtgtt ttgccacatt ggcaccctca tatttgtttt  90780
ttcaatcgtt gagagtgttg actgttgaag caaactttgc tccttgcttt ttttttttgt  90840
tttgtgggtg tgtgtggtgc tgaggagtga aaagtcttct gttcgggatt gtcgcctgga  90900
atgtccattt tgttgatatg gggagatcat accatgaaat tgtaaaaagt tttatccgtg  90960
tccttattgt aatgctccgt tgtattgtac tgtttgaatg ataggtcaat ttttaatatg  91020
atcatgtttt aagaattaag acactacata ttgtctgcaa taccttgaat ctttggtttg  91080
gtgaccattg tgcatagact aggtttatta tatgtctgac atattcatct actcagtgtg  91140
ttggcgggta tagagaagaa agctgtatat ttatccttac cacttcaaat cctggttatc  91200
atcatagtaa agggttcgac aatcatccag tcctgtgata gctgttgttt caagacattg  91260
ttttcttccc tcttttctga tttcattaca ctgtaccttt tgcactgagc tatttagatg  91320
tggttcgtta aattcatttt gttttgtaca aaaggattat ttatctcatg tattggaaaa  91380
gaatagttgc tactttgctg tccatcctcc agctagggtt agattaccgt agatgtttaa  91440
gcttgtgttg catttgtttt cacttactgc atattcagga cacagaatta ccaagatttc  91500
ccaagaagtg ttatttggac caacacaaag tcatattttc tcaacttttc attgttgttc  91560
atgataaaga aagttaagag atggtaaagt gtaggtgctg agtgagaatg agtttatggt  91620
accaggtttt ttcatgcata tattgaatat acatgcatct taggaaagat atcttacgtt  91680
gaatttttct gaaagatttt ttccccattt tatgctaatc caagatatgt aaacttctcg  91740
accaaaacct cctgatgaga tggaagtaat tgcatgatgc taatctttga gaaatgtgtt  91800
```

-continued tgtaaattag cattagttca ttcaaaaaga tacctttttt ggttcaacac tttgttttca 91860
ggcatattag ctttagggcc ggtctcttgg tatgaatgtg ccacttttag cttatgtgct 91920
cataatcttg ttgtcaatat tatggcagtt atggattgca cttgttgttg ctactaatag 91980
caatgcatgg tttggaacag cagtgctagt aaccaacatg aggaattttc ccctcagtag 92040
aggtactgtt gctggcatcc tcaaaggtta tgctgggatt gctgctgcaa tatatacagt 92100
gttatacaat atggtgcttc agaattctgc aacaacactc ctgctgttcc tggcacttgg 92160
gattccttta atctgcttag tcacaacata cttcatccgg gcatgtacac cagcttctgg 92220
agaagactct tcagagcatg gtcattttgt tttcacccaa gctgcaagcg tttttcttgc 92280
tatctatgtt gttgcaattt caataacaag cgattatgtt tctctaagcg atgctctttc 92340
ctacatatta gttgccataa tggttgtatt tatgctgtct ccattggcaa ttcctgtcaa 92400
aatgaccctt ttccctgcta ccaagaaacg tattcgatcg gccgactctt cagacagttt 92460
ggctcaagaa gggggtgatt caaccccaac agatcctttg ttgacaccat cttcatctgc 92520
tgcatatctt ggaagttttt acgagactga agatttctca gatgtggaga tacttcttgc 92580
cataggggag ggggcagtga aggagaaacg gagacccagg agaggggagg atttcaaatt 92640
aggtgaagct tttgttaagg ctgatttctg gcttctttgg tttgtatact ttctaggtgt 92700
tggagctgga gtcacagttc tcaacaattt ggcacaaatt ggggttgcat taggagtcaa 92760
tgatactaca gaattgcttt gtcttttcag cttgtgcaat tttgctggtc gccttggctc 92820
gggtgtgctg tccgaacact atgttaggtc attactctta tgctcttact taagaagcat 92880
caaactgggt agaaaatgca aatgttttct tgttttgttt gaaaagttcc aaaccacagt 92940
tgaagttttt gtgtcagcat acatgacatg atttcacctt gctaaaattt aaaattctta 93000
tactgtgcag tttacatgga ttctttcacc ttctttgttt ttgctctcac caagtcatgt 93060
tgccttttat ttagtatcta aaaacctgag gaagtgcatc ctggcaataa ttttcttaat 93120
tttcgaaaga tgattgtggt ttcttgacaa ttttttgaat tctgtcttca aaacaaaatt 93180
ccaaccatat ttttgtttga tgtgatacta tgggactgtt ggaagatctt ctccaatttc 93240
atttggaatt atcataattg cagatcaaaa gcgattcctc ggacagtttg gattacgtgc 93300
acgcatatta tgatgatctt gacattcctc ctgtatgcat cagcactcag tggtaccctc 93360
tatgctgcga ctatactgct tggagtctgc tgtggcgtca tatactcttt gatggttcca 93420
actgcctccg agctttttgg cttgaaacat tttggcctta tttataactt catactgctg 93480
ggaaatccta ttggtgcgct ccttttctcc ggactgcttg ccggtaaatt atacgatgca 93540
gaagctacca agcagggaag ttccacctgc ataggtgctg agtgctttag gcttaccttc 93600
ctggtcctag ctggagtctg tgggctaggc accatcctga gcataatttt gacaatcaga 93660
atccgacctg tttaccagat gctttacgcc ggaggctcat ttcgcgtgcc tcaagcatca 93720
gaccgctgaa atttacagaa tataatgatt atcaataaaa tccaggcatg cctatttttg 93780
ggttggtctg tccaccaatc ttattttttg ctctctagga agcagattgc cgcttgcatt 93840
ggctatatat atgatgttgt tgcatattat ctgggtgagt cagtgaccaa tgagtactat 93900
gaaacaatgg ccaagatttt gtggatacat agttaaaaca tcccatgatg ctgtacttta 93960
aacaggagca tgtgcactct cctgaattag atgctattga tcaatataat ataattgagc 94020
ttcgtccttc cccaagagga atttataatt tacagttttt ctttctgacg tcttattttg 94080
cattaggatc gtacttcaat gtattctttg gatcatgtac taattgtata cgttgtaaat 94140

-continued

```
attattgcaa catgaagtaa tagaaattta ccaatataaa aattctcagt aaatggaacc  94200
ttttaaaccc agacatttct ttgtcgttca taaatataaa atatgcggac gctcccattt  94260
gtgctttttt aaatttttgg tcaaaataca gctgccaaaa tccaatatta aatatgttta  94320
cacttcaata aaagtgacaa caccatcaaa agagtcaaga ttcacccaaa acaaatatat  94380
ctgaatattt ctgccagtac aaattttcag tattttcaac ccaaaaaacg gataaagata  94440
caattcttgc tacgtatttg gacatatgta acacaaattc ttttcaaaaa gacactaagg  94500
actagtgcat tcttgtctat caaaggtaaa aagaaaaaaa gattatagca tacaaaagct  94560
aagtggagac agcttgattg ccgaaacaga cccttgctgc ctaagtcttc ctttttatct  94620
tgacccacca ctaaagtaaa agatcaattc aatgatcttc ttctttaaca caccccctata  94680
aattaagtaa aaaattaata aaaaaataaa aatctggtgg aagaacccca aaaacccatc  94740
tctcaccatt acaatctaaa atcaaattca gaacgacata ttgaaaagaa aaaatttgac  94800
ctttcatgtg ggtttcaagt tctgaaacat tgtatcccat ctgatctctt caactcctgt  94860
tgaccaatac cgatcatcat ctgcaacctc atgatgatca tgatcatgtt catgatgatc  94920
ataaccattc atcttctcct ccttattatg atcataacta agtacagggc ttgaaaaact  94980
attgaccctt ccactggtga ggagcagtct tccgggttta ggcagcatca acttcttgtt  95040
cctcttcaac atggcacttc tccatcttgt gccataacta ggcttattag gcacaacaac  95100
aagagctgta gatgaatctt ctcttcgaac ccaagtcctc aaatacttag caagagatct  95160
ttttgttctc ttgatagcaa ctatgagcct tgacacaggc cttggaccag ctgctccctt  95220
ttcttttctt gccagcttga ggatctctag cctgtgcttg gctatagata tgcccatgct  95280
ttgaagaaac tcatggttga aataagctat gtcttcttct tctagctcat tgtgggcaaa  95340
agcaaggccg tattcataca cgagagttgg ctccaagcca gttttagaga gccatgaaaa  95400
ccagtccatg actctttgaa gtgtaatgaa atgaatgtgt gatgcgtgtt gaaagtttga  95460
gagatatgtg tgtctatata tatataaaga aggaaaagag gaaatggttt ttttttaaat  95520
aataaataat tttttttgcg cccctacgga tgagagagtc ttaaatggga tgcatgtgca  95580
taataaataa ataaataaat aaaaacatac agaaatgatt tagtgcagtg aaacaattta  95640
attcactgat gagtaactgg acatacgacg taattttata attttatttg aataatattg  95700
aaattgtgga tcaatcaaat aattttaata ttagtacggc tcattataat agtagtagca  95760
ttactcacta atagtaacat aatcaaataa aagtaacata atcaaataat ttttttatat  95820
atatattttt ctatcttcca ttttatgata tggttgttga aacttgagaa tgaataaagc  95880
agaaagaaaa gtttgaagtg gggtttgcat ggccaaatgg caatgttaac accaaaaaat  95940
gtgatcaagg agtgtgagcg aaggattgtt aattcttgga gagaaaatgg attgccatca  96000
atcacgctat gggaaaagag taacgtgtag ggaccccccc ccactacttc tgtttttgtg  96060
gaaaattttg gaataaaaat ttcaaacaag gcaactcgac ttgtgggaaa agatgggttc  96120
tctggttttt agtttaacta caagcaactc cctttgaatc aatgctacca actgatttga  96180
atgacaaatt ttattaatta gctctaactc atcaactact aatcctgctt aaagaatcta  96240
ttcaatttct tccgttgctt taagaccata ttgaataact tgtgaaaagc atggtttcat  96300
agttaagatc cattgagttt ctagattaat taatctcacc taacagaagt agattgggtt  96360
attgctaggt ccgtcctagg cttaggctta acttaggaaa ataaaagaaa gaaaaaaatt  96420
agttttgcaa attgacatgg gaaattttca atttttcttt ttaattttag aaaacaatta  96480
ctagttaatt atgatgtctt atagtatcaa tgatttgtag aaaagttctt ccaaatttga  96540
```

-continued

```
tcaagaaact actttataca aattggtcgg tttaaatatg agggaggttt acaataaaaa  96600
taagatgact tggttgacat aaaatttaat tgttaattat cattgtatta ggtgttgtcc  96660
gccatcacta actaattaat taccacttta ttatatttga acgctttatc ataaaaatta  96720
aaagcaaaaa ggaaaagagt tgacatcaca gctttgcctt aatttaattc ttaaatcctt  96780
acgactcccg aagaaaaact ttattgcata tgaatttctt ggattttctt tttggcagtg  96840
attcatttat taatatttga taaaaaaaaa attgtatccg tttggtttcc ataaatatat  96900
ataatgtaat tgattaattg ggttgaattt ggaaaagaaa ttaattctta tccatatact  96960
gttattaaaa tacatatggt aaattttttt tagaatcttt aaaaactcac ttgaatctaa  97020
ttttgttgaa tttataataa gattacaaac atgtaattta tttcttttaa aataattgta  97080
atttaattgt attagttgca ggcttgctgc ctgccatcac gtataagact attttattat  97140
tatcctgatt agcctaaaaa taatataaag taatccttca gttgaaagct taaactgttg  97200
acaatttaac ttaattatgc cgaagtatat aatctatatg ctgaaagaaa tttaaaacct  97260
tgtaatattg gtttcctaag ggttgagaat ttctaatccc ttgggttttt tttttttaa  97320
ataaaaaaag gtcgatgaca gagatatgaa aattattttt gttatatgca cgcacgcaca  97380
cataaagaat tgaagattaa aggtgtaaaa tgagtcggat caaaatgaca ctaatgagcc  97440
taatactgag aagaaaaaaa attacaactc aattcagaat gagagttcaa ataaattgat  97500
gaaattaaga atgatgaagg gatctaattt tttttaaatg agagaactca cagataagtt  97560
tataatcatt acaattgaaa aaaaaaaatt gcgagattca gagacggatt gctaatgatg  97620
cctagattga aagcatgcaa aaataaagat aaagccttaa ttagattaac tcctaaggaa  97680
cataatcata attaatttga cgcccaaatt atcacagaca gtccggccgc cttaccaaat  97740
acataatttc ttttatctat cttgtaatca ataatttaat acaaaatctt ccaaaaataa  97800
ttaacaaaaa taaagtaaaa aaagaaaaaa aatggtagat acgactcttt tgtttgtggc  97860
tccataacaa ttgggatata tggtatctac ttttgttact taatgacttt aaatcacttt  97920
cagtactaag cactatctca aaaccacatc ctttaaaagt gttttgttgg ttattcaatt  97980
ttcttccaca ttcacatgca tatctatcaa ttgtgtattt tactttttgt tgcttattaa  98040
accgtgtcaa ttcattctac ttaatttatg gcttcagcac taagcattat tgtttcaaaa  98100
gcacttcttt ataaaagtgt tttgtctgtt tttccaattt ttcacccaca ttcacatgca  98160
tgcatatatg ggttacattt tggactaaaa aaattctcac ggcctcacta gtgacttgtg  98220
agtgttgagt actatttgca tgtgagcgac aaatgttttt ttttttgtct tttttttttt  98280
aagtaaaaga acaatggtga gagttttaaa ctagaatttt tttttttaaa aaaggaatta  98340
attggctgtt aaacccttct attatttctt ttttagctca tgtgaagaag aatcttttca  98400
atgcctagag atttagattg caccataaca gagctatcta attaggatcc acaatgactt  98460
cttccgattt atgccctctc tcaaagttct aaatctggca gacagcagtc taaccaactt  98520
accagagggg atttcaaagt tggtttcact gcaacatctt gacctgtcaa aatccagcat  98580
agaagagttg ccactagagt taaaggcatt ggtaaatctc aagtgtttga atttggaata  98640
tacatggagt ttaactacaa tcccgcgtca actaatatct aatctttcaa ggttacatgt  98700
cctgagaatg tttgctgcta gtcatagtgc cttcgataga gcatcagaag acagcatttt  98760
atttggtggg ggtgaactca tagtagagga actgcttggt ttgaaatatt tagaggtgat  98820
tagcttcacc ttgagaagtt ctcatggtct ccaaagcttc cacttccaaa gattgtaatg  98880
```

-continued

```
gtaagtgctc ttcgagacct tacaaaaaac attacaagtc aaaaagccat aggaaaccct  98940

ttcttggaca tagggaaaat ttttataaga aacctactag gccttataaa aagtccagat  99000

tccctagaaa gaaagatttt aaagccacac caaaaactcc tttcaatttc aaggaagcca  99060

tttgtcatcg atgtggtata aaaggccata ctgcaaaata ttgcaaaatg aacaga      99116
```

<210> SEQ ID NO 2
<211> LENGTH: 58965
<212> TYPE: DNA
<213> ORGANISM: artificial
<220> FEATURE:
<223> OTHER INFORMATION: Poncirus trifoliata and Citrus grandis hybrid
<220> FEATURE:
<221> NAME/KEY: misc_feature
<222> LOCATION: (2145)..(2320)
<223> OTHER INFORMATION: n denotes unsequenced nucleotides

<400> SEQUENCE: 2

```
gatccattta actaacaaag atttcttatc atttataatg aaacaaaccg taaagctaaa     60

ttagaatttt ttttaactat taaaatccct caaatacttc ttggaaaaca aaaaaaaagt    120

ttacatatat atatatatat atattaaaaa gaatagtctc aaacacaaac atatctttaa    180

aatttgttga tttctattgt acataaatcg agtttaattg agatcccaca tgatcagttc    240

attcacgttg cacgcttatg gagacccatg caattttgag aaaataaata caagctcttt    300

ttgtcgttgc cattcctaaa taaaatgatc attcaaatgc ccagtgaggg cataatcaat    360

aatgcctact agccaacagt attgggatca attcttgtcc aagttaagtt agtttttcat    420

ttcttgtttg cttatgataa tgcaaatttc aacaaaataa acctttttttt taaaaataga    480

ccacttcctt taccgatgta tttagaatca gattcgaata gctatgaatc ctagtgtgtg    540

gttctctata tatatatatg agtaattttc tggtttggga tcataaaatg cgggaaacgt    600

ccgggaaaat tttaaaattg tgagatttta aaggtttaaa acttaaagcg tttaaaccgc    660

acggtttata cgtttttccg gacatttata cactttaaaa ttttaaatta aaatatttct    720

tttatatata tataatcctc tttagtgtag acgcctttat tttttttttt tcatacaaac    780

atgttattaa actatgagat ttaatagagt tagattttaa tactataaaa ctgcacagcc    840

taacaaagtg tatccatgaa aaaaatgata gtgtccgtac ttgagaatgt gtgtgtatga    900

gatctgttaa gagaaagatt tattcaaaag aaatcataac aattacatcc gatcacaaac    960

tacacgaaag ttgccccctt tttcatggcg atttgcccct cacaaagatg cactgagaaa   1020

cagaacaaac tgcttgtgaa ccagctaaga gacgctttca ttgggaccat cccacctttc   1080

gtggctagga aattccttat ttaaatttaa gtaatagctc atctagagaa tccctgacac   1140

acacacacag agacacacat gcacgcgcac gctcacacat agagactacg ttatgtatac   1200

tagggttgat gtaggaaatt ctaaaagaat ttgatattta atattagtaa atttgttaat   1260

gtaatgcatc gggttaagtt gagtaatttt taaatagttt tatttagatg actactttaa   1320

tttgaatttt gaattacgga atttgatatt taatattagt aaatttgtaa tgtaattatt   1380

cagggataaa gttagagtaa tttttaaata gttttattta gttcaccact taaattcgaa   1440

ttctgaatga gtaagggact aaaaaatcat caccttacct ttaaaaaaaa tattgttaat   1500

acaatatttc aaaaaaagaa atgctcatac aatttttata gtatttttaa aaattttttt   1560

tgataagtgt ggattggatg tgatcgatat atttactaat agacaaacaa acacaactgc   1620

gctatacata ctaaaacatt tacatcaata ttattgtatt ttagcgataa atataatgag   1680

tggtaagcca atattattta ttttgaaaaa aaaatgccca catcaatatt agtcactcat   1740
```

-continued gttgatttac aattggtttg gtaactagtg atgttgcttg ttatggacac taattaatta 1800
aaattatttt aagagaagtt tactaattgc atgctttcat aatcttttgc acctaattag 1860
tgatttttca aacataaaac taaatgaagt tagtaaacag gtgatgattt tgatgctttt 1920
actctatatg catgcgaatg taatttgttc ctaacttata aactaaggat atatatatat 1980
atatatatat atatatatat atatatatat atatatatat atatatatat atatatatat 2040
atatatatat atatatatat atatatatat atatatatag tcatatatat atatatatat 2100
atatatatat atatatatat atatatatat atatatatat atatannnnn nnnnnnnnnn 2160
nnnnnnnnnn nnnnnnnnnn nnnnnnnnnn nnnnnnnnnn nnnnnnnnnn nnnnnnnnnn 2220
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn ctttctaggg acccaaatta 2340
aatggagaaa gaggaagatg gaccaatatt tatgatatta aattgactgg agacgattgc 2400
aattgaaacc aatagaaatt gtcttcaatt gatattgttg tctacttaag tgtctttaat 2460
tgttactgca gactaccgat aataataatg cattcaattt taatctaatt ccatggtata 2520
aattcctaaa aagttttaag aactaattgg gaacgtttct tctttgctca agtttaaact 2580
aaaactttaa agcttgtgac ataagaagta gagaagaaga agcgatgaag aagcagccgt 2640
ttgtgatgag gtcggtttaa gtttcacgcg tttatttaga caagaaaacg atctattttt 2700
cttttaataa gaaaagtctt taaggtaaat tgaatctcac ccttaaaaaa agacttaaat 2760
aaccatgtaa catgtgttat gatcttttat agagtttagg aaagattaaa taaggagaga 2820
atttaaattc atcaatcgta ctacattaat ttgtacaaac taaatttata taatatttta 2880
taattgtatt attattcttg aaaaacaata acatacgtac taatatcttt tattctgttt 2940
acacaaataa gtttgagaac atcatcgacg gcggtattag ttatttgtaa attatattat 3000
ctttgttaaa tagaaatggt acgttaagaa tagttaaaaa atcctatgga taaacattat 3060
taacaatgat taagatcatc cactcatagt aacttttact tttactaaat acgtaaatgt 3120
agttggtggc cggttaataa aattaataaa aaaaatactt aaggtgagta tagaatagca 3180
aattacacat attagttaag tgtcactctc ttagtttttt tcacttaaac tgattaattt 3240
atcttttatt cattaaattc gttcaattca atcgtgtatc cactagtcat taaactcaaa 3300
tgcttttaac attctctaca ataaatctaa aagcttttgc atattccatg aattgattgt 3360
tttaattgag tttgatcagt cttaatcaaa gagacttgaa gccggaacca cgagttgatt 3420
ttctggtttt tatttgcgct atcatttcat caatgtctct aaaccaataa ttatcaaccc 3480
gcatttggat atttcttcaa tcaatgcacg acaagggcaa catttatggt catgagattt 3540
aaagtttctt atttgtctta cttagaattt tgaaatatct tacaccgctt gcatcatgac 3600
caaaacgtat ggtcaggatt tataataatc ctatcatttc tcaaataata ttttaagagt 3660
atctatcgca aagtcatgac attaaataga tgataaattt ttataaatta taaaattact 3720
ggttaaatca tcttattttt caaaagacga aaactccttt attttatcga caaataattt 3780
ttatacattt aaataactca cataagaagg gactcgattc ctctatgtgc attaatgagg 3840
tcatttttca tatatatgat cttaaagtgg attcgactcg tattagactc ttgatattaa 3900
tctaaacaat ggttttgatg aacttcttat tgccgttgct aattagagtt tatatagagt 3960
tccaaatttc ggaaaagaaa tgtcaaagag aaaggcccag cccagccctt attttctttg 4020
ttttcttgtc tcgaaactaa tgggctaggc ccaacataaa acgagatcgg gttatacccg 4080

-continued

```
tccagcaggg cccattttct ttcaattttc acttgcaaat ccctgaaagc aacacgaaaa   4140
ttagtaggaa acgaatcaaa atcagtgacg acaggaagac tacgaatccc tttcgcttca   4200
atcttcgtaa aagatggatg cagcgaggaa aaaggcgata tttcgcgcta aattgaatgc   4260
tcagaagaag gagaagcgga taaattctcc tcttgtaagg tgagaaaata aaaaatttta   4320
aaaaatattt tttattgaaa ttttcgtcag attagttagt gttattaatg atatgggttt   4380
cttttaaaaa tttatacagg tataacgaat ttgaccaacc tgtctgtcga gtttgtgatg   4440
ttgttttgaa atctgactcg cagtgggatg cccaccaagc ttctcgtaaa catcatgagg   4500
tgccccaatc tttttctcct caccgaaaac aaatttgatt aatggttcat ttattagttt   4560
ttctgagaat ttggtcataa ttgaattact tgcttatgtg tgttgctggg taggcaatta   4620
aaaatatcaa agcaggtgct actggaaata atagtcggat ggtgagtgat gctgcgaagc   4680
ctgaggctgg tagagagtct tctagaagtg aaagccgttc agcatcgcaa aatgtagaga   4740
ttgaaagctc ggcgaaattg ggtaaagctc gaacgtcttc tgtgcttcct tcgaatttct   4800
ttgatagtca ggaggtgaag agaccaaaaa ctggtgagaa cttgtttaac ttccaagtga   4860
ttactagaac attacttgtt tcctgctgga attgtgcaaa acgggaactt aatacatttc   4920
tgaataagtc tctaacggtt gcttttatcg tagttacatt ggttaacttc aaaatgctta   4980
tcttgtttag aattttcacc gtttacagtt tcttctatta atcttggcat tctaattcat   5040
ttgctgttgt tattaatagt attcagtatt tgaactaggc tggttgaaac tttgaacgtt   5100
tatttacatg ataaaaaata atgtactttt agccacagat tctgtcaagt tggtggatcc   5160
tgattcaaac aaaacgtctg gggtttctgc taaaactcag gcaatgaagt cagttgtctt   5220
ggaaaatgag atggatgagc tgcctaatgg taatgctgta gatgcaaaaa agggtcagcc   5280
tctcaaggag catccagaga aatcaaagca gaatgtagat tcggaagcca agcaaataaa   5340
gggagctctt cctgaaggct tcttcgataa taaagaagct gatttacttg cacgtggaat   5400
taagcctgtt aaaccagatg tcaagtaagt tccgatttga gatatgtata aatattattt   5460
ccaaacctgc caaaatattg ataaatagta aatgcattaa tagtttcttg tatggttatg   5520
tttttgagtg cattaatagt agtgtaaggc ctgtattttg ttattctcat gatcctaaac   5580
atggtgcctc tacttcattt agtttagaga tcgtaaagat tctgtaaaga ccttttcagt   5640
ctagagctgt gctgagataa gttgttgact gattcacgta gatatgctgc tgttttactt   5700
tatgggcttt ggtgttttcc aaaaaaaaaa ataaaattga tcaatagtgg ttttaaattt   5760
ctgtcttgtc attaatcaat agtttctatt tttaaaaaag aaattgcata attaaggatt   5820
gcaataagac tattaagaaa caatggctga agacgttgcg accaaatgtg aaatattgtt   5880
gttgtcgtga ttaagtgtga aagttgcgtg ctggatagca catctaatca gtcaataaga   5940
aacttccagt gttaagtttt agacttcatt ctgagtttcg aggaaagaag ggagtggaga   6000
gatatattat gatgtttact tacatcataa tacaaaggga aatgccagtc ctacacctaa   6060
aatttcattg ccgattttta ttgatttccc tatatactta gtcaatctgc tggcctcttc   6120
taccgtttag atatgatgga tttttttttcc cctattgtgt atttatacag atctacaact   6180
ctctagtaat cttgaattta tgtcaaatct tgatcagaga tgagtacaag gaatatgaaa   6240
agttgatcca agaggacttg aaacaggtgg atgaccgttt tgaagaagag gaggtgagct   6300
gtttttctcc cttttcccag tcgctgaacc attcctgtct tggcatttac atgtctggaa   6360
gaatattaat aatcttaaat ggacttgtga gatgcagatt gatgctgcag aaatgataga   6420
agagtacgaa tcagtggacc aaaagtaagt agcataatgt caacagcagc aaaatatcat   6480
```

-continued

```
cttctatttg ttatcttttt gaacttacga atttttattt tttatttttt taaatcaatc   6540
tataggacgt tcagcgagag agtggaagct ctaaggaaga agaaaatgga gtgggaagcg   6600
gcttccaggt cagcgaaaag cagaggtagt tctgaggttg ctcgcaaaga acctacaaaa   6660
gaagagttat ccagtgacga tgatagtgaa gagatctttg ctgttgattg gcgggctcag   6720
cacctgtgat gtctgccccc aaattttctg gtagaactct tctcgttttt caacttcttg   6780
tagtaacttt tataaaaaga tgagattggt ttgaaattaa gtatgttttc acagatctca   6840
atcaaaatct aaacacccaa ttggcatgat ggtgcatcat ttgcaatttt tgctcagttt   6900
catttgcttt tctctatttt tccagtatta aatatgtaaa tagcttttga atccaaaccc   6960
ataatcagtc atttaaaata aattttgcat tatctgttat cgataaagta tttatagtgt   7020
tatccattct tgatgactac tctttctcag atgcgcatat ccattgaacc aattgtctgt   7080
cttggctaga gtaaccagag tgcatcattt ctgaaatttt gtcacagaag gagccttact   7140
gcctacgtaa tcgatggaac ataacatgta aatagggcat taatcaagta aatctagctg   7200
ttgaaaggtc gttgacggga cttgctggct tactcaagag gttgttcaca gctttactag   7260
gagttgttaa cttacgtaga caagtttcac gttaagttgt aagttagtta tcgacgatgc   7320
aactaaattt ttgaatattg attcactcgc gacatttatg gagctgattg aacgatgaat   7380
aatgtaattg gggaatgtct gtaatctgta tgcgccttta gaaatggaga gatgagcaaa   7440
atgtgatgat catttgggaa atatttttcg attcttaatt ttgaaagaaa tatttgaaaa   7500
atacagggtt cgtttttcaa aattaatatt tatgcttaat tgtcgatatt tgaccctagt   7560
tttttttttc ttttttaaat gaaaaaaaaa actcctgctg tatatattct atggtacaat   7620
gaacaataca aattaatact tggaaaagag aactaaaatg aaacatagta agtgataaaa   7680
tacaaaatgc agagccataa ttgcaaagcc ccgaagggag tagagatgtt ttgccacgga   7740
tctgaaattg aagaaatcaa atcacgtact agctaattga tcaatcaagc caaaagtttc   7800
atagatgatt acaaagagga caaacattat taagaatctg tactcgtaaa attactttta   7860
gcaactagaa caagaaatgg gaatgcaaga aacagagtgt cttattttac gtgaagggaa   7920
ttaacaagat gatcaataca agaaaaagca ggcacaaaac cagaaatcaa atacaatctc   7980
tgctcaggaa tcaggatcgg aaccaatatc gaaccccatc gataagaaaa gcattttgag   8040
tggcctgatt ttcccattga agctgttccc accattctgt gtatccacga ataacaattt   8100
tccgctcctt tgcactactg gaatcgagcg ggatgtcacg ggatgagtgt tttgcgcagc   8160
taacccgtgc ggcacttaga caactttgcc gaatgttgct aagtaagcct agaaattctc   8220
aaacaagaga agagagcaat tgagccaaag aaagaacttg tattgcacaa agagagatta   8280
caatgcttaa agcttgttgg atacaaatgc ctaatgccat cccatattta taggggaggc   8340
ttggtcaaac ttggcctaac tttgccaaac tttgccaaac tctagagtat tctacaattt   8400
cctagctatt tacatgtgct ggaattgtat aaagcattct agaatattta catgttcaca   8460
tgtgctagat tttcctagaa ccttccggaa ttgggccaag ctagcactct tggctttgtg   8520
ttggctctct agcccgaaat tgtgggcatt tgggctagcg aattgggcgg tccgcaacat   8580
cctcccccac ttaagctcgc ggcgtcctcg tcgcgctttc gtgcttgaac ctctggatgt   8640
gttcagcgaa ttgccacaaa tcatcttcac gttcccaagt ggcttcgctc tcggggaggt   8700
ttttccactt taccaagtac tcgctatgtg ctggcacgcc cctccttgaa accgtgcggt   8760
ccgcaatgat gtagtccaca tctttgtcga atgcggtgac aacggcagtt ggcgcgcgcc   8820
```

-continued

```
tcgattctcc gcgacttggt tctcccatgt cttcgtgata tggcttgaga aggctcacat   8880
ggaagaccgg atggatcttg agtcttggcg gaagttggag ttgatacgag acgttaccca   8940
cacgtcgaac aactcggaag ggtccctcgt agcgcctcac taaccccttg tgaactttcc   9000
gcaaagtctt gaattgttgg ggtaggagct tgatcatgac ttgatcacct tccttgtact   9060
caacatgccg tctccttgta tccgcccact tcttcatttt cctcgcggct ttgtcaaggt   9120
aggctcgcgt gatgtccgct tcctcatgcc attcgcgggc gagcttgtgt gccgcggggc   9180
ttttccctcc gtaagtcgag gctatggcat tgggggtcat gggctggaat cccatgatga   9240
tctcgaacag actcttgccc gtagcctcac ttcgctgcaa attataagaa aattgggcga   9300
tgtcgagtag cttcgcccaa tcccgctggt gagcgctcac ataatgcctc aggtacatct   9360
cgaggaggcc attgatgcgc tcggtctgcc catccgtttg tgggtggaag cttgtcgaga   9420
acttgagatc agtccccaac atcttaaaga gctccgtcca aaaccgccca gtgaaccgag   9480
ggtctcggtc gctcacaatg ctcttcggaa ctccccatag cttcacaatg tgcttgacga   9540
atagacgggc tgcctcgtcc gctttgcaat caataggtgc ggcaatgaat gtagcatact   9600
tgctgtgtcg gtctacaatg accatgatgc ttccgcaacc ttcggacttc ggcagcgatg   9660
tgatgaagtc catggagaca ctttcccatg gccttgttgc tagtggtagc ggttccaaca   9720
atcctgctgg aagttgatga tccaccttgt cttgttgaca cacaaggcaa gttcgcacat   9780
atgcctcgat gtcatccctc atgtgcggcc aaaaatacga ggcttggact agtgcggtgg   9840
tgcgctcgat tcctggatga ccagcccact tggagtcgtg gcactccttg attacctcct   9900
tccgcaagtt accccacctt ggcacgaaca gccgatctcc cttggtgagg aggatgcctt   9960
cctcttgcca aaaccgcctt gtctttccct cgagcacctt ctccagcaaa tcctttgcta  10020
gcggatcttg ttggaggcct tccttgatgc gtgagacaag gtcggacttc ggttggctca  10080
tgctaagtgt tgccaattca gccttgcggc ttagagcatc cgcaacgaca ttggccttac  10140
ccggtttgta ctcgagccga tagtcgaatt ctgctaggaa atcttgccac cgtgcttgct  10200
tcggactcaa cttcttttgc gtctgaaagt agcttgttgc cacgttgtcc gtcataattg  10260
tgaagtgtga gccaagcaag taatgtcgcc acactcttag acaatggatg atggctgtca  10320
tctccttctc ttgcaccgtg tagcggcgtt ccgtgtcatt tagctttcga ctctcgaacg  10380
ctattgggtg gccttcttgc atgaggactc ctcctatagc gaaatccgag gcatccgttt  10440
gcacttcgaa gggctttgtg tggtccggaa gggcgagaac tggttcctcc gaaattgcct  10500
tcttcaattc ctcgaatgcg cgttggctct cttcggacca atgccatgtt ctgtttttct  10560
tgagcatatc cgtcaagggt gccgccttgg ctgaatagcc ctgaatgaag cgtcggtagt  10620
aattcaccag cccaaggagt gagcgaagct cgggcacttt cgagggaggt tcccattcga  10680
ggatggcctt tactttgtca ttctccatca tgatcttccc acccgcaatc ttgtgtccaa  10740
ggaactccac ctcttgttgg gcaaacgaac acttctctag tttgaggaag agctcgttgt  10800
ctcgaagtac ttggaggact tgtcgcaagt gttggacatg atcctcgagt gtggtgctat  10860
acaccactat gtcgtccaag tacacgacca caaagcggtc gaggaatggt tggagtacct  10920
tgttcatgag tgtgcagaat gtggcgggtg cattagtaag gccaaaaggc atcacaagaa  10980
attcgaaaga cccgtacctt gttgtgcacg ctgtcttcgg ttcatctccc ttggcgatgc  11040
gcacttggta gtaccctgag cgcaagtcaa gtttggtgaa gtaccgtgct ttgccgagct  11100
ggtcgaacaa gtccgcaatc aagggaatcg gatacttgtt cttgatggtg atcttgttga  11160
gcgctctata gtcgatgcac atccgcagcg atccatcctt tttcttttgg aagaggaccg  11220
```

-continued gtgcaccgaa tggggccttt gaggggcgaa tgtagcctgc gtccagcaag tctgtgagtt 11280
gtctccgcaa ctcttctaac tcgggtggcg ccattcggta gggcgccaag gctggtggct 11340
tcgcgccttg ttccagctcg atcgcatgat ctacctctcg tcgaggtggg agcttcttcg 11400
gaagttctgg aggcatcacg tccttgtact catcgaggac ggcttgaatt cgcggaggga 11460
cttggcttgg cgaagttccg ctatttcctt cctcatttag ttcccgaatg gagaccaaga 11520
agcttgggtc cttcttgaaa gcccttttga attgcatggc ggagagtgtc ttctcctcgg 11580
acttgcctcg ttccgtgggt accatgcatg ctttgcttcc gtcaaggatg cttagggagt 11640
ttgtagcggg cagcgggaag gcatggactt ggtcgaagaa ttccatgccg aggaccatct 11700
tgaagtcatc catgggcaca atggagaaat caagctttcc gctccatgta ccgagtgtga 11760
tgtgcacgcc ttgtgcaatt cccgcaattg gtttggcggg tgagtttact gccttcattg 11820
tgcctccttc tttggtggcc ttgaggccta aacgcttggc ctcgtctatg gacacgaaat 11880
tgtgggttgc tcccgtgtct agcagcgcgc gaacggactg gccgtttacc tttgcgctaa 11940
catacatgag ccctttcttg gctagtgcgg gctgttggcg gttgagtgcg ccaaggcatt 12000
ggagagaacc catgctgagt tggggttcct ccgtggacat tgtggggttg ctcttgagtt 12060
gtgcagcaag aacattaagc gaccgcttct ccggacagtc gcgtacccaa tgcggaccat 12120
tgcatatgaa gcatgggctt cgcggctttg gcgcctcctt cttgccctcc gattttcctt 12180
gccaaatctt gttgctaggt ggctttttct gcccccaatc cttgcggtag ttgcccttgt 12240
ccttgcgact ctctccacca cctttgcctt ggctaggctt cttgtccttg gattgggcag 12300
agtattcggt gagcgattcc gcaacggcta tggcgtcgtc aagtgtttga acaccacgcc 12360
tatcaagctc ggtcttggcc caatccttga ggccatcttg gaagtagaag agtgaatctt 12420
tgtcggacat gtcgcttatc tccagcatga gggtagagaa ctcgttgatg tagtcccgaa 12480
tgctacccga ttgcttgagg cgacgtaagc gcgctcgcgc ttccttctcc gcattgcttg 12540
gggcgaactg ctttcggagt tcttgcttaa agtcggccca agtgtcgatg gtgcaaatgc 12600
ccttgcccat ctcgccatgc ttgcgacgcc accatagttg tgcagcgcct ctaagatagg 12660
tgggtgcagt gcccactttc gatgcctcat ctcgtacacc tatggcatca aagtattgat 12720
ccagcccgaa caggaagttg tccacgatta tggcattgcg tgtgccatcg taggtgtcgg 12780
gctttggcac atcaatgcgg cgcgcatcac tcgagtttgc ggaagctgga cttgcggaga 12840
gtgtgcgctt gtgccatgcc caatccgagc ggacttcatc cacttccgca cggacagcac 12900
gtagttcgtc ttgaacaaaa ctacgaagtt tcagcaactc atcatggaaa gatcgaaact 12960
cacctcggag agtgttcgct tgctcatgca tgagagcctt tgtggccacc gtgaactcgc 13020
cgtactctcc ctcgagatcg tccactcttt tctccaatcc ctcaaggcta tcttgagcgg 13080
tggacaatgc tatttcgaga gtacctacac gaggctccaa cgcatccacg gatggggcct 13140
tggacttgcc acgattcttg ccttgggcgc gttctccctc tcggccgcgg cttggttctg 13200
gtggaacatc cacaccaaca acaccctctt gtgctacgtt cgaagggttg gccattgctt 13260
cgtgagctat ttgcgtgcgt gcaaacctta gctctgatac cacttgtcac gggatgagtg 13320
ttttgcgcag ctaacccgtg cggcacttag acaactttgc cgaatgttgc taagtaagcc 13380
tagaaattct caaacaagag aagagagcaa ttgagccaaa gaaagaactt gtattgcaca 13440
aagagagatt acaatgctta aagcttgttg gatacaaatg cctaatgcca tcccatattt 13500
ataggggagg cttggtcaaa cttggcctaa ctttgccaaa ctttgccaaa ctctagagta 13560

-continued

```
ttctacaatt tcctagctat ttacatgtgc tggaattgta taaagcattc tagaatattt  13620
acaggttcac atgtgctaga ttttcctaga accttccgga attgggccaa gctagcactc  13680
ttggctttgt gttggctctc tagcccgaaa ttgtgggcat ttgggctagc gaattgggcg  13740
gtccgcaaca gggagcttac ttaagcttat cgcaacaaat taccttcacc tctttcagag  13800
gtgggaaggg caggggcttc ctgtaaatgc cctgcaaatt tgacagacaa gataaaccaa  13860
gataatggag ttttgcaaac aggtttagat ttcgcatcac ctctggagca tcactgacga  13920
tttcttgaat ataacggcaa ccgtttactt taacacttga ggtttggagc gaaagcaagg  13980
aatgtgaagt ccttcaatta attacaatcg tctatttgaa tcttcttgag gctttggaaa  14040
acaaaaggtt ggctcctgtt ttgcactaca cctgtataat ccatcttcag ttcttccaat  14100
tcataacact ctacaatctg tactctgttt aggtgcttca ggtctgccaa agctgaaaca  14160
tcaagcgact tcgaacgttc aaagtctttt gaggaacaga acttgagtac aacttcgtaa  14220
cttatgcaag ctcgaaacac attggagagc tcgagaatta ttcgaggtca aggttaattc  14280
ccaacacatg caaacttgaa aaacgggata ttagtcgccc tggaattaca gttaccctcc  14340
atgcgttttc caaattcaaa gtcttaagat ttaccaacgc atttaactca ttctggcaac  14400
tctgctactt ctgtatctga aagatcaaga tgttgcaatg aaaccaactt tgaaatccct  14460
aaaggaaaaa gaagacagcc gtacagtacc tgacaggttt aaaactttga gacgagtcat  14520
agagtggaag aagtcactgt caattctctc taatcgttcg ttatcgtaaa gaaataaagt  14580
aagaaaatta aaacaccctt aaaatcatta gcctaaaata ctatttctct aaaatagata  14640
tacaataata gtaaaccaaa aaaaataaaa aataaaataa cctgtgttac aacttgcttg  14700
cctaagaggt agttcattaa catagacttg ttgagttgca aatagcctcg cccttaactt  14760
ggtttttgaa tagtcattcg tgacatacat gcaatgcagt tgattaaaag atgaatgtaa  14820
tgaagttgtt gtatgtctgt atgcagttga tttatctttc actgaactat aagaaatttc  14880
agaagattta acaatacttt cgtttcgtta aataaaaaaa tgaacaacgg agggtcggaa  14940
catcatttac tataaacgta gttaaatgat taaaaataaa ttaaagggta atttaataaa  15000
tggctacgat ggaaccctcc tcctgaggga gtctttaaat tgaaggaaaa tgctacttac  15060
cccgagtcaa atcctgggtc aaactccgaa attaacaaac cagagtgacg aacagtagag  15120
aaattctcaa acccatggaa ccaaaacaac gtaagatcaa aaaaactagc agactactca  15180
ctgaatagat acaaatatgt gcaaattcta acatcaccac agcccacttt attctctcgc  15240
tccttgcttg ctcacggagt ggcataccgg aaaaaaaaaa tggagaagaa aaatatgatc  15300
aatctcatct catagtgcca agatgaagaa aagaaataag aggtaatctt tttctaacta  15360
aacggcatcg ttttagatag aatgaaaaaa aaaaaagagg aaacggcgtc gtttcaatta  15420
atttcgggat ttgacccggg ataaatagca gaactctaaa ttgaataccg atgggtcctg  15480
aaggagctca agtactgcag gggttggcgg tttaattcga aatagcaaca gagagtgggt  15540
gacaggattc agcattaata ttggtgtatg tttatgggga atttattagg gactgttgct  15600
ggcttggcag gttggcattc gtaacattct catagaagct gatggtgagt gtgcaatgca  15660
aatgattgcc aagggttgta gtactgttaa tgcttgttat catctaattt gtgacataaa  15720
agggctgatg gatcgtaatt ggcgagtagt tttgcaccat gtttatagag aatcaaataa  15780
tgcagcggat tttatggctt ctcatgccct caagcttcct ctgggagttc atatatttgc  15840
gttccccccct ccagagatct ctacttggct tttgtatgat ggcctgggga tctcgatccc  15900
tcaccgagtg attgcttagc cttgtttggg ctgcgggctg cttgttgtac caaaaaaata  15960
```

-continued

```
aattaaaaaa aataaattag aggataatta ttatataatt actttatgtt tgccatgata  16020
tcaacatgat tgaaggagtt ccgcaagaca tataactaaa ctacaagaag tttaaaaaat  16080
gtacaattta attacgttat gtcactactt gttacctcat ttaattgagc gctgctatgg  16140
tacttataag agtgtgaaaa tttagcttta aaaaaaggga tattatcaat ttactaccaa  16200
acttttactg acatatcatg tcagtactaa ggtttgtgaa aagtgcattt aactaccaaa  16260
gtttttcgcg gttatcattt tactactaat ccgttaacaa cgttagaaaa ttgctgacgt  16320
gttgctgatg taataagggc ataaaagaca tttatggata caagggcatt aaagacattt  16380
tgagttgaag caaaacgcag cgttttgaca gaatatttaa gaacaaaatc gatcggcccc  16440
ctctctcatt ctgaaacctc cgtctccgat ctctcttcat cggtgctgag tgacggtcga  16500
ctccactacc atttgcgctc tccactgtga aacctccgtc tccgatctgt ctccctcaca  16560
gctgtgtgac ggctgactcc actggtgttt tgcgctctca attgtgagtt gttgactctg  16620
cctttttatt cgcttattgt tcattaattt tttcattaat taaattgtta ttgtttttttg  16680
ttgtgaataa tacttgaatt tcatagatta taatattaat tttgtagcat aattttttgt  16740
taatgtgttc tttgtcgttg tccatggtac taacattaga attttattaa tttttttgtta  16800
attctgttat tgttggagat ctagctttga taatttttcc ttattttttg tggatcttgt  16860
taccaatata agaatttttg ttattgtttg cttttgataa ttaagttgtg aattgtgtta  16920
tgttcatatt actagaatta acgttaccaa ttttggttca ctagttgctt tttgcagatc  16980
atgttaccaa aacaacttta tataatctac aaaggcaaga accattgtaa aaggttgatt  17040
gaaccagatg aatgcagtct actgcagctg aagaatgaag tggtgaagat tacaatttaa  17100
gatggattaa ccactcctga aagtgtgtaa ttagttgtca ccaacccaag gaataatgtg  17160
gaagttattg tagatactga tgcgatgtta cggattatgt tcacggcaca tgactcgtta  17220
caagtgccag tatttaaagt cactgtgttg ctaaccctac gtcttgattt agaacttggt  17280
ggggtgatac aatccctgct acatgcatta ggagttcagc tatctgcaga gcaagttgca  17340
tgggtaaatg aaagtggaaa tgaaccatta tctaggcgtg gaggcattca tgggccacaa  17400
acaaaccttg ctgagaatgt tgggtgtgag actgatgctg atgaagatga atcaccttcc  17460
aagagtgaag gcagagatga accacaaatt gttaggaatg agaatgttca gcagaatgtt  17520
gatgacaacg acgatgatga ttggttgtca gattttgaca aggaatttgc tgctgatggt  17580
agtcatataa atcaccaaaa catagctgat gatgcataag ttatggatga tgagggatct  17640
agctctgacg atgaatcaat tgatgcagat cctcaattat tggcgaatac atttgactca  17700
gattttgatt tgggtactac tcaattgaaa gattatattg aagtgcatat gtataagtca  17760
aggcctgatg gtaagcatag gttgaggtta ggagacgtgt ttgatgatgt tgaccacttt  17820
aggaaggtgt tgggtgaagt gatggtggat aaaagctttg aaattacaaa ggtgtacaat  17880
ggccgtatga gattttacag taaatgcaag actgatggtt gtccatggta tgtggtggga  17940
ggtaaaatca ggggtaaggg tggatttgta attaaggagt tgcaaaataa gcatgattgc  18000
agacagactg aaatgttagt gaatgtgacc agtaaatgga tagtagagaa aataaagagc  18060
aaagtcactg tggatcccca tgtgaagatt tatgttcttc acgagtttat gcaagagaca  18120
tttggtgtga ggatagggaa tttaaagctg tatagagcta gagagagggc aaggacagac  18180
attcatggag accatgcaag gggctatgag gactctttca atatgctgca gtaattctga  18240
agtatgatcc aggtgcaatt tgcaaagtac tttgcgatgc agtaactaag ccagaaaaag  18300
```

-continued

```
tgttatttca gagatttttt atggcatttc cagcccaaag aaatgcgctt cataatggtt  18360
gtaggccata cattggatta gacagatgtc atttgaaatc aaagtatggt ggagttcttt  18420
tagctgctgt aagtatggat gctaataatg gaatggttcc attagcaata acagtgtgtg  18480
agatagagaa cactgaaact tggacattgt ttttagagat tctgcattcg tatttcaata  18540
atggatcaga tcagatcacc ttttgcagcg ataggcaaaa gggtttgtta ggagcaattg  18600
ggaatacatg gccgactgca tttcataggc catgtgctag acatatatat tctaacttct  18660
ttaaagatca tcttggagtt actttgagga atctgttttg gagagctgtc agtagcacta  18720
ataagtttga ccatgcagct gcaatggaaa agttgaaaaa agagaagtta gaggcatgag  18780
agtggttgga gagagaactt gctgggttta cttggtcaaa atatgagtat gacaagaatt  18840
gcaaagtgga tcgcacaagt aataacactt cagagtgctt caacagctgg atcttacccc  18900
atagagataa gccttgcctg actatgcttg aagaaatccg atgcatgttt atgacactat  18960
tcacagaaag aagaaaagaa gcacaatctt ggtccaatat tctacctcga gtaaaaaaaa  19020
attagatgag gcttatgagt ccgaaagcaa aatgattgca atggcttctg gtgatcttca  19080
ctttcaggta taaatctaaa atatttttgt tttcaaatat atttttatat agttgaactg  19140
tttagagtaa aacacatatt tacaattcac aaagcacata ttataattgc ttgaaattac  19200
aatctgaatt cataaattct agtagagaaa gagttattgc tgaactgttt acaatttaca  19260
aattttatat agctgaactg tttacaatct gaattcacaa atgtttccct atatgctttt  19320
aattattgtg ctattgctct caggttaaag acaagagtta ttatccagcg aggaggttca  19380
tcgttgattt agtgagcagg tcctgcgact gtggtcattg ggaactatcc ggactcccct  19440
gtgctcatgc tatggctgca attagtcatg caagacacac aatagaagag tacctaccaa  19500
aatacttcac gaaacaggca tatttgaaca cttatgctgt gatgtttaag ccaattcttg  19560
ataaggttac ttgggacccg tgtgatagac caaaactttc tccacctgag attactaaga  19620
agattggaag gccgaagaag tcaaggaaga gggcagccac tgagccagtg aaaaaaaaca  19680
gatcattcta tgtatgctgc tccttttgcg gtgggatgaa ccacaatgtt tgaaagtgcg  19740
cattgaggcc ttcaatagca agacaaataa gagcttagaa tcaggtatca atgtattact  19800
tttttaatta tttttgtgta taccgagatt aattctttat taatatttgt tgaatatgta  19860
atttaaaata gggtgtcagt gggtcgggag aaagttctaa tgtagaaact acttcgaaga  19920
gaagaaaaag aatggtaaat gttggtttga atatggaata attttttgtt tgttgtagtt  19980
tttcataatt tttttatatt tatatatttc aatttaaata ggctgtgagt agtccagacg  20040
agaggtttat gcatagtagg ggaagatgag gtaacagggg tcgaggtagc agagtaagag  20100
gaggtgacag aggaagagga atggcttcta gaggtagagg tccaggtagc agagcaagaa  20160
gaggtactgt ggtgtttttt gatattgtta taattttctg aatacttcat agatactgaa  20220
gtatatatat atttgttaat acttcatata tatatatata tatatatata ttctgaatac  20280
ttcatatata tatatttgtg caggcagata tgaagctgac aatctatctc caaatccaac  20340
tcaaggctca caagcttcac agatcataga tagttagcag agttttattg ttaggatatt  20400
atgtatatga aatgcacaaa ctatcactag tgcattaggc tactgtggtg tttttttagt  20460
gcattaggct gctgtggtgt ttgttgattg cacaaactat tattagtcca ttaggctgct  20520
atggtgtttg ttgattgcac aaactattat tagtgcatta ggatgctatg gtgttttttg  20580
aattcacaaa ctgacagttt tgggaatagg catttcaagc acaaaatctt atttttcacc  20640
attgataatg gaagtacttt agattacttt tgactttgct tacatattaa attacttcta  20700
```

-continued

```
ttacattact ttctcataaa taagcctatc aagaggccac aaataaaaac tatgaccaat  20760
tttagcttcg ctttaatgca tcgtagtctt tcattcatct tcagtacatc ttcatttagg  20820
ttcaagccat aactagatgt gttgttacgc atttctaaat cttcttttgc tgcccattgc  20880
caaaaattac actttttata cctgcacatc caaaataatt tgttaggatt tgccgacgta  20940
gtagatacca tagcacatgc ctgtactcca cagttgcagt atttagggta gcaggttact  21000
tctacaggtt tcttagctcg acccgtagaa ctaatgcttg tgtggccgac ccgtagaact  21060
aatgcttgtg tggctgttgg aggccatttt tctgtttgaa tttatatgtg tgaagggtga  21120
aaaattgttt ggttttcact gaagatagga aagaggtgga tattgtgttt tcaatgaatt  21180
caagtatttg ttgtgcctta ttcttgttgt ttttgtatga caaaagtgtt taaatttcag  21240
tactttttgt gtgaggttgt tggtgtttag tctgaggttg caggtgttta ctatggggtt  21300
gctggtgtgt ttaagaattg caggtgttta gtctcaggct gctgttgata tagggttgtt  21360
agggttgaaa taaggccact ggtgtctttg aaataaggtt gttagttttt aagtgaggtt  21420
gctagtgtgt ttgaaaaagg gctgctgaga tggggttagt attcaagtga ggttgctggg  21480
gtgtttcaaa cgggtttgct agtgtgttta taaggctact ggtgttgatg aaatggtttg  21540
ctaatatgtt tgtaagcctg taaattctag cttttataag ccaagaaaat agtcgttttt  21600
ggttctaacg gctattttct tggccatttc ttgtcacttt tgtttttgtt gtttctttct  21660
tttcataggg taaaattatc ttttacgttt ctaggggcag aatcatcttt taacataatt  21720
tccgttgagc actaacgttt tgttaacgga ttggtagtaa aatgataacc gcgaaaaatt  21780
ttagtagtaa aatacacttt ttagtaaatc ttgatattga catgatatgt tagtaaaagt  21840
ttgatagtaa attaataata tcccttcaaa aaatatcaaa tgagcatata gggtagaaaa  21900
ttgtccaaag catatacaat gtaaacagac acacttaaaa gtaaatctca cgtcacgtca  21960
atgcgattga aagtaaataa cacatcagca tatatatttc acatcacagt taacatccgc  22020
gcagggcaac gaattttatt tttctgcttg attgaaacta aataatccgc cgctcgattg  22080
aaaccgcatc tcaaagagta ccttcaaagg gatcaaacca aaagattgtt agatgacaaa  22140
gaggatacca ttattaggaa tattgaagca ttgatgcacc atttttattc atttattttt  22200
ttttcccgac ttccacttgt ccaaaattat agtaatcaat tttcgtaact tttttttctca  22260
taaaattata tacagcaaat gaatgcaaga aaaagagtct tgtacatgaa ggaaattaac  22320
aagcagagtg taagaaaaag cacgcaccag aaattaatca aatgcgatct ctgctcaaac  22380
atctctgaaa cagcgaagaa aagcatttcg tgtggcttca tcctcccatt gaagctgttc  22440
ccgccaattt ctctctccag aaataactat tttacgctcc ttcgcgctgt tggaatctag  22500
tggaagcttt ttaagctttt tgcaatgcaa gaaactcatt gctttcagat gtgggaaggg  22560
cagggacttc cagtaaatgc tcttcaaatt tctagcacca gctacttcaa gattttggag  22620
tttttcaaat gggtttagat ttgccatcac ctctggaact tctgcaaatt ttccctcact  22680
tgcgatttct tccatagcat ggcaaattcc tactttaata gacttgaggt tcggagcgaa  22740
aacaaggaat gtcaagtcct tcaattgaat gcaattgcat atttcaacca tattgagact  22800
gcggaaagca aattgttgaa cttcctctgc ataatccatc tttaattcct ccaatattac  22860
actatttgca atctgcaatc tgttaagttg cttcagatcg gccaaagctg aaacttcgag  22920
cgatgtcgaa tctttgaagt gttggagcaa cagagcttga gtacaacttc gtaacttatg  22980
cgagttcaaa aagctttgga gaccataaga actcctcaag gtgagggtaa tcacctctaa  23040
```

-continued

```
atgtttcaaa ccaagcagtt cctctactat gagttcaccc ccaccaaata aaatgctgtt  23100
ttctgatgct tcatcaaatg cattatgact agcaccaaac attctcaaca cacgtaacct  23160
tgaaagatta gatattagtt gacgtggaat tgtaattaaa ttccttgtgt attccaaatc  23220
caaacactta agatttacca atgcctttag ctctcctggc aactcttcta tgtcggattc  23280
tgagaggtca agatgttgta gtgaaaccaa ctccgaaatc cccactggta acttggttag  23340
ttcgcagtgt gacaggttta gaactttgag agagggcata aactggaaga agtaattgtg  23400
gatcttccgt aagttatttt cgttaaggag caaagtaagg agatgaggac atgttggaat  23460
ctctgaaaga ttcctaattt gattctgcat caatgacaac ctccttgcct tttcccatcc  23520
tctgacatcg ggtgcttcaa ctaatccaac gccagcataa acaaaaaaat tctccttctc  23580
cctttcaatg tcgcatgcta tccataatgc catatctcga atcacgtcat gcatttttac  23640
ttcaccgtct cctccctctt ccagtaaaca ggcatgaaga agaatgccca gaatatggta  23700
tccttctttt tgttctccag tcctgtccct ttctgtcaaa agtctctcgc caatccaaca  23760
gtctatcaac ttctctttag aaatgcaata atcttctgga tataaactac aatataagtg  23820
acacgatcta attgtgtcac tcggcaaact atcgtaactg aattttaaaa gaggataaac  23880
ctcatttccc aaacctggga actgagaact tgatgttctt agcacctcaa ttgcgtaact  23940
ccattcttca ggtgtcttct tgcaagccat ggctcggcct atggtaataa gtgctagagg  24000
caaaccacca cactctctag ctgctgtttg ggctagttga agaatatcgg gatgactgtt  24060
catggtttct tctccaacgt tctgccgaaa caattcccaa gcatcgatat ttgacaggca  24120
cgccacttta aacctcgtgt gagctcccat caaaccacaa acttcttcgg aacgggttgt  24180
gaataccact ttggatgcat tattttgcgg gccaggaaga gggacgccca cttttgttaa  24240
atcaacccgc tgccataaat catctagcaa cagcaaaaac ttcttctgct tcaaaatcct  24300
gaagatgtct tgagctttct gttcaattct tttatttttc catgtatcgt ttaacaaacc  24360
aatctgctcc ccgatagttt cttgaatgtt ttcaagtcgc agatcttttg acgctacgac  24420
ccatatcaca taattaaaat tagttggact ctgaataaat ttattgtgga tatgagtcaa  24480
tagtgtggtt ttaccgacac cgcccatgcc gtataggcca acaattctgg ctgattcttc  24540
ttcaagacaa ttgcagactt gttcaaattg tgattgcaag cctactacgg ttggctcggt  24600
gggtctctca tctaccgcag gttgtggtac ttcctcagct accgcttcaa aagcttcttc  24660
agccattaaa gtcttgacat ctcccagctt tctagccact tgtttgccaa actcgtagct  24720
tgacttgcag ttcttggaac agtagcctcc aagacatagt ttcttaattt cttgagagcc  24780
acatgttatc aatttgtcac cgtcggattt agcagcttcg accctggaaa gccagccttg  24840
aactttgttc agccttttca tcattgggtg cctttcagcg gtgttgaccc tcctcatcac  24900
atcttccttt gcgtcgatta gttttcccaa ttcagtctcc aagtctgcaa gattttgttt  24960
gaggtttttt atatatgctg cttttccaag aaagcaatcc aggcaacggt taaagagagc  25020
gccgtcgcat gtgatttgga aaatgttacc catactttgg atgagaattc aaccaggaca  25080
aaccaaggaa attttaacga tggagttcga tgaatagaag ccgctgcgaa gagaacatca  25140
actttgaatt atgatctctt ttgtttgtgc ttgaaaagat tacccgtgtt cggtttaaac  25200
aactaaactt taatttcctt taacaaaaga gactatcccg cttgtaatta aataattaaa  25260
cgtctctttt gccagttgta attaagaaat taaactttaa tttgttgttt acagcgttac  25320
attgataaaa tatttgatga taaaattttg ataaagttat gaaagaaaca aaatattaaa  25380
gttgttacgc acaattttct tttagttaaa atatttctat ttttttata caatttggag  25440
```

-continued

```
gaagctatgt gctccgggtg cacggtaccc cttgtttttg gtaaattact ccctcttatt  25500
tgctgaaaag taaaaaaatt agaagttttg aaattttaac atataagtct aatatatttc  25560
tactatttac acttagagta tatttcaatt atttatattt gaatactaaa ccattgttga  25620
ttattatgaa attttttaac attgtcattt ggtcatatta ttattgataa attaaaattt  25680
aattatatat taaaattttt tattatagat taaattgata ttatattatt ttcaaaaaat  25740
aaaaaaattt atgtattcaa atttttttca agttattgca cttatactgt cattaatttt  25800
aatagtaaat taaatcaatt gatcaaaata taaaatttaa aaataatcta aaattatgtg  25860
tcaaaccttt gactattttg ctttttttgct tttttgaaaa actatagaga tgttaatgtt  25920
aaaatcaaag agaatacatc tatgccgttg aagtaagttc tatcttatat ctaacgggca  25980
actcatatat gaacaaaata cgggtaccat acaccaagtg cacggtagtt ggacctatat  26040
aatttacttt taattaaaat atttttatat ttttattttt tgaaaatttt ataaccgaag  26100
ttgttgtcaa aatagctttt tcaacaaaat agctttttttg ttaaacattt gtagattgta  26160
attaattata tcaactttca aatgccacta gcatttgcga tacaaacaat caacgcgtga  26220
taatactttt ttgaccaaag gttcaagggc ttatcataac aatggagaag tctatgttac  26280
agattctgta acatacatcc cccactccat gcactccacg tgtcccggca tgcggaaaca  26340
aagcaagcaa atgacaccct tgggggggctg gctaacctgg tctgtatgtt acagaatctg  26400
taccgtagcc agctcccata acatttggaa acgtccaaaa gacattcaca ctgaaatttc  26460
ttttataaaa ataaataaat aaagaaacat ttgtttatgg gaactttcca ttagatgaag  26520
gaagggatgg cgacattccc gcgagctccg ggacccgtgg gctcctgatg aatttcagtt  26580
tagtatgagt tctcaaaaac cttaaaaata gaataggagc tatttcgaga ataggcccaa  26640
gacctaatct aaattaagtt ttggatttag agattctttc gggcacccga atccgaacta  26700
ttaatatttt taattaaata aaaattatga aatagaacac aaaaagctct cttcctctct  26760
ctctcctcac tggcgtagta cttcttttgc ttaattaaat ataatatgtg tctatatgta  26820
tacgtatacg tatttgtgtg tgtgaaatta ttaatatttg ttatttgagc actacgcagc  26880
tcctctgttg tatctgaaaa aaatgaatac ataacaatca cgctaatgta ctacataatt  26940
gggcaataca attcaagaga tgagctttta acacccctct aaaatcttat aacacccatt  27000
ttgaatttat tttttaagat acctcagatt aatttataaa atacaaatcc atatattaaa  27060
gttaatcatc ttactcataa aatttcatcc taataacaag catttctttt aatgttttat  27120
ttacaaaatg catataaatc ctaaaatcta aaattatttt ttcttattat atagtttcta  27180
tctctataac tctaaattct tacaattttc taaaaaaaat taattgggtg gaaattgttt  27240
gctgtgtaaa ttggcaaact ttttgtttgg ttcataagaa tatccacgaa aaatgaaagt  27300
actagcaaaa ttatcatgtt ttaaaagctc ttaattgagt atatccagaa aattattatg  27360
ctttttaaga taaaatatat aaaaaaaatt ggggattgga cccgttttaa ccctggcctt  27420
attcggggat tattggggat gtccccaaac tataccgaaa atgaatttct gggtatgggg  27480
gtgggtttgg ggattgcttc taattccaaa tggggatggg ggtatggtcc ccatcccaaa  27540
cttatcccat tggcatccct agatcaagtg atttgcctaa gttatattta ctttaactta  27600
catcacatta aaaatatgcc tcaattatat gtagtgtaac cagcatgggg gatcgtgtgg  27660
ggctagaatc ttgttttggc ttatctttag tgggttataa gttacactaa tggtgcgttt  27720
actaaactgg aatcaaaatg gggtggaatc ggaatgggta ggaatggaaa tgggttggaa  27780
```

-continued

```
tcagaatagg gaatggaaat aagaataaat tgtttatttg aattataaga atcataattg  27840
gaatgagccg gattgccata tttactttgt tttaaaatag gaataaaaat gaattaaatt  27900
gtatcaaatt actaaaaggt acttaatgaa ctattgtcat aattattctt gtgtatttta  27960
attattgtga ttatttgttc aaaaatatta ttattagtaa ttattgttaa taatatatta  28020
atatattaat taattgtaaa aattttttat cgttaataat aataatagta attaacatta  28080
atatattaat taattataat atactaatta atcaaaataa tttttaactg aggacaaatg  28140
gacatttttt ttaattttat ggtggggggg taaaatagtc aattttagga atgggaggtt  28200
ggttcccacc accagccttg agaatcaatc tcccattccc cattcctaaa ttcgagtgag  28260
tcctacgatt ccaattctaa ttcctacctt tattttgtga agtaaatatt gttaataatt  28320
tcgattcccc atttcaaaaa gtaaacatac tataaatgga acttacagtg accacccctg  28380
ttcaagattc tatgaaagat tggattgtag aaataaacat tggtttctag gagttttcaa  28440
gtgcttttat ttcaagaatt acgaaaaata aataggtgca agaagtattg gtgtttgaca  28500
atttattgtt acattttaaa aaaaaatctt atatttaatt atctttttgt tatcacagct  28560
cttgaaatga ttacatcata tggatgtcac agggataaaa tcataaaaat aacttcgtac  28620
ttaaatttgt ccaaaggcac taatttttct atccattata aaacttcctt tacacattaa  28680
aaaataaaat aaagagaaaa aaattgttgt aacttatttc ttattcatta aatggtaaat  28740
tgatatttaa aacgttttta aggcatgcaa aggtcccatt aagtctcaaa gtctgtttta  28800
tggtgagact agaagccaag catgccagga tctattcgac caagcgaaga cgagtagacc  28860
ctcacatgtt ataaaaagtt tctaaggcat gcaaagacct tattaagtct taaagcctgt  28920
tttatggcga gaccggaagc caagcatgct aggatctgtt cgaccaaacg aaggcgagca  28980
aacccttaca tgttataaaa agtttctaag gcatgcaaag gccccattaa gtctcaaaac  29040
ctgttttatg gcgagaccgg aaattaaggt tgccaggatc aactcgacca agcgaaggcg  29100
aacagaccct caaaggttat aaaaagtttc taacgcatgt aaaggcccca ttaagtctca  29160
aagcctattt tatggcgaga ctgaaagcca agcacgccag gatctgttcg accaagtgaa  29220
ggctgttgag tgttagaaaa tgtatattta taaaggagaa aaccgtcatt ttacatttca  29280
agtattacta acaaccctta ctttttatgt atttaagttt cttgtaattt aattatgtgt  29340
tttattttaa ttaagtattt tatgtatttt agcggcatta tagtcatttc gcaataaact  29400
agagatcaaa cggtaaaaca gacatcactt ttgaactcag gacggtcgaa aaccttagca  29460
ggagcataaa aggaaaaaaa ggcactgttc acatgtacag tactattcac atgtacggat  29520
actgtctacg ttactgttca cggaactgtt tatatagacg gatcgatgac gtggcattga  29580
ccaatgacgt ggtattgact gatgaggtgt catgatcctg ttggtctgaa attcttatgt  29640
actgtttatg gtgacgtggc agcatattag tggaccaaga aatgtgcgta cggtacatgc  29700
aacacatgag attattttca accaaaccgc gtactgttca aacctcgtta ttgttcaaac  29760
cgcgtggtca aaccgtgtta ctgttcacac gtactgttga cgcgtactgt tgactgatga  29820
cgtggcgcaa tcctgagcgt ccaaactgtt tttaatccga tgaccatgat ttactccatg  29880
tatctataaa aggggacctc tccccccta a tttgatacct ctgaatccgt ttttggaatc  29940
cattttctat aattccttct ccatcttgta ttttctacgt attttaataa attcccattt  30000
ttcccctagt tcaattatga gtggctaatt ttctttcaag atttgattga aggtgaagtc  30060
tcaacatgtg tcatgggctt tatttggtaa atttattttc ttttcccctc tagtttttgt  30120
gaatgttttg acttctcgtc gacaaataat aatagtcttg tctagtaccg ccctggtttc  30180
```

-continued

```
accggctccc tagtacaagg ttattattat ttggcacgat aagcccttag caccatattg  30240
attagagcgt ggttcatgaa gagtggattc ccccttatg atttaattga aattaataag  30300
gattatttag cccatgatgc atgttgatac ggatccagat acccaagtac gtcatttcaa  30360
tagaattctg ttcaatttat tctcgccatt tcaattccaa ttttagaatt tattctcgct  30420
attttaattt aagttttagt atattccaaa taatttccac cacaaatcca atcacccatt  30480
tacaaaatta attctacaca caattaaaat ccacctcctc gtgggatcga cactcgtcac  30540
cattagtcta tactacaata gattcgtgcg cttgcgagta cattaaaatt tgcacaacaa  30600
aggtgagcaa atcatcaaat gtcacaaaaa gtttctatgc ggaaagattg cataagtctc  30660
caggcctgct tgatgacagg ataggaagtc gagcttttcg gtatctgctc gaccacaata  30720
taagcgaaca aaaaataaaa taacaatctg ccgagagcgg gaagcaaaga aaacaaataa  30780
gagcaatctt attaattcgc caacaattgt aaaaagctgc tagtcttaac acacaatatt  30840
tcaaaaaaga aacctacaac acaaggtaca attgctgatg cgagattcag tttttactc  30900
gtccacgacc aggatctctc ctcaactaac tcgtccagcg accatgatct ctcctcataa  30960
gacttcctct ccacggactt ctgcgcacac agaaaccggt cagagcaatc cggatgtttt  31020
cccggcgtaa acccttctac gctcaagtca gaaatgtagg tttacttttc tgggaaacac  31080
gaccactaat cttatggctc ttttatgatc tcccaataga acactctttt cctacgctct  31140
aatctcaaaa agtctaaccc ctttactgta acacctgtgg atgttaaagg aaaatgaggc  31200
ggttaaggag tttataagca aaggaataag ctggaaacag aggaaactta tgcacgtgta  31260
acacagagag agagagggag aagctgtcaa ctgacccaat ttcggacccg aaaacccgac  31320
ccaacccgcg acctttaccc ggtcatatct cccatttccg accactgttt tggccgagct  31380
tggtaccgat ctgaagctta gaagccgaca gtcgttcccc tgccatcctc gccgccgaaa  31440
acctatcgga acgccggcaa tcaaagcttg aaaccctcga ctgcttcact ttactccgcc  31500
gagattttcg ccggttttgg gtgacaccac cggttggatt ttgttcctca tgactccctc  31560
ttccatttcc gaccatccat aggcaccgag agtcgttatt ttgctgccgg tcaaattttg  31620
gaactcacgg ctgtcgagct agattccggc gtcgttgccg cgcgttggag ctcaccgccg  31680
gtaccattga actcagcgtg attggcactt taagatccac gagcgagaac cagaccgcgg  31740
acgtggacga taaccgaccg tgaacacctt cactgtgagt ggaatataca aaacttattt  31800
tcatagttag tgatgatagt aaagcatgtt tgcggaataa gtattttaaa tgttctgatt  31860
taatgattaa tgatttctag aaaatgattt aatgtgattt cctcgaaatg gattttactc  31920
acgtattggt attttattaa catgtttggt taatgatttt gcgtattgat tttgaataag  31980
catgatagta ttttaaagat aagaaaagtg gattcaaatg tggtatgaat taaagtatga  32040
tttaaagcat gatagtgatt gtttttgaaa tcattagaca ataccatttc cctccagata  32100
cagtattata tatgagatga gatgagataa gatagaggcc tttggggccc ctctgaacac  32160
acatagaggc tttgggccgt gtgtttgggc gcttttgcct tttgggggca tatgcatgcg  32220
gtatgatgat tacagtgata cagataagag atacagacat acattgagat accgatgata  32280
cagatatgag atacatacat acattgagat accgatgaca cagatattga gatacaaatg  32340
atacagatga gatacaggcc tttggggccc gtctgagtac acacagaggc tttgggtcgt  32400
gtgcttggac gcttttgtcc tttgggggct aaattatgca tgcagaaata tgatgagata  32460
tgagatgata tttccctatc tatccgtgta gctccggggc gtgacgttac ccagatagta  32520
```

-continued

```
cgtcattgcc tgtccgttga ggtccggata tgacgagatt atttccctgg gtacttgttt  32580
ggtgatgatt tcagatttgt gaattctata tgatatggtg atatgatttc tatggttggt  32640
aatctgattt aaatgattaa tgatttatca ctggtttctc gcttatggtt taatgaaatc  32700
ttgtttggaa atgatatgat tatttgtttt aaagtaagaa taaattttca aatctactat  32760
ccactcactg atctcactga gttttaaact caccccgttt ttattatatt ttcccccccct  32820
caccaggagg ttgcaggtac accagaccga cccaacgact gtatatattt tgagtcttgg  32880
ccacgtgatg gtgctagaat atgtttttgt tgggacatct tggtcatatt gttcttttgg  32940
ggttgtataa tataaaactc agcattttgg ttgaggatgt tgagcactgg agtttgttgt  33000
atattggatt tgtttttgga gtgttatatt catattgtaa attgggagtg ttatatatat  33060
ataaaggaga ctctgccgaa ttttcggcag actcttaacg aatagaatta ttttcaagtc  33120
cgttttgata tgactagata gactcgccta gggggctttc ggggcgagtc gtttcagttg  33180
gtatcagagc atggttttag attctgtaga ctttactgtc ttaatcagaa taagttttat  33240
ctttattaaa gttagaattt atcttttgta ggcaccatca tgcttcgtcg tagcagtaga  33300
cgtggccgta ctaggccaat agctgggttg acttctggta gtgtacctgc gggggaacgt  33360
gaacccccga atgaggggat agttgaatcc tccacgcatg gaattgcaca acatgaaata  33420
taagtgtgca acccaagagg ggggtgaatt ggaattttaa aatttatcct agcaaatcca  33480
cacaacaagc aatctaatgt cttaataaga attgaaagca ataagtttaa caaaagcaca  33540
ataattaaag agtaagggag aagagaaaca aacacacgaa tttttacgtg gttcggctat  33600
ccccacctac gtccacgcct tcaagcgatc caagcttgag gatttcacta tccaagcctt  33660
tccaaggctt caaccgatta caattgactt caaggtgtca atgaaccttt acaataaaga  33720
gattatctcc caatctcttc actcaagtgt ctcacacact caaactctta caattgagat  33780
gaataaatga aggttacaat gaaactcact caatgagtag atattcaaaa atgaagaaca  33840
agaaatgatt caatgtttat agtttacaag tttgaaggct caagatatct cgtgtgcttt  33900
ttgtttttgc ttgtttgagc ttgttggagc ttattggaga acttcaaaat gagttggatt  33960
tgagttctta tagtttgagc tcgaaaacta gcctttactc acattctggg caatccggtt  34020
tactgtttat ggaatccggt aagccagatt tttcttaccg ttaaggcaaa attttgaatt  34080
ttgccttaac cggcttgccg gatttggaat ccggtaagcc gttttcgttt tgggtgcatt  34140
ctgcccagtt tttggttttt tggattttga atccggtaag ccggatgcta cagtaacctg  34200
ctacagtgca ctattttcta aaattatagt gtgaccccaa aactttataa aactgtacta  34260
cgacccaaaa tgctatgaaa ctttacaaat aagaccaatt tcagaatttc taaataatac  34320
tttgttaatc ccaaaacttt ctgaaattat ggtatagccc aaaacggtat gacactcttc  34380
aaataagtcc tttaccaaaa tttcaagcaa tacttgttta ttttaaagtt ttcaaaattc  34440
tttcaattaa accataaact ttgaaaaaca accaatttca taaaatcatt tttattaaat  34500
atgaaacatt tataatgtga aaataatgat ttatttaaaa agaataaaaa caatcaattt  34560
cataaaatca tttttccatt aaatatgaaa catttataat gtaaaagtaa tgatttattt  34620
aaaatatatt tttcaataat ttgagcttaa aagattaatc attcttaatc ttatttgtta  34680
ttatcaaaat caaaattatg aaaacatata tgttaacaat cccccccttt ttgatgatga  34740
caaacatttt atgtatttaa acaatcattt ttcttaaaat catttttcca ttaaatataa  34800
aacatttata atgtgaaaat aatgatttat ttaaaatata taaaaaataa tttgagctta  34860
aaagattaat cattcttaat cttgtttgtt atcatcaaaa tcaatattat gaaaacatat  34920
```

-continued

```
atgttaacaa tctccccctt tttgatgatg acaaacattt catgtattta aaaaatgatt  34980
ccacaaattg ctcctcctaa atataatatt ctcttacaat ttgccaatta actaaattaa  35040
tgatttaaat acatggattt ttctccccct catcatcaaa aagaaaaact taattggcaa  35100
agacaaaagt ggcaaatttt taaaaatttg aaaacatgta ttcttctccc ccttcatcat  35160
aaaaaaaaaa aaagaaaacg aaaaggaaaa gaataagagt aggaaatttg ttacccatgt  35220
tgttcgaata gaaatttcga caaaatctcc ccctaacaac aatcaccacc tcaaatataa  35280
gattagcaat atcacatcca aattattata aatcattata caagccaact ccatacacaa  35340
atcatcacac aaaaatatca tgaaccatta ttccatcaat tactaagtca acaactcata  35400
acataaattt atcatataaa atacccatgt aatcaaatca tcatatctca aaattatcat  35460
aatcataatc ataatcaaat atcaattatc aaaacaatta cttaaaatgc atatgattca  35520
aaatcatatt gtatgctccc cctaaatata tggccaattt aaaaatttaa ccgaaaagat  35580
tttatccaaa aacatatcat atttatctcc cccttcatcg taaaaaggaa agatagatgc  35640
aatcaaaaca agatcataaa aaataattcg ataaagatat tacccatttt gtacgaacaa  35700
aaatttcggt aaagtctcct cgtaaaaaaa ataaattctc aaatgcacaa catggttaaa  35760
aagatataaa cttcaacaat tataacaacc aacaactcca tcaattcatc aagcaatgca  35820
catataatca ttaatcatca aaatcaatat gaattcccca acacttgtaa caattaaatc  35880
caagaattcc ataatcatat atcaaccatt aaaagaatgc tcaaaatgca tgttatttcc  35940
cccaatttac atcattaaaa tgatttatta ttttgtctcc ccctttggac aataaaaatg  36000
ttcaaaaagc atattatcca aaatagaaca agtaataagc taagcaaggg aatgcaaaag  36060
tcataagagt ataatgacaa tatatagatg atcaaaatca acatatgctt aagaatctca  36120
aagtagatgc atttctccct tacatctcat atctccctct tgatcatcaa aaagtcaaga  36180
taagcacatt agttccatat tatccaaata taaaacatcc aaatagcaaa caataatcat  36240
catcaatcac aatgaaagca acaatgcata tgaaaatgta agtgcataat ataatagaaa  36300
actatggtaa aatccataag gagaacacac tacggaagtg gtaatttgaa atactcaaaa  36360
tgcacaaatt cgaatttttt taagatattg agtaaaaagt gtaagtttga atcaattaaa  36420
acgattctag agatgatttt agacacaaga atggatgaga ataatttata tgaatcaatt  36480
tggattgaaa acgaatgaga atgatggatt ttggaatgaa atcaagtgtg gagtaatcgg  36540
cttttagtga gagagagaga gaaccggaat gccgaaagag agggagaaga tgaatagatg  36600
aaatagctcc cgaatccggc ttgccggatt tcctaaccgg ctggccagtt attgggcaga  36660
aacgtgaagc ccataaacgg atagccggat gcctttaacc ggaaatccgg ttgtgtttca  36720
acaaatccaa tcacgcgaat tcggcttgcc ggttttcgag aaccgttagg ccagttgcga  36780
ggcaatgagc attcaaaatg catccggttt tccggattag aagaaccggt tatccgaatg  36840
ttgtccaaag agcaaccaaa gcaaatccgg ttttccgaat tgaaaatccg gttatccgaa  36900
atttgacccg agggaaatca ataataagaa taaataaaaa atttccggat gagtggaaat  36960
ggaatatcgg ctagctcttt tacttgtaca acgcacacca tttcattttt ggtctttaaa  37020
aaaaaaactg attaattcta aatcattttg agatttaaaa cttttcaata agccatttaa  37080
tgcatgaaat ataaatgcat acaagaccaa acatatgaaa tcgtattaaa caatgatgtc  37140
aattttataa atgaatgatg atataacaca attaacagca caagaattca cacatataat  37200
tcattcatca tgtgtatatt ttacacaatc atgaaacata taagcattca aaacttaata  37260
```

-continued

```
aaatacagaa aggtcaaatt cggaataaac tctgtattga ttgagccaga agtaatgtgc  37320
aagctatata ccgttggaaa gataattacg ttagctttcc aataaatttt acagaacttg  37380
atttggagtt ctttagaata agttatgacc aattcattac aacttgtgca gactagagat  37440
tttcacaaaa attaaacata taagcattca aaagtgaata aatcaaacac accacttatc  37500
tatcatgctt aaacacttta taaacattaa catcaaacaa atccatcatg atgagttgat  37560
aagctatcat catatatata taaccttgta tcatgataaa acactcaatg ttaaacataa  37620
tgataattca atcatgtaaa catacaagta tattatcaca aattcaagct actatccatt  37680
tttcatgatt cactcaacat gataccaaat gaattattaa atacttacta agcttagaag  37740
accatcactc ataatcaata aggcaataat tgttatcaaa acaattaaac catcttgcct  37800
cattattttt gcctagacca tgatcatcct cacaagcttc atcaaggaac tctccaccat  37860
tccttgtttg tggtacctac aaaaaaaata ttcaagttgt actcttggta cccaaatgct  37920
cttgggtcct tgagtgttag caatggttcc ttttggaatc caaacacatt taactccata  37980
atacacattt cttttaattg gacatctatt cttcatataa ccattttgat tgcaataatg  38040
acatacaatt tgatcatttg tggaggtagc cttaacaaaa taattcttat aatatttttg  38100
tttcaaattt ggtttgtaac caatgccact tttgtcaaat acgcattttt gtgaatttag  38160
caaattgtcc aacatctttt gcccatttgt aaattttaac acaatttgat ttagctcacc  38220
actcttcttt ctaagcactt cattttcttt tattaattca tcaccatatg atttctcatg  38280
ctcatatgaa gtactttgtt tacatgtgaa tgatgcaatt ctatcatgta acatttcatt  38340
atctaattct aatttttttta tcttttcatt taatgaaaca ttggattttt gcaaggcatc  38400
tttttcattt ttcaagtcat ttacatgtga ttctagatgc ttgtgtgaag tgctagattt  38460
atcatttgat aatgcaactc tatcatgcaa tgttttattt tctaattcta ggcatgtgat  38520
ctttgcacta aatgattcat tttcattctt aagttccatc atcttctttt taagacatat  38580
attcttttta ccaatcttca ttaactcatc atgcaaatcc ttaaaagcat catgtaattc  38640
atcatatgta ggaagatcat ttacctcttc aagttcatca tccgagtcat ctccaattgc  38700
cataagtgcc aaattcgaca cttcatgaaa ttcctcctcc tttgtagtct cctcatacac  38760
aattttgagt tttctccaaa tttcataagc attagaacaa tttgaaactc tatgaaattc  38820
ctttttatct aaggcacaaa ataaagcatt catagctttg gaatttaaag acatattttt  38880
cttatctaac tcacttaaag cattctttct aggaatgagt aaatcatcac aaacaacttc  38940
ccaaatttca taatctaaag cttgtaaata aattctcatc ttagttttcc aataaggata  39000
atcatttcca tctaaaaatg gaggtcttgt gatagattgt ccttccatga tagatgagct  39060
aatttgggtt actatggatt tttaactcta gatgattaag tctgcacaag agcacctcgc  39120
tctgatacta attgaaatat aagtgtgcaa cccaagaggg gggggggtga attggaattt  39180
taaaatttat cctagcaaat ccacacaaca agcaatctaa tgtcttaata agaattgaaa  39240
acaataagtt taacaaaagc acaataatta aagagtaagg gagaagagaa acaaacacac  39300
gaatttttac gtggttcggc tatccccgcc tacgtccacg cctccaagcg atccaagctt  39360
gaggattcca ctatccaagc ctttccaagg cttcaaccga ttacaattga cttcaaggtg  39420
tcaatgaacc tttacaataa agagattatc tcccaatctc ttcactcaag tgtctcacac  39480
actcaaactc ttacaattga gatgaataaa tgaaggttac aatgaaactc actcaatgag  39540
tagatattca aaaatgaaga acaagaaatg attcaatgtt tatagtttac aagtttgaag  39600
gctcaagata tctcgtgtgc tttttgtttt tgcttgtttg agcttgttgg agcttattag  39660
```

-continued

```
agaacttcaa aatgagttgg atttgagttc ttatagtttg agctcgaaaa ctagccgtta  39720
ctcacattct gggcaatctg gtttgctgtt tatggaatcc ggtaagccag atttttctta  39780
ccgttaaggc aaaattttat ccggcttgcc ggatttggaa tccggtaagc cgttttcgtt  39840
ttgggtgcat tctgcccagt ttttggtttt ttggattttg aatccggtaa gccggatgct  39900
acagtaacct gctacagtgc actattttct aagattatag tgcgacctca aaactttata  39960
aaactgtact acgacccaaa atgctatgaa actttacaaa taagtccaat ttcagaattt  40020
ctaaataata ctttgttaat cccaaaactt tctgaaatta tggtattacc caaaacggta  40080
tgacactctt caaataagtc ctttaccaaa atttcaagca atacttgttt atttcaaagt  40140
tttcaaaatt ctttcaatta aaccataaac tttgaaaaac aaccaatttt ataaaatcat  40200
ttttcattaa aaatgaaaca tttataatgt gaaaataatg atttatttaa aaagaataaa  40260
aacaatcaat ttcataaaat catttttcca ttaaatatga aacatttata atgtaaaagt  40320
aatgatttat ttaaaatata tttttcaata atttgagctt aaaagattaa tcattcttaa  40380
tcttgtttgt tattatcaaa atcaaaatta tgaaaacata tatgttaaca atctccccat  40440
ttttgatgat gacaaacatt ttatgtattt aaacaatcat ttttccatta aatataaaac  40500
atttataatg tgaaaataat gatttattta aaatatataa aaaataattt gagcttaaaa  40560
gattaatcat tcttaatctt gtttgttatc atcaaaatca atattatgaa aacatatatg  40620
ttaacacaac agacaccggg ggattccccg aatattgagc agtcatttga tcggctagct  40680
caaatcatga ctatagttgt gcaaaatcag acttaagcgc atgtcggtaa tgcaaatact  40740
attgagcgag tgaggagttt aggggtggga aggtttaatg gttccggaga accacctggg  40800
gctgagttat ggtttgttaa gttagagcgt atttttgacg tgatgaagtg ttcagaggat  40860
gatagattat ccttcgccac tttcttgctt gaggatagag cttaccattg gtggcagaca  40920
gtcgagagat gatatcaagg tcatgctgcg attacttggg ccattttctg caaggaattc  40980
tacgatcatt attttcctgc tgtatatcag gatattaaac gaaatgaatt ctttcggttg  41040
gtttagggat ctctgacagt tgaggaatat gagaagaaat ttttagacct ctctagattt  41100
gctacatctg tagtcggtga tgagagagag agatgcagac ggttcgagga tggtctccga  41160
tttaagattc gtaccgccgt gactgcatca cgatatactg agtttggaga ggtagttgag  41220
gcaaccagga gagtagagca cagtattgca gaaggacgta gatttcatgc actaaagcaa  41280
aagcgtagcc agagttggtc agagggtggc tctagtagta ggccgcccaa gagaggggt  41340
attcctacga gttattctga tagtatgcaa aggagtcaga gtacaggctt caggggggac  41400
tcgagacaag ctgttagtca cagctctatg caaccatcag tggggagtaa tactaggaat  41460
cagggatagt acgaccgtag tggtggggga tatcgtgatg atcgttctag gagttttcag  41520
cagatgtctt gcccttcata tggcaggaat catcagggcc catgtcgtgt tggagacaga  41580
gtttgttatt tatgtggtca gcctggacac atcaggagat tctgccctac tttatctcag  41640
ggtgatagct ctacaggagg gacagcctca cggtatcggc cttactctgg ccagactcag  41700
ggtcagagag gagtgcagac atgaggttct acatctacct ttaggggtca gacgactgct  41760
ccaagtcaga gaggtcagcc tggttgacct catactcagg ctcgagtttt tgctttgatg  41820
cagcaggagg cacgtgctgc accagaagtt attatgggca tattatctat ccttggccgc  41880
gaggctcata ttcttattga ttctggatcc acacactctt ttgtttctcg tacttttgct  41940
atacacttag ggcaagagcc cgaattgcta gattgcgaat tagttgttcg tacacctact  42000
```

-continued

```
ggagagtcat tacttgctca gagtgtgtat cgagattgta tgattggaat gggtgaacat  42060
gaatttgagg cgaatttgat ttccttagag atttatgact ttgatgctat tttgggcatt  42120
gattggcttg aatctcatta tgctacggta gattgtttca aaaaagacgt tgtgtttaaa  42180
aaactaggga aagctgaggt gatattttgt ggggagcgca aagttctacc ctcatgtgtt  42240
atatctgcta ttagtgcaag acggttgcta agaaaaggct gctcagctta tttagctcat  42300
gtgatagata cagaagctcg ataattaaga ttggaggata ttacagcagt taaagaattt  42360
ccagatgtat ttccaaatga actacctggg atgccaccta acagagaagt tgagttttct  42420
attgacttag tccctggaac atctccgata tgtatggcac cgtacagaat gactccagta  42480
gaattgaagg aactgaaggt tcaattgcaa gagtttgtgg aaaaagggtt tattagacct  42540
agtgtgttcc cgtggggagc tccagtcttg tttgttaaga aaaaggatgg gacttttaga  42600
ctctgcatcg actacaggca ataagtatcc acttccacgt attgatgact tgtttgatca  42660
actccaagag gcaaaagtat ttctaagat tgatttgcgc tcgggttacc atcagcttag  42720
aattaaagat gttgacgttc ctacaacagc attcagaacc cgttataggc actatgagtt  42780
cttagtgatg ccatttgggt tgacaaatgc cccagctgct tttatggacc tgatgaatag  42840
ggtatttcgc ctgtacctgg atcggtttgt gattgtattc attgatgata ttttggtgta  42900
ttcctgaagc gaggaagagc atgcagagca tttgtgaact gttttgcata ctttgagaca  42960
gaagcagttg tatgccaagt tcagcaaatg cgagttccgg ttggatagag tagtatttct  43020
gggctatgtg atatcagttg aaggcattta tgttgatcct caaaagattg aagcaattgt  43080
gaaatgggaa cgacctacaa atgtcacaga ggttcggagt tttcttgggt tagctggtta  43140
ttattgtaga tttgtggaag gattctctaa gattgctact cctctgacac agttaaccag  43200
aaagaatgct aagttccagt gggatgatga ctgtgagaaa agttttcaaa aacttaaaac  43260
atgtttgacc tcagcaccag ttcttacact tccatatggt aataaaggat ttgtggtata  43320
cagtgatgcc tctaggcagg gtttgggttg tgtattgatg cagcatggga aagtggtggc  43380
ttatgcctct agacaactta agaagcatga acaaaactat ccaacacatg atttagaact  43440
agcagtagta gtgtttgcac tcaagatatg gcggcattac ttatatggag caacatgtca  43500
gatttttacc gatcataaga gcttgaagta tttgtttact cagaaggagt tgaatttgag  43560
acaaagaaga tggattgagc tgattaagga ctacgattgc actatagatt atcatccggg  43620
caaagcaaat gtggtagctg atgcactaag tagaaagttt tccagctcta tcgctcactt  43680
gcgagtgaaa tatgtacctc tattgatcga gttgagatct ttagaagtcg agttgaatac  43740
tgacaatcgt ggagctttga tagctaattt ccaagttagg ccgaacttga ttggcaaagt  43800
tcactagatg caagctcaag acccacagtt aatgaagttg aaagaggatg tgcagaaggt  43860
ttatgaaccg attttatggt gagagatgac ggagttttat tcatgggtaa tagactttgt  43920
gtacctgata ttaaagatct gaaagaagag attatggaag aagctcactg ttcagcctat  43980
acgatgcatc ctggtagtac gaaaatgtat cgtaccctga gagatcatta ttggtggcag  44040
ggcatgaaga gagagatagc agaatttata tctcgatgtt tagtttgtca gcagattaag  44100
gctgaatatc agaaacctgc agggttttct caatcgcttc ctatccctga gtggaaatgg  44160
gagcacatca ccatggattt tgtggcggga cttccacata cccagagtgg tcatgatagt  44220
gtttgggtag ttgttgatcg acttacaaaa tctgctcact ttttaccatt caagaccacc  44280
tattcgatgg acaagttggg gaatattttt gtggccgaga tagttcgact tcacggaaca  44340
cctgtgtcta ttgtttcaga tagagattcc caatttactt ccaagttctg aactagcttg  44400
```

-continued

```
caaaatgctt taggcaccaa gttgaacttc agtataactt ttcatccaca gactgatgga  44460
cagtcagagc gtactattca aactctagag catatgttgc gagcttgtgt tatggagttt  44520
aaaggaaatt gggacaatta tttacctctg atggagtttg cttacaacaa cagttatcaa  44580
gctagtatcg agatggcacc atatgaggct ttgtatggca gaaaatgcag gactccagta  44640
tgttgggatg aggttggtga gcagaggtta ttcggtctag aactaatcca ggatatgaat  44700
gagaagatac aattgattcg gggtagatta aaagtggccc aagatagaca gaagagctat  44760
gcagacaagc gtaggtggga acttgaattc aaagttggtg atcgagtttt catacggata  44820
tctccttgga aaggagtgct tcgatttggg aaacgtggga agttaagtcc acgttacatt  44880
ggaccatatg agatcgtgga gcgtattggt ccgttggcat accgataagc tctaccgcct  44940
gagttatcca gaatccacga tgtgtttcat gtttcgatgc tccggaagta catatatgac  45000
ccgagtcatg tgttatcaaa gcaaccaatt cagttgaagg aagatttgac ttacgaaaag  45060
gaaccagtgg agatactgga agagaaacac caagttctac gttctaagac cattcctcta  45120
gtaaaagtgc ggtggaagaa tcatgcaaag gaagaagcta cttaggaacg cgaagactta  45180
atgcgagctc aaaatcccta tcttttctta tcaggtacgt aaatttcgag gacgaaattt  45240
ttataagggg ggaggattgc aacacctatg gatgttaaag gaaaatgagg tggttaagga  45300
gtttataagc aaaggaataa gctggaaaca gaggaaactt atgcacatgt aacagagaga  45360
gagagagaga agctgtcaac tgacccaatt tcagacccgg aaacccgacc cgacccgcga  45420
ccttgacccg atcatatctc ccatttccga ccaccgtttt ggccgagctt ggtaccgatc  45480
tgaagcttag tagccgactg tcgttccttc accaccgaaa acctaccgga acgtcggcga  45540
tcaaagcttg caacccgcga ctgcttcact ttactccgtc gagattttcg ccagttttgg  45600
gtgacaccac cggttggatt ttgttcctca tgactctctc ttccattttc gaccatccat  45660
acgcaccgag agtcgttatt ttgctgctgg tcgatttttg gaactcacgg ctgtcgagct  45720
agattccggc gtcgttgccg cgcgttggag ctcaccgccg gtaccattga actcagcgtg  45780
attggcactt taagatttga gcttcctggc cagtgttgac caatttctgg tgaccgttga  45840
ccgacaaggg cattttggta atttcacact atgagggaaa ttctgtcatt tctgagcctg  45900
tggatatttt agtaattcct aaaattgaga attgggtgta attcggtgat ttacaatttc  45960
ggagcatgtt aatgatttac ggactcaagg gcattttagt aattttatcg acacgggagt  46020
tgtaaattat ggataaatgt tcgtttcgaa tttattgctt ataattagtc gtcattccga  46080
tttacagaaa ataattatgt cgtttccttg atttaggagg atccatgagc gagaaccgga  46140
ccgcggacgt ggacgataac cgaccgtgaa caccgtcact gtgagtggaa tatacaaaac  46200
ttattttcat agttagcgat gatagtaaag catgtttgcg gaataagtat tttaaatgtt  46260
ctgatttaat gattaatgat ttctcgaaaa tgatttaatg tgatttcctc gaaatggatt  46320
ttactcacgt attggtattt tattaacatg tttggttaat gattttgcgt attgattttg  46380
aataagcatg atagtatttt aaagataaga aaagtggatt caaatgtggt atgaattaaa  46440
gtatgattta aagcatgata gtgattgttt ttgaaatcat tagacaatac catttccctc  46500
cagatacagt attatatatg agatgagatg agataagata gaggcctttg gggcccctct  46560
gaacacacat agaggctttg ggccgtgtgt ttgggcgctt ttgccttttg ggggcatatg  46620
catgcggtat gatgattaca gtgatacaga taagagatac agacatacat tgagacaccg  46680
atgatacaga tatgagatac agacatacat tgagataccg atgacacaaa tattgagata  46740
```

-continued

```
cagatgatac agatgagata caggcctttg gggcccgcct gagtacacac agaggctttg  46800
ggccgtgtgc ttgggcgcat ttgtcctttg ggggctagat tatgcatgca gaaatatgat  46860
gagatatgag atggtatttc cctgtctatc tgtgtagctc cggggcgtga cgttacccag  46920
atagtacgtc attgcctgtc cgttgaggtc cggatatgac gagattattt ccctgggtac  46980
ttgtttggtg atgattttca gatttgtgaa ttctatatga tatggtgata tgatttctat  47040
ggttggtaat ctgatttaaa tgattaatga tttatcactg gtttctcgct tatggtttaa  47100
tgaaatcgtg tttggaaatg atatgattat ttgttttaaa gtaagaataa attttcaaac  47160
ctactatcca ctcactgatc tcactgagtt ttaaactcac ctcgttttta ttatatttta  47220
ccccctcac caggaggttg caggtacacc agaccgaccc agcgactgta tatattttga  47280
gtcttggcca cgtgatggtg ctagaatata tttttgttgg gacatcttgg tcatattgtt  47340
cttttggggt tgtataatat aaaactcagt gttttggttg aggatgttga gcactggagt  47400
ttgttgtata ttggatttgt ttttggagtg ttatattcat attgtaaatt gggagtgtta  47460
tatatatata aaggagactc tgccaaattt tcggcagact cttgacgaat agaattattt  47520
tcaagtccgt tttgatgtga ctagatagac tcgcctaggg ggctttcggg gcgggtcgtt  47580
tcatttacct ttgttgatta catttttata gccttctttc aaatccaacc cttcccaaga  47640
tccacgtccg tcacctccct caactctcag aagtgggtgc ttcactatcg tagttgtggc  47700
tgagtgggct tcatgccttg attcttggat aggagtgcac gtcttgtcaa ctgtcatgga  47760
tcgggtctac ccacttcagc ctttagcagg aatggctttc tgatcctagt aggaggccag  47820
ctcatgctgt ggtcccgagg agggtgtctt cgtgaacgag cagaatattc ctacttgtgg  47880
aaacctacta ccagacttct tgtaaggttt aattctctca cctaaatata gtagaattca  47940
ttttgagcta acaagcccct ttaagtatta aaataatatt aatatataat atttattttt  48000
aagagaagta gtgacataag tgatgatgca atgattacgt aataatgaca taatctatga  48060
cataagtgat gatgtaagag aagttgtagg gatagataag aattctagaa actcgtaaga  48120
tatttatgaa ggataatttc aaccattgat caagagttat ggtggcaaaa tcttagccat  48180
ccattagcct taaggaatcc tataaatacc ccctaacccc ctttcatttt caatccaact  48240
taggaattaa aacatttgtt taggagaatt aaagcaattg gtattggagg tgattgagac  48300
ttttagagac ttagaagtgt gttagttcaa atccctttat cgaggtaagt aacttcattc  48360
ctagtatact tgatatgaat aaatattttg atattattat aataagtata aatgtttcta  48420
tactacttag aagattaatg gattttcata acaaaattaa cttatgaaaa tgttttcaaa  48480
acctaaattc tttttaacaa aagtatttta taaatgcttt ttagtatgaa agttatttta  48540
cattaccatt tatgatttta tctataaaat aatttgcaag cctaaattat tgttatagac  48600
ttttatgaat ctggtacgaa tgttttgtac tcatgtctga tttcaattgt tgaaaattgt  48660
atgagattcc taatgttttg gctcattgtc catagttatt ctgattctga ttctaatcgt  48720
aatacacgat atatctctgg actagttctg ggtttctgtt ttgagtgcgc acacaatatt  48780
ctgattctgc ttctggccgg gtcaccggga ctataggtga cactatgtga catgaactaa  48840
ctatccgttt tctatgaatg tgatatatga tttgctttca taagtaacta tgcttttgat  48900
attctgagat acaattaatt tatgttattt tatcgtgata tatcgtttta tgaaatttat  48960
gaattataac atatatgttt caaataaaag aaggcttgca atatttttgg tatcggttgg  49020
gctagtttgt taggaatggt tttacttaca gagacggctc acccttcgtc attacttttt  49080
gcatattaag ttccgtttga aaggtgtgcc tagctttgga tttagtgatt tcatttccgg  49140
```

-continued

```
ttgctatttg aataaaaaga agaatgaact catgtttttt atttagttta tttctgatat  49200
gaacttgtaa tttggagttt gagacttttg ttaatgttat gttttgggag agattattaa  49260
gtgttaaacg ttaaaatttg tggatttgtt tgaataagaa tttgaggtat ttcagtttgg  49320
aatttatgaa taaggattac gatttgtaag taacattctt cttgaggtgc tccgcacgtg  49380
ttagttttgg ggtgttacac ttctgctcat ctgctccatt ataaggaggc tggctcctca  49440
tttagggcat gaatggtctt gtggaagtat atccccccaaa caccggtccc ccagtttttg  49500
gtgtttggta atgtagtgga ccaatagtag aaactcaata gctctggctt gctcaggata  49560
agaaacggct ttgaagagtc gtgtcgcatt taattgcggg cgaggtaatg tggctgtgat  49620
ctgtccctcc agtgaatttc aaaccgatgg ttataaaacc cttggaattc gtgtcgttaa  49680
atgctgataa accaagagtt tgttcctcat tagggaaccc aaaacctcaa aaaggaaact  49740
tctctcttag ccttcttctt cctcttcggt gactgagtta tttctctccc tcggcgtaaa  49800
agctacattc cttgtctcta ttcagcttgg ctacaactgc atgtattatt tctatttctt  49860
cggtcttaga taattataga aaatttcttt tttctctttt ttgtttgggt agcgtttggt  49920
ggtattactc tagtcatagt ttggagaatg tcaaaaggca aagagaaagt aattgaggtt  49980
gataatgacg agttagactt cttgcctggt ctactcactg atcctacctt tgaccctggg  50040
atccattcag aaccgactag atctagtgtt gggactagtg ttaggagaat gtctcctcaa  50100
ataacctcct tacccagcaa taacggcaat aagggatctt ctggttcgga agatatcctg  50160
agtgaggacc cgggtgaaga ttatggtgaa atgtcctcac cgggaatatt gcgaccagat  50220
aggaaaagca aagtaggagg tagggcttta tcagagcact acgctattga cttcttgacc  50280
tgcacgacta cagtagaaga cctcgtcgaa ctccgaacta ggtagacatt cctgatggta  50340
taccccttag aatttcagga aaaaaaatac tcccagccga cctcccaggg gatatgttac  50400
tctatttctg gaaagcttta agtttgggat gaggctcccc ctgcaacctt attttgtcca  50460
gatgcttaat gagttaaact tagctcctag tcaacttaac cttaacggat agagggtact  50520
ttctggtctg ttcattttgt gggacagatg ctgccagagt gagctcacgg ttgatgaagt  50580
caaacaccta taccagttaa agaacagacc taaagacgtc ggttggtact atttcatgtc  50640
gagtactaag actatgaaac ccataactga tcttccaata ggtggtggtg ggaattggaa  50700
gaaaaaattc tttttactg ggggtcccta gggtcaagtt gcacagattg atgggaagaa  50760
ttatcgcgtc ccaagcaagg gagttgatat caaatatggt tgccaacgca caacaatttg  50820
gcagcaggca agatctcact tcaaggaagg tgaatgaggt aaatatttct tatgttgaac  50880
aacgtttaga taaacttact tctcttgtgg aaaagtttgt tgtaggtaat gtgcaacagg  50940
cgaagacttg tggcatttgt tacaatatgg gtcattcaac tgatatgtgt cctacactac  51000
aagaagaacc cgttgaacaa gccaatgcag ttggaggatt tccaggcatg cctcagagga  51060
ggtatgatcc ttatgcacaa acatacaatc cgggatggaa tgatcatccc aacttcagct  51120
atggagtttg gcaatcagga ttctcacaac agtatccact aagacaacca gtacctccac  51180
agtcaaactc caagtcaggt atatctcttg aagaaattgt taaatcactt gcgactaaca  51240
ctcaacaatt tcagcaggca actacagtaa gcattcagaa tttggagaac caaatgagtc  51300
aattggcgac tacaatgagc cgtctggagt ctcaagtatt agggagattg ccttcacaat  51360
ctgaggtgaa tccaaagcaa aatgttagtg ctgtcatcct tagaagtggg acggagttgc  51420
aagagcctag taagaaagtg acaaagcatg tagaagatga gcttgagaag aatgaattga  51480
```

-continued

```
tacctcaata tcaagatgcg caacccacca gagcgaaacc cctacctatt gtgatacctc  51540
ctcctttgcc aagccggttt gcaaaatcca agaaggagga acaagagaaa gacatccttg  51600
agacatttcg caaggttgag gtaaatattc ctttattaga tgctataaaa caaatacctc  51660
gatatgctaa agtctttaag gaactgtgca cctccaagag aaaattaaga ggagatgaaa  51720
aagttcacat gggggagaat gtttcagcag ttctacaaaa gaaactacct cctaagtgca  51780
aggatccagg tatgtttact atcccttgta aaattgatag tgttagaatt gaaaaggctt  51840
tgttagatct cggagcttct attaatgtca tgcctcgttc catttattca tctttcaatg  51900
ttggtccatt aaaagaaact ggcgtgataa ttcaactagc tgataggtct aatggatatc  51960
ctgatgggat attagaagat gtcttagtac aagttaatga gttggttttt cctactgatt  52020
tttatgtact tgatatggaa gaggataact cctctaattt tgtcccaatt ttgttaagaa  52080
gaccttttct taagactgct aggactaaaa tggatgtaca taaagggact ctcactatgg  52140
agtttgatgg agaggttata gaattcaata tgaatgatgc catgaaatat cctagtaagg  52200
aacatttggt attttctgtg aatgttatta accctatagt gcaggaagtt ttttacaagg  52260
aaaaaacgaa gacatttcat gatagaatga ttttgagaaa ggagttctct attggtcaaa  52320
aagttcttct ttttcattct aagctgaaac ttttttcggg taaattacgt tcttgctggg  52380
ttggacattt tattgttatt aatgtttttc ctcatggtgc agttgagatt cggagtccga  52440
cctctgacaa agtttttaag gttaatggtc atcgctgaaa accttttttat gaaggttttt  52500
cggtgaatat tgtggaggat atggctctcg agagtcccaa ttatggagat tggtgcataa  52560
atgtgtctag ccaaagacat aaaacaaagg cgctttttgg gaggcaaccc aaatgattta  52620
tttattttgg ttttttttat atcttctttt aattttgatt cagtttttttt tttaaataat  52680
gtgtttgctt atttggtcag aagaaaattt ttgataaggc gtgcccacgt cttaactaat  52740
aagtacttct gtgattttta aagcaaaatg gttttaaggc gtgcccacgt gcttatgaga  52800
aaagtacttc tgaaattttt agtgtctcaa gtgattcatc actaaaaaaa aaaaatcgtt  52860
ttctttccca acaaccagct gctccagcct tcaccagagc aacaactgca ttcaccgagc  52920
agccgtgcac acccagcaac ccatgcatct caacatctcc cgtagcagca gcccgtgcgc  52980
aactatccca ccatttccgc caagcccata ggcgttatga ggatcaaagc tcacaattca  53040
gggaagtttt tgccttttaa tcttttatcc ttacgcttta atttttatgt gagctttgat  53100
gatcttacat tggggacaat gtaagttctt ggtgtggggg agggattttt gcattattga  53160
tgtctggaag tattattttc actctactca tccttaaatg attttggagt tagtatgctt  53220
catatattat tatttttctt ttcttttctt tctcactact cttttcccat ctatctcaaa  53280
ttatttacat ttatttatat atcactactc tttcatcact cacattttat ctttcttttt  53340
tttactacat acatctttat cgcttattat ccttttttacc tttcttttta tatatcactc  53400
ataccttcct ctcattctac accactattg atggttgatt catttgaaga gtgtacatga  53460
tttgatggta aatttaccaa ctttgtgagg attttagcct atgagcaacc gctttgctct  53520
aattattatt tttatgtgaa tatcaatctt agtttgttta ttctagaact tgctttgtta  53580
tgcatgttga agccgcatta tgggatttta tgcattaaaa tgataagggc aaaccatttt  53640
ccatttttct attctcgtat ttttttttct ctacccaaag acctttattt gctacctttg  53700
tttgagcctt aaccattacc catctaattc tctctgttta cttaaccatt tttcttgttt  53760
ttgagcctca atttaaggag atttttggac tcattgtgtg gatatatttt gtatatattt  53820
tgttgctttt ttctaccttg tattaaagtt tctcaattag atcaacaagc attatgcttg  53880
```

-continued

```
aattaaattg tgcaaggttc gtttcttttg ttttaaaaaa aagaaaataa ataaaaaaag  53940
agaaaaataa aaaaaaaaga aaaaaaatgt ttacattctt aacaccgtga ggtagaaata  54000
agcattttga tatcataagt tcattcaatg agttcattct tctcattttg atcttttttt  54060
tctttcgtag acgtttgttt ttcattaaac ctatttaacc ccattacaac ctttttaaga  54120
cccttagatt tttgcatttt attcatgttt tgtggattga gatgtaatat atgagcaagc  54180
ttatggtaat agcattcttt gatttgattt gagtgaataa atgacaccct aaacactttg  54240
agtgcatgga gtgaagtcga tgagagggtt attaaatctt gttgcacttg aattttgaat  54300
ggatcttctt ggtggttgaa tgttattatt ctatcttatg agattctatg ctttaaaaat  54360
ccttgtctct ggaatattga tgaaaattga gtggagattt gggattagtc ttgagttata  54420
tgcttgagga caagcatcat cttggtgtgg gagaatttgt tagagtgcaa tttatgcact  54480
aggtttgcat tgtttactgc ccttaatatc gatgttttgc acttaataat aatgatttac  54540
atgtgtttta cttttgtagg tgcaattcta ttgatttgtg ataaaattga gctataagat  54600
gatgtttaaa gatgattgtt ctcttggaga aatttagaga gtcagaagaa ctttgttgat  54660
aaggcgtgag cgcgtgttgt caactgcgga cctgcaattt ttagttttac gtgttttata  54720
tttttggtta tttttgtaat tactaattta atatttcaga tattagtatt ttattttaaa  54780
tagaactcta aaagagaaga gagagagtat ttaagggagg aatctattgt gaaaaagggg  54840
atttgttttt tgggaggaaa agaaggaaac cctagatcta atttttctct tctctctatg  54900
aagaactaaa cctatttttc tggttgaagg ttaatgaagc tttgattcat cactactgtg  54960
agatctttct tatgctttaa ttgttttatt actttttggg tatttgttta ttctctgaat  55020
tagtttcatg attatgtttg ttaattaggt aattgactac tatttaatta tcaatttaat  55080
ctattgtcaa ttaaaggatt catcgtatga agattttaat gtttgtgaca aataacatag  55140
cagtgagttg tgttatgaga ataaacaatc taatttaaat gaatcatcat atgtgttgat  55200
taggatttgg gtctctctgg ttttttaggc tgtcaattga ttaaatccta tgatcgtatc  55260
tagggttgtc tattgattag ggaaatatcc aacggtcgta ccttggttat cgactagtta  55320
aggagagatt ggctattaga gggtctcaat agctataacc ggtctattca taagtaataa  55380
taatctatat ttgaatcaat gatcagtagt cgaatcaagc tgagttaatt ccttcaacca  55440
gagctttctc caatttgaat tacaacttta atttgcatta ttgttatttt aatttgattt  55500
ttattattgt caacaaaacc cccattttat gttttatgtt tcaaaaggag ctgaataagg  55560
tcaaagagga cttgcagagg caaaaggata cttaccaagc tcggctcgaa tccctcaagg  55620
attctcacca gattcatgtc gaaaacatag agaaggaaac agacaactag tataaccaga  55680
ggcttcgaca ttcttatcag tacatcatgg ccgttctcgg aaagcagcat cctgatctga  55740
agatggatga acttgccact ggtgttgctc aatacataga tgaggaggca accaaagaag  55800
atgtcgaaga gttggagcca aatacgactg aggagggaac ctctcctccc cgtgcagccc  55860
ctactgatgt tgccgaagca agtacccccc aggtgcaact agtgagaccc tctgctcctg  55920
aggtggacca gccagcggag acagctcagc ttactgaccc gctttcctct tgattgtacc  55980
ttgtgttgta ggtttctttt ttggaatatt gtatgttaag actaaaagct ttttacaatt  56040
gttggcgaat taataatatt gctcttattt gttttctttg cttcgcgctc ttggcagatt  56100
gttattttat ttttttcctt atattatggt cgagtagata ccgaaaagct cgacttccca  56160
tcctgtcatc gagcaggcct ggagacttat gtaatctttc cgtgccatag aaactttttg  56220
```

-continued

```
tgacgtttga tagttgcctc gcctttgctt ggtcgagcag atcatggcat gcttggcttg  56280
tagtctcgcc ataaaaaaag ttttgagact taatggggcc tttgcatgcc ttagaaactt  56340
ttataacctt tgagggcctg cttgccttcg cttggttgag cagatcctgg caagcttggc  56400
tttcggactc gccataaaac aggctttgag acttaatgga gcttttgcat gccttagaaa  56460
ctttttataa catgtgaggg tatgctcgtc ttcgcttggt cgaacagatc ctggcatgct  56520
tggcttctgg tctcgccata aaacaggctt tgagacttaa tagggctttt gcatgcctta  56580
gaaacttttt ataacatgtg aggatctgct cgccttcgct tggtcgagca ggtcctggca  56640
tgtttggctt ccggtctcgc cgtaaaacag gttttgagac ttaatgaggc atttgcatgc  56700
cttagaaact tttataaaca tgtgaggatc tgctcgcctt tgctggcatg tttggcttcc  56760
agtcttgcca taaaacaggt tttgagactt aatgtagcct ttgcatgcct tataaacttt  56820
ttataacatg tgagggtatg ctcgtcttca gttggtcgag cagatcctga caaacttggc  56880
ttccggactc gccataaaac atgctttgag acttaatggg gcatttgcat gccttagaaa  56940
ctttttataa catgtgagga tctgttcgcc ttcgcttggt cgagcagatc ctggcatgct  57000
tggcttccag tctcgccata aaataggttt tgaaacttaa tgaggcattt gcatgcctta  57060
gaaacttttt ataacatgtg aggatctgct cgcctttgct agcatgcttg gcttccggtc  57120
tcgccataaa acaggctttg agacttaata gggcctttgc atgccttaga aactttttat  57180
aacatgacaa ctgactgaaa ttcttccact tttcgttaat tactaaattc ggcttacatg  57240
aaattgatta agcataaaac gaataacaac aagaacgaat agaaataact ctaaagcatg  57300
attgggtctg actggaaata tttcttgagg tgtgctgcgt tccatgggcg tttcacctcg  57360
tggccatctg cgcaaacgag cttataggct ccggatccag cgacctgctt gaccctatat  57420
ggcccctcct agtttggacc gagtacttct tgtgtcgagt cttttgtgct ctaattcacc  57480
cttctaagta cccaatcgct gaccttgaac tgtcgtatac gcaccttctg gttgtaataa  57540
cgagtaacca tctgctggta ggtggctgat cgcttcgatg cttgctccct cttctcagtc  57600
agcagatcca gattcaagca catctggtcg ttgttttcct gctcatcgaa gcgatctgtc  57660
tggtgcatgg ccgcccctat ctccacgggt acaacagctt catgtccgaa ggccaaagca  57720
aatggagttt caccggttgc tgtcttgtgg gttgtcctat atgcccataa tacacttggt  57780
agctcattag cccatgctcc cttctttgct cctaacctgg ctttcaaaag cctcttgttg  57840
gcagcttcta cttgtccgtt aaactgaggg tgagcaagcg agcaaaactt cagctctatc  57900
ctgaggtttt ggtaggagtc tctgaagtta tgattgtcaa actgcctgcc attgtctgct  57960
atcaggacat aagggatccc atatttacag accaggtttc tccatatgaa gtcagtcgtc  58020
tttttctctg ttatcctatt gagggcttat atctctacct gcttcgtgaa ataatcaatc  58080
attactattg catgcgttgc tgcccctcat cctttgggta acggtccaat caaatcaatt  58140
ccccattaag caaatggcca tggcgaggcc atagaagtga gcttctctgg tggttgggta  58200
gagaaattta caaaattcat gcaactcctg gttttctctt gtgcatcgtc acccagaaat  58260
atccctgcct aagagccttg tgggcaaggg atctcgcacc agcatggttt ccgtaaactc  58320
ctttatgtac ttctctcagt acgtaatctg catcgtccta atccaagtat cgaaggaacg  58380
gtagagtgta tccccgctga tataacatcc cattaatcat ggtgtatctc gacgcttgag  58440
ctttgatctt gtgagctcat aacttatctg gtggtaatac accatcccgg atgtaccaga  58500
gtattgggtc catccatgag cacttctatt ctacccacag cacctctaga ttctgctcga  58560
tgctggggct agactttacc tccaaaggga catacttcag atatgctgca actgccattc  58620
```

-continued

```
tagccagaat atctgcttga taattctcat atcttgggat ttgtatcact ttcataaact  58680

caaacttccc catcatctgt cttaccttct ttaggtactg ttctatcttc ccatctctcg  58740

gttgaaatct ctcactgacg tggttggcaa cgagttggga atatgttcgg actctcactt  58800

tattcgtttt cactatctta gccaattcta accccgctat caaagcttcg tattcggcct  58860

ggttgtttgt ggccgtgaac ttcaatctta caacataaga gatctcatcc ccttctggtc  58920

ctaccaaaac aatccccgct ctagacccct gctcccctga ggatc                  58965
```

<210> SEQ ID NO 3

<211> LENGTH: 78333
<212> TYPE: DNA
<213> ORGANISM: artificial
<220> FEATURE:
<223> OTHER INFORMATION: Poncirus trifoliata and citrus grandis hybrid

<400> SEQUENCE: 3

```
aagcttcatg ttaagctttt ctagatgcat gcctgcttgt tacatcatat gtgtatgaat     60

tgcaagagga aacttccata tgcgatggtc gaacaactaa acaggtggtc aacatgaaaa    120

acaatccagt ctagcactca tgcaaacatc atctctgcag gttccgattc cgtgattgaa    180

tacgcacttt cacattgaac tattagctaa ccaataaaat gttgtgcaag agtaagagct    240

gctagtcaag tcaagacgta caaacacaga actcatcaag gcggtcactc cacatattaa    300

aacccttcat ctaattcctc actcgtagaa gaaaataatg acaaaggaat tcatttcaat    360

ggcagtattg ttcttgcatt tttacaatga taagtagcga aaacattcaa cagtatcacc    420

tcccgggaat caatcatcag gcttgctttc caaactatat atgtttctag taactccaac    480

aaagcttact gcaatagcca atatatacta acatctgcct tgacaggaac ttctccccaa    540

ggcataaacc gctaatatgt aaatttgaaa gcagtccaat tgttgggagt catggtagag    600

aacaacacca aaagcatccc tgtcaaagct aaagacctct gcctactctc cgaaaatgga    660

gttgctccct catagaataa ggcatccctc gaggaatcaa tgtttgctaa atgattaatc    720

aaaccaaaag tttcatagat taaaaagagg atagcattat gtaaatattt agagtatgaa    780

aatactattt tccatatttc attcattcta caagttacat ttaaatagaa tgtagaaaac    840

aaactcttaa tagatatccc ctaattgtag gatacttatc taaacttgaa ttttaaaaaa    900

taattatcta aaacttcatt ccgataagac tttaaaacta aactaattat ctaaaacttt    960

attatgataa gactttcaaa ctaattgaaa aatcctaact tcttgacact ctccctcaag   1020

ttggtgcgta gatgtcaatc attcccaact tgctgacaag atgtccaaag ttagttttga   1080

ggagtccctt ggttaggata tctgctgttt gttgtttcgt tggaacaaac aatagaaaaa   1140

taatcttatt ctcaagtttc tccttgatga agtgacaatt aatttcaaca tgcttgatcc   1200

tatcatgttg cactgggtta tgtgcaatgc tgattgctgc tttgttgtcg cagtataacc   1260

tcataagtag aactataggt cttctcaaat cctctaaaac ttgtttcagc cacaatattt   1320

cacaaagccc atgtgccata gctctaaatt cagcttcagc agtacttcgt gcaaccacat   1380

tttgttttct actcctccaa gtcactaaat tcccccatac aaaagtgcaa tagccagtag   1440

tagacttcct gtctgtaact gaacctgccc aatcagcatc agtgtatacc tcaatacctc   1500

tattctctgt tattttaaac aaaagtccct ttcctggagt actttttaga tatttgagaa   1560

ttctgtaaac agcttcaaga tattcttccc gaggatgatg catgaagcga cttactatac   1620

tgactgcaaa agcgatgtct agtctagtat gagacaagta aataagtttt cccaccaaat   1680
```

-continued

```
tctgatatcg gcgtgcatcc actaaggctt tttctccttc acctagtttt agattgtact   1740
ccacaggtgc atcaattagt ttgcagccac tcattcaagt ttcctttaat aaatcaagga   1800
tgtatttcct ttgtgagaca actatacctt tcttagaatg agcaactttc attccaagaa   1860
agtatttcaa ggcactaagt ccttgatttc aaaatcagtt aggctttgct tcaatctgtc   1920
catttcaact aaatcatctc tagtaagaat aatgtcatcc acaaacacta taagcacaat   1980
gattttacct ttagttgaaa ctctagtgaa cattttgtga tcagccttac tttgtttgta   2040
accttgtcta ttcacagctg tagtaaattt ctcaaactaa gccctaggca attgtttgag   2100
accatataag gacttttgca acttgcacac atttgaccta aatttttcag agaaaccagg   2160
aggaggatcc atgtatgctt cttcttttaa atctccgttg agaaatgcat tcttcacatc   2220
caattgttgt aatggccaat ttaggtttgt agcaatagac aagagaactc gtccaatgtt   2280
taactttgct actggtgcaa atgtctccga atagtcaatc ccataagttt gagtaaactc   2340
ctttgccact aggagagcct tgtatctctt aagtgaacca tctgaattgt atttgacagt   2400
aaatacccac ttgtagccaa ctgttgactt ccctttaggc aaattgacca ccttccaagt   2460
gtgattcttc tcaagagcat tcatctcttc aaggacagtt gcctttcatt caggtacact   2520
tagagcatcc tgtacattct ttgaaatttc tacacttgaa agttgtgagg taaatgcata   2580
taaataaggt gataggttgt gatacgaaac aaagttagat aatgggtatt tggcacaact   2640
tctagtacat tttctaagag caatatgtat gtccaaatca ctaagaacct gagaatttga   2700
atttaactca taagaatgat tagattagaa ttacctgaag aagaagaagt ctgatttgac   2760
cttggatttg agtcatggcc ttgctacaaa gtagggttat ctcttctttg attagtgccc   2820
tttcttagta aacaataaac tcagattgtt tattaccctg tcttgcacac aaatatggtt   2880
ctaatagcac attagaaggc tgtccaggtt tattagcatt ttcattatta gatttagtga   2940
ggttttctta tagttcgggt gcattaggtt ttaatatggg atcaagaatg gtagaactag   3000
gtataacagt atttggaaca tgtacgataa tattaggttt aggtatggca gcctcgagac   3060
ttttttctgg atggagtgag tctagcacat aagaaataga aggggttttt aggtgaatag   3120
tgttaaagat agaatcttca ctcctatttt ccccctaaag atgattatct acatactatc   3180
ttcgttttaa aaaaaatata acatccatgg taacaaacat tttttaaaaa aaataggatc   3240
aaaacattta taaccctttt gtgttggaga atatccaaca aaaatgcatt ttctagcctt   3300
tggagcatgt ttgccctgat tctggttgtg aatatggaca aaagcaacac aacagaatat   3360
tttgggcgga agtgtgactg aaattcttga ggtagataaa cattgattaa agaaatcaga   3420
tggagtttga agttatagaa cttttaaagg aattcgattt atcaaatagg cagcggtgag   3480
tacagcttcc ccccacaaat acataggaac ttgagttgta aaaagtaagg atctagcaac   3540
tttaaagaga tgcttatttt tgcgttcagc aattccattt tgttgagggg tattcgtaca   3600
tgaactttga tgaaatatgc cattttccac aaaataatct cccaaaaact tgttaaagta   3660
ttctttccca ttgttagtgc ggaaaacttg aattttagtt tgaaactgag tttgtaccat   3720
attgttaaaa gttttaaaaa gcattcccac atctgatttt tccttcatta aatataccca   3780
agaaatacag gtatgatcat caatgaaggt aataaatcat ctttttcctg ttaatgtaga   3840
aattctatta ggtccccaaa catcactatg gatcacagaa taaggttttg aggctttgta   3900
tggttgggaa ggaaatgatg catgataatg ttttgctaat tcacaaattt cacatttaaa   3960
ggaataagaa ctttaattag caaacaagtt gggaaataaa tattgtaaat actgaaaact   4020
```

-continued

```
gggatggtct aacctaaagt gccacaacaa aacttcattg tcattattaa tagcagaaac   4080
agaattgaaa taagtacgtg gaggttgttg tctcaaactt ggtacttctt caaagaaata   4140
tagcccccca ctttgtctag cactgccaat catcttcctc gaggtcaaat cctgaaattc   4200
acaatgattt tggaagaaat tagcacaata gttcaggtta agagttaatt tactaataga   4260
caaaagattg caagataggt taggaacatg cagaacatta tgaagagtga gagtggaaga   4320
aagaatgata cacctttttc cagcaatagc caagagggat ccgttagtga tcttaatttt   4380
ttgatttcct gcacatggct tataggcaga aaacaaagat ggagagcatg tcatgtgatc   4440
ggttcctcct gaatcgataa tccaagaaca aggattcgaa tgatgacaaa caagggaagc   4500
agaaagataa ttaccttttt gagctaatga acaagaggga gtagatgaat taaaggataa   4560
ggattgaaac aatttataca agtgctctaa ttgatccttg gtgaaaggtg atgactctga   4620
agaacctgat tgctcttgat ctgaagtagc ttggaaggct cgtccatcac ctccttgttt   4680
cttcttcaca taaggaggct tgccatgtag cttccagcaa gtttctcttg tatgccaagc   4740
ccttttacag aagtcgcacc aagggttctt tgaattcctt cgatctccat caggttcagg   4800
tgcctttgaa ataagagcaa aactctctga actctctact tcattggtgg ctttaacatc   4860
attaagcatg acattccatc atgcttcttc tcttcttacc tcagaaaaca cttcttgaat   4920
agatggaagg ggtttcctac tcagaattct gcctctcact tcgtctaaat cacggtttag   4980
cccagccaag aacacatata ctctgtcatt ttccaacatc ttcttatacc ttacactatc   5040
actcaaacag tcccactgct catcatagca aagatctaat tcctgtcaaa ggatcaacag   5100
ttcattgtag taagttatga cctcccgatt accttgcttg gactgccaca gtcgagtttt   5160
caactcaaat atctgagatg aattttctaa atcagaatag gtatcttgga ctgcatccca   5220
catcgccttg gctgtcggta agaacagata aggcttacca atcccaggct ccattgagtt   5280
tatcaaccac gcaataacca ttgaatttgc tgatctccag gtcggaagag aaggatctcc   5340
agcagctagt tttattactt caccagtcaa atgccccagt tttccctttc catcaattac   5400
caacttaacg cattgtgccc actctaagta attttttcca ttcaatttat gaacagttag   5460
ttgcaaagaa gagttatcct ggttatattc agactgttgc aacaacggct gaggagttgt   5520
ggtgttacta tcatcatctt cggcggtaga tgccgatgag ctctttgtag ctccagtcat   5580
ggcagttttc accattgaaa aatagacctc taaatattca ttgctctgat accatgtaaa   5640
tatttagagt ctgaaaatac tattttccat atttcattca ttttacaagt tacacttaaa   5700
tagaatgtag aaaacaaact cctaatagat atcccctaat tgtaggatac ttatctaaac   5760
ttgaatttta aaaaatgatt atctaaaact ttattccgat aaaattttaa aactaaacta   5820
attatttaaa actttattct gataagactt tcaaactaac tgaaaaatcc taacttcttg   5880
acacattata agggatatta aagccatgaa gtaaatattt tactttaaaa attatctttt   5940
tgctagtact ttaaaatgct agtaaccaat tttcatactt tttgctctca taaaactatt   6000
tcagcagata gaacaagaaa tgagaaagca tgaaatagag tgtttcttac atgaagggaa   6060
ttgacaagta gaatgcaaga aaatgcaggc accacagcag aaatcaaata taatattcgc   6120
tgttcaggga gtaaaaactc cactcagaat gacttgaaac aggggagaaa agcattctga   6180
gtggcttcat cctcccattc aagctgtttc caccggtctg gttctccacg aatatcaatt   6240
ttacgctcct tggcagtatt ggaatcgagt gtaagcttgt cgcaattaaa caagttcaat   6300
tctttcaaat gtgagaaggg caggggcttc cagtgaatgc tgttcagatt tggcagagca   6360
gctaattgga gatattggag tcttgcaaaa gggtttagat ttccatcacc tctggaacat   6420
```

-continued

```
cagcaaattt tcccacacat atgatttctt ccatggcaaa acaacttctt acttcaatag   6480
acttgacgtt tgacgcgaaa ccaaggaatg tcaagtcctt caattctttg caatagtcta   6540
ttacaaccac gcgaaggctt tggaaacaaa actgttgtac tccccctttc taatcaatct   6600
tcaattctac caattcggga cagcctgcaa tccgtaatct gctgagcagc ttcaggtctg   6660
ccaaacctga aacatcaagc gatgaatctt tgaagcgatg gaggaagtac aactttgtaa   6720
cttacgcgag gtcaaaaaac ttttgagagc atgagaagtt cgcaaggtga agctcaatgc   6780
ctctaaatgt ttcaaaccgg gcaattcctt tactatgagt tcgtccccag catataaaac   6840
gctttattgc gtcaccgaac attctcagca catgtatcct tgaaaaatta gatattagct   6900
tcccaggaat tttaattaaa tcaaatgtgt attccaaatt caaacactta aaatttacca   6960
acgcctttaa cccctctggc aactctctta tccgtgagat tgaaagatca agtagttcaa   7020
ttgaaaccaa ccttgaaata tctgaaggta attcgaatag tacctcatta tgtgacaggc   7080
ttaaaacttt gagagaagac atatactgaa agaagacatc agggatcctc aacttatcat   7140
tattggtaag aaataaagta aggagatgag ggcatctagg catctctaat atatctttaa   7200
tttgattttc catcaatgac aatctcctca cctttttccca ccaagcctct cgtaaacatc   7260
atgaggtgcc ccaatctttt tctcctctcc aaaaacaaat ttgattaata gtcaattatt   7320
agtgtctctg agactttggt cataattgaa ttacttgctt atgtgtgttg ttgggtaggc   7380
aattaaaaat atcaaagcgg gcgctactgg aaataatagt cggatggtga gtgatgcagc   7440
gaagcctgag gccggtatag agtcttctag aagtgaaagc cgttaagcat cgcaaaatgc   7500
agaggttgaa agctcggcaa aattgggtaa agctcgcccg tcttctgtgc ttcctttgaa   7560
tttctttgtt agtcaggagg agaagagacc aaaaactggt gagatattgt ttaacttcgt   7620
aagtaattac tagaacatta cttgtttgct actagaattg tgcaaaacgg gaacttaata   7680
catttctgaa taagtttcta atggttgcta ttacggtgct acattggtta acttcaaaat   7740
gcttatcttg gaaggtttag aattttcacc gtttgcagtt tcttatatta atcttgacat   7800
tctaattcat ttgctgttgt tagtaatagt ttccagtatt tgaattaggc tggagtcagt   7860
tgaaaccttg aatgtttatc tacatgataa agaataatgt acttttagct acagattctg   7920
tcaagttggt gaatcctggt tcaacaaaag ctctgagatt tctgctaaaa ctcaggcaat   7980
gatgtcggta gtcttgggaa atgttaagga agctcacatt gcagtcaaag gagtggcaca   8040
tttagcacat gtgaaccaag gccaagacag caaagtttgc taagaagcta tgccagctca   8100
gcaagtttgt taaacatact tttcattctg ttttttgttg ttaagcttac tgaattcggt   8160
tttgcttttg tattacgctt agtataaata ctgatgtaga ttcacttttg taataaattg   8220
agaaaagaaa aaaaagtaaa gaaaaacttc cagaatgttc atttcctttt cttggctccc   8280
aaacacattt tacagcttca agcttttagt tttcaaatag gaaatgagat agatgagttg   8340
cttaatggta atgctgtaca ttcaaaaaaa ggtcagcatc tcgaggagca gctagagaaa   8400
tcaaagcaga atgcaggttc agaagccaaa gcaaataaag ggagctcttc ctgaaggctt   8460
cttcgataat aaagaagctg atttacttgc acgtggaatt aagcctgtta aaccagatgt   8520
caagtaagta cctattctag atatgtatta atattatttc caaacctgcc aaaatattaa   8580
taaatagtaa atgcatttat agtttcttgt atggttgtgt ttctcagtgc attaatagta   8640
gtgtaaggcc tgtattttgt tattctaatg atcctaaaca cggtgcctgc acttcattta   8700
ttttagaagt gctaaagatt ctgtaaagaa attttcagtc tagagctgtg ctgagacgag   8760
```

-continued

```
ttgttgactg atttatgttg atatgctcct gctttacttt atgggttttt gtgtttacga   8820
gaaatttttt ttttttatca atagtggttt taaatttctg tgttatctgt gctcaatagt   8880
ttctatttca aaagagaaat tgcgtaattt aggattgcaa taagactatt aagaaacaat   8940
ggctgaagtc gttggaacca aatgtgaaat attgctgtta ttgtgattta agtgtgaaag   9000
ttgcatgctg gatagcacat ctaatctgtc aataggaaac ctccggtgtt aagttttaga   9060
cttcattctg agtttcgagg aaagaaggga gtagagagat atattatgat gtgtacttac   9120
accgtaatac aagggaaata tcagtgctac acctaaaatt tcatggccga cttttattga   9180
tttcccgatc tattggcctc ttctaccgtt tagatatgat ggatttattt tttttcccct   9240
ttatgtattt atatgaatct actactgata agtgcatatt ttctatttat tttgctatta   9300
atttctccat ttttttcttc ttttgctctt aaaaattcta gttatttcag ttaatttttt   9360
atttagttat tttgttaaaa ttatatttta ttatgttaat ttttatctta atttttttaa   9420
ttttgttatt ttagatataa tttggaatta aagagaaatt aaatcagagc attcagaaaa   9480
gaaatctgat tcaaagaatc agaataggaa aaaaattgaa aatttagaga caaaaataca   9540
caagagatca agaattgaaa agaattaaag aaataaagaa tattttccaa ttagaaatta   9600
tacgggccaa gcaaaattaa tcttgctcat ggaactaaaa atagactaag aaagtcaaaa   9660
aggaagccaa gtcaattaac aagctaagcc atcacataag agcaaaattg aaaaaaaaaa   9720
ggaaattgtc aaagtggcca gcacgtgaaa ggaaggaaaa taaagcattt tggctttagg   9780
aaatcatggc caatcacaaa agcttgtgca tgaggacgaa aaaggaaaac gaaagttcaa   9840
accttaatta ctaaggttgg tggcttaagc actataaaag ccaccttctg gcttttgatt   9900
tgaagacaat gggcagccac acatactcaa caatttgcag ccatcaagga gaagaaaaaa   9960
tagaggaggc agccatttaa attaatcttt atgtctggtt ttattaattc ttttattccc  10020
aatttaatta tgttagacta agttttttat ttggttgatg atgaattcaa aatccttaac  10080
atgctatgca attaattttt aatttctatc atttaattta tttaattgag attatttata  10140
ttcttctata attaatattt atgattttat tcttgttttt tttagtggcc aattagatag  10200
gacttgaaca aattctattg ttatattaaa attcttgatc cgtaattgtt ttaatatttt  10260
aatcattagt agcaggttgg aatcagtgat ttcaattgga gaacataacc tagactaaat  10320
aattcgagct tgtgtgttta ttgtctaaat caacctaaca tctttctctg cttaatactt  10380
ccattatctt aaatttaaag agattgtttt aaattattta atggttagag attaggtgaa  10440
gagtttgttt ttcctaacga cacactaaga aaagattgag actaacagaa cttattatta  10500
tctacggttg atagtttcaa tataaattat gatagaattg atatattatg tgcatatttg  10560
gtggtagcga atgattcttt gaccaaagtt ttcatcatta ttatttcttt ctcctttaat  10620
tagagtttta ttgttggtag ttttaatttc tttatttctt tctatttatt taaaaattca  10680
taaagccccc tttttattta tttataattg gtattttctt tagttagatt aatttatatt  10740
gttattacta ttattattac tagtattatt ttattttaaa tccttcctta gagttgataa  10800
tatatataac tagcataatt ttcgtgggat cgatctttac ttgctatgta ctagttattt  10860
atattagtag taaagtttta aatttgatac acccttatga cactaccaac aactctctgg  10920
taatcttgaa tttatgtcaa acctgatcag agatgagtac aaggaatatg aaaagttgat  10980
ccaagaggac ttgaaactgg tggatgacta tttagaagaa gaggaggtga gctagttttt  11040
tttccctttt accagtcgct gaaccattcc tgtcatggga tttacatgtc tggacttata  11100
ttaataatct aaaatgcact tgtgagatgc agattgatgc tgcagaaatg atagaagagt  11160
```

-continued

```
atgaatcagt ggaccaaaag taagtagcac aatgtcaaca gcagcaaaat atcatctgtt  11220
gtttgtttat ctttcttaac cttctccccc cccccccccc ccaaatcaat ctgtaggacc  11280
tacagggaga aggtggaagc tctaaggaag aagaaaatgg agtgggaagc agcttccatg  11340
acacgaccca taattgtttt acgtgtctga tttgaggcga atcgtgcgga ctaataacta  11400
aaacttgtgg cacatattta attcatgaaa atatgtttat aatatgacat ttcctataaa  11460
tacataacca cctctgtgcc ttttctgaaa tcataaatgt attcaaaact tgcataactt  11520
atgtctcatt gtacatactg acattacatg tatatttaca cataaaacat aggcaacata  11580
aacgtgctca aaatgcaaga catgcagcaa tgcgtctcgt ggcccaacct caactaacta  11640
gaactaatct gcacgaaatc ctgcggaatc ctgagaggaa atggataaat agtaaaatag  11700
ttagcttgcg gctcagtgag tggatgtaat attatattaa aaatattaac aataataatt  11760
ataataaagt atgtgtacta gtgcttatac ataatcatgt aacataactc tatattgaat  11820
accacacatg agcaaacatg gaattcatac atacatccat cacaaactgc accaaatagt  11880
acccagagga aataactctc aatactcgtc gggatcatca tcgcacgagt agagcggggg  11940
gaaaacctct caataccctg cggaatttag ctacatcact cagatagagt aacctaactc  12000
tcaatacgca tgcacagagt ctacggggac gggtacaaat atggtaacta gcaatcacat  12060
ctcatgactc aaataaacat ataatatgcg tacatgtaat tcataacatg atattaaatc  12120
aaaatatcat acataaatgc ttcacagaat acataatagt aataatagta ttaactcaca  12180
tattgtgttt cactctgggg ttcgttgggg ctcttgtaag ttcctggatt ctcgagttcc  12240
tcctaaaata caaggttcga aaattaattg ttagaactga tataaaagct tatacgtatc  12300
atgcaaactg taacataatt gctcaaattt cataaatcta ttacccactg gtttaactgg  12360
atttaatcta actatccagt tctaatttcc gtattatttc ctcttaattc cactttattt  12420
ctcacactct cggcttattc cttttcctta ttccttttct tttcttcttt tcttcttttc  12480
ttcttttctt tttcttttcc ttctcttttc tctcggtttc tcttcgtttc ttctctttgt  12540
tttgctctcg gttttccaat ttggtgaatg gaagcataaa tgagagctgc tttcaattat  12600
atccaattat atatacatgg ccaccgactc acaagtgaag catgcatgtc aaatatgcat  12660
gtgccaagca aggagggaac ttggcatgtg gagaagtggt gaagcaagca gctggctgtt  12720
gcttttgaaa tcagccacgt ttggctcttt tttttttttt ttcaagcggt gcatgacatt  12780
ccaggtcagc gaaaagcaga ggtagttctg aggttgctcg caaagaacct acaaaagaag  12840
agttatccag tgatgatgat agtggagatc tttgctgttg attggcgggc tcagcacccg  12900
tgatgtctgc ccccaaagtt tccagtagaa ctcttttcat tttttgatct tgctgtaata  12960
acttttatac aaagagtgaa atctaacgac caactggcat gatggtgcat catttgcaat  13020
ttttgttcag tttcatttgc ttttctctat ttttccacta ttaaatatgt aaatagcttt  13080
tgaatccaaa cccataacct gagtcattaa aagaaatttt gcattatctg ttatcgataa  13140
agtatttata ttgttatcca ttcttgattt ctcagatgtg gatatccatt gaaccaattg  13200
tctgtcttag ctagagtaac cagagtgcat catttctgaa atgttgtcac agaaggagct  13260
ttactgtata cgtaatcgat ggaacataac atgtaattag gccatttatc aagtaaatct  13320
gtctgttgaa aggtcgttga gggacttgct ggttggctga agaggttgtt cacagtttta  13380
ccacggactt gttgacttac atggggaagt ttcgcgttaa gttgtaagtt ggttatcaac  13440
ggattcaact caattttttta atattgattc actcgtgaca ttcatgcagc tgattgagcg  13500
```

-continued

```
atgaataatg taattggtga atgtttgtaa tctgtttgcg catctttagg aaaggaaaga  13560
tgaagaatac aaataatact ccgaaacatt ttcagatgtg atgatcattt gggatacatt  13620
tttctattct caattttgaa agaaatattt gaaaaataca agtttcattt ctcaaaatta  13680
atatttatgc ttgagtgttg atatttgacc atttaatttt tttttaataa aaaaaaggca  13740
ctcctgctgt atatatttta gggtacattg aagaatacaa attaatactt ggaagacaaa  13800
atataaataa aagtgataaa atacaaaatg caaagctata attggaagtt ccaaagagtg  13860
tagggatgtt ttgccatgca tctgaaattg aagaaatcat atcccatgct agctaatgat  13920
caatccagcc aaaagttaca tagattatta caaagaggat aaacattagt aagaatctgt  13980
actcggaata ttatgtttag caactagaac aagaaatggg aatgcaagaa acactctcat  14040
tttacatgaa gggaattaac aagatgatca attctagaaa aagcaggcca cctaatctgt  14100
ttaggaatca ctatcgaact aattgataga ccggaaacat ggacgaaaag cattttgagt  14160
gtcttgatcc tcccattgaa gctgttccca ccattttgtg tatccacgaa taacaatctt  14220
acgctctttt gcactattgg aatccagtgg aagctttcta agctcatcac aactatttac  14280
agtcaaatct ctcagacatg ggaagggcag cggcctcttg taaatgctct tcaaaacggt  14340
taggccacct aatctaagag aatagagttg tgcaaaaggc tttataattg gcatcacctc  14400
tggaaaatca gcaaatttta cctcacttat gatttcttcc atagcaaagc aactgctaac  14460
ttcaatagac ttgaggtttg gagcaaagag aaggaatgtc aagttcttca atctatggca  14520
tccgtatatt tgaatcttct cgaggctctg gaaaacaaaa ggttggcgag ccatcttcaa  14580
ttcctccaat tcttcacatt catgaatcca taatctgttg aggtgctcca gacctgccaa  14640
agctgaaaca tcaagtggct ccgagcgttt gaagctgtga aggtatagag cttgagtaca  14700
actgcgtaac ttttccgagt tcaaaacaca ttggagatct tgagaattat tcaaggtcaa  14760
gcttaatacc tccaaatgtt tcaaaccacg caatgcctcc actaaaaggt cacccccgct  14820
aaataaatcg ctgtcatttc tttttccatt aggagaccaa tcaccaactc cgaacattct  14880
taacacaact aaacatgaaa aacgcgatat tagttgccgt ggaattgtaa ttaagtaatg  14940
tgtctggtcc agattcaaac tcttaagatt ttccaaagca tttaactctt ttggcaactc  15000
ttgtattgct gtacctgaga gatcaagatg ttgtaatgaa accaacactg aaacccctaa  15060
aggaaaagaa gacatccgtc tagcacccga caggtttaag actttgagac aaggcattga  15120
tttgaagaag tcaccagtga tcatctctaa ttcttcatta aagacaagaa ataaagtaag  15180
aagatgaagg catgtaggaa cctctgatag attcctaatt tgagtttcca tcaatgacaa  15240
tctcttcgca ttttcccatt ctctgacatt tggcgcctca gttaatccag caccttcata  15300
aaccaaatag ttctctttct tcttctccgt gtcttccgtc ttctcagtgt cacaagctat  15360
ccataaagtc atatcacgaa tcacatcgtg cattttgact acatcatctc cttcctcttc  15420
taataaacac gcatgaacaa tattacccaa aatagtgtgt cctctgtctt gtaattcata  15480
tttgccagtt acttttagga aaccttcccc aatccaacaa tctatcaaat tctctttata  15540
aatccgataa tcttcaggaa ataaacaaca atacaagaga caagatctag ttgtgtcgtc  15600
tggcaaacta tcgtaactga attttaaaac acgaagcaca ttattttcca aacctggaaa  15660
ctcagaagct gatgtttgta acactttaat tgcgtctctc cattctgctg gtgttttctt  15720
gcaagccata gctcggccag tgacaataag agcaagtggc aagcacccac actctttggc  15780
cactctttcg gctagctcaa gaattttagg ttggccattc agagtttctt ccccaacatt  15840
ctgtcgaaac aattcccaag cgtcgttggc tgataagcac tccacttcaa tttttttgtg  15900
```

-continued

```
agctcccatc ctaccgcaaa cttcagtgga acgagttgtg aataccactt tggaggcact  15960
cttgtctcgg ggaggaatag ggacgcccac tgttgcaaaa tcaacccgct gccatacgtc  16020
atcaagtaac aatacaaact tcttctcctt caaaacgttg tagatgtcaa cagctctctc  16080
tgcaagattt tttttcatcc aggaatcatt aaacaaaccc accttcttcc cgataatttc  16140
ttgaattttt tcaatttgta ggtcctttga cactacaacc catatcagaa aatcaaaatg  16200
aaaatctctc tggccgagaa atttattgtt gagatgggtc agtagtgtgg ttttaccgac  16260
accgcccatg ccgtataggc caacaattcc aactggttct tctacaagac atctccaaac  16320
ttgttcaagt tgtgattgga tgcccaccgc tggctcgata ggcctttcat ccgctacaga  16380
ttctggagct ctctgagcta ccactgcaaa ggatccttcg gccaataaaa tcttgacatc  16440
gcttagcttt ttatccactt gtttgccaaa ctttttgctt gacttgcagt tcttggaaca  16500
gtagcctccg agacacagct tctcaatttc ttgagagcca attcttatca attcatctgc  16560
tcctgctgta acagcgtcca ccctcgaaag ccacaattgc acttcgttca gccttgtcat  16620
catttgttgc cgttcagcgt tgacgaccct cgccatcaca tcgtcctttt tagcgattag  16680
ttttggcaat tcatttttca aggcttcaac attttttttgg aggtttctta catatgctgc  16740
tttgccaaga aagcaatcca ggcaacgatt gaaacaagta ccatcgcacg agatcgagat  16800
ttgcaaaatg ttgcccatta ttaggataaa aattcgacaa gacaagtcaa taaaatttga  16860
acaaaagctg ctgcggattg aaatattttg tgtttctgga aatttataaa agataattag  16920
gcatgtaaca ttggtgaata ctttacttgc cttcaacatg gctagccttt cgctttaaat  16980
taaatactta acttgtaatt tgaaaaaaga attccacttt tgttttaagt ttgtgctgta  17040
tgatcttgct ttttattgtt ccgtttgtaa ttaaatataa cgtctttctt gtaccgttaa  17100
cgtttaaatg aaaaaaaaaa tcaaagtata atattacttt tgtgaccaag gtttatcatg  17160
atatttggga aaaaaattaa tatatcattt aaataaatcc ataaaataaa gtagaattcc  17220
tgtatatttt gcattaaaat agcgccatct atcgagcagg agaaataaaa aaaaaattga  17280
actcattaac aaagtatttg aaattcttta ttccaatcta aaattcttgt tcatttattt  17340
tatttacaac actaacgatg ttgatgaaca caatctgcag tggaagtgta tatcaaaaat  17400
taaaaaagat tagacgtgtt ccattcctgg cggctttaat tgccttttat aaaagagcat  17460
attgcttttg taattaaata tttagccttg aaatttgata aaagaatcct gttgttttgc  17520
ttttgtgcga catgatcatg ctctctcttg taacacaaca ttcaagtcac tagccttgta  17580
gttgcccagt ggcgtgattt ctactactgt acggttggat ttctgatatt acatcccact  17640
agaaagggag tgcttaagtt atatgtaatg tgtgggtgta aattatatta catgtaattt  17700
aatgtttatc cactaaaaat atgtaaaatt gagtaactag catgtgagat tatgtggggc  17760
catcttattt tgacttattt ttagtgggtt gagagttaca ttggtgtaac actgtaactt  17820
aaggagactc ttgaggaaga ttctatgaaa aattggatta tagaaacaaa aattggtttt  17880
taggaacttt caactgcaat ttttttttta acacacaaca gtttatttat taattaagag  17940
agacaaaata tatagataca gataaagaaa atctcttgca tatatcaaga gattgtacta  18000
gttaaaacaa acttatattc atataattaa catgtaataa aatatacatc tttttattga  18060
ataaaacata atacgaaaga aaacactaca tgcatttaac cagtataatt aaaaaaaatt  18120
tcatattgag ggactacaag aaataaagat tgtcatcttt tatgtcctcc tcatcaacaa  18180
tactaaacac acgatgatac ctccaaccct ccaacccatt gatctttctt gcgcgaggag  18240
```

-continued

```
tttccatata ttcttcaaat tagaaaggga aagttctcgg ctagcttctt gtgaaccgta  18300
atcaaaagta agtagtagag cttgagcgag ttgttatttc tgctggtttc atatgatgtg  18360
tagatcacgt gaccaacaat gccatggtat tgattatgaa tcaacggcac ggatcagcgg  18420
ctgaagtttt attatccata aaattgccaa gattaagggc tatggctagg gttaaaagat  18480
tgcgatgagt ccgaaatatg tatgggctgg tccaaaataa tatcaaaaac tgcacaaaca  18540
aagtgaatag acaacggatc aacaaatgtg aaacatattg tctgatctgg tccacaatgc  18600
tatcggtaac atttttaact tgcgaacaaa agcaaagcaa taatgcatgg tatagacaat  18660
ggagcaacaa atgtgaacat atggcctgat atggtccaca aaatatataa ttgtcaaaaa  18720
gaagacgaac aaaaagaatc aagccattgc gagccttttt ctcatggaag gaccagacca  18780
accaacttct taaacaagag ttggggacaa ccataccgag ctctcctgga ccagcagcgt  18840
atctccttta gttcctttaa attgaaataa aagcagagaa agcatgatca tgtcgcacaa  18900
aagcaaaaca acgggattct tttatcaaat ttcaagggta aatatttaat tacaaaagca  18960
atatgctctt ttataaaagg caattaaagc cgccaggaat gggagattgg gacatgccta  19020
atgttttcaa attgcctacg aaggcaaaaa taaccaagat tcttttatta actcttttttt  19080
ttcaaatgaa aagaatagga ataagaaaag tggtaggcta gtttattaaa ggcaattaaa  19140
gccgtcagga atggaacgcg tctaatccta ttttaatttt atttaagttt ttatatacac  19200
ttccgctgca gattgtgttc atcaacatcg ttaatgttgt aaataaaata aatgaacaag  19260
aattttagat tagaacaagg aatttcaaat acttagttaa tgagttcaaa tttttttttg  19320
atttctcctc ctcgatagat ggcgctattt taatgtataa tatacaggaa ttctacttta  19380
ttttatggat ttatttaagt gatatattaa tttttttccc aaatatcatg ataaaccttg  19440
gtcacaaaag taatatcata ctttgatttt ttttttaatt aaaaagttaa ctgtttaaga  19500
aagaagttat atttaattac aaacggaaca ataaaaagca acattataca gcgcaaacgc  19560
aaaacaaaag taccaatggg ccagtgcaag gttcgactta gaggagtaca tgatagaaaa  19620
aatgtctcaa ttgtataatt tattaataca gtatcaaaaa aaaaagcaaa acaaaagtag  19680
aattcttttt tcaaattaca agataagtat ttaatttaaa gcgaaaggct aacccgttga  19740
aggcaagtaa agtattcatg aatggtacat gcctaataat ccttttttata tttacagaaa  19800
cacaaaaaat tttcaatccg cagcagcttc tgctaaaatt atcttggatt tttagttgat  19860
ttctattatc caaaaaaaaa aatgggtaac attttgcaaa tcgcaatcga tggtgctgtt  19920
ttcaatcgtt gcatggattg ctttctcgga aaagcagcat atataagaaa cctgcaagaa  19980
aatgttgtag ccttggagac cgaattggga aagctaatcg aagcaaagaa cgatgtgatg  20040
gcgagagtcg tcaacactga aaggcaacca atgatgacaa ggctgaacaa agttcaaggc  20100
tggctttcgg gggtggacgc tgttaaagct gaagccgatg aattgataag acatggctct  20160
caagaaattg agaagctgtg tctcggaggc tactgttcca agaactggaa gtcaagctac  20220
aagtttggca aacaagtggc taaaaagcta agagatgccg ggactttaat ggccgaagga  20280
gtctttgaag tggtagctga gagagctcca gaatctgcag cggtgggcat gcaatcacga  20340
cttgaaccag tttggagatg tcttgtggaa gaacccgttg gaattgttgg cctttacggc  20400
atgggcggtg tcggtaaaac cacactactg acccatctca acaataaatt tctcggccag  20460
agagattttc attttgattt tctgatatgg gttgtagtgt caaaggacct acaaattgaa  20520
aaaattcaag aaattatcgg gaagaaggtg ggttttttta atgattcctg gatgaaaaaa  20580
aatcttgccg agagagctgt tgacatctac aacgttttga aggagaagaa gtttgtattg  20640
```

-continued

```
ttacttgatg acgtatggca gcgggttgat tttgcaacag tgggcgtccc tattcctccc  20700
cgagacaaga gtgcctccaa agtggtattc acaactcgtt ccgctgaagt ttgcgtttgg  20760
atgggagctc acaaaaaatt tggagtgggg tgcttatcag ccaacgacgc ttgggaattg  20820
tttcgacaga acgtcgggga agaaactctt acgagtgatc atgatatcgc tgagctagcc  20880
caaattgtgg ccgaggagtg tggtggtttg ccactcgcac ttattactat tggtcaagct  20940
atggcctaca aaaagacagt agaggagtgg agacatgcaa ttgaagtgtt aagaagatca  21000
gcttctgagt ttccaggttt tgataatgtg cttcgtgttt tcaaattcag ttacgatagt  21060
ttgcccgacg acacaactag atcttgtttc ttgtattgtt gtttatatcc caaagattat  21120
ggcattctta aatgggactt gattgactgt tggattggtg agggattctt agaggaatct  21180
gccaggtttg ttgcagagaa ccagggatac tgcattgtgg gcactcttgt tgatgcgtgt  21240
ttactagaag agatagaaga tgataaagta aaaatgcatg atgttgttcg ttatatggct  21300
ctatggatag tctgtgaaat tgaggaggag aagagaaact tttggttcg tgcaggtgct  21360
ggattagaac aggcaccggc tgttaaagaa tgggaaaatg tgagaagatt gtcattgatg  21420
caaaatgaca ttaaaattct gtcagaggtt cctacatgcc ctgatctcca tactctattt  21480
cttgcctcta ataataattt gcagaggatc accgatggct tcttcaaatt tatgccttct  21540
ctcaaagttt tgaagatgtc acactgtggg gatttgaaag ttttaaaatt acctttgggg  21600
atgtcaatgt tgggttcact agaacttctt gatatttcac aaaccagcat aggagagtta  21660
ccagaagagt tgaagttgtt ggtaaatctg aaatgtttga atttaagatg ggcaacttgg  21720
ttaagtaaaa ttccacggca actaatatca aattcttcaa ggttacatgt gttgagaatg  21780
ttcgctactg gctgttcgca ttctgaagca tcagaagaca gcgtttttatt tggtgggggc  21840
gaagttttaa tacaggaatt gctcggtttg aaatatttag aggtattgga gttgaccttg  21900
cgaagttctc atgctctcca attatttttt agctcaaata agttaaaaag ttgtattcga  21960
tctcttctcc tcgacgaggt cagaggtaca aagtcgatta ttgatgctac ggctttcgca  22020
gatctaaacc acctcaatga attgcgcatt gattccgttg cggaagtgga agaattgaag  22080
attgattata cagagatagt acggaaaagg cgggaacctt ttgttttcgg cagccttcac  22140
cgtgttactc tagggcagtg ccttaaattg aaagatttga cattcctcgt ttttgctcca  22200
aacctcaagt ctctccagct actcaattgc cgtgctatgg aagaaataat cagcgtcgga  22260
aaatttgctg aggttcctga ggtgatggga catataagcc cttttgaaaa tctccaaagg  22320
cttcatttat tcgatttgcc acgtttgaag agcatctact ggaagccatt gcctttcact  22380
catctcaaag aaatgagggt acatgggtgt aatcagctta aaaagcttcc actcgattcc  22440
aacagtgcaa aatttgttat tcgtggagaa gcagaggggt ggaaccgact tcaatgggag  22500
gatgatgcca ctcaaattgc ttttcgttcc tgtttccaac cttatccctg agcggtggtt  22560
gcaacatttg atttctggtg agtgcatttt tgttaacgct tatatatata ccagtcattt  22620
gcttcgtgca aaagactatg tcttttgttc tctgttttta ttccagtgtg tttttcttct  22680
ggcttctgca aatcacaatt aaatgttgaa taatatggaa tcaatgcttt ataaattttc  22740
cggcgcggcc atttcctttt ccctttttat tttttttggg cgtgggtcga attgatgctc  22800
tagtttttta ctttttgtcg tcaactttgc tctggttttt caaattgatg cttgaatata  22860
tgaatttaat tgccgtaaaa ggatataatt aggctgaaat tcgcacttct agaatgaata  22920
gaattgaaac agagaaaata ttaagcacac tagccctctt taaacccctt ataatttctt  22980
```

-continued

```
ctgttctaac gataaccaaa tcctttgctc taaggattga taatagtcca ccaaaataat  23040
gaacgcttgg atgctgcttt aagggtctct aatcaatagc tggaagcaaa tgagaagttg  23100
gtcacaactc tgtaaaaagc catgcagcaa ttgctattca tcttaataat tatgaagctt  23160
ttgttaaatt ttcaaacaaa gttgacatgt tattttgaga tttggttcct gattttgtat  23220
gaatatcatt gcttggtttg agttgggtgt gaattcaaat tcaaatattc tttgtttttc  23280
aattctgaac tcaatttctt tttctcatgc atgttatgca gaaatgattt ttactaaata  23340
atttttgata aactatttaa attaaacaat tggattaaca aattgtgacc atttatcata  23400
agcgtgctaa tataataact tgttttatga acgattagtt aatccattaa tattaaaata  23460
tatattagtc agttagctat gtgtaacatt tgtcatgttt aaaaaattat ttatttatat  23520
ttcaaataat gtttaaaaaa ttattcattt cgggttcggt tcgggttagc gtacgaaatc  23580
taatcgggtt agcctatata ttcacacaca tatgctcaaa cgttgcttcc tttccttcaa  23640
atccctaatg cctcttcttt gcgctttcac atttgcgctc cacaacagca cagccagcac  23700
gtagcagtga gcacagacac tcacacatga catacccatg tgccgctgcc gctgttgatt  23760
ccgttcagag caccgacgtc gcaggcttgc agcttctagc ccttcctcct cccttgagtc  23820
gatctggttc ctcattcaag acttcaagct actgtcgcct tgagccaatc ttgaatcgtt  23880
tgcgtctgct cagtctgctg ccgtcactgc ctccagcttc attcacggtc gtcagctgca  23940
caagtttatg tatgcggttc caaatggtgt atgaatggtt gtttgtaaat caatcttctt  24000
ttgggcatgg gtaagaggca ttactggcac tgaaactgtt caatcttctt ttgtgtaacg  24060
atggttgttg ttttcaacag attttggggc aagaaaatcc aaaatcaatc ttgaacaatg  24120
aatttatatt ttttgggaag atggggtacc tcactagtat gttgtgtgcg gtgcggtgta  24180
actgaaattc gggggaggtg agaaagggag agagagtggt aacaatggtg aaaggtttag  24240
aactgagagt ggtatccttc gaaataggtt ccacacctgc aaaacagtga aatagaggtt  24300
agaggtgaag ccggggtacc ccggcgttca cactccgacg ctcaagttag caaactcaag  24360
cttttgtggc aaagagagct agctagccct ctgtaaatta gggtttaagg ttgaagaaaa  24420
cctctttttt ggagtgtgag tgtttttggt gagtgagagc ctcctggaga atgaaaccta  24480
ggcgccttta tatatggagt aattcagctg ccacgtggcg taccettttt ggctaacgtc  24540
cttttacctc tttataattt tttttgggcc gttatctgca tgttcgcggc gtatcccatc  24600
ttttggaaac gtggcacgcg ctggagagtg gtccagggta cctctgcagt agctgtcggg  24660
taggcggctg gggaccactg tccttgggaa agtgtccttc acttttggca gaggtagcag  24720
gcggctgtcc ccccctttg gtacgacgtt cttgattcat aattctgaca aaatcgaata  24780
atatctttta agagatggag acgtttctca tggcggatat tttcggagga ttatcttgca  24840
tccgctttgc cgggtacctc gagttacgtg gggtacccct attacgcggg gtacccctat  24900
ttgtatgggg tacctctatt tgtatggggt acctcatatt atatggggta cctttatttg  24960
tgtgggatac ctctaattct gcggggtacc tcaaatcacg ccgggcacct cggatcgtgc  25020
ggggtacctc ggattgtgct ggaaccattc cattggtcga cacgtggcgc ttcactgcct  25080
ttcctatttt tccctcaaac agttgtaatt gttcctgatt cggtttctta acattgaaat  25140
ttttgttgta ttgagtgtta atggtgatgg gtattaatgt attatatatg ttgtcatttg  25200
gtgtcatttt tgctttcatt tttgcatctg gagttgggct ggtgtttggt tttggaattt  25260
taggcgctgc ctgggtggga ttgattcatt ttgaaattga attaaatttt ggaagaggtt  25320
gtcacccgaa ttagaatcca aaccaaaatc ttgacttgaa ttttgaatcc gatccaaccc  25380
```

-continued

```
gaaattcgaa ccaaattggt ttgtgtttcg aacgcggatt gggttgaatt ctccaaccca  25440
aatgggttgt aacccaagcc gaaaccgaac aaccaaactg aaacccgatt tgtccaccat  25500
taattttttt cattcaatta tttttgttct agaaaaatgt aagaaatatt gagaaatgtt  25560
aagagctata attttgaaac tttgcctaaa attattatca ttacttattg tttcttattt  25620
aaggagatcc tggaagcatg aaatgattat tctatggcgt aactacaaca agagaagagt  25680
agagataatt tgtagtaaat taattgatca ttttgatgca aatgattccc tattaaaaaa  25740
ttcaagtcag agctgaattg cacagccgtt agtcgtgctt gcacttcgaa ttaagtgttg  25800
tattttccgc ctggtttggt tgattaaact atgtgcattt gcataacgga gatgcttatg  25860
aatgttgtag tatagaaatc gaagcatctt gtcttctgcc aagcccagaa gcaaagttct  25920
ttatattgta ctcatcactt ttattcgttc tcttcgttga aattttatcc aaacaacgat  25980
ttcttcttat ttatgccttc tcttacactt ttaaatctat caaagaaccg ctactcggga  26040
agattgccat cgggaaattc gaaattgatt tcactacaat accttaatat ttcagatact  26100
tccatcactg agttggcaaa agagctaaaa gccttggtaa atcttaagtg tttaaactgg  26160
agtacacaaa ttatctctct acaatgctga tttgttactt ttcaatgcca catgttctgc  26220
gaatattcgg ttttggttat cttgttgaaa caccagaaaa tagcgttcta tttgtggtag  26280
tgaattcttg gttggggtgt tgcttagttt aaaacgttta aatgtattaa gcatcacctt  26340
aaaaggtttt tctgctccaa aaacttataa gctcccaaaa gtttcaaagc tgtacaaaat  26400
gtttggagct tatagactgt gatgattcaa agttgtttgc cttggcagag ttgaagcatc  26460
ttgaaaaact aggtttttca aattttggaa atttggaaga gtttaagttc tgctgtgtcg  26520
aggctggaaa agctcgagaa tgttttatgt tttcatttga acagccttca ccgagttaag  26580
ataaaggctt gtcataaatt gagagaagtg acatggcttg tatttgctcc atatcctaag  26640
gttattcaaa tagaaaaaat gtatggagat ggaaaaaata atcagtgtaa ggaaattggg  26700
tgaagttcca gagatgatgg caaacctata cccttttgca aaactccaat cccttggcct  26760
acgagttcta ccaaaattaa aaagtgtcca ttggaaggag ttgccctctc cacatgtcag  26820
ggaaattttt gtatctgaat acccaattct caagaatctt tcaatcggtt ttaacaatgc  26880
aaaggaatct aaaattgtca ttgggggaga ggaacactgg tggaatgagc tgcaatgggg  26940
ggatgaagcg accctcaatg cttttctttc ttgtttggat ccatttgacg ggcatcaaca  27000
tggattgata ttttgctgtg gacaaattcg aataaaattt atggtaagtg cttctccatt  27060
tattgcatgt ttatatctaa cttttgtttt cctttgtggc tgaattttac tccatatctg  27120
ttgttgtacg gtgacattct cgtttcaatt attagctttt taattctctt ctcacattaa  27180
ctacccttct aatcatggag gatatgccga tgtcaaagag tcgtaatttg ggacacaaat  27240
gtaagaatta gacagatgac atgttgtttt gaaggtctca aagtactagt gaaattagga  27300
gattaagggt gcgtttggga ttgaggttgg gtagttgtag cttaaaagct acagcactaa  27360
agtgtttggt aaacactagc tgctgtagtt tttaagctat tttgatatga tttttcactt  27420
gtataatata aaatttatta tatctttaat aattttatca aaattattat ttaaaattta  27480
tttttactat atattattaa cttttgtttc ataattacag cttttttttc acagcagtta  27540
taccttaaat gctatatcac ctcaatccca aacgcaccct tattaataag ctcctcgttt  27600
tgaaaagtac cccagtttaa ctgatgatgg tccctttttg ggattcttct ttcgctaggc  27660
tgcaattcgg atatgtacat aatagacaat cttttgtggg tttagcatat cttctctgat  27720
```

-continued

```
tttgtcttct attccccaat tttacaatta cccaccatga atgttgggtt gattgaacag  27780
aaaattgttt tagaacaaaa gcattgtgaa ggagtttcta cgctataagt tagtggcttc  27840
tgttttattg gcgttaattg agtagattac gtgttacagt gattcaattt gtgatccaga  27900
ctttgctttg attttctctt ttccctaatt atttatgtca aatttaactc cagaagcatg  27960
taccgatttt ttttcttttt gtatttattt gtgaagttta tttggaatgg aagtatctgg  28020
gtttaacaga ttaaattatg acattgagga gaaggcacta aagggtttgc ttgacacatt  28080
tggttctatg ttaactctgc aagaaatagc tttttcttat tgcaatgcag ggggaaatcc  28140
cgatttgact ggtgaatttt tttgtgacaa actggcaaac acctcaacct cttctgttca  28200
tccttctgct ggtgaggcaa ggggtaaaga gtcttcaaaa tcatcaaata gcaacatctc  28260
tgagaattta tttatgcaaa tggaaaatct agaccttcta aggcaaaatg gcgtccggta  28320
tctggaggta ccatttcaag ttttcttagt aaagattatg tttaacctac atagcaagct  28380
aatggcactt ttctagcatc aaagccattg tagttggatc caaaggagtt tcccatgtct  28440
gtactttgta gagaagaaac taaatcgaaa caatcaaagg atgaccattt gtagagggat  28500
atggaagatt ttccgtttaa attgctagga gaaggcttcc agctgaacaa ggatgtgatt  28560
aaggaagttc tcggtaatgt cttaaatata tttatgccaa tttaatacat cttgtccttt  28620
tcattgttct ttctttcttt ctcttctttt attcttcatc ttcttcttct cctcctcctc  28680
ctccttctcc tcctcctcat tctttttctt tcttttcgtg tgcaagtgat cactaattta  28740
gtattataat taacttgcag atagttgtgg atatgatatg caaaaggtaa ggactatatc  28800
ttcctgaatg aggcctctgc tttttccctt ctatgtaatt tggcaaatcg catcttcctt  28860
tgcgatagaa actcaaatat ttgtgtcggg cagtcgagaa acctaagaga aaatgaaaga  28920
aaatctcata atagaaactt cttattaatc aaatgaatac agcttacata tgtatatagt  28980
aagagagcca agcttgttat agatcgttag taatttgtta catgcaagtg atacaactta  29040
aatcaaaata actaactaag ccacgtcagc tgagcaagct atttagctgc tattagatgc  29100
acaataatag catatactcg tttcctctgt ttcttcacat tttattaact tcactaacat  29160
cccttcttga actggagttt cttcttttct tattacttcc ttcctctgct cttcacatat  29220
tatcagcttc actagcatcc cttttagagt tggagtgtat aggttgaaca tttagcttac  29280
tgcgcaagta atgaaattga gtgaaagtga gagccttagt taagacatct gttgttcgat  29340
cttcactcgg cacaaaacaa actgttattt cctttgatgc caccttatct ctgattaaat  29400
gaatgtccag ttcaacatgc attgtttttg catgataaac tggattataa gctaaggcaa  29460
ttgcaccttg attgtcacac cacataagtg gtgttgtgct tagttgaatc tgtaactcag  29520
caagtaaaga ctatatccaa ataacctctg attagggatg gtcccctccc cattgccatc  29580
cctacctctg atgcagcatg ggccaaagct ctatattcag cttatgtact tgaccttgag  29640
acagctgact gtttcttgga ggaccatgaa ccaagctggg tatcatctcg atcacagacc  29700
caatttgagt cggagaagca gtttatttgc atagctccat gttgtgcaaa ttttaatgta  29760
ttcgcaagcg cacgaatcta ttgtagtata gactaatggt gacgagtgtc gatcccacga  29820
ggaggtggat tttaattgtg tatagaacta attttgtgaa tgggtggttg gattttgtgg  29880
tgaaggtgac ttagattatt ctaaaattgg aattgaaatg gcaagaataa attgaagaga  29940
aattctatta aattgacgca ctttggtatc tgaatccgta tcaacatgca tcataggcta  30000
aataatccgt attaatgccg attaaatcat gagggggggaa tccacacctc atgaaccaag  30060
ctctaatcaa tatggtgcta agggcttatc gtgccaaata ataataacct tatactagcc  30120
```

-continued

```
tactagggag ccggtgaaac caggacggta ctagacaaga ctattattat ttgtcgacga  30180
gaagtcaaaa catccacaaa aactagaggg gaaaagaaaa taaatttacc aaataaagct  30240
tatgacacat gttgagactt caccttcaac ccaagcttga aagaaaatta gccactcata  30300
attgaactag gggcaaaatg ggaatttatt aaaatacata gaaaatacaa gatggagaag  30360
gaattacaga aaacagagtc caaaaatgga ttcagaggtg ccaaattagg gggggagagg  30420
tccctttttc atagatacat cgagtaaatc atggccatcg gattaaaaac agtttggatg  30480
ctcaggattg cgccacgtca tcagtcaaca gtacgcgtca acagtaacac ggtttgacca  30540
cggtttgaac agtaacgcgg tttggttgaa aataatccca tgtgttgcat gtaccgtacg  30600
cgcatttctt ggtccactaa tatgctgcca cgtcaccatc aacagtgtat aagaatttta  30660
gtccaatagg atcatgacac ctcatcaggc aatgccacat catcggtcaa tgccacatca  30720
tcgatccatc tatgtgaaca atgccgtgaa cagtaacgta gacagtaccc gtacatgtga  30780
atagtaccgt atatgtgaac agtaccattt tttcttttat gctcctccta aagttttcga  30840
ccgtcctgag ttcaaaaatg atgcctgttt tgccgtttga tctctcattt attgtgaaat  30900
gactatgata cccctaaaat acacaaaata cttaattaaa atcaaacaca cataattaaa  30960
ttacaaaaag cttaaataca taaaagtaaa ggttgttagt aagacttgaa atgtaaaata  31020
acaattttct cctttataaa tatacatttt ctaacactca acactccaca attgtaaaat  31080
tggagttcaa aatgaattgt gccttttaga tatcttaata gtcttttgca agcctctcaa  31140
tgtgaaattc taggattaga tagaaattaa ctaagtttac tgacagtgaa tgctatctct  31200
ggtctaggga gagtaactta ttgtagtgcc ccaataatgc ttctatattg agaaacatta  31260
gtaatgtcag tacctgagtt tttagtgaga tactgacctg tagacatggg tgttggtatt  31320
ggactacaat tagtcaagtc atgtttggcc aaaatgtcag caatgtatta gcttgtgata  31380
aatgaattct ataatgaagt tttgaaactt caatgcttaa gaaataactg agttctccaa  31440
gatcttttaa ggcaaaggtt ttctgcatat catgaataac ttgctaaact tttgttgagc  31500
tatagccagt ggtgataata tcattgacat ataccaacac caagagcaaa tgatcaattt  31560
ctctcctgta aaagagtgaa ttgtctgatt tagaatttta aaaatgccac taagaaacca  31620
tggatgtttt gaatctagca aaccaagctc ttggagcttg tttcaagcca tagataactt  31680
tcctcaactt gcatgtgtgt tgaggtttat gaggattaat aaaatcctca ggttgtgcca  31740
tatagacttc ctcatcaaga atgccattta aaaaggcatt gttcacatct atttgcctaa  31800
gagcccaatt attcatgact acaatactta gaactactct gacagtggaa gcttttacta  31860
ctggactaaa ggtttagatg ttgaaattgt tgctaaagga gcttgaagtt gaataacaaa  31920
agaggatgaa gaggaacgct caaaatttgt ttgagaagat attgtgattg aaaagtctat  31980
accatggaca tagggaaatg atttttcatt aaagaccaca tggttagaaa tgtagactct  32040
cctagatgag tgaagacact gagaaccctt atggtttgaa ctatatccaa taaaaataca  32100
catgctagtc ctgaattcat atttgtgtct gttataaggt ctgagataag agaaacatgc  32160
acaaccaaag attctgagac tagagtaatc tagtttttta tggaaaagtt tctgatatgg  32220
tgaaatattg tgtaaaactg gtgtagaaag tttgttgatt aaaaagatag cagtatgaaa  32280
ggcattccac caaaatttta aagggagatg tgcttaagca agtaaggtaa gtcctacatc  32340
aacaatttgt ctatatttgc tttcaatcat accattttga tgatgaatat aaggacaagg  32400
atgcctaaat tgtatccctg agttgttgag taaagatgaa aagaatctga atttcccacc  32460
```

-continued

```
cattcagttt gaactacttt aatattcctt tgtaaatgtt tttcgataaa agtcttaaat  32520
ttgacaaaca ttgttagtgc atcagacttt gaacttagtg gaaatatccg agtaaactgg  32580
ctgaaatcat ctataatgga tagataataa gcataacctt gggtagaagt aacatgtgaa  32640
ggtcccaaaa gatctacata aagtagttaa aaaggttcta tagatttaga ttgaacagag  32700
ttaaaatgta acatacgatt cttaccaaat tggcaagcat cacagaattc taagttttgg  32760
aatttttta acaccacaaa acgtattaca tgagtttagg attgttttca agacatgaat  32820
agtaagatgc cccaatattt tatagagaag atttacaaaa aacgaacaag accttttatt  32880
ttcgtgagag gaatttgaac aaaacatttc acaagttgaa tgagaaagac aagcaaaaag  32940
agactgaaaa tcaagatagc caaaagaaca tgccacttga aaatcaagag gagcaacacg  33000
aagaaataaa tgcggagtaa aatgaaggta ctttctcata cattcccaaa gagtggatgt  33060
atatttcttc tcaccttaag aaattaattt tgaaagatcc atcacaaggt gtaactacta  33120
tatcatcact taaaaatata tgtgagcatt tgtaataacg gatttaatca cttgttcttt  33180
aactcataat tatggctttt cttaatagtt atgttgattt tgatgatcta tatattggca  33240
tatgttgatt ttgatgattt atatattgcc attacatact tatgttttta cttaagtttt  33300
gatgataaag aatgtgcatt gatgattaca ttgtatttga tgaagctttg atcttatgca  33360
atctatgatt agtgaatgaa tgcatttttt gtactttatc gatgtattgt tgaatatgtc  33420
ttacttattt taaatgatat cgaataaggg agaaatacat atacttcgag aattttaagt  33480
atatgagatt ttttttgtta tattgaatgt cacattagat atttgatgag tttagttgtc  33540
tttatttata aaatgtgatt gataattatg gagcttgaat atttgataat atacatgcca  33600
atttggtaaa gaaatcaaaa cctctttgcg aagaagaatt ttcaaaaatt ctgcataaac  33660
ttggaatgat ttgatttctt gatgattttg gtaattgatg attatatgtg cgttgcttga  33720
tgaattgaag gagttgttgg ttggttatta ttgtttaagc ttatatggaa gtgtttttaa  33780
ccatgttgtg tatttgagaa tttgttcatt tttaaggggg agacaaatat aatatgtttt  33840
tggataaaat catttcggtt aactttttaa attggccata tatttagggg gagcatataa  33900
tatgattttg gataatatgc attttgattt tttttttgt tgtccaaagg gggagacaaa  33960
ataatatatc attttgatgt tattaaaagg aggagaatat tatgcatttt gagtaattat  34020
tttgattatg gtgatgattt gatgtttttg agatatgatg attacatggg tgttttatat  34080
gataatttca tgttatgagt tgttgatttg gtgattaatg gaataatggt tcatgatatt  34140
ttggtgtgat gatttgtgta tggagttggc ttttatcatg atctataata atttgggagt  34200
aatattacta atcttgtatt tgaggtaatg cttgttgtta gggggagatt ctttcaaaat  34260
ttctactcaa acaacatggg taacaaattt gctactttta ttcttttcct ttacgctttc  34320
ttttttata atgaaaaggg agaagaatac atgttttcaa acttataaaa atttgctact  34380
tttttctttg ccaattaagt ttttcttttt gatgatgagg gggagaaaaa tccatgtatt  34440
taaatttgtt aatttagcta attggcaaat tgtaaaagaa tattatattt aggagcaatt  34500
tgtggaatca ttctttaaat acatgaaatg tttgtcatca tcaaaaaggg ggagattgtt  34560
aacatatatg ttttcataat attgattttg atgataacaa acaagattaa gaatgattaa  34620
tcttttaagc tcaaattatt taatattctt tttaaataaa tcattatttt cacattataa  34680
atgttttata tttaatggaa aaatgatttt atgaaattga ttgtttttat tatttttaaa  34740
taaatcatta ttttcacatt ataaatgttt catatttaat ggaaaaatga ttttatgaaa  34800
ttggttgttt ttcaaaattt atggtttaat tgaaagaatt tttgaaactt tgaaataaac  34860
```

-continued

```
aagtattgct tgaaattgtg gaaaaggact tttttgaaaa gtgtcagcat tttgggctat  34920
accataattt cagaaagtgt tgggattaac aaagcattac ttagaaattc tgaaattgga  34980
cctatttgta aagtttcata acgttttggg tcatactata gttttgtaaa gttttggggt  35040
caaactataa ttttagaaaa taatttcact gtagcaaacg gctaaccgat aatttccaga  35100
aagcatgttc tgcataatat tgttaaaatg atgattctag aacataacga tgaaccgttt  35160
actgaaaacg gttaaccgat tattttcata ttgctaatct tgaactgttt agtaagaacg  35220
gttaaaccaa atttgttttg caggtctctg gaatttaacg gcgaaaggaa aatcctaaac  35280
ggtaaaccgt ttatttaaaa attggcccaa cggtaacttt gaccagccta aacggttaac  35340
cgttaatggt taacggtgaa ccgttttcta gcagacagtc tataacggct agtttttcag  35400
ctccaactat aaataagctc aatccaattc aaacaagaag ttttccaacg atcatcattg  35460
agcaaaatat tgagaataca actttcattg agatttaaat ccttgtattc atctaattca  35520
ttcacacatt gagctttcac ttgtgatcaa acacattgtg tgtgagacat tcatttgtaa  35580
tcctttttgt aaaatcaagt taaaagattg taagtgttgg gatacacttg gattaagaga  35640
ttgggaataa tctcttgttg taaaggtcca ttgacacctt ggaagtcaat tgtaagcgtt  35700
tgaagccttg agaggttagc ttagtgaaat cctcaagccc agtgagcttg gaggcgtgga  35760
cgtaggcggg gattgccgaa ccacgtaaaa atcattgtgt ttgttttctc ttcccttact  35820
cttttaatat tgtgcatgat tgaatttatt gttttcaatt tgattaaggc aatagattaa  35880
attgttgtgt gatttgtcta gaataatttt taaaatccca attcaccgcc cctcttgggt  35940
tgcctagtta gtatttcacc agaggtgtaa ttaagaggag tatagccagg gataaaggca  36000
ggatctgagt atgccatatt ggcttgaaaa gcatctactc ttggcatata ggaattccta  36060
aaattaggtc cacaaaatgc tgaccctctg ccaaaaccat taaatgatct gcctctacaa  36120
tattgacctc tgaaatttcc tctaccaaaa ttcttctgag gaacaaatga aggataaaat  36180
atgttcttgc atctatttgc tctatgtcta ggaatgaagc aaatttgaca gataacattt  36240
gaaaagtttc ttccaccaac aaattgagat gcattatcgt taaaaccacc accgaaattt  36300
ggactatcac ttccaaaatt gcctctagaa tttttctgaa atccactatt atttttacca  36360
aagtatgaac ctttctgagc tacatttgca gacatatgat gcataacatc actaacaatt  36420
ttgcctttct tttgttcaat tctattttca taattgacaa gtagttagta caaatcatct  36480
aaggtaatag ttccttctct ggctagaaca acagttatta aagactcata gtcagaggag  36540
tcaagaccag tcaacacatg cataataaaa tcattcaact caactggttt ccctactgag  36600
gctaatgtat ttaatatacg tttgatttta gcaaaataat cacccataca catagatcat  36660
ttttttaata gtttggattt gcattctaag agtttgaatt cgagcttgac attgagagat  36720
gaacatattg ttaagtgatt cccaaagttg ctttgaatat ggatgacaat ggggagggga  36780
ccaacatccc cgcacccatc cccgatgttc ttcatatatc ctcatcccct cctcgtcccc  36840
tccccgaata ataagagggg atccccaaga gtccctgatc cccgaataat tgatacattt  36900
ttaatttctg aacttgattt aattatatta aaataaaaat ttaaacaaag gtaaggtttg  36960
acaatatatc ttagattaac attaattcat tttaaaaatt acactacaaa atacaaatca  37020
ttagaataat tatcttcctc aaccttcata atcctataat aaaaagaaat tactcttata  37080
tcaataatga aataaatgaa atgggtagag atactgaaat taatattttt aataaaagca  37140
tttactcttg tatcttatac ttatcttatt ctttctcgag gaatattgga aattgaaaga  37200
```

-continued

```
tagcatcaga tttcaaatct aaaaaaaata aaaatagtat aagcaatatg actcataatc  37260
taaaatagtt ttgggccaag acctttgaaa taaagtatgg tcaaatagta attcaggact  37320
acaactagtt aaccagcctt gaaatttttt atagtagatg tgtataaata ttttgatatt  37380
tgttatttat actaatattt aacatttttt aatttaaatt ttattattca tttattaata  37440
attctaaaaa ataaaatcaa aataaaaaat taatatgagg aaatggggaa atgggtaggg  37500
gatgaggatt ccaactcatc cccgtccctt ccttgaataa aagcctgggt aaaaaatcgt  37560
ccatgtccgt tccctaaata agaaatttgg tataagatta tcctcatacc ctccccgaat  37620
agggaaaatc cccaagggtc cccgtcccta tggggatttt taccatcctg cctttgaagt  37680
tgcacaatca atcacagttg acaataagct ttacatcatc tagcttaaga gaagttgatt  37740
tgttttcatc caagcaatga acttaggatt tgcagatctt aatttactta catatgattt  37800
tgaagcttca ccagtactgg taagtgaaag aaactgctct ggacacttca gaccgccatt  37860
aatgaaacct tctaaattgt ttcctttgat tgatgtcaaa acttgtgttc tccacaaaat  37920
aaaattgttt tgacccaatt ttacaggtgt aacaaagata taagataaat tggagtgagt  37980
cacgtttgcc aatattggct ctgataccat gatagaaact caagtatttg tgtttggcag  38040
tcgagaaagc aaagagaaaa tgaaagaaaa tctcataata gaaacttata gaaacttctt  38100
attaatcaaa tgaatacagc ttatatatat atatatagca agagagccaa gcttgttaca  38160
gattattagt aatttgttac acacacgtga ttgttgtgca aattttattg aactcgcaag  38220
tgcatgaatc tattgtataa tagatcaacg gtgacgagtg tcaatcccac gaggaggtgg  38280
attttaatta tatgtagagt taattttcta agtgggtcat tggatttgtg gtgaaagtga  38340
tttagactat cctagtattt aaattagaat ggcaggaata aattaaaatg aaaactatta  38400
aaatgaagcg tttaggtctc tagatttgct atcaacatgc actatgggct taatattcct  38460
tattaatgcc aattaaatta tgagggagat ttccactcct tatgagcctc actcaaataa  38520
atatagtgct aagtgcttat cgtgctaaat aataataatc ataaactagg gagacagtta  38580
ttccaatgca atatctagat aagattatta ttatctatcg acgaaaagtc aaaacatcca  38640
cacaaattag aggggaagag aaagtaaatt tactaaatta agcccataga acatattgag  38700
acttcacttt caacccaagt ttgaaagaaa attagttact cataattgaa ctaggggtaa  38760
aatagaaatt tattaaaata catagaaaat acaagatata gaaggaatta caaaaaaatag  38820
agctcaaaaa tgaattcaag ggtgccaaat tagggggaag ccccctattt atagatacaa  38880
tgagtaaatt atggtcatca gattaaaaca atttaaacac ttagaattgc aacacgtggc  38940
gagttctgat tggatagaac acatcatcag ggctgtcatt ccgtatatat gcatgtaccg  39000
tatgtgaaat acgaatgtgc aacccaagag gggggtgaat tggaatttta aaaaattaat  39060
cgaacaaatc cacacaacaa gcaatctaat gtcttaataa aaatgaaagc aataaattca  39120
atataagcac aataattaaa gagtaaggga gaagaaaaac aaatacacga atttttacgt  39180
ggttcggcaa ttcccgccta cgtccacgcc tccaagcgat ccaagctcga agatttcact  39240
atccaagcct ttccaaggct tcaacaaata caattgactt cgaggtgtca ataaaccttt  39300
acaacgaaga gattatctcc caatctcttc cctcaagtgc ctcacacact caagttctta  39360
caaatgaaat gaagaaatga agattacaat aaagctcact caatgagtag ataatcaaag  39420
atgaagaaca atgaatgatt caatgatttt tgtgttttac aagttgaaga cccaagatat  39480
cacgtgtgct ttttgttctc gcttgttgga gagagcttca aaatgagttg gattggagtt  39540
tttatagttt gagctcgaaa actagctgtt actcacaatc tggggaatcc ggtctgcggt  39600
```

-continued

```
ttatggaatc cggtaagccg gattcgatct ggcgcattct gcccagtttc cggtttgccg  39660
gatttggaat ccggtaagcc ggattcgaaa tgaaaacttt ctgcctcgta atcggatttt  39720
cggattttgt attcggtaag ccagatgcta cagtaatcta ctacagtgct acaatacctg  39780
ctacagtgat atttttcgaa tttttcaatt ttgaccctaa aactttataa aattgtagta  39840
tgacccagaa cgttgtaagc attggcaaat aggtcctaat ttcataattt taaataatgc  39900
tttgtcaagc ccaaaacttt ctgaaattat aatttcgccc aaactttgtg aaattataga  39960
atggcccaaa aacgtttaaa taatttcaaa tgggtccaaa tccgaaattt aaaaatacaa  40020
tcaaatattt taacaaagct ttcattttaa tccaaaatgc ttaaattcca taacatcatt  40080
ttattattat agaagcataa tttataaatc tttgcttaat aaaaacatgt ggtttgttat  40140
catcaaaatc aatatttata gccatatagg ctaacaatct ccccattttt tatgatgaca  40200
aagcacatta aaaatataat atagttatga aaagctcccc ctcaattaat gcaagttaaa  40260
aaatgatttg aaaataattt aataaaactc cccctgcata catgcatact ccccctagat  40320
acatgcatgt tttcataaca catattaaat cattctcccc cttcatcata aaaaagaata  40380
aaagctcccc ctatcaatca tcaaatatcg caacataagc tcattagtaa aaaaaatcca  40440
taagcataag agaatccata taatccataa tgatcaataa aaacaaatcc ataacatcca  40500
acataaatag tcacaacaaa tcatccataa tgaaaaacaa atccataaca tccgaaaaca  40560
aatacataaa ccgaaaaaca taataaccac ccagagagtc gaaaataaaa taacacacaa  40620
tgcaacaaat gagatgtagg tgtgtccaag tacaagtata agatactact caggtggtga  40680
ggatggagat gatggtggcg gaaacggata tggaatgccg aagtgctcaa agagaagtcg  40740
ctgaccatga atgagctgct gctgctgttg ctgaaactca gtctgccgca cagagagggt  40800
ccgcacttca tccatcagat gctgaagagt gacctcttca gaggtaggag gatgcggagg  40860
tgatgaagcg gaggcagatg cactaggtgc tgaagcatcc gtggaagaaa cacggcgtct  40920
acgttgtcct cgaaatgaga gtgagaaaac tggaagctga tcagcaggta tcacggcatt  40980
aagtggccga tcatcacttg gggctagaaa agtaaacttg ttgtcgctgt atttgaccca  41040
agtgccatcc ttccactcaa agcctaaccc aataataacc tcatctccga tacccttgga  41100
cggcctacac gaaggttcta gaatcggcac ttcaaagaat ttaagaatgc gggtaatgaa  41160
gtgaccataa ggaagagagc gggtaatcaa gggaggaatg ctcaacatgg tatggacgat  41220
ggtatagccc aagttaaccg ggcgacatct aagaatacaa tcaatcatgg caacatccat  41280
atgagaaacc tcatctagat gaccggatct aggaagtaca atggactgaa tgatacgaag  41340
caaaatgcga gtttgaagac aaagacactg agtacggaaa tgaatggtac agtcttcaac  41400
cgaaagatca ttacgccgac aaatattgcg aacggcatca acatgagtaa aaccggtaag  41460
tttaggggat ttcctacacg aaaagatttc taggccaaaa tcggatgaac ctaggataga  41520
gttcaacaag gaaacatcga aatcaatctt aactcctccg acagtggtga ttactcgagt  41580
cttattctcc tcggaaactt ccatgttcga gtaaaacact ttcaccaagt cgggatacac  41640
attctcctca atcaacaaag catcaatcca accaacatct cccaacaatt gaaatatgtt  41700
tctataacta atcttgagag tatgcataac atccggtaaa acgaagaaag agttgagtac  41760
ctcacgagtc cgaaagtttt gttgaaaccg attgatcaag tgttgtttgt tctgaaagtg  41820
aatggactca aaggtggatt gatttgagat gacccttgct tcctgtggcc gtgtggtttg  41880
ttgaaccggt tctttgcctt ttcttcgaac cggcctagaa cttgacatgg tgattttgat  41940
```

-continued

```
ggatttgaag ataaaaacac caaatagaat gaagatgatg aagattggaa gtgatttggt  42000
gaaacaaatt tgatcaaaaa cggcttgaga gtgagaaatc tagagagaga aaattcagcc  42060
caaacctagg ttgaaattgg gatctaagga tttagatgtt gaaaatgaat tttaagaatg  42120
gtttcgtgtt cttaaggaga tggggaatga ttttcttgat tcaatttgaa gtgaaaatga  42180
tagacaatgg aggaatttgg agtgagaaaa agagaaaatg gaaacagttt ttagagagag  42240
agtggaaacg gattgccgaa acaagaggat aatgaatagt tcttgaaaat cacgaatccg  42300
gcttgccgga tttgctaacc ggcaagccgg ttattggaca gaattgaagc catcgaaaac  42360
ggccttccgg attgccaatt cggtgagccg aaaataaaac cgagagcagc cattttgaac  42420
aaatataatg ggcacgaatc cggcttgcca gatttgctaa ccggcaagcc gattaaggga  42480
cagatttaaa caaagccgaa aacggcttac cgaaagtgag atccggaaat ccggaaatga  42540
gcccgagaga agaaagaagc aattcggctt accggtttcc tgaaccggct agccggtttc  42600
gagaaccaca agcaaatccg atttttcggt tttgttccag cacaaaccca aggcaaattc  42660
agctttccgg attgaagaac cggtaaaccg gttatgaggc agagaccaac caaagctaat  42720
ccggtttttc ggattgaaaa tccggttgtc cggaatttgt tccgagagag atcaatagga  42780
aataatgttt ttccggaaga atggaaagag aatttttgct agcttttata cttgtatgac  42840
acaccatttt atttccggct tttaaaaatt gattaatttt aaatcatttt aagatttaaa  42900
actctgcaat aagccattta atgcatgcaa aacaaattca taaaattaca agccaatcaa  42960
gctatctaat ttatgatgca taaatccata tgataacaaa catatcaagc catacgaaac  43020
atgaattaag attcaacatt catcattcca agctcatgtc ttatctttat aaaatgctct  43080
tcgcaaagag gttttgtaaa gatatccgca agttgatttt cagtggaaac aaatttaatc  43140
atgacatctc ctttttgaac atgatctcta aggaaatgat gtctaatttc tatatgctta  43200
gttctagaat gttgaatggg attcttggaa agatttatag cactagtatt gtcacataag  43260
ataggaattt gatcaagttt aatgccatag tctctaaggg tttgtttcat ccataaaatt  43320
tgcgcacaac aactacctgc ggcaatatat tctgcctcgg tggttgaaag cgcaaccgag  43380
ttttgtttct tactaaacca agagacaaga taatgaccta ggaagtgaca tgttccacta  43440
gtactctttc tatcaacctt atacccagca aaatcagcat ccgaataaca agttaaatca  43500
atatgagttc ctctaggata ccaaaggcca agattaatag tgccaattaa atatcgaaaa  43560
atgtgtttga cagcaagcat gtgagactct ttaggacaag attgaaatct agcacacaac  43620
aaacactaaa cataatatca ggcctactag cagtcaagta gagtaaggat ccgatcatac  43680
ctcgatatgt cttgatgtca acttccttac ctttctcagc tttgtccagc ttgatggtgg  43740
tgctcatagg agtgcttttt gccgttctat tatcataacc aaatcttttg agtagatctc  43800
tcacgtactt ggcttggttt atgaaaattc cttcctcgtt ttgtttgatt tgaagtccaa  43860
ggaaatactt caactctccc atcatactca tctcaaactc ttgactcata catgatgaaa  43920
aatctttaca caacaactca ttagtaaaac caaaaaataat atcatcaaca tatatttgaa  43980
caataagtat gtcttgattc ttatgcttaa caaaaagagt tgtgtccgct tttcccattg  44040
aaaaatcatt atccaacaaa aaatttttaa gcatatcata ccaaactcta ggtgcttgtt  44100
ttaaaccata caaagccttg gataacttat acacatgatc tggaaatttt tcattttcaa  44160
aaccaagagg ttgtttcaca tacacttcct ccataatgta tccatttaag aaagcacttt  44220
tgacatccat ttgatacaaa ataaaatcct tatgacatgc atatgctaac aacatcctaa  44280
tggattccaa tcttgctaca ggtgcaaagg tttcatcaaa atcaattcct tcttcttggt  44340
```

-continued

```
tgtaaccttg agccactaat ctagctttat ttcttacaac cacaccggat tcatccattt  44400
tgtttctaaa tacccattta gtacctataa tggattaata ttccggatta ggaactaact  44460
cccacacatt atttctctca aattgattca actcctcttg cattgccata atccaagatt  44520
catcattttc cgcatccgca aaggattttg gttcaatttg agaaataaat gcagcatgct  44580
cacatgtgtt cctaagagat gatctagtgg taacgcctcg tgagggatct cctaaaatta  44640
catctttagg gtgagaagat acatacctcc actccttggg gagtgtttga aaagtacctt  44700
cattttgctc cacatttgtt tcttcatgat gttcctcttg aattccatgt gacgcgtctt  44760
cttggttgtc attcgatgtt ccttcttgtt gttcttcttc tgcattatca tcaacaacaa  44820
ctttctccgt agaggagggg ttagactcat caaatgtaac atgcatagat tcctccacaa  44880
ctaaagttct tttattataa actttataag gtttgcttga atttgaataa ccaagaaaaa  44940
taccaacatc agattttgaa tcaaatttac caagattatc ttttgtattc aacacaaaac  45000
atttgcatcc aaaaacttta aaatatccaa tgttgggttt tctatctttc caaagctcat  45060
atggagtttt attgagatta cgtctaatca acacccggtt taaacataac aagcggtgtt  45120
gacggcttcg gcccaaaaat acttaggcaa agaattttca ttcaacatgg tcctaaccat  45180
ttcttgaata gacctattat ttctctctac tactccattt tgttgtggag ttctaggtga  45240
tgaaaattga tgttcaatgc caaagtcatt ataaaaattt tcaaatgcat gattttcaaa  45300
ttctccacca tgatcacttc taatacaagt gatagagtaa cccttttcat tttgaatctt  45360
tttatagaaa attcgaaatg catcaatggc atcatcctta ttagctaaga acaataccca  45420
tgaatatctc gaataatcat ccacaattac aaatgcataa tatttgccac ttaaactagc  45480
atatctagaa ggtccaaata aatctatatg aagcaattga agtggttttg aagtggaaac  45540
atgattcttg cttttgaagg aagttttgat ttgttttcca aattgacatg cttcacaagt  45600
tttatctttt tgaaaattga tttttggaag actttttacc aaatcatttt tcacgatttt  45660
ttaaatcaaa tccatgcttg catgacctaa tcttctatgc cacaaccagc catcatcatg  45720
cattgcggag agacatttat catgtattga tgcacaatct atattaatgg tatagacatt  45780
aacacatcta tttcctacaa acaagtcttt cccatcacat gcattctcaa taacacattt  45840
tgattcatca aagataactc tatatccttt atcacataat tgactaatgc taagcaaatt  45900
gtgtttcaag ttctcaacca aacacacatt ctcaatgagg gtagaggata cattaccgac  45960
atttccaatt ccaatgattt ttccttttga attatcctca aacgaaatat ctccaccatt  46020
ttcgatcttg gtaaagcttg aaaaccaaga ataattccct gtcatgtgtc ttgaacagcc  46080
gctgtccaag taccacttat tcttcttctt ctttgatccc tgaaagaaaa atctcaagtt  46140
ttaggtaccc aaaccttttt gggtccttga aagttagcaa tggttccttt cggaacccaa  46200
atacatttca taccataata agcatttctc tttatagcac atctattttt catatggcca  46260
tcttgattgc aataatggca tacaatttta ttgttaatag atgtattctt cacaaaatag  46320
ctcttgtaaa atttttgttt caaattcggt ttataaccta ggccactttt gtcaaataca  46380
catttttgtg agtttagcaa attgtccaac atcttttgcc catttgtaaa tcttaacaca  46440
atttcattta gctcattact cttttttcta agcatttcat tatcattttt caagtcattc  46500
atgtgtgact ctaagttctc atgtgaagtg ctagaattct tgagtaatgc aatactatca  46560
tgcaatgtct tattttctaa ttctaagcat gtaatctttg cactaaatga atcattttca  46620
ttcttaagct ctatcatctt ctttttaaaa cttatattct ttttaccaat cttcattagc  46680
```

-continued tcatcatgca aattattaaa ggcatcatgc aattcatcat atgtaggaag aatacttacc 46740
tcatcaagtt catcacatga ttcttcccca atagccatga gagccaaatt tatcatttct 46800
tgttgctcat catcatcact tgtttcctct tcgttatcat cccatgtggc caccatagcc 46860
ttcttcttga gtttgttgag aagaggacac tccggccgta tgtgtctggg ctttttgcat 46920
tcataacagg tgatgggctc cttcttctcc ttcttattct tgtagtctct gaattttctc 46980
tgctcattgt tctttttgta aaattttctg aatcttctag ccaacatagc cagctcctca 47040
tcatccattt cgctttcctc atcactctca cgttttgaag ccttgagagc aatgttcttc 47100
ttcttttcct catgcccttt ttctgctgcc aaatcttctt catatgaaat aagagagcca 47160
atcaaatcat caataggtaa tacatttaga tccttggctt tctcaatggc agtccttttt 47220
tgtctccact ccttaggtag agatctaatg attttcttga ctttttcgct atttgaaaaa 47280
gtctttccta gggctcctag agtgttcact atgtccgtga atctagtata catagagtac 47340
acattttcat tttgttccat ttgaaacaat tcgtattgtc gagtgtatct acttatttta 47400
gattctttca cttggttcgt accttcatag acaacctcaa gtttgtgcca aatctcatta 47460
gcactttcgc aactagacac tctatgaaac tcttacttat ctagtgcaca gaacaaggca 47520
ttcatggcct tggaatttag agaagctttt ctcttatcga attcattcca atcccgtgaa 47580
ggttttggaa tatcttctcc tacttcattt ttagtcaaag gcatgaaagg gccatcatta 47640
acaatttccc aaatctcgta atctaaggct tgcaagtaaa ttctcatcct agttttccaa 47700
tatgggtaat cattaccatc aaagtaaggg ggtctagtgg tggactgtcc ttccctaaat 47760
gtggaatcat tttgagttgc cattgatctt tagctctaga tggttaaatc tatataagag 47820
caccttgctc tgataccaaa tgaaatacaa atgtgcaacc caagagggga gtgaattgga 47880
attttaaaaa attaatcgaa caaatccaca caacaagcaa tctaatgtct taataaaaat 47940
aaaagcaata agttcaatat aagcacaata attaaagagt aagggagaag aaaaacaaac 48000
acacgaattt ttacgtggtt cggcaattcc cgcctacgtc cacgcctcca agcgatccaa 48060
gcctttccaa ggcttcaaca aatacaattg acttcgaggt gtcaataaac ttttacaacg 48120
aagagattat ctcccaatct cttccctcaa gtgcctcaca cactcaagtt cttacaaatg 48180
aaatgaagaa atgaagatta caataaagct cactcaatga gtagataatc aaagatgaag 48240
aacaatgaat gattcaatga tttttgtgtt ttacaagttg aagacccaaa atatcatgtg 48300
tgctttttgt tcttgcttgt tggagagagc ttcaaaatga gttggattgg agtttttata 48360
gtttgagctc gaaaactagc cgttactcac attctgggga atccggtctg ccgtttatgg 48420
aatccggtaa gccggattcg atctggcgca ttctgcccag tttccggttt gccggatttg 48480
gaatccggta agccggattc gaaatgaaaa ctttctgccc cgtaaccgga tttccggatt 48540
ttgtatccgg taagccggat gctacagtaa tctgctacag tgctacaata cctgctacag 48600
tgatattttt cgaatttttc aattttgacc ccaaaacttt ataaaactgt agtatgaccc 48660
agaacgttgt aagcattggc aaataggtcc taatttcata attttaaata atgttttgtc 48720
aagcccaaaa ctttctgaaa ttatgatttc gcccaaactt tgtgaaatta tagaatggcc 48780
caaaaacgtt taaataattt caaataggtc caaatccgaa atttaaaaat acaatcaaat 48840
attttaacaa agctttcatt ttaatccaaa atgcttaaat tccataacat cattttatta 48900
ttatagaagc ataatttata aatctttgct taataaaaac atgtggtttg ttatcatcaa 48960
aatcaatatt tatagccata taggctaaca gtatgcacat ttttcggtcc actaacatag 49020
tgccacgtca tcggtcaacg ccacataaac attttagtcc aatagaatcg tgacacataa 49080

-continued

```
ttggtcaata ccacataagc aatcaatacc acatcattcg tccaaacaaa tgttgtcacg  49140
tcatcagtca atgccacatc atcggtcatt gtcacatcat cggtcaattt cacattattc  49200
atcaatgcca catcatcgta ctgtatatgc gaacgatgtc atgaacagta ccatgaacat  49260
taccgtacat gtgaacaata tagtttatcc ttttatactc cccctaaagt ttttgactgt  49320
cctgagttca aaattgttgt ctgttttgct atttgttctc tcgttcgttg tgaaatgacc  49380
atgatgcccc ctaaaataca taaaaactta attataataa aacacacata attaaatcac  49440
aaataactta aatacataaa agtagaaatg ttagtgagac ttggagtgta aaatgatgat  49500
tttctccttt ataaatatac actttctagc actcaatagt gataccgctt aaatcaaaat  49560
aactaagcca cgtcagctga gtgagttgtt tagctgctat cagatgcaca ataatagcat  49620
gtacttgttt tctctgtttc ttcacatttt atcaacttca ctaacacttt gtgattgtta  49680
tatcatatca aagtcaagtc ttaaatacta atgtcatatg ttaaggttca tctttcattt  49740
tgattagcat tcatttgctg ctgcttccaa cagggagaat gagatatttt ggttaatttc  49800
ggtagttgaa cccaatagag tactttattt agatcttcct ggttcaaagg cctgaaaaaa  49860
cttgccagta aatgtaaaat gactttctgt gcttttaatg caatagaggg aacaaggaag  49920
tattgctttt ggaaaaagca tggactgata actacggaga gatttattat ttaagtgata  49980
aaaatttccc ataacccacg gtcaagaaaa tttcagatag ttaaagactc cagtttgttt  50040
caccaaaaaa tgtttgtttc gattgaagac ttgaaccatt ttcattaaac ctgattgtga  50100
tgcattacgt tatgcatgtt cctctcaatt taagaaaagt tgaggtcatg attttatatt  50160
tctatattgt aacttgaaat aataattggc ctgctagctt ctgtagcttg ataacatgaa  50220
ttttccttct caagtcttca aagaaaatag cgtgttgaaa ctaattgatc actcggcagg  50280
gcctttgggt tagaagataa aatttcttgg taaatcctct gaaaaggtat gcataattcc  50340
acgagtatta aataacccat ggtcacaatt tttgtacacg actctttttg tggagaccgt  50400
taaaagtggt tgatgatcca ttttgtaata tcatagaggg atcatcaatt ccttttcttt  50460
tctgtggcta ggcaacactt cgggccaaaa cacgaagcat cttgatcagt ttgggctaac  50520
tctggaatat caggatgact atcaagagtc tcttttccga ccttctttag gaaaaattcg  50580
caagcatctt gatctgccaa acactgcacc ttgaacattt tttgagcttc catgaggcca  50640
ctgacgtcca caagacgagt tgtaatttgt aaatactatc tttgatgcat ttcttgaact  50700
agcaggagaa gggacaccca cttggactaa atcaatcttt tcccatatat catctaacaa  50760
tagcagaatt ttcattttgt tcaataaatg gaatatactt atgaaattgc atttgctgtc  50820
ctctgccgta gctaccaaaa ttgccactgc ctattggaaa gcctctggat gaccgttaaa  50880
gaacatgcct cgaccaaagt ttgatcctct tccaccaaaa ttaccattaa aaccatgaaa  50940
tccacttcca tatgatcctc ttctagcatt acacctgatt tgtgagtaat ttgcatttat  51000
catgctaaag tttgcattaa acatatcctt agcattctaa ctttgtccca atcgagcctc  51060
atgtgttagg agtaaggcat atgcttcatc ataatccatt ttattgaagc taaatctaag  51120
taaccaggca ctaaacattc aatattctca gcatcaatct tttccagtta tggagtctcc  51180
agcacattca gcaagcattt tcacctttcc acaatattct tttatagaca ttgaatcgtt  51240
ccttaaaaaa ttcattttat atcgaagttg cattgcttta gcttcaaatt acactccaaa  51300
ttgtttttca atagatctcc aaatgttaaa tgaagtgtca cagccaagaa cagagctcaa  51360
aataccttta ctaatggtag ataacggcca actgagaagg atccgatctt gagctcacca  51420
```

-continued

```
attgatctag gctagatttt cagctctctg ctctgaacca ccaactgatg aatttgggag  51480
atactgatct ggtacagttt gagtttctga aataaagctt tccagccgat tgtctcttat  51540
ggatgaaagc acttgctttt accaaagtat gatattatat cgatcgcgtt ttacaggagc  51600
agtgaatgta gatgaagtat gtgaaggctg attttggtta agatcggttg aatttgagtt  51660
cgttgtaatg gaattggcca tgtctggctc tgataccatg aaggaaagca agaaaagtga  51720
tgtttggctt gagaaaatct caaagaaaat attttcttga ttttggaact tccatcgact  51780
aacttatttt cttgattttg gaacttccat cgactaactt atgtcaattt acatcttata  51840
tttatacatg ctaattaatc ataactactt gtaactaatt acacttaacc aattataata  51900
tctagcaaaa cttcagcagt atacattcaa tacattacaa caattttaac taactatgct  51960
gaggctgttg tattgctcag tagcttttga tgatgtggca cagctgggca ttataggttt  52020
aagcttggtc ttcttattct ctgcataatg agctgccata acaattcttg atcaaaatct  52080
gaacacccaa tttgcatggt ggtgcatctt ttgcatattt tgttcagttc caattgcttg  52140
tctttatttt tccaccacta aaactgcaat ccacaaccat aaccagaatc attaaaagaa  52200
attttgtatt atctgttatg gataaagtac ttaaagtgtt atcccttctt gatgactctt  52260
tctcagatgc agacatccat taaaccaatt gtcttgacaa gagtcagtta accagagtgc  52320
aaacgcctgt cacagaagga accctactgc atatgtgatt gatggaacat ttgggcagat  52380
tgaaacgagt caaaacacct aagacgtcag ttctatgttt aaatttaatt gattctggga  52440
aaaagctacc cacacaatta aagtttgctt gaatggaata tgaaaaattg ataccagagg  52500
acttgcaaca ggtagatgac cggagtgagc tgcttctttc ccgacactga accattcttg  52560
tgttctgatt tacacgcctg gactcatagt cataatctaa aaatgcatgc gcttgtgaga  52620
tgcacattga tggtgcagaa atgatagaag agaatgaatc agcgcaccaa aagagtaagt  52680
gccacatgtt caacagcagt aaaatatcag ctgctgtttg tttatttatt tattttgaat  52740
catcataagt caaagtctga acagccaaat tggcataaag atgcatcatt tccaagtttt  52800
gttcagtttc gtttgctttt tctttatttt tccgtaaata gctttagaat tcaaaccccc  52860
ataaccagtg tcccatatca aaagaaattt tgtgttttct atccgttatc gataataaag  52920
tacttttcgt gatatccatt gttgatgact ccttccggga tgcagatatg caaataacca  52980
actgtctgtg ttaagaggag tcagttaacc agagggcaaa tgcgtgatca tttctaagtg  53040
attgcacata acatgtaaat agggcattaa ccgagtaaat ctggctgtga aaatgttgtt  53100
aatgggactt gctggctggc tcaagaggtg gttcatagct ttaattaccg agactcatta  53160
acttacgtgg acaagtttca cttcagttct aagttgacta tcgttggatt caaattaaat  53220
tttgaatatt gctgattcac ttgtgacatt cattcagctg attgaaagac gaataattaa  53280
tgaatggtat aatcagtagg cgttcattgt tcaagcaatg atccttattt agtgtttatc  53340
cacagtggct aaaatatttt atccctgctc caggaaaatg aaagtccaat cagttgaaac  53400
gttgtttgat taggatatga ggattcaaac tgccatgcaa ataaaggatt ctggttttca  53460
attataacag taattattgt attacaaata caaataaaca gtataaattt ttattgtact  53520
gtgaagaatc caaattaata cttggaaaag aaaaaagaaa agctaaatga aacataaaag  53580
tgataagata caaaatgcac atgtctcaaa gagtgttagg atgttttgcc atgtttatga  53640
aaattgaaga aatccaagca attaacatac aagctaacta acgatcaatc aaaccaaaag  53700
tttcatagac taccaaaaag gataacatca ttaggaatac taaagctttg aagtacctat  53760
ttttattaat ttatttattt ttcctaatga tgttatcctt tttggtattt ttcacatgaa  53820
```

-continued

```
ggaattaaca aggcgcctca ctaaaaatca aatgaaatct ctgctcagaa atcaacacca  53880
ttgaagctgt tcccgccact ctctgtcaac tacatcagaa agataggaaa catgggcgaa  53940
aagcattttg agtggcttga tcctcccatt gaagctgttc ccaccgtcct ctgaatccac  54000
aaataacaat tttccgctcc ttcgcaatat tggaatcgag tggcagactt ttaagcacat  54060
cgcaatgact taccttcatc tctttcagat gtgggaaggg caggggcttc ctataaatgc  54120
tcttcaaatt ttgcagacta aataatccaa gatattggag ttgagcaaat gggtttagat  54180
ttcccatcct cacctctgga acatcattga cgatttcttc caaaggcttg caatcgtctg  54240
ttccaataga cttgaggttt ggagcgaatg caagaaatgt caagtccttc aatttattgc  54300
aatagtatat ttgaatcttc ttgaggctgt ggaaaacaaa gggttggctc gtgttttgcc  54360
acttttataa tcatcttcaa ttctgcctaa ctcataacac acgctaatcc ttaatacgtt  54420
tggtataatt ttttaaataa aacttattta agtaaaactt ttattaatag aggttaaaag  54480
agattttaac taaaaatttt agttgtttga tggtagatga gaacttttat taaaaattat  54540
ataattaatt taatagacaa gtatttttga agttatgtta taaaaagaat gaaataagat  54600
tgttaaataa gtaaatgata ttttagacat tttatattaa aaaaaacttt tcaacctcta  54660
ttatcaaaag tctaaaattt gagacaaaat gacttattta atcttcaaaa ctctacttaa  54720
aaaaataata aaaattttga tacgggctta tgagattaaa gaaaaactta tgattattaa  54780
ataagtaata ccgaatagac attatatcaa caaaccccaa cgaaaaggct atacatatca  54840
aatggctcca ccaaagcgaa tcggtgcttg ttagcaagta acaactcctt aaaacttcac  54900
ttgtcacttt caaaaatttt cacttggagg tggtgctttg tgttatgctt ggtactttgt  54960
gttgtgagtg acattttata ctatgcatga cactttgatg cacactagcc ctcaagagat  55020
cgcccttgca tgccctaaga ggtggcccta tacaacttca agaggtgacc ctcatacaag  55080
ctttcataaa cataacataa taacaaattt cataaattgc aaacacaatt aataaacata  55140
attcatctta ttatgtaaat acttataaga aacatttgca tgtccatgct tatgccaaag  55200
catatatcaa acacattttg aaaaaatttc ataatgcaca tgttaaaata atatttacaa  55260
attccacacc aatgaatatg tccattgtga ttccaattta aagttctcat ttacttatct  55320
cttggtggta acaacaaact taacctcata atataacagc tatagcctaa cattaaagat  55380
tggactctca tgaacatcat aatcacttaa aaaggtggta aaaatctatt ctccttaagg  55440
agttatttcc tgtaacttca tgaatcaaaa gggtttcatt cttagaatcc agaataaaat  55500
aaaatattaa tccgaaaatc ataaaacttt taagggcttc attcttcgat ttttataaaa  55560
taaaatatta atttgaaaat catggaactt ttcggggctt aaacagacac ataaatatac  55620
atgcgtaaaa atttcaaggc caaaaatata ttccaaatta attttatttg aagaccatta  55680
aatcctgaaa tctaaaatct gtaacgaagg gccatttact catcgacaca caacaattaa  55740
aatacaaggg attaagatcc caattttgga tatgatatat tagacatata taggggtaaa  55800
tctgaaaagt ttcatatttt tcgggtaatt ttttatcagt caaaacattt ttctcattct  55860
ataacactgt agaaattttc gatttcagaa tccttgtgtc taatttgaaa attcattaaa  55920
aatagaatat gaaccatttt cttgatgaaa taaatcctat gtaacccttt aaaatgtcta  55980
gctttatcag atataaacaa attttcataa cccaaaagtc ataattctaa aaaaaatttg  56040
gagtgagtga cagtcacata acattctgca cacatttcat tattcctcgt gaatttctct  56100
taatcaataa tttcttgaga cataatgtcc atgaaaatca tacaatcaca taaagattca  56160
```

-continued aaactcccaa atcctaatct tataaagatc aaatacaata aatctaagtt tatacaagaa 56220
ataaaggaca taaatgtaat agaattgcaa accttaacca cctccacaat tacccaacgc 56280
tgttactcga aggataaaag ccaagaaaat gcttcggccg accactttga gagaaagagg 56340
agctagcgtt ttcgctagta ggcttggtgg ggctcgattg agtttgactt aaaactagag 56400
tttgactttt agcgcccctc caaaaatctc ttaataccca tccttcaatc ataccccact 56460
taatgccaaa aatatccttt tctgtataat tcctgttttt gattaactaa gcaatgtcaa 56520
gtgcttgaac agaaattgca gggcttgggt ccctgctata taaacaatat ccaaaatctt 56580
gtagtcgagg gagtctttgg taatggaaga tgcaatattc tgttaattgg agggtttggt 56640
gatggacgat gctatactct gctacatgta ataataatac attcattttg ggtcaataat 56700
tcattaattt gcgaatttga aagcaattcc agttttcata tatataagtg gagtaaatac 56760
caatggaaag atgacatgga gatagagatc aacgattaat gctaatttaa aaggaaaatt 56820
atctatgcat tatctttctt ttgtcatatg tatatttaac cattataaaa ttttgacata 56880
tactttacac cacttttatt tttaaatttg tatcaatcaa ctattttagc actaaaaata 56940
accattttat ccctaaatga attaaaattt tattttattc tttaaaattt tgaaaaataa 57000
aaaactataa ttacaagaat acccttaaat tcaataaaac taaaaatcta aaatgatatt 57060
ttttaaatga aattataatt ataaaaaaat aacatcttgt aattacattt ttttgtaatt 57120
agaattttat ttgattttta taattaaatt aagtataagg aagtttacaa aaattaacat 57180
gaagagaaaa gctccctata attttttttt attttttaaa atttatagaa taaaatggcc 57240
ttttgattca tttagagata aaattggtat tttctattgt ctaagtagtt gattgataca 57300
aacttaaaaa caaaggtagt gtaaagtaca tatcaatatt ttgtagtaat tagtatacat 57360
atgacaaaaa aaaatagtat agagataatt tcccaattta aaatggcgtg agttcatgat 57420
tgaagatgaa aatgatgaac agaggatatc aagcctagga gttattagga aaaacctgat 57480
gctgagcaag aaattgaaga aatcctaatt atattgaaat ttataatatt taagaatatt 57540
ctaattaatt tgtattatag tttaatttag ttacatgttt acagtcttat tgtttaggta 57600
ttcctttttt ggattgtatt ttttatatgg atataagtct tattaaaaca agtttttcta 57660
atcaaattag ggtaaatcat aattagtata aataagtatt ttttgtaact tttacaaaca 57720
tgtcttgatt atttattatt aattattcct tggaataaac acgaaattcg agtttaataa 57780
tattttaatt ttcaaatctc tgtatgagtt ttgagttcag ttcattttcg atattttgta 57840
aaatcaatga gttttaattc ttaaattcgt tgtattcttt gactcaatgt gaatttaatt 57900
tgttctttta ttctgatatt ctctaaaatc aatagaacat tttaaacatt taaaattccg 57960
ctgcattaat ttggtatcaa agtcaaaccc tagttctaaa ttatcctcaa ttcctatcct 58020
ttttttcctt taaactcggt agcttaaaac aaaaaaatca gaaaacccaa taaaaaagac 58080
aagatacaga aacgtctgtc gtgtcagcca ccatccacag ccgccggctt ttattttccg 58140
tcaccgtttc ggtcgcaacc atcagcattc caatcagaca aagccgccga tcctatccca 58200
ttgatcaaac tctccttcct gccaccaaag ccaccggaaa acaatcaaat tagccgcaaa 58260
gccgccgctg taccaattag ctcttctcca tgagctcgat ctttcccacc attcctcacc 58320
gcctatcgac tctcaaattg ccggagatcg aagccctcaa aatcaccgca acttatctca 58380
aatttccagc caaaccaccg ctttttggac aaaacgccac tgccatcaca ctcatcgtcc 58440
tcaactcttc tagatccaac catctttatc caattttccg accaccgtcg ccgataaccc 58500
tattttttgt ttatttacaa ctttgaccca gttctttcat ttataccatt attgcgcttt 58560

-continued

```
tgttttgtga tcttagcaaa acaaaaccca accaaacaac aaaaaaagga gaaaaaaaga  58620
gagaaaacag taaaaaaatt gaatcatgaa attacatcgt cgtgaagatg ttatcttgaa  58680
agaagatgtt ttaattagaa tgtttaggat tttgagttcg actactgaag atttagagaa  58740
attttgaaat agaaaatctt ttcaaataaa gtaaagatat ggatttgacg aagttgttcg  58800
tgataatgca tgttgtgagg aataataagg agaatggtaa ctttacttta cttgacaata  58860
gtattccttc cagggagatt gttaattggc cattcacgtc tacaacaaat tctccacata  58920
catacatcga tttggatcaa ccgccaaaat ttgatgacta cattgatctt gtggaacaag  58980
atgagctagc aattaataca gtctcatatt attcattcga ttcaaatggg gagaggtatc  59040
ataacatttt tcaacaagtg gaagatttta agaagcattt ttttaaaagg taagggggtg  59100
gggcaaaccc aaataatttt tattttcccc ttacctccgc tcaaacctag gtggttagct  59160
actacaagct tcatgctatt accaacccga ccatgctctt aggggactaa gacacactct  59220
ttcgttactg gtttttctaa gagcttggaa ggatgttaca acagggtatt cttagaaaaa  59280
ttattgattg aagattttat cttgcgttgt tgaacaaatt ggatggatat agtcaccaag  59340
gttggaaagt tcagggttat tcatcagcat cgacgttgta atttaaagat taatcttaag  59400
gcaaataaag attatcttgg agactacaac gagcaaattt ccaagatgaa ttttctccaa  59460
cctggcggga atgatgtaga gtaaaaaatt aaagaaatcc taattacatt gaaatttata  59520
atatttagga atattctaat taatttgtat tctaatttaa cttagttgcc tatttacaat  59580
cttattgttt aggcattccc tagttgagtt gtattcctaa tctaggtata agtcttattc  59640
aaataagttt ttctagtcaa attagggtaa atcataatta atataaataa gtgtttttttg  59700
tagcttctac aaacagatct tgattatttg ttattgatta tttcttgaaa taaacttgag  59760
attcgagttc aataatattt taattttcaa atctctgtgt gagttttgag ttcaattcat  59820
tctcaatatt ctacggaatc aatgagtttt gacccctaat tcgtcgtatt ctttgaatca  59880
acgtgaaatt actttgttct tttattccga tattctttag aatcaacaca atattttgaa  59940
catttaaact tctattgcat caaaacctat tagtttaata gattgtattt tgaatttaaa  60000
aaaaatcata cttgtgcatg ttaaagaaat tgaagagctt atttaagaaa aaaaatagag  60060
tgaaataaaa aatatagtgg gactaatttt attatatttg tcttcagata tgatcgtaat  60120
attctaataa aatagggggtt ttaagatatc agtgaagcag tacaaatact ccaacactaa  60180
acttggccca acaaaaatcc taagctcaaa attaagtata agcactatta ttatatcaat  60240
atgacaatat ccacgttgat gttattgatt gtaataaaat aatagttaac agtaataata  60300
acgcaacgga aaaacaatta ggaaaataac taataatcat aacaatacaa tcaaaataat  60360
attaataatt actcacttgg tttccgggca ttatatttac agattttact tttagaattt  60420
ttttattgtt catttccata attctttcaa cgacaaaact ccaagattgt tgatgttata  60480
gactctctta gactctttac attgttaaac accatttatg gaaaaaagaa atcttgaaaa  60540
aatttcttat gttcaattga aacttttttt aagatttatt tgtctttaag ataaatttca  60600
tacttgaaaa aatttaattt agctcaatat actaaaaaaa ttcttggctt tgacctgaac  60660
aattaatcat aactgaattt taaaagcgga taaacctcgt tttccaaacc tagaaactga  60720
gaacttgatg ttcttagcac ttgaattgcg taaatctggt cttcaagtgt tttcttgcag  60780
gccgtagctc gggcaatggt aataagtgca agtggcaaac cctcgacact ctttttgcca  60840
ttgccactgt ttccgctggc tcaagaaatc aggatggcat ctcaaagttt cttcccaagc  60900
```

-continued attgttatct aataagcaca ccactttaaa tatcttcgac gacttttggc tcaaatatcc 60960
tgtcttgtga aaggtcagca gttaccgaac cattcctgtc ttgtgattta cgtgtctgga 61020
cttgtattca taatccaaaa tgcacttgtg agatgcagat tgatgctgga gaaacgatag 61080
aagagtgtga atcagtggac caaaagtact acatggtttt ggtctacatg gtcaacagca 61140
gcaaaatatg atctgctgtt tgtttatctc ttttaactta cgatttttgt tttcaaacaa 61200
tctgcaggat ctgcagggag aaagtggaag ctctaaggaa gaagaaaatg gagtgggagg 61260
cgagctgcca ggtcagccaa aagcagaaat atttctgagg ttgcgtacta aagaacagtt 61320
atcgagggat gatgatagtg aagcattttt tgctgttgat tggcaggtga tgtcttctcc 61380
caaagtttcc ggtacaacta ttcttgttct tcatcttatt gtagtagctt ttcataaaag 61440
agtggaattg gtttgaagtt cggaatgttt tcacaaatct caatcaaaat ctgaacaccc 61500
aattggcacg attactggca taaacatatc ttttgtaatt ttcagtcata aattaatata 61560
aagtatttat tgcctccatt attatgtgtc cacgttcaaa cgctttctta ttaagacatc 61620
agcaattgaa catataagta atttttaaag agaaatttta tcaaacacgt aacgtgcatt 61680
caaataataa gacaagataa gaacccaaat taataacaat atgtaatctg ctccaagaga 61740
agaaagaaaa gaaaatttc ttaggttacc tgaacgataa atcaaccaaa aactgaagag 61800
aagtttatta atcgaagata aattaaattg attatttcga aattgagaat gaaagtgtga 61860
gttcgtcgtt ttttgaatgg aacagagctg aatcttagaa ttaattaaat ttaaccctag 61920
attgattaaa gaacaattaa atcaagccat aaccccaaaa ttatcaaaat tagaggagaa 61980
aagtaaaaaa attaaattaa aaaaaaaaac tgaaattcga gaagcaaatg aagttgaagc 62040
atgatggaat cctttgtgat tcttcgttcc tgaaaagaat ggagatgaga ttcgaaaatg 62100
aatttcattt aaaaatactc atgacgtttt atgaagtaag tgacaattat attatacatt 62160
tatagaataa ttacaattta ccaaatacct tttacttcta ttgactcaag gaaaaaaaat 62220
attgtcattt atatttcaca atcactcatt ttttaacata atgccaaata tacttaatat 62280
ttcctaaaaa ctgacaaaat aaaaaatgtc aagtatttta ctttttcttg tagtgcgcat 62340
ccttataaat ggagagatga aaaatacaag taatacttgg aaacattttc agatgtgatg 62400
atcatttggg aaccattttt ctattctcaa tcttgaaaga aatatttgaa gaatacaggg 62460
ttctttttcc aaaattaata tctatgcttg agtgttgata tttgatccct aatttattaa 62520
gaaggaaaaa aaattcctgc tatatatatt ttatggtaca atgaagaata caaattaata 62580
cttggaaaag aaaactaaaa tgaaacacaa aaagtgataa aatacaaaat gcaaagctat 62640
aattggaacg tcccgaagag tgtacgggtg ttttgccatg catctgaagt tgaataaaca 62700
aatcacatac tagctaatga tgaatctaac caaaagtttc atagattatt acaaagagta 62760
taatcattat taagaatctg tactcgtaaa attattttta gcgaatggaa caagaaacgg 62820
gaatgcagga aacagagcgt cttatcttac ataaagggaa ttaacaagat gatcaataca 62880
agaaaaagca ggcaccactc cagaaatcaa atacaatatc tgctcaggaa tcactatcag 62940
aatcaatatt gaaccgcatc gagagactag aaacatggaa taaaagcatt ttggtggctt 63000
gattctccca ttgaagctgt tcccaccttt ctctggatcc acgaataaca attttccact 63060
cctttgtacg gttggaatcg agtggaagct tcttaagctt aaggcaatga ataaccttgt 63120
tgtgaaatta acccttatat gtcaagatta atcacacccc aagacctaac tcagacttaa 63180
aggcacaaga accaacctta tgcaaacaaa ggacaaagat cacagcctaa agaacaaaga 63240
acacacagag cttaagtgat tcagcacttg taagggtgcc tacatcctct ggagaaaatc 63300

-continued

```
aacacaggga gcagttttat taagctttca aggttacaga gaaatcatgc acaatacaga  63360
gaccactcag ttaagctttt ctctcactac agatgcctta tctctctctc cttgatcacg  63420
caacataaca ccagaaccag ctcgtttata tatcagttgt gcaggtgaaa cagatccaga  63480
tttccctcca aatctaacgg cctttcaacc aacctgttac gagcttctca cgcgctatta  63540
taaagctttc cttaaacgac tgctagctct gccatttaag cttaagtaag gcatgcgtta  63600
gacacgtgag gtttaaaggt cttgaacgac attggcaatt tgtcagttct gttatattgc  63660
ttaaatgaaa cgacattgca ctcatcttca caacttacaa acgacacgtt gtgctgacga  63720
gtttaagttc atttcaacaa tctccacctt aaactcaaca ctcccagctc cctcctttca  63780
cgttgtcttc tccccatctg caacttctta aactctgcag atacctacta agttcatgca  63840
aatgatgaac ttggcagttg gcacaacctt ggttaacatg tcagctggat tttcttcagt  63900
gtgaatcttc agcaacttta cagctcccct tgacacctta agcctcacga aatgcaactt  63960
aacatctata tgttttgttt tctcgtgatg ggactgattc ttgctaagat gtatagcact  64020
ctgactgtca ctgtatactg ttacagactc ttgttttgct cccaactcag ttatcatgcc  64080
tttcagccaa attgcttctt tgagagcttc agctgctgca gtatactcag cctctgttgt  64140
ggacaatgcc accacattct gtaatgttgc cttccaactg actgtgcagc cttccagagt  64200
aaacagatac cctgtttgtg acctcctttt atcaagatca ccagcaaaat caacatccaa  64260
ataaccaatc aatgtgtgtc cctttttgtc ttctccacca tagaccaaac ccacttccag  64320
agtccccttc agatacctca taatccattg aacaactctc tagtgttcat atccaggatt  64380
tgccataaac ctactcacca aactcacaga atgtgagata tcaagtctgg tgagtatcat  64440
ggcatacatg aggctaccta ctgcactaga gtagggtatg caagccattt tctgttgttc  64500
tgcttcagtt tgaggacact gagcagcaga taacttgaag tggcctgcca atggtgtctg  64560
cacttgctta gcatcatcca ttccaaatct caccagaacc ttctaaatgt agctctgttg  64620
agttaagaac aaactcttct tgctcctgtt tttgattata tccattccca gaattctctt  64680
ggcttctcca agctccttca tttcaaattt cctgctcaaa agcttcttta aatgattgat  64740
ctcttccatg tcatggcatg caatcagcat gtcatctaca tacagcagaa gatatatcat  64800
ccctcctcca cttgtctcct tgaagtacac acagcaatca tagctgcacc tgttgaaggc  64860
atgtgttatc atgaagttat caaacttcag ataccattgc ctaggtgact gctttaaccc  64920
atacagagac tttttaagta agcaaacaca atcttctttt ctagatgtta catacccttc  64980
aggctgctgc attacaattt cttcttgtaa ctcactatac aggaatgctg tttttacatc  65040
catctgctca agatgcatat cttgaatagc cacaagtgca agaataactc tgatggaagc  65100
atgtctcact acaggagaaa attcttcagt gaagtcaatt ccctcctttt gtgtgaaacc  65160
tcttgccacc agtctacctt taaatcttct aggttcagct ccaggtatac catctttaat  65220
cttgaagatc cttttacagc ttattatttt cctcttggct ggtttttcaa tcaatgtcca  65280
ggtctggttt tttatcaggg atgtcatctc ttcatccatt gccctcttcc attccagctt  65340
gtttttgcct gtgatagctt cttgataagt cttaggttca tcatcattca gctcttgagc  65400
agcattcaaa gcatatgcaa tcaagtcagc tactgcatat cttttatgtg gtcttattgt  65460
ccttctcttt ctgtctctag ccaactaata ggtgtcctct tcactttctg ctaattcatg  65520
ttcaacatta gcttcaaatt ctgcttcagc accatcagtt tcaggctcag gttctttcaa  65580
gttttgaggc tccacctgaa acttcacttt atcagtctca gtgtctgatt caatgttgtt  65640
```

-continued

```
accagggctc cttggtttat tcaataactc tttttcatgg aatcctacat ccctgcttat  65700
gatgcattgt ggtggttttg agtcaacaca ccataatcta tagcctttga caccctctgg  65760
ataccccaga aacctacatt ttaatgccct tggttccagc ttaccctgct tcacatgagc  65820
atatgttgtg cagccaaaaa ttctgagttt tgtatagtca acccttcttc ctgaccaaag  65880
ttccattggt gttttacaat ctatagcagt tgatgggctc ctgttgacta ggtagcatgt  65940
tgtgtttaaa gcttctgccc aaagggtttt tgggagctta gagtagatta gcatgcatct  66000
taccttctcc accaaagtca tgttcatcct ctcaacaagg tcattttgtt gaggggcata  66060
ggtgacagtt ttgtgcctct gaataccatt tttttcacat aattcttcaa acagcttgtt  66120
acagtactcc aagccattgt ctgtcttcag agttttcact ttcagaccag tttggttttc  66180
aacaaaaatt ttccagtttt tgactttttc cagaacctca tctttgcttt tgagtgcata  66240
gacccaaacc atccttgaaa aatcaaagtc gaggtcggac ttcaggtcag ccaactcact  66300
ctcaagctga aaagacttgg attcagcaag agcaacttcc tcttctaggt ccatgacctg  66360
cctgtacagc tcgagcatct tctccttaga gcagtcagta gattcaacct ttttctttag  66420
gtcctgaatc tctgcctgct atttctctc atgacgtgcg gtcctaagtt tgtagcaaga  66480
agccaatgta gcaagcttga aagcagccct ttagtgagaa ccccccaact cgccaagatc  66540
catgctctca acatctttaa ccattttttg cctcactgat ttggtgcatt tcctctggta  66600
agtggccaaa tgatcgcatc ggtcataagg cgagggcgac gaagtccgat ttctggattg  66660
aacgctgccc ttatgactct tttcacgaag tttctcccca ccattctttc gggtcggatg  66720
agggggcaga gcaggagcag aagttttgga agggccggta ttgcttttct tctgagaaaa  66780
gggagcgatg ctggattcgc ccgacacctg agcacgtttc cttgacatgg cgctggggat  66840
cttattatcc atcccagcaa ctacgtcaac tagacgagat tcgacgagac tggtaggtga  66900
taaaagatcc tggcagttga aggcgttaac cagagcaatt tcgactttga ccagtggctc  66960
gtcgtcgagt ttactgacta ggccccacga gtccgaaaac atagacaagg ttaaataaac  67020
aaataagtga cgaccagaga catgaagtgt aaagaaaaat aaacgacgtg ggtgacaaa   67080
acgcgtggga aggtgaatat caccaccaag cgactgaatc gctaggtacc agtttcccca  67140
gcaaagaaga acttgttctt ccaattttta catgaagagg gaaacccggt gatgggtttc  67200
ctctttgcat agctcattgg gttttatatt ccctcctctt gtggcattaa gattaaggaa  67260
ggaagggccg ggtttaagcc tttgggagaa gttcctctta gggctgatgt tagtattggc  67320
tattgtagta agctttgttg gagttatcgg aaacatatat agcttggaaa gcaagtctga  67380
tgattgatcc ctgagaggtg atctgtggga tgcttttgct aagttttaat ttggcaaatc  67440
tatatttgaa gtcacgggtg ggactgagct ttagtttttc tgacgtcatt cctttagtct  67500
tagttggttg attttgctaa gatgtggcga gaaaagcttg gaaatatctg gtgccatgca  67560
cacattactg atacaatgtg gttatatatg cttcatagga gctgtaataa gttgactcac  67620
cattggagta tttagggaga atacttccac ggacatgccc cagatgtaag ttaatcaaac  67680
atttttttcc ccgcccaata aatccatcaa tatcttgtcc tagtttttat ttttattttt  67740
atttttttgt catttttttc catttctcta gaataatgtt atacttgtat aaatgcaaga  67800
acaatactgc tattgaaatg aattccttcg tcattatttt cttttacaag ttaggaattg  67860
gataaaaggt tttagtattt ggagtgactg cttttacggc ttatgtgttt ctgcatttcg  67920
atttgattaa caactcttac tcttgcacaa cattttattg gttgtctatt tgtgaaaatg  67980
catattcaat catggaatag gaacttgcaa agatgatgtt agaacaagtt ctagactgga  68040
```

-continued

```
ttattgtttt tcatgctgag cccttgttca gttgtttgat tgtcatgtat gtaccagtgt  68100
ccatctgaga ttaatacata tatggtgtac caaccaagca tgcctctaga aaatcgtgta  68160
ggcttggtat cagttgatcc aattgaatcg cttaattttt ccgatggctt tgatttaagt  68220
aattttagca tgttacagca attagatttt aagccactag aagaaacaaa tttctcacag  68280
cagtaacagt tcgttattca gtaatgcagt tgttaccatg taaggttcga actccggacg  68340
cctccttgtt gacgatattc agtaatgcag gagcagaagt tttggaaggg ccggtattgc  68400
ttttcttctg agaaaaggga gcgatgctgg attcgcccga cacctgagca cgtttccttg  68460
acatggcgct ggggatctta ttatccatcc cagcaactac gtcaactaga cgagattcga  68520
cgagactggt aggtgataaa agatcctggc agttgaaggc gttaaccaga gcaatttcga  68580
ctttgaccag tggctcgtcg tcgagtttac tgactaggcc ccacgagtcc gaaaacatag  68640
acaaggttaa ataaacaaat aagtgacgac cagagacatg aagtgtaaag aaaaataaac  68700
gacgtggggt gacaaaacgc gtgggaaggt gaatatcacc accaagcgac tgaatcgcta  68760
ggtaccagtt tccccagcaa agaagaactt gttcttccaa tttttacatg aagagggaaa  68820
cccggtgatg ggtttcctct ttgcatagct caacatgaaa taatatcagc ctgcctcttt  68880
tggactactc ctcagttgat acaagctctt tatttccata atggagggtt tcccgagctg  68940
acaccattcc cacaacacaa acaggcctgc gagtaccatt cgcccgttag ggtgaagctg  69000
actaggagct agatgcatgc cacccacaat cttgacaaaa taaggttgaa agggtaatct  69060
agctcctaat ttgaagctct ccagattcaa agttatataa cctctaggag gacgactaag  69120
aacatcacct ttcccaggat agcaaggaaa acatcgttgg ggatttgata aagggttctc  69180
aatttaaata ggtcagaatg ggtggtggta catttgaggt aatcaatggg gtaagaatcg  69240
gcttccattc tatgatcgag atttcttttc ttggctggtc ggctcagctc ggagttactc  69300
tcctcattgc caccctttc tccagggatc tcagtcccgt cagaactgcg attctcccca  69360
gaaccagatg cttgcccacc acggttccca ttgagctcac aatcataagg tggcggaata  69420
gcttctggtt gggagtacct aagagtgttc tttctagaag aaggacctac attactggaa  69480
gggttttggg gatcaatggc tctcaaaaaa ttagggtacg aatctatctc ctcatcgctc  69540
tcaactacga ttatttttcc ttttcgtctt aacatagtga agttttaaga ggaaagtact  69600
gcaaatccag acatcagagc acgaaagaac agtataaaac tcacgcaaca acaaccagag  69660
agggggttaa gggcgatacc taggtagatg ggcactggtg gcgtcgctgt gacggcgagg  69720
gagccaagca aaaggaaatc tccggcatag aaagtgtgtt taatttcata aaatgagttg  69780
gttcacgata gaatgatgga aaatggaacg ccgtaaaaac cttcgaatta gggattttac  69840
gcgggaaaga gaatggaagc gtttaagtaa cgtgggtgtc cattcaatca gcatgtatcg  69900
agggtagata aattgtcatt tcaaatttca aacacatggt gtaaatagtg ccacgtcatc  69960
gacatttaag acgacgtgac aggatgttag cctagtagca tatgtggaga cactaacata  70020
catctacatc ctgactagaa atcctctaaa tagaaagcgt caccttaaat ccatcacaac  70080
aaagcaataa ataggaagac gcaacccgga tgtggccagg ttcgactctt aatttctaat  70140
cttaactagc cttactcgca atactagaaa cttggggact agtattcaat aatgaaaaag  70200
catcagtcat acatgtcctc atttcctagc cagggggcga atctcctcga ctaaatggta  70260
tgaatagatt cctggtgatg tcttcttcat ggagcacgta acagccgacc agaaacgagt  70320
accgaccaga aatgagtacc gaccatagac gcatgccgac tagaagcttg tcattcaaaa  70380
```

-continued

```
agaatgcacg atcccgcaac aatgcgatag tttcgccacg ccccaaaccg ctggggagaa  70440
cacgtgccct acatttactc acgtttaata gttggaaccc gttagggccc ttgaccgccc  70500
gagtatgatg gacgtgggaa atgctctatg aacatgggac aatttcctat aaaagttagg  70560
aaaatcgatt gagaaggggg agaaaaagaa aaagagaggg aaaattctgc caaattgaca  70620
tcagaatttt acttcataaa aacctttaat acacttttct ttgagaacat tgctgctagt  70680
gtgcacgaac ttaaattaca cagttttccc aaaaaccctg catactaact taagcattgg  70740
agggtttttg ccgaaaaaac caccggcccc tgtgatttgt ttctgtgaac gcaagtcttg  70800
aaggaggaaa aatggtgatc taagcctcaa gagtttgtgt aattgcaaaa gcttgtggag  70860
tgtagtgttt tcatcattgt cagtacaatc gttggtgagc caatctagtc gggcaaagag  70920
aaaccagatt tcagcatcaa catcttccac actttaccca tttcttcaat cggaattccc  70980
ttggtctccg ccaagaaaaa gtagatgaag aatgacatca ccattacgaa gaacccgaag  71040
aaaaggaaca agccaaactt aagatggcat agcttgttca agaacacttg cgcaaccaag  71100
aatgtgcata acatgttgac agaaacattc acactctgtg ccgctgatcg tattttgagt  71160
ggtaaaattt cactaggcac caaccatcca agaggacccc aagaccaggc aaatccagca  71220
acgtatatgt agaagaaaag cactacaaca attgcgtacc acttcggtag ctccccagga  71280
ttcccatcaa ttccaaattt agcaccaatg caagcagcaa caacagcctt cgcaatcaga  71340
gaatgagtta aaagccatcc ctaatggaaa gattaagtga ttcaattgga tcaaatgata  71400
ccaacctaca caattttcta gaggtattct tggtcggttc actatatata tatgaatctc  71460
atatggacac gtatacatac atatgcgact atcaaacaac tgaacagggc tcaacttaaa  71520
aaacaataat ccagtctaga gcttgtgcaa atatcgtttt tgcaagttcc tattccatgt  71580
ttgaatatgc actttcacat ataaacaacc aataaaatgt ttacaagagt aagagttgct  71640
aatcaagtca aggagtagaa acacagaact caaatattaa aaccttttat aataaaataa  71700
tgacaaaggc attcatttcc atggcagtat tgttcgtgca tttatacaat taaaacagta  71760
atctagaaaa atgaaaaaaa ataacaaaaa ataaaaataa aactaggaaa aggtattgac  71820
aaaaaaatgt ttgatattaa ttgcctttaa taaattagcc tatcactttt cttattctta  71880
ttcttttctt tttgaaaaaa aaaaagaaat taataaaaga atcttggttg tttttgcctt  71940
tgcgcattat gatttgaaaa gattaggtat cctattcctg atggctttaa ttgcctttta  72000
taaacttgca tatcgctttt gtgcaatata atacttgctt tttctcgaaa cactacattc  72060
aagtccctcg gggctcatag gcttatagtt taccaatggg gctcatttct tttatctaag  72120
tagatttagt catagagtag atataaatgt aattgactct aaataaaaat tttatggatc  72180
aactcttctt gatcaaattt gagtatttcc taagtagaag cttggtaaac tggcatgatc  72240
tcccttcagt tcaaataccc aagaaatatc gtcaacaagg aggcgtccgg agtttgaatc  72300
ttacacagtt acaactgcat taccgaataa cgaactgtta ctgctgtgag aaatttgttt  72360
cttctagtag cttaaaatct aattgctgta acctacacga ttttctagag gtatgcttgg  72420
ttggtacacc atatatgtat gaacaccata catgtatgaa tctcagatgg acacacatac  72480
atgacaatca aacaactgaa caagggctca acatgaaaaa caataatgca gtctagaatc  72540
tgtgctgaca tcgtctttgc gagttcctat tccatgattg aatatgcact ttcagaaata  72600
aacaaccaat aaaatgttct gcaagtgtga aagttgttaa tcaaattgag acgcaaaaac  72660
acataactca taaaagtagt cactccaagt attaaaacct tttatccaat tcctaacttc  72720
tagaagaaaa taatggcaaa ggaattgatt tcaatagcag tattgttcct gcattcatac  72780
```

-continued

```
aattataaca gtaactagga caagatattg atggatttat tgggcgggga aacaaatgtt  72840
tgattacctt acatctgggg catgtccgtg gaagtattct ccctaaatac tccaagggtg  72900
tgtcaactta ttacagctcc tatgaagaat atataaccac attgtatcag taatgtgtga  72960
atggcaccag atatttccaa gcttttgtct ccacatctta gctaaatcaa cagactgaga  73020
ctaaaagaat gatgtcagaa aaactaaagc tcagtcccat ccgtgacttc atatatagtt  73080
catatatagg tttgccaaat taaaacttag caaaaacatc ccacagaatc acccctcagg  73140
gatcaatcat cagacttgct ttccaagcta tatatgtttc ccataactcc aacaaagctt  73200
actagaatag ccaatactaa catcagtcct gacaggaact tctccccaag gcttaaacct  73260
ggcccttcct tccttaatct taatgccaca agaggaggga atataaaacc caatgacacc  73320
gccgtagttg cccctgtaaa cttgaaagca gtccaaatgt ttggaatcat tgtggaacca  73380
aagtaaatca acaccagaag caaccctgtc aaagccaaag acctcttcct actctccaaa  73440
agtggatctt gaaccaacgt gtaattattg taagcaccag attcaatcat caaggagaga  73500
cctgatccga catcaaaggg ctgagatgaa gagctagcat tagagagaaa tctagaaaga  73560
cctagaaatt tggttcaaga taagggttgt gagctggtca tcaagcaatg agacaaaatg  73620
taccagagtt aagaggttgt tatgctttct tgtaatgtag tgagaataaa tcagggccct  73680
tgcactataa atagtgatgt tatgaatgag aatggaagca gcaaaatcat tttcttattc  73740
attgcggtat gtcttataat tctttttttt ttttttccaa aactagcttt gtttcatttc  73800
attattgaat atcctattgg atagatgtgg gactccgaag gatattaatt tggtgcttca  73860
ggatattttt cagcggatgg ttgcagttta gcatttccgc aaatggcaga ctcatgtttt  73920
attcaagttt gatttgacgg ttaatgtttt ttgttgtttg actgaattaa ttgccattgg  73980
gaattcgaca ctgctttacc tagaattgtt aattttagtt gtcagttggt gagcattgga  74040
ttaatccaat caatagtaag gagcggcctt cctaagctaa ggtctagctc tactgttcca  74100
atcctaagtt cgatcttcaa tgattgtgtg agttaataat aaaattaaaa aaggttggat  74160
tctacttact tttcacatgc agctgattga aagatgaata taattggtgt ttgtctgtag  74220
gcacatttcc agcaaagtaa aaatgaacaa tatatattca agcatgagta atggccttca  74280
tttagtgttt tgttacttct gcacaaaggt gcagcagaat tttacagaga ttgatttaat  74340
ttgcaccaat ctaagcaagt ttatgatgtt gaagaagaaa gaaacgtcta taataatgaa  74400
atcaagccgt aaaaatagta ttttatttaa cttggagaag cacgcaccag aaattaatca  74460
aacgtgatct atgctaaaga ttgaaaacag gaaagaaaag cattttgcgt ggcttcatcc  74520
tcccactgaa gatttctcca ccagtttgca gctccacgaa taacaatttt atgctccttt  74580
gcactgttgg aatcgagtgg aagcttcttc agctcatagc agtcacttac agtcaattct  74640
tctagacatg ggaagggcaa gggcttccag taaatgctct tcagatttgg cagatttcct  74700
attccaagat attgcagttt tgcaaatgcg tttggatttc cagcaaattc tcccacactt  74760
atgatttctt ccatagcctc gcaatctgtt acttcaatgg acttgaggtt tggaatcaaa  74820
acaaggagtg tcaagtcctt caatttagag caatagttta cttcaaaact ctgaaggctg  74880
tggaaaccat aacgttgtac ttcccctgca taatcaatct tcaattctac caattcataa  74940
cagtctgaaa tccgtaatct tttgagccgc ttcagatctg ccaagcctga aacatcaacc  75000
gaagtcgaac cttggaagtc ttggaggagc atagctcgag tacaacttcg tagcatatgt  75060
gaggtcaaaa aactttggag ggcacgagaa cttcccaagg tcaagctcaa tacctctaga  75120
```

-continued

```
tgtttcagac caagcaactc ctctactaag agttctcccc caccaaacaa aacgctttct  75180
attggataat tgccgtacga aaaataagca ttaccgaaca ttctcagcac atgtaacctt  75240
gaaaaattag atattagttg cagaggaatt tttaataaac gaccagtgta ttccaaattc  75300
agacatttaa gatttaccaa cgcctttaac tcttcaggaa tctcagatat aagtgaggtg  75360
gaaagatcaa ggtattcaag tgaaaccaac tttgaaatcc ccaaaggtaa taccaataat  75420
cccatgtaac gagacaggtt tagaactttg agacgaagca tagattgcaa gaagtcactg  75480
ttgattctcc ataagatgtc gtcactgtta agaaataagg taaggagatg agggcatgta  75540
ggaacctccg atagattctc aatttgattt tccatcaatg acaatctcct caacttttcc  75600
cattctatga catctggcgc ctcccttaat ccagcacctg cataaaccaa atagttctct  75660
ttctcctttt cagcgtcaca agctaaccac aacgccatgt cccgaatcac gtcatgcatt  75720
tttacttcgt cttcatctac ctcctccagt aaacaagagt gaacaagaat gcccacaacg  75780
tggtatcctt gctcatgaga tcctaacgtg acacttccat tcaaaagacc ctctccaatc  75840
caacagtcta ccaaattctc tttagaaata caacaatctt ctggatatag acaacaatat  75900
aagagacaag atctaattgt gtcatttggc aaattatcgt aactgaattt caaaagagga  75960
taaacctcgt ttcccaaacc tggaaactga gaacttgacg ttcttaacac ctgaattgcg  76020
taactccatt cttcaggtgt tttcttgcaa gccatggctc ggccaatggt aataagagcg  76080
agtggcaaac ccccacattc tttggtcact gtttgggcta gctcaagaat atcatgatgg  76140
cagttcagag tttcttcccc gactttttgt cgaaacaatt cccaagcatc attgcctgat  76200
aagcactcca ctttaaactt cttgtgagcc tccatcaaac cacaaacttc ttcggaacgg  76260
gttgtgaata ccacttttga tgcacttgtt tgtgaattag gaagagggat gcccactttt  76320
gctaaatcaa cccgctgcca tatgtcgtct agcaacacaa caaaattctt ccccctcaaa  76380
atcctaaaga tgtcaagagc tttctgttca attcttctac tcttccatgc atcattcagc  76440
aaacctatct tctccccaat aacttcttga atactttcga gtcgcaggtc ttttgacact  76500
acgaccaata tcactaaatc aaaatttgtt ggactcccaa gaaatttgtt gttgatatgg  76560
gtcaatagtg tagttttacc gacaccgccc ataccatata ggccaacaat tccaactggt  76620
tcttctacaa gacatctcca aacttcttca agttgtgatt gcaagcctac cacggttggc  76680
tcagtgggtc tctcatctac agcaggttct ggtactttat cagccaccac ctcaaaaact  76740
ccttcgccca ttaaagtctt gatgtctctc agctttctag ccacttgttt cccaaacttg  76800
tagcttgact tgcagttctt ggaacagtag cctccaagac ataatttctc aatttcttga  76860
gtgccgtctc caataaatgc atcagcttcc gtttcaacag tttccaccct tgaaacccac  76920
acttgcactt ggtccagcct tctcatttgt tgccgttcag catcgttaac cctcctcatc  76980
agatcgttct ttgctgcgat tagtttcctc aattcagtgt ccaaggcaac aagattatct  77040
tggaggttac ttatgtatgc tgcttttcca aggaagcaat ctaagcaacg attgaaaaaa  77100
gcaccatcgc acgagattga gatttggcaa atgttaccca tactttggat aagaattcaa  77160
ccaagagaaa tcacaaaaaa aatttaaaga tattgatgaa cacaatctgc tgcggaagtg  77220
tatatcaaaa ttaaaaatta aaaaaaaaat agacatgtta cattcctgag tcctgacagc  77280
tttaattgcc tttaataaaa ttagcgtatc acttttttta ttcttattct tttcttttga  77340
aaaaaaaaaa gaaaaagaaa ttaataaaag aatcttggtt gtttttgcct tcgcgcagaa  77400
tgatttgaaa agatttgaaa ggcatcctac tcctgatggc tttaattgcc ttttacaaaa  77460
tagcatatcg cttttgtgca atatgttctt gctttttctt gaaacactac atttggggcc  77520
```

-continued

```
cattcgtttt atgcaagtaa atttagttat agagtagata taaatataat ttactctaaa  77580
taaaaatttt atcgatcaac aagagttgat caaatttgag tatcccccaa gtagaagctt  77640
aggggtgtta aaaaaactgt cccgaccgga cccgggcaaa acccaaatcg tatacacaaa  77700
aaatcagatc tgagtttaaa attctcaaac tcggatattt ctgggcttgg gtccgaactc  77760
aacacaaaaa aaaaattgaa atccgaacct ggtttcttaa taaattaaaa atatatattt  77820
tatataaata tataattatg aatttatgat atgttggatg ttatttagat ttattttata  77880
attattgtat tcaatttaat ttaatttttt ttatatagat tgaatgagtt tagattggaa  77940
attagatgcc tctaggtatt agaaagtaga ttgaaataat ttttatttat tatttgtgta  78000
aaatttacat tgttagtatg ttatatattt gtatttgact tttttttaaa gcttgaaatt  78060
gaatgagttt atttgactat tttctttttt aaaatttgta ttgttagaaa aatgaaagaa  78120
aaaattaaag aaaaaaaatt aaagttatca catgcgggct tcgaagccca aatgaaaaac  78180
ccgaactcgg ggggtgccga gcttgagccc agaccacatc tggaaaaatc ggattttaac  78240
ccgggtccga tcttgcgttt cactcatccg gtttgattcc aggcaacacc aaaacctgga  78300
ccagacccgg gttttgccaa gcctaagaag ctt                               78333
```

<210> SEQ ID NO 4
<211> LENGTH: 3900
<212> TYPE: DNA
<213> ORGANISM: artificial
<220> FEATURE:
<223> OTHER INFORMATION: Poncirus trifoliata and Citrus grandis hybrid

<400> SEQUENCE: 4

```
tgtaaatcat ttgccgtcaa ttattagtcg ttgcgtgaaa gctcactgct ttaattttgg    60
ggaccttgat atttaaatca tttaatttat tttccgtcaa ttcccatttc actctattct   120
tgtggtgtcg tgatggtttg gtaatcacat ccaaacgggc tctagactaa agttcttcca   180
tcagactctt gtttttcttt atcgaaatct catacaaaat atgggtaatg ttattggaat   240
ccagttctca tgtgatgcca ttttgtctca cggcctaaat tgtactctcg gcaaagcagc   300
atgcataagc cagctcgaag ataatcttgt tgatttgcag actaaattgg aaaaattaat   360
tgaagcaaag aatgacgtga tgatgagggt tgtaattgct gaaagacaac aaatgagatg   420
cttgaaccaa gtgcaagggt ggctttcaag ggtgcagtct gtggagaccg aagctggtca   480
actgataaga gatggctctc aagaaattga gaaattatgt cttggtggct actgttccaa   540
gaactgcaag tccagctaca actttgggaa agaggtggct caaaaggtgc aacttgtgga   600
gactctaatg ggagaaaaag attttgcagt ggtggctcag aggtctcaag aatctgtagc   660
agatgaaaga cctactgagc caattgtagt aggcctgcaa tctcagcttg aacaagtttg   720
gagatgcctc gtagaagaac cagctggaat tgttggccta tatggcatgg gtggtgttgg   780
taagactacg cttttaactc atatcaacaa caagtttctt caagtgccaa acgattttga   840
ttgtgtgatt tgggttgttg tgtccaaaga ctggcgtctt gaaaatattc aagagattat   900
tggggggaaa ataggtttga tgaatgagtc atggaagagt aaaagcctcc aggagaaatc   960
actagacatc ttcaagattt taagggagaa gaagtttgtt ttgttgctag atgacttatg  1020
gcagcgggtt gatttaacaa aagtgggcgt ccctcttccc agcccacaaa gtagtgcatc  1080
taaagtcgta tttacaaccc gttctgaaga aatttgtggt ttgatggaag cccaaaaaaa  1140
gttcaaagtg gcttgcttat cagataaaga tgcatgggaa ttgttttgtc acaaagttgg  1200
```

-continued

```
agaagaaact ctgaacaatc atcctgatat tcctgagctg gcacagacag ttgccaaaga   1260
gtgtgggggt atgccacttg cacttattac cattggccga gctatgtctt gcaagaggac   1320
gctgcaagaa tggagacacg caattcaagt gttaagaaca acagcttccg agtttccagg   1380
tttgggaaat taggtgtatc ctcttttaaa attcagctat gaaagtctgc ccaatgatat   1440
tgttagatct tgtctcttgt actgtagttt atatccagag gattatcgaa tttctaaaga   1500
gaatttgata gattgttgga ttggtgagag ttttctgaat gaaagggtaa aatttgaagt   1560
acaaaatcaa ggatactata ttttgggcat tcttgttcat gcatgtttac tagaagaggt   1620
gggagaagat gaagtaaaaa tgcatgacgt gattcgggac atggctttgt ggatagcatg   1680
cgacagtgag aagaagggga agaaattttt agtatgtgca ggtgctggat tgactgagga   1740
cccaggtgtt aggggatggg aaaatgtgag tagattgtca ctgatgcaaa atcgcattaa   1800
gaatctgtca gagattccta agtgccctca tctccttact ttatttctta acagtaatga   1860
gttaaagata atcactaatg acttctttca gtttatgcct tctctcaaag ttttaagcct   1920
atcacgcaac agacgactaa ccaacttaca gttagggatt tcaaagttgg tttcactcca   1980
acatcttgat ctttcactta caaacataga aaagttgtca ggagagttaa aggccttggt   2040
aaatctcaaa tgtttgaatt tggaatacac atggagttta gtgacaattc cacagcaact   2100
aatagctagt ttttcgaggt tacatgtgtt gagaatgttt ggtgttggtg atgatgcatt   2160
tgaagtagca tcagaagaca gcgtttttatt tgatgggggt gaatttttag tggaggaatt   2220
gcttggtttg aatcatttag aggttttgag cttgaccttg agaagtcctt atgctctcca   2280
gagctttttg acctcgcata agttacaatg ttgtactcaa gctctattcc ttcaatactt   2340
caaagattca acatcgcttg ttgtttcatc tttggcaaac ctgaagcgcc tcaacgtatt   2400
acggattgca gactgtgaaa aattggaaga attgaagatt gattatacaa gggaaataca   2460
acattttggt ttccgcagcc tttgtaaggt tgaaatagcc aggtgccaaa aattgaagga   2520
cctgacattc cttgtttttg ctccaaacct cgagtctatt gaagtaaaaa gttgccttgc   2580
attggaagaa attgtaactg atgttccgaa ggcaatggga aatctaaacc tatttgcaaa   2640
actccaatat cttgaattgc ttggtctgcc aaatttgaag agcatttact ggaagcccct   2700
gtccttccca cgtctgaaag aaatgacaat aatcacttgt aataagctta aaaagcttcc   2760
agttgattcc aacagtgcaa aggagcgtaa aattgttatt cgtggagaca gagaatggtc   2820
gcgacagctt caatgggagg atgaagccac tcaaaatgtt tttcttccct gtttcaaatc   2880
tctactggag attactgagc aaagattgta atggaattct ggtgagtgct atttcttaca   2940
ttaattcttc ttgttaattt cctccatgta acaaaatact ctgtttcttt ccttcccatt   3000
tgttgtatgt tgtgacacag cttgatcaaa gcagccttgt tgattgttac aagatatttg   3060
cagaattatg aggtttcata tgacaatttt cctattttca gaactgaaca agaaaatatt   3120
tatcaaaaaa gtctaatgca ttcctctgta tttaatatgt gtatttagat gagttgcagt   3180
cacctgttaa gcccttgtgt ttgcttgttc ctacaaatga ccctaattgc tctccaatgc   3240
agttagagaa gttttcagtt gaaatcaggt aagggaatgc tacatttcat tttgagtttt   3300
ctttttttgat tttggaagtt cgtgtgttac ttatagcgca ccagctcctc gtgttaatta   3360
ttttaataaa ctcactaaaa ttttgctcca gtactttcat ttttgtttat tttgaaatta   3420
atctccaata gtttttttcc gatggtgaca cctaatcatg aggagacgtg gtgagccttg   3480
tagtaataaa ttgtaaattg attctacatg atgtatattt tgaacttgtt attctacttt   3540
tatatgtgtt tgattgaatg atatttcagt gtgttatcaa agagtaataa aatattatta   3600
```

-continued

```
caacttaggt taaaacttag gcctatttga tattaaggta ctataatttt caagcacaac   3660

tgatgtttaa aaaaaaaact ataattataa aacaaaaact gatagcgttt agtaaatatg   3720

attttaagta attttttgac aaaaaataat aaagatatta tagatttttc atcgtataag   3780

tgtgaaatga aatcaattta actttgtagc cccaataaca agtatttatc aaacactcaa   3840

gtggtgatac aactaatcaa tctcaatagc aatcagggct ttagtattct ttagatttta   3900


<210> SEQ ID NO 5
<211> LENGTH: 863
<212> TYPE: PRT
<213> ORGANISM: artificial
<220> FEATURE:
<223> OTHER INFORMATION: Poncirus trifoliata and Citrus grandis hybrid

<400> SEQUENCE: 5

Met Gly Asn Val Ile Gly Ile Gln Phe Ser Cys Asp Ala Ile Leu Ser
1               5                   10                  15

His Gly Leu Asn Cys Thr Leu Gly Lys Ala Ala Cys Ile Ser Gln Leu
            20                  25                  30

Glu Asp Asn Leu Val Asp Leu Gln Thr Lys Leu Glu Lys Leu Ile Glu
        35                  40                  45

Ala Lys Asn Asp Val Met Met Arg Val Val Ile Ala Glu Arg Gln Gln
    50                  55                  60

Met Arg Cys Leu Asn Gln Val Gln Gly Trp Leu Ser Arg Val Gln Ser
65                  70                  75                  80

Val Glu Thr Glu Ala Gly Gln Leu Ile Arg Asp Gly Ser Gln Glu Ile
                85                  90                  95

Glu Lys Leu Cys Leu Gly Gly Tyr Cys Ser Lys Asn Cys Lys Ser Ser
            100                 105                 110

Tyr Asn Phe Gly Lys Glu Val Ala Gln Lys Val Gln Leu Val Glu Thr
        115                 120                 125

Leu Met Gly Glu Lys Asp Phe Ala Val Val Ala Gln Arg Ser Gln Glu
    130                 135                 140

Ser Val Ala Asp Glu Arg Pro Thr Glu Pro Ile Val Val Gly Leu Gln
145                 150                 155                 160

Ser Gln Leu Glu Gln Val Trp Arg Cys Leu Val Glu Glu Pro Ala Gly
                165                 170                 175

Ile Val Gly Leu Tyr Gly Met Gly Gly Val Gly Lys Thr Thr Leu Leu
            180                 185                 190

Thr His Ile Asn Asn Lys Phe Leu Gln Val Pro Asn Asp Phe Asp Cys
        195                 200                 205

Val Ile Trp Val Val Val Ser Lys Asp Trp Arg Leu Glu Asn Ile Gln
    210                 215                 220

Glu Ile Ile Gly Gly Lys Ile Gly Leu Met Asn Glu Ser Trp Lys Ser
225                 230                 235                 240

Lys Ser Leu Gln Glu Lys Ser Leu Asp Ile Phe Lys Ile Leu Arg Glu
                245                 250                 255

Lys Lys Phe Val Leu Leu Leu Asp Asp Leu Trp Gln Arg Val Asp Leu
            260                 265                 270

Thr Lys Val Gly Val Pro Leu Pro Ser Pro Gln Ser Ser Ala Ser Lys
        275                 280                 285

Val Val Phe Thr Thr Arg Ser Glu Glu Ile Cys Gly Leu Met Glu Ala
    290                 295                 300

Gln Lys Lys Phe Lys Val Ala Cys Leu Ser Asp Lys Asp Ala Trp Glu
```

-continued 305 310 315 320

Leu Phe Cys His Lys Val Gly Glu Glu Thr Leu Asn Asn His Pro Asp
325 330 335

Ile Pro Glu Leu Ala Gln Thr Val Ala Lys Glu Cys Gly Gly Met Pro
340 345 350

Leu Ala Leu Ile Thr Ile Gly Arg Ala Met Ser Cys Lys Arg Thr Leu
355 360 365

Gln Glu Trp Arg His Ala Ile Gln Val Leu Arg Thr Thr Ala Ser Glu
370 375 380

Phe Pro Glu Asp Tyr Arg Ile Ser Lys Glu Asn Leu Ile Asp Cys Trp
385 390 395 400

Ile Gly Glu Ser Phe Leu Asn Glu Arg Val Lys Phe Glu Val Gln Asn
405 410 415

Gln Gly Tyr Tyr Ile Leu Gly Ile Leu Val His Ala Cys Leu Leu Glu
420 425 430

Glu Val Gly Glu Asp Glu Val Lys Met His Asp Val Ile Arg Asp Met
435 440 445

Ala Leu Trp Ile Ala Cys Asp Ser Glu Lys Lys Gly Lys Lys Phe Leu
450 455 460

Val Cys Ala Gly Ala Gly Leu Thr Glu Asp Pro Gly Val Arg Gly Trp
465 470 475 480

Glu Asn Val Ser Arg Leu Ser Leu Met Gln Asn Arg Ile Lys Asn Leu
485 490 495

Ser Glu Ile Pro Lys Cys Pro His Leu Leu Thr Leu Phe Leu Asn Ser
500 505 510

Asn Glu Leu Lys Ile Ile Thr Asn Asp Phe Phe Gln Phe Met Pro Ser
515 520 525

Leu Lys Val Leu Ser Leu Ser Arg Asn Arg Arg Leu Thr Asn Leu Gln
530 535 540

Leu Gly Ile Ser Lys Leu Val Ser Leu Gln His Leu Asp Leu Ser Leu
545 550 555 560

Thr Asn Ile Glu Lys Leu Ser Gly Glu Leu Lys Ala Leu Val Asn Leu
565 570 575

Lys Cys Leu Asn Leu Glu Tyr Thr Trp Ser Leu Val Thr Ile Pro Gln
580 585 590

Gln Leu Ile Ala Ser Phe Ser Arg Leu His Val Leu Arg Met Phe Gly
595 600 605

Val Gly Asp Asp Ala Phe Glu Val Ala Ser Glu Asp Ser Val Leu Phe
610 615 620

Asp Gly Gly Glu Phe Leu Val Glu Glu Leu Leu Gly Leu Asn His Leu
625 630 635 640

Glu Val Leu Ser Leu Thr Leu Arg Ser Pro Tyr Ala Leu Gln Ser Phe
645 650 655

Leu Thr Ser His Lys Leu Gln Cys Cys Thr Gln Ala Leu Phe Leu Gln
660 665 670

Tyr Phe Lys Asp Ser Thr Ser Leu Val Val Ser Ser Leu Ala Asn Leu
675 680 685

Lys Arg Leu Asn Val Leu Arg Ile Ala Asp Cys Glu Lys Leu Glu Glu
690 695 700

Leu Lys Ile Asp Tyr Thr Arg Glu Ile Gln His Phe Gly Phe Arg Ser
705 710 715 720

Leu Cys Lys Val Glu Ile Ala Arg Cys Gln Lys Leu Lys Asp Leu Thr
725 730 735

-continued

```
Phe Leu Val Phe Ala Pro Asn Leu Glu Ser Ile Glu Val Lys Ser Cys
            740                 745                 750

Leu Ala Leu Glu Glu Ile Val Thr Asp Val Pro Lys Ala Met Gly Asn
        755                 760                 765

Leu Asn Leu Phe Ala Lys Leu Gln Tyr Leu Glu Leu Leu Gly Leu Pro
    770                 775                 780

Asn Leu Lys Ser Ile Tyr Trp Lys Pro Leu Ser Phe Pro Arg Leu Lys
785                 790                 795                 800

Glu Met Thr Ile Ile Thr Cys Asn Lys Leu Lys Lys Leu Pro Val Asp
                805                 810                 815

Ser Asn Ser Ala Lys Glu Arg Lys Ile Val Ile Arg Gly Asp Arg Glu
            820                 825                 830

Trp Ser Arg Gln Leu Gln Trp Glu Asp Glu Ala Thr Gln Asn Val Phe
        835                 840                 845

Leu Pro Cys Phe Lys Ser Leu Leu Glu Ile Thr Glu Gln Arg Leu
    850                 855                 860


<210> SEQ ID NO 6
<211> LENGTH: 5910
<212> TYPE: DNA
<213> ORGANISM: artificial
<220> FEATURE:
<223> OTHER INFORMATION: Poncirus trifoliata and Citrus grandis hybrid

<400> SEQUENCE: 6

tttttaact tccagtgtct cttatgacat atattgttat cgctgcttgt tgataaaacc     60

tggagtataa atgattttta accgatctgt tgatttcatt gactaatact agagaaattc    120

attgtgagcc tgaagagtat ttgtgatcct tttcccaacg ttgtgtaatt ataccaactt    180

tatcaacttt atgtttttaa ttttgaaccc atactggcaa gattaataaa caagtaatta    240

gatacatcgt agcgttgaac attagatcta atggtttgat tttaaaaaag atcaaaatca    300

aaccttgggt taaattatag ttttatagac caaaataaac aaacaaaaga agggaagtga    360

tgagcctttc tccttgtata ttttgtacag tgcaaagaag aatacaagca ttaaaacaga    420

ttaaaaaaaa gaaaaaggta gaaaaccgaa tggaatgcaa cgaacgcatc cgctgagcaa    480

acataaaaga gacaaaaata caaaagaatg gcactgagca aatttttgat tggagcgtct    540

ccaagagtct tgcaataaga gagagatgaa gcggcacttg atgacgataa aacctgaatc    600

tggatctctg agagagtacc ttcaaacgat cagaccaagt tacatagatt acaatgaagg    660

agattaacaa gaggaactaa taaaaattaa taacatattg tgtaagtaga gtaagttatt    720

aggtgcagat gtctgcatga aggaaattaa tgagaagaac taatgtaaga gaaagcacgc    780

accagaaatt aatcaaatgt gatctcagtc caaagttttg aaacagggaa gaaaagcatt    840

tcgagtggct tcgtccaccc attcaagctg atcccaccat tttgtgtatc ccctaataac    900

aatgttacgc tctcttgcac tattggaatc gaatggaagc tttttaagct tatggcaatt    960

cattgccctc aaatatttca gaagtgggaa ggacaggggc atccagtaaa tgctcttcaa   1020

atttattgca ccaactaaat caagatattg aagctttgca aatgggttta gatttgccgt   1080

cacctctgga actgcggcaa attttcccac acttaccatt tcttccatag caacgcaacc   1140

taatacttca atagacttga ggtttggagc gaaagcaagg aatgtcaagt ccttcaattt   1200

attgcaattg acaatttcaa ccttcttaag accgtggaaa acaaattgtt gaactactcc   1260

tggataatcc atctttaatt cttccaactt tttacattca gaaatccgca atcggttgag   1320
```

-continued

```
ttgcttcaga tcggccaaag ctgaaatttc aaggaatgtc gtatctttga agtgttggag   1380
taacagagct tgagtacaac ttcgtaactt atgcgagctc aaaaaacttt ggagagcacg   1440
ggaacttctc aagttgaagc taatcacctc caaatatttc aaaccaagca gttcctctac   1500
aacgagttca cccccgccca ataaaacgtt gtcttctgat gctttgtcaa aagcattatg   1560
acgagcaccg aacattcgca acacatgtaa ccttgaaaga ttagagatta gttgacgtgg   1620
aattgaaatt aaataccttg tccattccaa attcaaacac ttaagattta ccaatgcctt   1680
taactcttct ggcaactctg atatatctga ttcagaaaga tcaagatgtt gcagtgaaac   1740
cagctctgca atccctacgg gtagttcggt tagttcggcg tgcgacaaat ttaaaacttt   1800
gagagagggc ataaattgga agaagtcatt gtggatcatc cgtagcttat tttcgttaag   1860
aaacaaagta aggagatgag ggcatgtagc aacctcagac agattcgtaa tttgattgtc   1920
catcaatgaa attctcctca cattttccca acctttgacc tctggcgctt ctgtcaatcc   1980
aacacctgca taaaccaaaa cgttcccctt ctcattttca atgtcgcatg ctatccataa   2040
tgccatatct cgaatcacgt cgtgcatctt tacttcaccg tctcctccct cttccagtaa   2100
gcaggcatga agaagaatgc ccagaatatg gtatccttgg ttttgttctc caaaccggtc   2160
cctttcagtc aaaaatccct cgccgatcca acaatctatc aaattctctt tagaaatgca   2220
ataatcttct ggatataaac tacaatataa gagacatgat ctaattgtgt cattgggcaa   2280
attatcataa ctgaatttta gaagagggta aacctcgttt cccaaacctg caaactgaga   2340
acttgatgtt cttaacactt ggattgcgta tctccactct tcaggtgtct tcttgcaagc   2400
catagctcgg ccaatggtaa taagtgccag tggcaaacca ccacactcct tagcaactgt   2460
atgtgccagc ccaagaatat cagtatgact ctgtagaact tcttccccaa ctttctgtcg   2520
aaacaattcc caagcattga tatctgataa gcatgccact ttaaacttct tgtgagcttc   2580
cattaaacca caaacttcct cggaacgggt tgtgaatacc actttggatg tactactttg   2640
tgggccaggg agagggacac ccacttttac taaatcaact cgctgccata agtcatctag   2700
caacaaaaca aacttcttct ccttcaaaat cctgaagatg tctagagctt tctgttcaac   2760
acttcttttc ttccatgcat cattcagcaa accaatcttc tccccgatag tgtcttgaat   2820
gttttcaagt cgcaagtctt ttgacactac aacccatatc acatttccta ttaaaattag   2880
ttgtactctc aagaaatttg ttgttgatat gggtcaatag tgtagtttta ccgacaccgc   2940
ccatgccgta taggccgaca attccagctc gttcttctac aagacatctc caaacttgct   3000
cgagttgtga ttgcaagcct attactgttg gctcgatagg cctttcattc gctactgatt   3060
ctggagctct ctcagctacc acttcaaagg ctccttcggc cattaaagtc ccgacatatc   3120
ttagcttttt ggtcactttt ttgccaaact tgtagcttga atggcagttc ttggaacagt   3180
agcctccaag acatagtttc tcaatttctt gagagccttg tcttatcaat tcatcagctt   3240
cagctttaac agcgtccacc ctcgacagcc agccatgaac tttgttcagc cttgtcatca   3300
ttggttgcct ttcagcgttg acgactctcg ccatcacatc gttctttgct tcgattagtt   3360
ttcccaattc agtctccaag gctacaacat tgtcttgcag gtttcttata tatgctgctt   3420
ttccaagaaa gcaatccagg caacgattga aaatagcaca atcgattgcg atttgcaaaa   3480
tgttacccat ttttttgga taatagaaat caactacgag aaaccaagat aattttaaca    3540
caagctgctg cggattgaaa aaattttgtg ttttgtaaat ttagaaagga ttaggcatgt   3600
accattcctg actgctttac ttgccttgaa taaattagcc ttttgctttt gtaattaatt   3660
taacatttat cctcagcttg taatttaata aaagaattct tcttgttgtc attatgacct   3720
```

-continued

```
tgctttttgt tgttccattt gtaattaaat atggaaaatg atagctgaac aacaaaatga   3780
agacagaaac aattgttttc attcacttac cattttctct gcatttgccg gccccacagt   3840
tatattaaaa tattaataaa aaaagaaaac gaaatcccca ccttatctct aaattaggag   3900
gagaagttat caaagcaacg tcatctaatt tgaagagagt actcagcggt tttcattatt   3960
tgaatgtaat gagagtaggg ttggaagaaa agtcccggtc caggtccgcg ggctttaagt   4020
ccggcccgtg atttgaaatt atgggtaagg gctcaaagtt agtaaagccc ataacatatg   4080
gactcagtca agagcctaaa tgaaaagctc ggactttata ataaataata aattttatat   4140
atatatataa tatattatgg ataatggctt tatatatata ttaaaaaatg tataatatat   4200
tataaaatta aaaaaaatta attgctttac aaaataaata tatgtattat aatatatata   4260
tatatatata tatatatata tatatatata tatatatatg tataatatat atatatatat   4320
attaaaaaat gtataatata ttataaaatt gaaaaaaatt aattgcttta caaaataaat   4380
atatgtatta taagatatat atatatgtat aatatctata ttatctgaat catcctgtaa   4440
atgtttttgt aaaagaagtt ggatggtttc agaatcactt ttttgttttt ctttcaaatc   4500
tttaatttcg gacttaatat ccttaatctc tttttggagg tcttggatat tagggaccga   4560
tttttttggtt ttctttttat ctaaaatttc agtaagatca taagaattct tttttacgat   4620
tggaactttg gaagtctcag gtttgttgaa atccattgtt tttaaaagct tttcaagata   4680
ttctttttgg agatttggat cagaaatatg ctttacaagt tcaagaaaag tctcttggtc   4740
tttagtcaaa acattaattt tctttaaata agactctgat tcagaatcac tactgttaga   4800
tacagaagta tctgaatcaa ttaactcatc aatttgtaaa gaatcactat cccctgacat   4860
agaggattca gaattcgaag actcaatcat aagaggggca attttggaaa ggatgtcgtc   4920
atcaagacca agttcatgaa gctttctgtt cattttgcaa tattttgcag tatgaccttt   4980
tataccacat cgatgacaaa tggcttcctt gaaattgaaa ggagtttttg gtgtggcttt   5040
aaaatctttc tttttaggga atctggactt tttataaggc ctagtaagtt tcttataaaa   5100
attttcccta tgtccaataa agggtttcct atggcttttt gacttgtaat gtttttttgta   5160
aggtctcgaa gagcacttac cattacaatc tttggaagtg gaagttttaa aaggatcata   5220
attgaattgt ttacagaaac taccaagttc tcgcttagac tgcctaagct cttgttttag   5280
tcgtttctgt aacttcaaat cttgacaaat ctttaaacct tccttattaa cgaaactgac   5340
aagttcacca taggtgagct catcataagg aattcgattg tcataaaggg ctttgatgga   5400
atttctaacc ttttcaccta aaagggtagg tagacctgct aagaatttct ctttccaagt   5460
agtatgattc gcatcatctc taagaaagag tctggtgaag aaggtggttt tgtataattg   5520
gaaatcacta agtttcctac atcttaaatt atgtagtaac tcagcatttt tgtctctgag   5580
gtgagaaggg tcacctataa aatggaggga aatggtaagg attaaggtag caacagcatc   5640
ctggatagga ttgttgaatt gatcgagaat aggtatctta ttttcatcaa tttggataac   5700
attaagaata tccatttgtt gctgcctagt gagaagatga tcccaccaac cttttaattg   5760
accagtaaaa ccggcgataa gaatctctgc aatagccatg tcagaggttc cggattgagt   5820
tttataggca ttagctgcca tggtcatttg ttgcaagact cctaagatat tgtattcgga   5880
catgccatca atattccatt catagacaga                                    5910
```

<210> SEQ ID NO 7
<211> LENGTH: 1335
<212> TYPE: PRT

-continued

<213> ORGANISM: artificial
<220> FEATURE:
<223> OTHER INFORMATION: Poncirus trifoliata and Citrus grandis

<400> SEQUENCE: 7

```
Met Ala Ala Asn Ala Tyr Lys Thr Gln Ser Gly Thr Ser Asp Met Ala
1               5                   10                  15

Ile Ala Glu Ile Leu Ile Ala Gly Phe Thr Gly Gln Leu Lys Gly Trp
            20                  25                  30

Trp Asp His Leu Leu Thr Arg Gln Gln Gln Met Asp Ile Leu Asn Val
        35                  40                  45

Ile Gln Ile Asp Glu Asn Lys Ile Pro Ile Leu Asp Gln Phe Asn Asn
    50                  55                  60

Pro Ile Gln Asp Ala Val Ala Thr Leu Ile Leu Thr Ile Ser Leu His
65                  70                  75                  80

Phe Ile Gly Asp Pro Ser His Leu Arg Asp Lys Asn Ala Glu Leu Leu
                85                  90                  95

His Asn Leu Arg Cys Arg Lys Leu Ser Asp Phe Gln Leu Tyr Lys Thr
            100                 105                 110

Thr Phe Phe Thr Arg Leu Phe Leu Arg Asp Asp Ala Asn His Thr Thr
        115                 120                 125

Trp Lys Glu Lys Phe Leu Ala Gly Leu Pro Thr Leu Leu Gly Glu Lys
    130                 135                 140

Val Arg Asn Ser Ile Lys Ala Leu Tyr Asp Asn Arg Ile Pro Tyr Asp
145                 150                 155                 160

Glu Leu Thr Tyr Gly Glu Leu Val Ser Phe Val Asn Lys Glu Gly Leu
                165                 170                 175

Lys Ile Cys Gln Asp Leu Lys Leu Gln Lys Arg Leu Lys Gln Glu Leu
            180                 185                 190

Arg Gln Ser Lys Arg Glu Leu Gly Ser Phe Cys Lys Gln Phe Asn Tyr
        195                 200                 205

Asp Pro Phe Lys Thr Ser Thr Ser Lys Asp Cys Asn Gly Lys Cys Ser
    210                 215                 220

Ser Arg Pro Tyr Lys Lys His Tyr Lys Ser Lys Ser His Arg Lys Pro
225                 230                 235                 240

Phe Ile Gly His Arg Glu Asn Phe Tyr Lys Lys Leu Thr Arg Pro Tyr
                245                 250                 255

Lys Lys Ser Arg Phe Pro Lys Lys Lys Asp Phe Lys Ala Thr Pro Lys
            260                 265                 270

Thr Pro Phe Asn Phe Lys Glu Ala Ile Cys His Arg Cys Gly Ile Lys
        275                 280                 285

Gly His Thr Ala Lys Tyr Cys Lys Met Asn Arg Lys Leu His Glu Leu
    290                 295                 300

Gly Leu Asp Asp Asp Ile Leu Ser Lys Ile Ala Pro Leu Met Ile Glu
305                 310                 315                 320

Ser Ser Asn Ser Glu Ser Ser Met Ser Gly Asp Ser Asp Ser Leu Gln
                325                 330                 335

Ile Asp Glu Leu Ile Asp Ser Asp Thr Ser Val Ser Asn Ser Ser Asp
            340                 345                 350

Ser Glu Ser Glu Ser Tyr Leu Lys Lys Ile Asn Val Leu Thr Lys Asp
        355                 360                 365

Gln Glu Thr Phe Leu Glu Leu Val Lys His Ile Ser Asp Pro Asn Leu
    370                 375                 380

Gln Lys Glu Tyr Leu Glu Lys Leu Leu Lys Thr Met Asp Phe Asn Lys
```

-continued

```
385                 390                 395                 400

Pro Glu Thr Ser Lys Val Pro Ile Val Lys Lys Asn Ser Tyr Asp Leu
            405                 410                 415

Thr Glu Ile Leu Asp Lys Lys Lys Thr Lys Lys Ser Val Pro Asn Ile
            420                 425                 430

Gln Asp Leu Gln Lys Glu Ile Lys Asp Ile Lys Ser Glu Ile Lys Asp
        435                 440                 445

Leu Lys Glu Lys Gln Lys Ile Asp Phe Tyr Tyr Pro Lys Lys Met Gly
    450                 455                 460

Asn Ile Leu Gln Ile Ala Ile Asp Cys Ala Ile Phe Asn Arg Cys Leu
465                 470                 475                 480

Asp Cys Phe Leu Gly Lys Ala Ala Tyr Ile Arg Asn Leu Gln Asp Asn
            485                 490                 495

Val Val Ala Leu Glu Thr Glu Leu Gly Lys Leu Ile Glu Ala Lys Asn
            500                 505                 510

Asp Val Met Ala Arg Val Val Asn Ala Glu Arg Gln Pro Met Met Thr
        515                 520                 525

Arg Leu Asn Lys Val His Gly Trp Leu Ser Arg Val Asp Ala Val Lys
    530                 535                 540

Ala Glu Ala Asp Glu Leu Ile Arg Gln Gly Ser Gln Glu Ile Glu Lys
545                 550                 555                 560

Leu Cys Leu Gly Gly Tyr Cys Ser Lys Asn Cys His Ser Ser Tyr Lys
            565                 570                 575

Phe Gly Lys Lys Val Thr Lys Lys Leu Arg Tyr Val Gly Thr Leu Met
            580                 585                 590

Ala Glu Gly Ala Phe Glu Val Val Ala Glu Arg Ala Pro Glu Ser Val
        595                 600                 605

Ala Asn Glu Arg Pro Ile Glu Pro Thr Val Ile Gly Leu Gln Ser Gln
    610                 615                 620

Leu Glu Gln Val Trp Arg Cys Leu Val Glu Glu Arg Ala Gly Ile Val
625                 630                 635                 640

Gly Leu Tyr Gly Met Gly Gly Val Gly Asn Val Ile Trp Val Val Val
            645                 650                 655

Ser Lys Asp Leu Arg Leu Glu Asn Ile Gln Asp Thr Ile Gly Glu Lys
            660                 665                 670

Ile Gly Leu Leu Asn Asp Ala Trp Lys Lys Arg Ser Val Glu Gln Lys
        675                 680                 685

Ala Leu Asp Ile Phe Arg Ile Leu Lys Glu Lys Lys Phe Val Leu Leu
    690                 695                 700

Leu Asp Asp Leu Trp Gln Arg Val Asp Leu Val Lys Val Gly Val Pro
705                 710                 715                 720

Leu Pro Gly Pro Gln Ser Ser Thr Ser Lys Val Val Phe Thr Thr Arg
            725                 730                 735

Ser Glu Glu Val Cys Gly Leu Met Glu Ala His Lys Lys Phe Lys Val
            740                 745                 750

Ala Cys Leu Ser Asp Ile Asn Ala Trp Glu Leu Phe Arg Gln Lys Val
        755                 760                 765

Gly Glu Glu Val Leu Gln Ser His Thr Asp Ile Leu Gly Leu Ala His
    770                 775                 780

Thr Val Ala Lys Glu Cys Gly Gly Leu Pro Leu Ala Leu Ile Thr Ile
785                 790                 795                 800

Gly Arg Ala Met Ala Cys Lys Lys Thr Pro Glu Glu Trp Arg Tyr Ala
            805                 810                 815
```

-continued

```
Ile Gln Val Leu Arg Thr Ser Ser Ser Gln Phe Ala Gly Leu Gly Asn
        820                 825                 830

Glu Val Tyr Pro Leu Leu Lys Phe Ser Tyr Asp Asn Leu Pro Asn Asp
    835                 840                 845

Thr Ile Arg Ser Cys Leu Leu Tyr Cys Ser Leu Tyr Pro Glu Asp Tyr
    850                 855                 860

Cys Ile Ser Lys Glu Asn Leu Ile Asp Cys Trp Ile Gly Glu Gly Phe
865                 870                 875                 880

Leu Thr Glu Arg Asp Arg Phe Gly Glu Gln Asn Gln Gly Tyr His Ile
                885                 890                 895

Leu Gly Ile Leu Leu His Ala Cys Leu Leu Glu Glu Gly Gly Asp Gly
        900                 905                 910

Glu Val Lys Met His Asp Val Ile Arg Asp Met Ala Leu Trp Ile Ala
    915                 920                 925

Cys Asp Ile Glu Asn Glu Lys Gly Asn Val Leu Val Tyr Ala Gly Val
    930                 935                 940

Gly Leu Thr Glu Ala Pro Glu Val Lys Gly Trp Glu Asn Val Arg Arg
945                 950                 955                 960

Ile Ser Leu Met Asp Asn Gln Ile Thr Asn Leu Ser Glu Val Ala Thr
                965                 970                 975

Cys Pro His Leu Leu Thr Leu Phe Leu Asn Glu Asn Lys Leu Arg Met
        980                 985                 990

Ile His Asn Asp Phe Phe Gln Phe  Met Pro Ser Leu Lys  Val Leu Asn
    995                 1000                1005

Leu Ser  His Ala Glu Leu Thr  Glu Leu Pro Val Gly  Ile Ala Glu
    1010                1015                1020

Leu Val  Ser Leu Gln His Leu  Asp Leu Ser Glu Ser  Asp Ile Ser
    1025                1030                1035

Glu Leu  Pro Glu Glu Leu Lys  Ala Leu Val Asn Leu  Lys Cys Leu
    1040                1045                1050

Asn Leu  Glu Trp Thr Arg Tyr  Leu Ile Ser Ile Pro  Arg Gln Leu
    1055                1060                1065

Ile Ser  Asn Leu Ser Arg Leu  His Val Leu Arg Met  Phe Gly Ala
    1070                1075                1080

Arg His  Asn Ala Phe Asp Lys  Ala Ser Glu Asp Asn  Val Leu Leu
    1085                1090                1095

Gly Gly  Gly Glu Leu Val Val  Glu Glu Leu Leu Gly  Leu Lys Tyr
    1100                1105                1110

Leu Glu  Val Ile Ser Phe Asn  Leu Arg Ser Ser Arg  Ala Leu Gln
    1115                1120                1125

Ser Phe  Leu Ser Ser His Lys  Leu Arg Ser Cys Thr  Gln Ala Leu
    1130                1135                1140

Leu Leu  Gln His Phe Lys Asp  Thr Thr Phe Leu Glu  Ile Ser Ala
    1145                1150                1155

Leu Ala  Asp Leu Lys Gln Leu  Asn Arg Leu Arg Ile  Ser Glu Cys
    1160                1165                1170

Lys Lys  Leu Glu Glu Leu Lys  Met Asp Tyr Pro Gly  Val Val Gln
    1175                1180                1185

Gln Phe  Val Phe His Gly Leu  Lys Lys Val Glu Ile  Val Asn Cys
    1190                1195                1200

Asn Lys  Leu Lys Asp Leu Thr  Phe Leu Ala Phe Ala  Pro Asn Leu
    1205                1210                1215
```

-continued

```
Lys Ser  Ile Glu Val Leu Gly  Cys Val Ala Met Glu  Glu Met Val
    1220                 1225                 1230

Ser Val  Gly Lys Phe Ala Ala  Val Pro Glu Val Thr  Ala Asn Leu
    1235                 1240                 1245

Asn Pro  Phe Ala Lys Leu Gln  Tyr Leu Asp Leu Val  Gly Ala Ile
    1250                 1255                 1260

Asn Leu  Lys Ser Ile Tyr Trp  Met Pro Leu Ser Phe  Pro Leu Leu
    1265                 1270                 1275

Lys Tyr  Leu Arg Ala Met Asn  Cys His Lys Leu Lys  Lys Leu Pro
    1280                 1285                 1290

Phe Asp  Ser Asn Ser Ala Arg  Glu Arg Asn Ile Val  Ile Arg Gly
    1295                 1300                 1305

Tyr Thr  Lys Trp Trp Asp Gln  Leu Glu Trp Val Asp  Glu Ala Thr
    1310                 1315                 1320

Arg Asn  Ala Phe Leu Pro Cys  Phe Lys Thr Leu Asp
    1325                 1330                 1335
```

<210> SEQ ID NO 8
<211> LENGTH: 4221
<212> TYPE: DNA
<213> ORGANISM: artificial
<220> FEATURE:
<223> OTHER INFORMATION: Poncirus trifoliata and Citrus grandis hybrid

<400> SEQUENCE: 8

```
ctctatatat atagaaacaa ttattacctc ccacttatct ttcccttata tgtcgaaatc     60

tcatacgaaa aatgggtaac agtttcggaa tccaattcac ttatgatgca attgtactct    120

caacaaagca gcatacggat gcaagcttga acagaatctt gttgatttgc agactaaatt    180

gaaaaagtta attgaatcaa agaattatgt gatgataagg gttgtaattg ctctatgact    240

gcaaatgaga cccttgtaat tcatagtgtg gggttcaagg gtggaagcaa tagatggatt    300

gctgtggtgt atatttttaa cttgttattg tactattatt tgtgtttagt tgattgaagt    360

ttcattttat tttcaaaaag caagaaaatg ttattttaac ttaggccact tacagttctt    420

aagattttat acttaagttg atggccctta gaaatttaat tgcaagtgcc aatgagagta    480

aagtggcatg cacaacagat gagagaagac ttttagctta aggtcctttt ctttactagt    540

aaaatagggg atgtactaca cacaacttgt ggccgtctac aataagataa atgttgatga    600

caaattggtc gttgcattta cttttcatat atctgaaagc acagtattta atttgaaatt    660

aggggccact tttaatatat ttttggctct aacgtaacaa gaacaataac aacaataata    720

aagattacga ggtttgtttg catctcacta tctatcatag caattatttg acataaataa    780

tcatgttacc acaaataaaa aagttaattt atttgtgcat agataggcac gcacccagta    840

gctattgaat gaacaattat tactcactaa gaatcaatct ttccctcata ctcaaatact    900

ttttcttcaa tcccaattag tagaaatctc aaagaaatta tgggtaacgt ttttggagtc    960

caaataccat ggagcaacat tttccctcgt tgcctagatt ggattctcaa cgaagcaaaa   1020

tatataagcc agcttgagga taatcttgat gatttgcaga ctaaattgga acaattaatt   1080

gaagccaaag acgatgtgat gaatagggtt gaaattgctg aaaggcaaca aatgagccgc   1140

ctgaatcaag tgcaagggtg ggtttcaagg gtggaagctg ttaaagctga ggctgatcaa   1200

ctgataagag ttggctctca agaaattgag agattatgtc tttggggcta ctgttccaag   1260

aactgcaagt caagctacga ctttggaaaa aaggtgacta aaaagctgca acttgtggag   1320

actttaatgg gcgaaggaat ttttgaggtg gttgctgaga aagtaccagg agctgctgca   1380
```

-continued

```
actgagagac ctactgagcc aacagtaata ggcttgcaat cacaacttga gcaagtttgg   1440
agatgtcttg tagaagaacc agctggaatt gtcggcctat acggcatggg cggtgtcggt   1500
aaaactacac tattgaccca tatcaacaac aaatttcttg agagtacaac taattttaat   1560
tatgtgatat gggttgtagt gtcaaaagac ttgcgacttg aaaacattca agaaactatc   1620
ggggagaaga ttggtttgtt gaatgataca tggaagaata gaagaattga acagaaagct   1680
ctagacatct tcaagatttt gaaggagaag aaatttgtgc tgttgctaga tgacttatgg   1740
cagcgggttg atttagtaga agtgggtgtc cctctccctg gcccacaaag tagtacatcc   1800
aaagtggtat tcacatcccg ttccgaagaa gtttgtggtt tgatggaagc tcacaagaag   1860
tttaaagtgg cgtgcttatc agatatcgat gcttgggaac tgtttcaaca gaaagttgga   1920
gaagaaactc tgaagagtcc cgatattcgt caactagccc aaacagcagc caaggagtgt   1980
ggtggtttgc cactagctct tatcaccatt ggccgagcta tggcttgcaa gaagacacct   2040
gaagaatgga cttatgcaat tgaggtgtta agaacgtcaa gctctcaatt tccaggtttg   2100
ggaaatgagg tttaccctct tttaaaattc agttacgata gcttgcccag tgacacaatt   2160
agatcatgtc tcttatattg ctgtttatat ccagaagatt attgcatttc taaagagatt   2220
ttgatagatt gttggatcgg cgagggattt ttgacagaga gggacaggtt tggagaacaa   2280
aaccaaggat accatattct gggtattctt cttcatgcct gtttactgga agagggaggc   2340
gatggtgaag taaaaatgca tgatgtggtt cgagatatgg cattgtggat agcatgcgcc   2400
attgaaaagg agaaagataa ttttttggtt tatgcagggg ttggattaat tgaagcaccc   2460
gatgtcagcg gatgggaaaa agcaaggaga ttgtcattga tgcacaatca aattacgaat   2520
ctatcagagg ttgctacatg ccctcatctc cttactttgt ttctgaacga aaatgagcta   2580
cagatgatcc acaatgactt cttccgattt atgccctctc tcaaagttct aaatctggca   2640
gacagcagtc taaccaactt accagagggg atttcaaagt tggtttcact gcaacatctt   2700
gacctgtcaa aatccagcat agaagagttg ccactagagt taaaggcatt ggtaaatctc   2760
aagtgtttga atttggaata tacatggagt ttaactacaa tcccgcgtca actaatatct   2820
aatctttcaa ggttacatgt cctgagaatg tttgctgcta gtcatagtgc cttcgataga   2880
gcatcagaag acagcatttt atttggtggg ggtgaactca tagtagagga actgcttggt   2940
ttgaaatatt tagaggtgat tagcttcacc ttgagaagtt ctcatggtct ccaaagcttt   3000
ttgagctcgc ataagttacg aagttgtact cgagcgctct tactccaatg cttcaacgat   3060
tcgacatcgc ttgaagtttc agccttggca gatctgaagc aacttaacag attatggatt   3120
acagagtgta aaaagttgga ggagttaaag atggattata caaggaagt tcaacaattt   3180
gttttccaca gtcttaagaa ggttgaaata ttggcttgct ctaagttgaa ggacttgaca   3240
ttccttgtct tcgctccaaa cctcgagtct attgaactaa tgggttgccc tgctatggaa   3300
gaaatggtaa gtatgggaaa gtttgcagaa gttccagagg tggtggcaaa tctaaaccca   3360
tttgcaaaac tccaaaatct taaattattt ggtgctacaa atttgaagag catttactgg   3420
aagcccctgc ccttcccaca tctgaaatcg atgagtttct cgcattgcta taagctcaaa   3480
aagcttccac ttgattccaa tagtgcaaga gagcgtaaca ttgttattag tggaaccaga   3540
agatggtggg aacagctcga atgggtggat gaagctactc gaaatgcttt tcttccctgt   3600
ttcgactctt gagcagagat cacatttgat tgatttctgg tgcgtacttc ttctcgcatt   3660
aatcttttat aataatttcc ttcatgcaga agtctgcacc taataacttg ttacttcaat   3720
```

-continued

```
gtgttcttaa ttgtttgaag gtactctgag aggtgcagat tcaatttttt atcaagtggc   3780

gaatcattta gctattgcgg gactcgattt cactcctgtt gcaagactct tggagagact   3840

caaatcataa atttgatcag tgattttgct cctatatgtg tgctcagcgg atgtgttcat   3900

gcattcaatt aggttttcta cctctttttt ttttttttctt taacttttgg gcttttatat   3960

ttgtattctt cttcgtacca tgcatccaaa agttgcagaa gttgttccaa ggtagtgatg   4020

tatttaatta tttaatacaa atttcgaatt gtctcaaact ttttataatt aatcctgcta   4080

tcaaaaaatc ttgtatcttc agacttggtg ttctaaagat tcatctctgg tagtctttta   4140

tcggttcaat ttattttgat tcactctaat gaacggctcg attcttgatt ttcagttttt   4200

ttttttaat ttttaaataa a                                              4221
```

<210> SEQ ID NO 9
<211> LENGTH: 890
<212> TYPE: PRT
<213> ORGANISM: artificial
<220> FEATURE:
<223> OTHER INFORMATION: Poncirus trifoliata and Citrus grandis hybrid

<400> SEQUENCE: 9

```
Met Gly Asn Val Phe Gly Val Gln Ile Pro Trp Ser Asn Ile Phe Pro
1               5                   10                  15

Arg Cys Leu Asp Trp Ile Leu Asn Glu Ala Lys Tyr Ile Ser Gln Leu
            20                  25                  30

Glu Asp Asn Leu Asp Asp Leu Gln Thr Lys Leu Glu Gln Leu Ile Glu
        35                  40                  45

Ala Lys Asp Asp Val Met Asn Arg Val Glu Ile Ala Glu Arg Gln Gln
    50                  55                  60

Met Ser Arg Leu Asn Gln Val Gln Gly Trp Val Ser Arg Val Glu Ala
65                  70                  75                  80

Val Lys Ala Glu Ala Asp Gln Leu Ile Arg Val Gly Ser Gln Glu Ile
                85                  90                  95

Glu Arg Leu Cys Leu Trp Gly Tyr Cys Ser Lys Asn Cys Lys Ser Ser
            100                 105                 110

Tyr Asp Phe Gly Lys Lys Val Thr Lys Lys Leu Gln Leu Val Glu Thr
        115                 120                 125

Leu Met Gly Glu Gly Ile Phe Glu Val Val Ala Glu Lys Val Pro Gly
    130                 135                 140

Ala Ala Ala Thr Glu Arg Pro Thr Glu Pro Thr Val Ile Gly Leu Gln
145                 150                 155                 160

Ser Gln Leu Glu Gln Val Trp Arg Cys Leu Val Glu Glu Pro Ala Gly
                165                 170                 175

Ile Val Gly Leu Tyr Gly Met Gly Gly Val Gly Lys Thr Thr Leu Leu
            180                 185                 190

Thr His Ile Asn Asn Lys Phe Leu Glu Ser Thr Thr Asn Phe Asn Tyr
        195                 200                 205

Val Ile Trp Val Val Val Ser Lys Asp Leu Arg Leu Glu Asn Ile Gln
    210                 215                 220

Glu Thr Ile Gly Glu Lys Ile Gly Leu Leu Asn Asp Thr Trp Lys Asn
225                 230                 235                 240

Arg Arg Ile Glu Gln Lys Ala Leu Asp Ile Phe Lys Ile Leu Lys Glu
                245                 250                 255

Lys Lys Phe Val Leu Leu Leu Asp Asp Leu Trp Gln Arg Val Asp Leu
            260                 265                 270
```

-continued

```
Val Glu Val Gly Val Pro Leu Pro Gly Pro Gln Ser Ser Thr Ser Lys
        275                 280                 285

Val Val Phe Thr Ser Arg Ser Glu Glu Val Cys Gly Leu Met Glu Ala
    290                 295                 300

His Lys Lys Phe Lys Val Ala Cys Leu Ser Asp Ile Asp Ala Trp Glu
305                 310                 315                 320

Leu Phe Gln Gln Lys Val Gly Glu Glu Thr Leu Lys Ser Pro Asp Ile
                325                 330                 335

Arg Gln Leu Ala Gln Thr Ala Ala Lys Glu Cys Gly Gly Leu Pro Leu
            340                 345                 350

Ala Leu Ile Thr Ile Gly Arg Ala Met Ala Cys Lys Lys Thr Pro Glu
        355                 360                 365

Glu Trp Thr Tyr Ala Ile Glu Val Leu Arg Thr Ser Ser Ser Gln Phe
    370                 375                 380

Pro Gly Leu Gly Asn Glu Val Tyr Pro Leu Leu Lys Phe Ser Tyr Asp
385                 390                 395                 400

Ser Leu Pro Ser Asp Thr Ile Arg Ser Cys Leu Leu Tyr Cys Cys Leu
                405                 410                 415

Tyr Pro Glu Asp Tyr Cys Ile Ser Lys Glu Ile Leu Ile Asp Cys Trp
            420                 425                 430

Ile Gly Glu Gly Phe Leu Thr Glu Arg Asp Arg Phe Gly Glu Gln Asn
        435                 440                 445

Gln Gly Tyr His Ile Leu Gly Ile Leu Leu His Ala Cys Leu Leu Glu
    450                 455                 460

Glu Gly Gly Asp Gly Glu Val Lys Met His Asp Val Val Arg Asp Met
465                 470                 475                 480

Ala Leu Trp Ile Ala Cys Ala Ile Glu Lys Glu Lys Asp Asn Phe Leu
                485                 490                 495

Val Tyr Ala Gly Val Gly Leu Ile Glu Ala Pro Asp Val Ser Gly Trp
            500                 505                 510

Glu Lys Ala Arg Arg Leu Ser Leu Met His Asn Gln Ile Thr Asn Leu
        515                 520                 525

Ser Glu Val Ala Thr Cys Pro His Leu Leu Thr Leu Phe Leu Asn Glu
    530                 535                 540

Asn Glu Leu Gln Met Ile His Asn Asp Phe Phe Arg Phe Met Pro Ser
545                 550                 555                 560

Leu Lys Val Leu Asn Leu Ala Asp Ser Ser Leu Thr Asn Leu Pro Glu
                565                 570                 575

Gly Ile Ser Lys Leu Val Ser Leu Gln His Leu Asp Leu Ser Lys Ser
            580                 585                 590

Ser Ile Glu Glu Leu Pro Leu Glu Leu Lys Ala Leu Val Asn Leu Lys
        595                 600                 605

Cys Leu Asn Leu Glu Tyr Thr Trp Ser Leu Thr Thr Ile Pro Arg Gln
    610                 615                 620

Leu Ile Ser Asn Leu Ser Arg Leu His Val Leu Arg Met Phe Ala Ala
625                 630                 635                 640

Ser His Ser Ala Phe Asp Arg Ala Ser Glu Asp Ser Ile Leu Phe Gly
                645                 650                 655

Gly Gly Glu Leu Ile Val Glu Glu Leu Leu Gly Leu Lys Tyr Leu Glu
            660                 665                 670

Val Ile Ser Phe Thr Leu Arg Ser Ser His Gly Leu Gln Ser Phe Leu
        675                 680                 685

Ser Ser His Lys Leu Arg Ser Cys Thr Arg Ala Leu Leu Leu Gln Cys
```

-continued

```
    690                 695                 700

Phe Asn Asp Ser Thr Ser Leu Glu Val Ser Ala Leu Ala Asp Leu Lys
705                 710                 715                 720

Gln Leu Asn Arg Leu Trp Ile Thr Glu Cys Lys Lys Leu Glu Glu Leu
                725                 730                 735

Lys Met Asp Tyr Thr Arg Glu Val Gln Gln Phe Val Phe His Ser Leu
            740                 745                 750

Lys Lys Val Glu Ile Leu Ala Cys Ser Lys Leu Lys Asp Leu Thr Phe
        755                 760                 765

Leu Val Phe Ala Pro Asn Leu Glu Ser Ile Glu Leu Met Gly Cys Pro
    770                 775                 780

Ala Met Glu Glu Met Val Ser Met Gly Lys Phe Ala Glu Val Pro Glu
785                 790                 795                 800

Val Val Ala Asn Leu Asn Pro Phe Ala Lys Leu Gln Asn Leu Lys Leu
                805                 810                 815

Phe Gly Ala Thr Asn Leu Lys Ser Ile Tyr Trp Lys Pro Leu Pro Phe
            820                 825                 830

Pro His Leu Lys Ser Met Ser Phe Ser His Cys Tyr Lys Leu Lys Lys
        835                 840                 845

Leu Pro Leu Asp Ser Asn Ser Ala Arg Glu Arg Asn Ile Val Ile Ser
    850                 855                 860

Gly Thr Arg Arg Trp Trp Glu Gln Leu Glu Trp Val Asp Glu Ala Thr
865                 870                 875                 880

Arg Asn Ala Phe Leu Pro Cys Phe Asp Ser
                885                 890
```

<210> SEQ ID NO 10
<211> LENGTH: 7528
<212> TYPE: DNA
<213> ORGANISM: artificial
<220> FEATURE:
<223> OTHER INFORMATION: Poncirus trifoliata and Citrus grandis hybrid

<400> SEQUENCE: 10

```
tccgtctata taaacagttc cgtgaacagt aacgtagaca gtatccgtac atgtgaatag     60

tactgtacat gtgaacagtg cctttttttc cttttatgct cctgctaagg ttttcgaccg    120

tcctgagttc aaaagtgatg tctgttttac cgtttgatct ctagtttatt gcgaaatgac    180

tataatgccg ctaaaataca taaaatactt aattaaaata aaacacataa ttaaattaca    240

agaaacttaa atacataaaa agtaagggtt gttagtaata cttgaaatgt aaaatgacgg    300

ttttctcctt tataaatata cattttctaa cactcaacag ccttcacttg gtcgaacaga    360

tcctggcgtg cttggctttc agtctcgcca taaaataggc tttgagactt aatggggcct    420

ttacatgcgt tagaaacttt ttataacctt tgagggtctg ttcgccttcg cttggtcgag    480

ttgatcctgg caaccttaat ttccggtctc gccataaaac aggttttgag acttaatggg    540

gcctttgcat gccttagaaa ctttttataa catgtaaggg tttgctcgcc ttcgtttggt    600

cgaacagatc ctagcatgct tggcttccgg tctcgccata aaacaggctt taagacttaa    660

taaggtcttt gcatgcctta gaaacttttt ataacatgtg agggtctact cgtcttcgct    720

tggtcgaata gatcctggca tgcttggctt ctagtctcac cataaaacag actttgagac    780

ttaatgggac ctttgcatgc cttaaaaacg ttttaaatat caatttacca tttaatgaat    840

aagaaataag ttacaacaat ttttttctct ttattttatt ttttaatgtg taaaggaagt    900

tttataatgg atagaaaaat tagtgccttt ggacaaattt aagtacgaag ttatttttat    960
```

-continued

```
gattttatcc ctgtgacatc catatgatgt aatcatttca agagctgtga taacaaaaag   1020
ataattaaat ataagatttt tttttaaaat gtaacaataa attgtcaaac accaatactt   1080
cttgcaccta tttatttttc gtaattcttg aaataaaagc acttgaaaac tcctagaaac   1140
caatgtttat ttctacaatc caatctttca tagaatcttg aacaggggtg gtcactgtaa   1200
gttccattta tagtatgttt actttttgaa atggggaatc gaaattatta acaatattta   1260
cttcacaaaa taaaggtagg aattagaatt ggaatcgtag gactcactcg aatttaggaa   1320
tggggaatgg gagattgatt ctcaaggctg gtggtgggaa ccaacctccc attcctaaaa   1380
ttgactattt taccccccca ccataaaatt aaaaaaaatg tccatttgtc ctcagttaaa   1440
aattattttg attaattagt atattataat taattaatat attaatgtta attactatta   1500
ttattattaa cgataaaaaa tttttacaat taattaatat attaatatat tattaacaat   1560
aattactaat aataatattt ttgaacaaat aatcacaata attaaaatac acaagaataa   1620
ttatgacaat agttcattaa gtacctttta gtaatttgat acaatttaat tcatttttat   1680
tcctatttta aaacaaagta aatatggcaa tccggctcat tccaattatg attcttataa   1740
ttcaaataaa caatttattc ttatttccat tccctattct gattccaacc catttccatt   1800
cctacccatt ccgattccac cccattttga ttccagttta gtaaacgcac cattagtgta   1860
acttataacc cactaaagat aagccaaaac aagattctag ccccacacga tcccccatgc   1920
tggttacact acatataatt gaggcatatt tttaatgtga tgtaagttaa agtaaatata   1980
acttaggcaa atcacttgat ctagggatgc caatgggata agtttgggat ggggaccata   2040
cccccatccc catttggaat tagaagcaat ccccaaaccc acccccatac ccagaaattc   2100
attttcggta tagtttgggg acatccccaa taatccccga ataaggccag ggttaaaacg   2160
ggtccaatcc ccaatttttt ttatatattt tatcttaaaa agcataataa ttttctggat   2220
atactcaatt aagagctttt aaaacatgat aattttgcta gtactttcat ttttcgtgga   2280
tattcttatg aaccaaacaa aaagtttgcc aatttacaca gcaaacaatt tccacccaat   2340
taattttttt tagaaaattg taagaattta gagttataga gatagaaact atataataag   2400
aaaaaataat tttagatttt aggatttata tgcattttgt aaataaaaca ttaaaagaaa   2460
tgcttgttat taggatgaaa ttttatgagt aagatgatta actttaatat atggatttgt   2520
attttataaa ttaatctgag gtatcttaaa aaataaattc aaaatgggtg ttataagatt   2580
ttagaggggt gttaaaagct catctcttga attgtattgc ccaattatgt agtacattag   2640
cgtgattgtt atgtattcat ttttttcaga tacaacagag gagctgcgta gtgctcaaat   2700
aacaaatatt aataatttca cacacacaaa tacgtatacg tatacatata gacacatatt   2760
atatttaatt aagcaaaaga agtactacgc cagtgaggag agagagagga agagagcttt   2820
ttgtgttcta tttcataatt tttatttaat taaaaatatt aatagttcgg attcgggtgc   2880
ccgaaagaat ctctaaatcc aaaacttaat ttagattagg tcttgggcct attctcgaaa   2940
tagctcctat tctattttta aggtttttga gaactcatac taaactgaaa ttcatcagga   3000
gcccacgggt cccggagctc gcgggaatgt cgccatccct tccttcatct aatggaaagt   3060
tcccataaac aaatgtttct ttatttattt atttttataa aagaaatttc agtgtgaatg   3120
tcttttggac gtttccaaat gttatgggag ctggctacgg tacagattct gtaacataca   3180
gaccaggtta gccagccccc caagggtgtc atttgcttgc tttgtttccg catgccggga   3240
cacgtggagt gcatggagtg gggatgtat gttacagaat ctgtaacata gacttctcca   3300
```

-continued

```
ttgttatgat aagcccttga acctttggtc aaaaaagtat tatcacgcgt tgattgtttg   3360
tatcgcaaat gctagtggca tttgaaagtt gatataatta attacaatct acaaatgttt   3420
aacaaaaaag ctattttgtt gaaaaagcta ttttgacaac aacttcggtt ataaaatttt   3480
caaaaaataa aaatataaaa atattttaat taaaagtaaa ttatataggt ccaactaccg   3540
tgcacttggt gtatggtacc cgtattttgt tcatatatga gttgcccgtt agatataaga   3600
tagaacttac ttcaacggca tagatgtatt ctctttgatt ttaacattaa catctctata   3660
gtttttcaaa aaagcaaaaa agcaaaatag tcaaaggttt gacacataat tttagattat   3720
ttttaaattt tatattttga tcaattgatt taatttacta ttaaaattaa tgacagtata   3780
agtgcaataa cttgaaaaaa atttgaatac ataaattttt ttattttttg aaaataatat   3840
aatatcaatt taatctataa taaaaaattt taatatataa ttaaatttta atttatcaat   3900
aataatatga ccaaatgaca atgttaaaaa atttcataat aatcaacaat ggtttagtat   3960
tcaaatataa ataattgaaa tatactctaa gtgtaaatag tagaaatata ttagacttat   4020
atgttaaaat ttcaaaactt ctaatttttt tacttttcag caaataagag ggagtaattt   4080
accaaaaaca aggggtaccg tgcacccgga gcacatagct tcctccaaat tgtataaaaa   4140
aaatagaaat attttaacta aaagaaaatt gtgcgtaaca actttaatat tttgtttctt   4200
tcataacttt atcaaaattt tatcatcaaa tattttatca atgtaacgct gtaaacaaca   4260
aattaaagtt taatttctta attacaactg gcaaaagaga cgtttaatta tttaattaca   4320
agcgggatag tctcttttgt taaaggaaat taaagtttag ttgtttaaac cgaacacggg   4380
taatcttttc aagcacaaac aaaagagatc ataattcaaa gttgatgttc tcttcgcagc   4440
ggcttctatt catcgaactc catcgttaaa atttccttgg tttgtcctgg ttgaattctc   4500
atccaaagta tgggtaacat tttccaaatc acatgcgacg gcgctctctt taaccgttgc   4560
ctggattgct ttcttggaaa agcagcatat ataaaaaacc tcaaacaaaa tcttgcagac   4620
ttggagactg aattgggaaa actaatcgac gcaaaggaag atgtgatgag gagggtcaac   4680
accgctgaaa ggcacccaat gatgaaaagg ctgaacaaag ttcaaggctg gctttccagg   4740
gtcgaagctg ctaaatccga cggtgacaaa ttgataacat gtggctctca agaaattaag   4800
aaactatgtc ttggaggcta ctgttccaag aactgcaagt caagctacga gtttggcaaa   4860
caagtggcta gaaagctggg agatgtcaag actttaatgg ctgaagaagc ttttgaagcg   4920
gtagctgagg aagtaccaca acctgcggta gatgagagac ccaccgagcc aaccgtagta   4980
ggcttgcaat cacaatttga acaagtctgc aattgtcttg aagaagaatc agccagaatt   5040
gttggcctat acggcatggg cggtgtcggt aaaaccacac tattgactca tatccacaat   5100
aaatttattc agagtccaac taattttaat tatgtgatat gggtcgtagc gtcaaaagat   5160
ctgcgacttg aaaacattca agaaactatc ggggagcaga ttggtttgtt aaacgataca   5220
tggaaaaata aaagaattga acagaaagct caagacatct tcaggatttt gaagcagaag   5280
aagtttttgc tgttgctaga tgatttatgg cagcgggttg atttaacaaa agtgggcgtc   5340
cctcttcctg gcccgcaaaa taatgcatcc aaagtggtat tcacaacccg ttccgaagaa   5400
gtttgtggtt tgatgggagc tcacacgagg tttaaagtgg cgtgcctgtc aaatatcgat   5460
gcttgggaat tgtttcggca gaacgttgga gaagaaacca tgaacagtca tcccgatatt   5520
cttcaactag cccaaacagc agctagagag tgtggtggtt tgcctctagc acttattacc   5580
ataggccgag ccatggcttg caagaagaca cctgaagaat ggagttacgc aattgaggtg   5640
ctaagaacat caagttctca gttcccaggt ttgggaaatg aggtttatcc tcttttaaaa   5700
```

-continued

```
ttcagttacg atagtttgcc gagtgacaca attagatcgt gtcacttata ttgtagttta   5760

tatccagaag attattgcat ttctaaagag aagttgatag actgttggat tggcgagaga   5820

cttttgacag aaagggacag gactggagaa caaaaagaag gataccatat tctgggcatt   5880

cttcttcatg cctgtttact ggaagaggga ggagacggtg aagtaaaaat gcatgacgtg   5940

attcgagata tggcattatg gatagcatgc gacattgaaa gggagaagga gaattttttt   6000

gtttatgctg gcgttggatt agttgaagca cccgatgtca gaggatggga aaaggcaagg   6060

aggttgtcat tgatgcagaa tcaaattagg aatctttcag agattccaac atgtcctcat   6120

ctccttactt tgctccttaa cgaaaataac ttacggaaga tccacaatta cttcttccag   6180

tttatgccct ctctcaaagt tctaaacctg tcacactgcg aactaaccaa gttaccagtg   6240

gggatttcgg agttggtttc actacaacat cttgacctct cagaatccga catagaagag   6300

ttgccaggag agctaaaggc attggtaaat cttaagtgtt tggatttgga atacacaagg   6360

aatttaatta caattccacg tcaactaata tctaatcttt caaggttacg tgtgttgaga   6420

atgtttggtg ctagtcataa tgcatttgat gaagcatcag aaaacagcat tttatttggt   6480

gggggtgaac tcatagtaga ggaactgctt ggtttgaaac atttagaggt gattaccctc   6540

accttgagga gttcttatgg tctccaaagc tttttgaact cgcataagtt acgaagttgt   6600

actcaagctc tgttgctcca acacttcaaa gattcgacat cgctcgaagt ttcagctttg   6660

gccgatctga agcaacttaa cagattgcag attgcaaata gtgtaatatt ggaggaatta   6720

aagatggatt atgcagagga agttcaacaa tttgctttcc gcagtctcaa tatggttgaa   6780

atatgcaatt gcattcaatt gaaggacttg acattccttg ttttcgctcc gaacctcaag   6840

tctattaaag taggaatttg ccatgctatg gaagaaatcg caagtgaggg aaaatttgca   6900

gaagttccag aggtgatggc aaatctaaac ccatttgaaa aactccaaaa tcttgaagta   6960

gctggtgcta gaaatttgaa gagcatttac tggaagtccc tgcccttccc acatctgaaa   7020

gcaatgagtt tcttgcattg caaaaagctt aaaaagcttc cactagattc caacagcgcg   7080

aaggagcgta aaatagttat ttctggagag agaaattggc gggaacagct tcaatgggag   7140

gatgaagcca cacgaaatgc ttttcttcgc tgtttcagag atgtttgagc agagatcgca   7200

tttgattaat ttctggtgcg tgctttttct tacactctgc ttgttaattt ccttcatgta   7260

caagactctt tttcttgcat tcatttgctg tatataattt tatgagaaaa aaagttacga   7320

aaattgatta ctataatttt ggacaagtgg aagtcgggaa aaaaaaataa atgaataaaa   7380

atggtgcatc aatgcttcaa tattcctaat aatggtatcc tctttgtcat ctaacaatct   7440

tttggtttga tccctttgaa ggtactcttt gagatgcggt ttcaatcgag cggcggatta   7500

tttagtttca atcaagcaga aaaataaa                                      7528
```

<210> SEQ ID NO 11
<211> LENGTH: 892
<212> TYPE: PRT
<213> ORGANISM: artificial
<220> FEATURE:
<223> OTHER INFORMATION: Poncirus trifoliata and Citrus grandis hybrid

<400> SEQUENCE: 11

```
Met Gly Asn Ile Phe Gln Ile Thr Cys Asp Gly Ala Leu Phe Asn Arg
1               5                   10                  15

Cys Leu Asp Cys Phe Leu Gly Lys Ala Ala Tyr Ile Lys Asn Leu Lys
            20                  25                  30
```

-continued

```
Gln Asn Leu Ala Asp Leu Glu Thr Glu Leu Gly Lys Leu Ile Asp Ala
        35                  40                  45

Lys Glu Asp Val Met Arg Arg Val Asn Thr Ala Glu Arg His Pro Met
    50                  55                  60

Met Lys Arg Leu Asn Lys Val Gln Gly Trp Leu Ser Arg Val Glu Ala
65                  70                  75                  80

Ala Lys Ser Asp Gly Asp Lys Leu Ile Thr Cys Gly Ser Gln Glu Ile
                85                  90                  95

Lys Lys Leu Cys Leu Gly Gly Tyr Cys Ser Lys Asn Cys Lys Ser Ser
            100                 105                 110

Tyr Glu Phe Gly Lys Gln Val Ala Arg Lys Leu Gly Asp Val Lys Thr
        115                 120                 125

Leu Met Ala Glu Glu Ala Phe Glu Ala Val Ala Glu Glu Val Pro Gln
    130                 135                 140

Pro Ala Val Asp Glu Arg Pro Thr Glu Pro Thr Val Val Gly Leu Gln
145                 150                 155                 160

Ser Gln Phe Glu Gln Val Cys Asn Cys Leu Glu Glu Glu Ser Ala Arg
                165                 170                 175

Ile Val Gly Leu Tyr Gly Met Gly Gly Val Gly Lys Thr Thr Leu Leu
            180                 185                 190

Thr His Ile His Asn Lys Phe Ile Gln Ser Pro Thr Asn Phe Asn Tyr
        195                 200                 205

Val Ile Trp Val Val Ala Ser Lys Asp Leu Arg Leu Glu Asn Ile Gln
    210                 215                 220

Glu Thr Ile Gly Glu Gln Ile Gly Leu Leu Asn Asp Thr Trp Lys Asn
225                 230                 235                 240

Lys Arg Ile Glu Gln Lys Ala Gln Asp Ile Phe Arg Ile Leu Lys Gln
                245                 250                 255

Lys Lys Phe Leu Leu Leu Leu Asp Asp Leu Trp Gln Arg Val Asp Leu
            260                 265                 270

Thr Lys Val Gly Val Pro Leu Pro Gly Pro Gln Asn Asn Ala Ser Lys
        275                 280                 285

Val Val Phe Thr Thr Arg Ser Glu Glu Val Cys Gly Leu Met Gly Ala
    290                 295                 300

His Thr Arg Phe Lys Val Ala Cys Leu Ser Asn Ile Asp Ala Trp Glu
305                 310                 315                 320

Leu Phe Arg Gln Asn Val Gly Glu Glu Thr Met Asn Ser His Pro Asp
                325                 330                 335

Ile Leu Gln Leu Ala Gln Thr Ala Ala Arg Glu Cys Gly Gly Leu Pro
            340                 345                 350

Leu Ala Leu Ile Thr Ile Gly Arg Ala Met Ala Cys Lys Lys Thr Pro
        355                 360                 365

Glu Glu Trp Ser Tyr Ala Ile Glu Val Leu Arg Thr Ser Ser Ser Gln
    370                 375                 380

Phe Pro Gly Leu Gly Asn Glu Val Tyr Pro Leu Leu Lys Phe Ser Tyr
385                 390                 395                 400

Asp Ser Leu Pro Ser Asp Thr Ile Arg Ser Cys His Leu Tyr Cys Ser
                405                 410                 415

Leu Tyr Pro Glu Asp Tyr Cys Ile Ser Lys Glu Lys Leu Ile Asp Cys
            420                 425                 430

Trp Ile Gly Glu Arg Leu Leu Thr Glu Arg Asp Arg Thr Gly Glu Gln
        435                 440                 445

Lys Glu Gly Tyr His Ile Leu Gly Ile Leu Leu His Ala Cys Leu Leu
```

-continued

```
    450                 455                 460

Glu Glu Gly Gly Asp Gly Glu Val Lys Met His Asp Val Ile Arg Asp
465                 470                 475                 480

Met Ala Leu Trp Ile Ala Cys Asp Ile Glu Arg Glu Lys Glu Asn Phe
                485                 490                 495

Phe Val Tyr Ala Gly Val Gly Leu Val Glu Ala Pro Asp Val Arg Gly
            500                 505                 510

Trp Glu Lys Ala Arg Arg Leu Ser Leu Met Gln Asn Gln Ile Arg Asn
        515                 520                 525

Leu Ser Glu Ile Pro Thr Cys Pro His Leu Leu Thr Leu Leu Leu Asn
    530                 535                 540

Glu Asn Asn Leu Arg Lys Ile His Asn Tyr Phe Phe Gln Phe Met Pro
545                 550                 555                 560

Ser Leu Lys Val Leu Asn Leu Ser His Cys Glu Leu Thr Lys Leu Pro
                565                 570                 575

Val Gly Ile Ser Glu Leu Val Ser Leu Gln His Leu Asp Leu Ser Glu
            580                 585                 590

Ser Asp Ile Glu Glu Leu Pro Gly Glu Leu Lys Ala Leu Val Asn Leu
        595                 600                 605

Lys Cys Leu Asp Leu Glu Tyr Thr Arg Asn Leu Ile Thr Ile Pro Arg
    610                 615                 620

Gln Leu Ile Ser Asn Leu Ser Arg Leu Arg Val Leu Arg Met Phe Gly
625                 630                 635                 640

Ala Ser His Asn Ala Phe Asp Glu Ala Ser Glu Asn Ser Ile Leu Phe
                645                 650                 655

Gly Gly Gly Glu Leu Ile Val Glu Glu Leu Leu Gly Leu Lys His Leu
            660                 665                 670

Glu Val Ile Thr Leu Thr Leu Arg Ser Ser Tyr Gly Leu Gln Ser Phe
        675                 680                 685

Leu Asn Ser His Lys Leu Arg Ser Cys Thr Gln Ala Leu Leu Leu Gln
    690                 695                 700

His Phe Lys Asp Ser Thr Ser Leu Glu Val Ser Ala Leu Ala Asp Leu
705                 710                 715                 720

Lys Gln Leu Asn Arg Leu Gln Ile Ala Asn Ser Val Ile Leu Glu Glu
                725                 730                 735

Leu Lys Met Asp Tyr Ala Glu Glu Val Gln Gln Phe Ala Phe Arg Ser
            740                 745                 750

Leu Asn Met Val Glu Ile Cys Asn Cys Ile Gln Leu Lys Asp Leu Thr
        755                 760                 765

Phe Leu Val Phe Ala Pro Asn Leu Lys Ser Ile Lys Val Gly Ile Cys
    770                 775                 780

His Ala Met Glu Glu Ile Ala Ser Glu Gly Lys Phe Ala Glu Val Pro
785                 790                 795                 800

Glu Val Met Ala Asn Leu Asn Pro Phe Glu Lys Leu Gln Asn Leu Glu
                805                 810                 815

Val Ala Gly Ala Arg Asn Leu Lys Ser Ile Tyr Trp Lys Ser Leu Pro
            820                 825                 830

Phe Pro His Leu Lys Ala Met Ser Phe Leu His Cys Lys Lys Leu Lys
        835                 840                 845

Lys Leu Pro Leu Asp Ser Asn Ser Ala Lys Glu Arg Lys Ile Val Ile
    850                 855                 860

Ser Gly Glu Arg Asn Trp Arg Glu Gln Leu Gln Trp Glu Asp Glu Ala
865                 870                 875                 880
```

-continued

Thr Arg Asn Ala Phe Leu Arg Cys Phe Arg Asp Val
885 890

<210> SEQ ID NO 12
<211> LENGTH: 3195
<212> TYPE: DNA
<213> ORGANISM: artificial
<220> FEATURE:
<223> OTHER INFORMATION: Poncirus trifoliata and Citrus grandis hybrid

<400> SEQUENCE: 12
ttttataaat ttccagaaac acaaaatatt tcaatccgca gcagcttttg ttcaaatttt 60
attgacttgt cttgtcgaat ttttatccta ataatgggca acattttgca aatctcgatc 120
tcgtgcgatg gtacttgttt caatcgttgc ctggattgct ttcttggcaa agcagcatat 180
gtaagaaacc tccaaaaaaa tgttgaagcc ttgaaaaatg aattgccaaa actaatcgct 240
aaaaaggacg atgtgatggc gagggtcgtc aacgctgaac ggcaacaaat gatgacaagg 300
ctgaacgaag tgcaattgtg gctttcgagg gtggacgctg ttacagcagg agcagatgaa 360
ttgataagaa ttggctctca agaaattgag aagctgtgtc tcggaggcta ctgttccaag 420
aactgcaagt caagcaaaaa gtttggcaaa caagtggata aaaagctaag cgatgtcaag 480
attttattgg ccgaaggatc ctttgcagtg gtagctcaga gagctccaga atctgtagcg 540
gatgaaaggc ctatcgagcc agcggtgggc atccaatcac aacttgaaca agtttggaga 600
tgtcttgtag aagaaccagt tggaattgtt ggcctatacg gcatgggcgg tgtcggtaaa 660
accacactac tgacccatct caacaataaa tttctcggcc agagagattt tcattttgat 720
tttctgatat gggttgtagt gtcaaaggac ctacaaattg aaaaaattca agaaattatc 780
gggaagaagg tgggtttgtt taatgattcc tggatgaaaa aaaatcttgc agagagagct 840
gttgacatct acaacgtttt gaaggagaag aagtttgtat tgttacttga tgacgtatgg 900
cagcgggttg attttgcaac agtgggcgtc cctattcctc cccgagacaa gagtgcctcc 960
aaagtggtat tcacaactcg ttccactgaa gtttgcggta ggatgggagc tcacaaaaaa 1020
attgaagtgg agtgcttatc agccaacgac gcttgggaat tgtttcgaca gaatgttggg 1080
gaagaaactc tgaatggcca acctaaaatt cttgagctag ccgaaagagt ggccaaagag 1140
tgtgggtgct tgccacttgc tcttattgtc actggccgag ctatggcttg caagaaaaca 1200
ccagcagaat ggagagacgc aattaaagtg ttacaaacat cagcttctga gtttccaggt 1260
ttggaaaata atgtgcttcg tgttttaaaa ttcagttacg atagtttgcc agacgacaca 1320
actagatctt gtctcttgta ttgttgttta tttcctgaag attatcggat ttataaagag 1380
aatttgatag attgttggat tggggaaggt ttcctaaaag taactggcaa atatgaatta 1440
caagacagag gacacactat tttgggtaat attgttcatg cgtgtttatt agaagaggaa 1500
ggagatgatg tagtcaaaat gcacgatgtg attcgtgata tgactttatg gatagcttgt 1560
gacactgaga agacggaaga cacggagaag aagaaagaga actatttggt ttatgaaggt 1620
gctggattaa ctgaggcgcc aaatgtcaga gaatgggaaa atgcgaagag attgtcattg 1680
atggaaactc aaattaggaa tctatcagag gttcctacat gccttcatct tcttacttta 1740
tttcttgtct ttaatgaaga attagagatg atcactggtg acttcttcaa atcaatgcct 1800
tgtctcaaag tcttaaacct gtcgggtgct agacggatgt cttcttttcc tttaggggtt 1860
tcagtgttgg tttcattaca acatcttgat ctctcaggta cagcaataca agagttgcca 1920
aaagagttaa atgctttgga aaatcttaag agtttgaatc tggaccagac acattactta 1980

-continued

```
attacaattc cacggcaact aatatcgcgt ttttcatgtt tagttgtgtt aagaatgttc   2040

ggagttggtg attggtctcc taatggaaaa agaaatgaca gcgatttatt tagcgggggt   2100

gaccttttag tggaggcatt gcgtggtttg aaacatttgg aggtattaag cttgaccttg   2160

aataattctc aagatctcca atgtgttttg aactcggaaa agttacgcag ttgtactcaa   2220

gctctatacc ttcacagctt caaacgctcg gagccacttg atgtttcagc tttggcaggt   2280

ctggagcacc tcaacagatt atggattcat gaatgtgaag aattggagga attgaagatg   2340

gctcgccaac cttttgtttt ccagagcctc gagaagattc aaatatacgg atgccataga   2400

ttgaagaact tgacattcct tctctttgct ccaaacctca agtctattga agttagcagt   2460

tgctttgcta tggaagaaat cataagtgag gtaaaatttg ctgattttcc agaggtgatg   2520

ccaattataa agccttttgc acaactctat tctcttagat taggtggcct aaccgttttg   2580

aagagcattt acaagaggcc gctgcccttc ccatgtctga gagatttgac tgtaaatagt   2640

tgtgatgagc ttagaaagct tccactggat tccaatagtg caaaagagcg taagattgtt   2700

attcgtggat acacaaaatg gtgggaacag cttcaatggg aggatcaaga cactcaaaat   2760

gcttttcgtc catgtttccg gtctatcaat tagttcgata gtgattccta aacagattag   2820

gtggcctgct ttttctagaa ttgatcatct tgttaattcc cttcatgtaa aatgagagtg   2880

tttcttgcat tcccatttct tgttctagtt gctaaacata atattccgag tacagattct   2940

tactaatgtt tatcctcttt gtaataatct atgtaacttt tggctggatt gatcattagc   3000

tagcatggga tatgatttct tcaatttcag atgcatggca aaacatccct acactctttg   3060

gaacttccaa ttatagcttt gcattttgta ttttatcact tttatttata ttttgtcttc   3120

caagtattaa tttgtattct tcaatgtacc ctaaaatata tacagcagga gtgccttttt   3180

tttattaaaa aaaaa                                                     3195
```

<210> SEQ ID NO 13
<211> LENGTH: 899
<212> TYPE: PRT
<213> ORGANISM: artificial
<220> FEATURE:
<223> OTHER INFORMATION: Poncirus trifoliata and Citrus grandis hybrid

<400> SEQUENCE: 13

```
Met Gly Asn Ile Leu Gln Ile Ser Ile Ser Cys Asp Gly Thr Cys Phe
1               5                   10                  15

Asn Arg Cys Leu Asp Cys Phe Leu Gly Lys Ala Ala Tyr Val Arg Asn
            20                  25                  30

Leu Gln Lys Asn Val Glu Ala Leu Lys Asn Glu Leu Pro Lys Leu Ile
        35                  40                  45

Ala Lys Lys Asp Asp Val Met Ala Arg Val Val Asn Ala Glu Arg Gln
    50                  55                  60

Gln Met Met Thr Arg Leu Asn Glu Val Gln Leu Trp Leu Ser Arg Val
65                  70                  75                  80

Asp Ala Val Thr Ala Gly Ala Asp Glu Leu Ile Arg Ile Gly Ser Gln
                85                  90                  95

Glu Ile Glu Lys Leu Cys Leu Gly Gly Tyr Cys Ser Lys Asn Cys Lys
            100                 105                 110

Ser Ser Lys Lys Phe Gly Lys Gln Val Asp Lys Lys Leu Ser Asp Val
        115                 120                 125

Lys Ile Leu Leu Ala Glu Gly Ser Phe Ala Val Val Ala Gln Arg Ala
    130                 135                 140
```

-continued

Pro Glu Ser Val Ala Asp Glu Arg Pro Ile Glu Pro Ala Val Gly Ile
145 150 155 160

Gln Ser Gln Leu Glu Gln Val Trp Arg Cys Leu Val Glu Glu Pro Val
165 170 175

Gly Ile Val Gly Leu Tyr Gly Met Gly Gly Val Gly Lys Thr Thr Leu
180 185 190

Leu Thr His Leu Asn Asn Lys Phe Leu Gly Gln Arg Asp Phe His Phe
195 200 205

Asp Phe Leu Ile Trp Val Val Val Ser Lys Asp Leu Gln Ile Glu Lys
210 215 220

Ile Gln Glu Ile Ile Gly Lys Lys Val Gly Leu Phe Asn Asp Ser Trp
225 230 235 240

Met Lys Lys Asn Leu Ala Glu Arg Ala Val Asp Ile Tyr Asn Val Leu
245 250 255

Lys Glu Lys Lys Phe Val Leu Leu Leu Asp Asp Val Trp Gln Arg Val
260 265 270

Asp Phe Ala Thr Val Gly Val Pro Ile Pro Pro Arg Asp Lys Ser Ala
275 280 285

Ser Lys Val Val Phe Thr Thr Arg Ser Thr Glu Val Cys Gly Arg Met
290 295 300

Gly Ala His Lys Lys Ile Glu Val Glu Cys Leu Ser Ala Asn Asp Ala
305 310 315 320

Trp Glu Leu Phe Arg Gln Asn Val Gly Glu Glu Thr Leu Asn Gly Gln
325 330 335

Pro Lys Ile Leu Glu Leu Ala Glu Arg Val Ala Lys Glu Cys Gly Cys
340 345 350

Leu Pro Leu Ala Leu Ile Val Thr Gly Arg Ala Met Ala Cys Lys Lys
355 360 365

Thr Pro Ala Glu Trp Arg Asp Ala Ile Lys Val Leu Gln Thr Ser Ala
370 375 380

Ser Glu Phe Pro Gly Leu Glu Asn Asn Val Leu Arg Val Leu Lys Phe
385 390 395 400

Ser Tyr Asp Ser Leu Pro Asp Asp Thr Thr Arg Ser Cys Leu Leu Tyr
405 410 415

Cys Cys Leu Phe Pro Glu Asp Tyr Arg Ile Tyr Lys Glu Asn Leu Ile
420 425 430

Asp Cys Trp Ile Gly Glu Gly Phe Leu Lys Val Thr Gly Lys Tyr Glu
435 440 445

Leu Gln Asp Arg Gly His Thr Ile Leu Gly Asn Ile Val His Ala Cys
450 455 460

Leu Leu Glu Glu Glu Gly Asp Asp Val Val Lys Met His Asp Val Ile
465 470 475 480

Arg Asp Met Thr Leu Trp Ile Ala Cys Asp Thr Glu Lys Thr Glu Asp
485 490 495

Thr Glu Lys Lys Lys Glu Asn Tyr Leu Val Tyr Glu Gly Ala Gly Leu
500 505 510

Thr Glu Ala Pro Asn Val Arg Glu Trp Glu Asn Ala Lys Arg Leu Ser
515 520 525

Leu Met Glu Thr Gln Ile Arg Asn Leu Ser Glu Val Pro Thr Cys Leu
530 535 540

His Leu Leu Thr Leu Phe Leu Val Phe Asn Glu Glu Leu Glu Met Ile
545 550 555 560

-continued

```
Thr Gly Asp Phe Phe Lys Ser Met Pro Cys Leu Lys Val Leu Asn Leu
                565                 570                 575

Ser Gly Ala Arg Arg Met Ser Ser Phe Pro Leu Gly Val Ser Val Leu
            580                 585                 590

Val Ser Leu Gln His Leu Asp Leu Ser Gly Thr Ala Ile Gln Glu Leu
        595                 600                 605

Pro Lys Glu Leu Asn Ala Leu Glu Asn Leu Lys Ser Leu Asn Leu Asp
    610                 615                 620

Gln Thr His Tyr Leu Ile Thr Ile Pro Arg Gln Leu Ile Ser Arg Phe
625                 630                 635                 640

Ser Cys Leu Val Val Leu Arg Met Phe Gly Val Gly Asp Trp Ser Pro
                645                 650                 655

Asn Gly Lys Arg Asn Asp Ser Asp Leu Phe Ser Gly Gly Asp Leu Leu
            660                 665                 670

Val Glu Ala Leu Arg Gly Leu Lys His Leu Glu Val Leu Ser Leu Thr
        675                 680                 685

Leu Asn Asn Ser Gln Asp Leu Gln Cys Val Leu Asn Ser Glu Lys Leu
    690                 695                 700

Arg Ser Cys Thr Gln Ala Leu Tyr Leu His Ser Phe Lys Arg Ser Glu
705                 710                 715                 720

Pro Leu Asp Val Ser Ala Leu Ala Gly Leu Glu His Leu Asn Arg Leu
                725                 730                 735

Trp Ile His Glu Cys Glu Glu Leu Glu Glu Leu Lys Met Ala Arg Gln
            740                 745                 750

Pro Phe Val Phe Gln Ser Leu Glu Lys Ile Gln Ile Tyr Gly Cys His
        755                 760                 765

Arg Leu Lys Asn Leu Thr Phe Leu Leu Phe Ala Pro Asn Leu Lys Ser
    770                 775                 780

Ile Glu Val Ser Ser Cys Phe Ala Met Glu Glu Ile Ile Ser Glu Val
785                 790                 795                 800

Lys Phe Ala Asp Phe Pro Glu Val Met Pro Ile Ile Lys Pro Phe Ala
                805                 810                 815

Gln Leu Tyr Ser Leu Arg Leu Gly Gly Leu Thr Val Leu Lys Ser Ile
            820                 825                 830

Tyr Lys Arg Pro Leu Pro Phe Pro Cys Leu Arg Asp Leu Thr Val Asn
        835                 840                 845

Ser Cys Asp Glu Leu Arg Lys Leu Pro Leu Asp Ser Asn Ser Ala Lys
    850                 855                 860

Glu Arg Lys Ile Val Ile Arg Gly Tyr Thr Lys Trp Trp Glu Gln Leu
865                 870                 875                 880

Gln Trp Glu Asp Gln Asp Thr Gln Asn Ala Phe Arg Pro Cys Phe Arg
                885                 890                 895

Ser Ile Asn


<210> SEQ ID NO 14
<211> LENGTH: 3980
<212> TYPE: DNA
<213> ORGANISM: artificial
<220> FEATURE:
<223> OTHER INFORMATION: Poncirus trifoliata and Citrus grandis hybrid

<400> SEQUENCE: 14

aacaataaaa agcaacatta tacagcgcaa acgcaaaaca aaagtaccaa tgggccagtg      60

caaggttcga cttagaggag tacatgatag aaaaaatgtc tcaattgtat aatttattaa     120
```

-continued

```
tacagtatca aaaaaaaaag caaaacaaaa gtagaattct tttttcaaat tacaagataa    180

gtatttaatt taaagcgaaa ggctaacccg ttgaaggcaa gtaaagtatt catgaatggt    240

acatgcctaa taatcctttt tatatttaca gaaacacaaa aaattttcaa tccgcagcag    300

cttctgctaa aattatcttg gatttttagt tgatttctat tatccaaaaa aaaaaatggg    360

taacattttg caaatcgcaa tcgatggtgc tgttttcaat cgttgcatgg attgctttct    420

cggaaaagca gcatatataa gaaacctgca agaaaatgtt gtagccttgg agaccgaatt    480

gggaaagcta atcgaagcaa agaacgatgt gatggcgaga gtcgtcaaca ctgaaaggca    540

accaatgatg acaaggctga acaaagttca aggctggctt tcgggggtgg acgctgttaa    600

agctgaagcc gatgaattga taagacatgg ctctcaagaa attgagaagc tgtgtctcgg    660

aggctactgt tccaagaact ggaagtcaag ctacaagttt ggcaaacaag tggctaaaaa    720

gctaagagat gccgggactt taatggccga aggagtcttt gaagtggtag ctgagagagc    780

tccagaatct gcagcggtgg gcatgcaatc acgacttgaa ccagtttgga gatgtcttgt    840

ggaagaaccc gttggaattg ttggccttta cggcatgggc ggtgtcggta aaaccacact    900

actgacccat ctcaacaata aatttctcgg ccagagagat tttcattttg attttctgat    960

atgggttgta gtgtcaaagg acctacaaat tgaaaaaatt caagaaatta tcgggaagaa   1020

ggtgggtttt tttaatgatt cctggatgaa aaaaaatctt gccgagagag ctgttgacat   1080

ctacaacgtt ttgaaggaga agaagtttgt attgttactt gatgacgtat ggcagcgggt   1140

tgattttgca acagtgggcg tccctattcc tccccgagac aagagtgcct ccaaagtggt   1200

attcacaact cgttccgctg aagtttgcgt ttggatggga gctcacaaaa aatttggagt   1260

ggggtgctta tcagccaacg acgcttggga attgtttcga cagaacgtcg gggaagaaac   1320

tcttacgagt gatcatgata tcgctgagct agcccaaatt gtggccgagg agtgtggtgg   1380

tttgccactc gcacttatta ctattggtca agctatggcc tacaaaaaga cagtagagga   1440

gtggagacat gcaattgaag tgttaagaag atcagcttct gagtttccag gttttgataa   1500

tgtgcttcgt gttttcaaat tcagttacga tagtttgccc gacgacacaa ctagatcttg   1560

tttcttgtat tgttgtttat atcccaaaga ttatggcatt cttaaatggg acttgattga   1620

ctgttggatt ggtgagggat tcttagagga atctgccagg tttgttgcag agaaccaggg   1680

atactgcatt gtgggcactc ttgttgatgc gtgtttacta gaagagatag aagatgataa   1740

agtaaaaatg catgatgttg ttcgttatat ggctctatgg atagtctgtg aaattgagga   1800

ggagaagaga aactttttgg ttcgtgcagg tgctggatta gaacaggcac cggctgttaa   1860

agaatgggaa aatgtgagaa gattgtcatt gatgcaaaat gacattaaaa ttctgtcaga   1920

ggttcctaca tgccctgatc tccatactct atttcttgcc tctaataata atttgcagag   1980

gatcaccgat ggcttcttca aatttatgcc ttctctcaaa gttttgaaga tgtcacactg   2040

tggggatttg aaagttttaa aattaccttt ggggatgtca atgttgggtt cactagaact   2100

tcttgatatt tcacaaacca gcataggaga gttaccagaa gagttgaagt tgttggtaaa   2160

tctgaaatgt ttgaatttaa gatgggcaac ttggttaagt aaaattccac ggcaactaat   2220

atcaaattct tcaaggttac atgtgttgag aatgttcgct actggctgtt cgcattctga   2280

agcatcagaa gacagcgttt tatttggtgg gggcgaagtt ttaatacagg aattgctcgg   2340

tttgaaatat ttagaggtat tggagttgac cttgcgaagt tctcatgctc tccaattatt   2400

ttttagctca aataagttaa aaagttgtat tcgatctctt ctcctcgacg aggtcagagg   2460

tacaaagtcg attattgatg ctacggcttt cgcagatcta aaccacctca atgaattgcg   2520
```

-continued

```
cattgattcc gttgcggaag tggaagaatt gaagattgat tatacagaga tagtacggaa   2580
aaggcgggaa ccttttgttt tcggcagcct tcaccgtgtt actctagggc agtgccttaa   2640
attgaaagat ttgacattcc tcgtttttgc tccaaacctc aagtctctcc agctactcaa   2700
ttgccgtgct atggaagaaa taatcagcgt cggaaaattt gctgaggttc ctgaggtgat   2760
gggacatata agcccttttg aaaatctcca aaggcttcat ttattcgatt tgccacgttt   2820
gaagagcatc tactggaagc cattgccttt cactcatctc aaagaaatga gggtacatgg   2880
gtgtaatcag cttaaaaagc ttccactcga ttccaacagt gcaaaatttg ttattcgtgg   2940
agaagcagag gggtggaacc gacttcaatg ggaggatgat gccactcaaa ttgcttttcg   3000
ttcctgtttc caaccttatc cctgagcggt ggttgcaaca tttgatttct ggtgagtgca   3060
tttttgttaa cgcttatata tataccagtc atttgcttcg tgcaaaagac tatgtctttt   3120
gttctctgtt tttattccag tgtgtttttc ttctggcttc tgcaaatcac aattaaatgt   3180
tgaataatat ggaatcaatg ctttataaat tttccggcgc ggccatttcc ttttcccttt   3240
ttattttttt tgggcgtggg tcgaattgat gctctagttt tttacttttt gtcgtcaact   3300
ttgctctggt ttttcaaatt gatgcttgaa tatatgaatt taattgccgt aaaaggatat   3360
aattaggctg aaattcgcac ttctagaatg aatagaattg aaacagagaa aatattaagc   3420
acactagccc tctttaaacc ccttataatt tcttctgttc taacgataac caaatccttt   3480
gctctaagga ttgataatag tccaccaaaa taatgaacgc ttggatgctg ctttaagggt   3540
ctctaatcaa tagctggaag caaatgagaa gttggtcaca actctgtaaa aagccatgca   3600
gcaattgcta ttcatcttaa taattatgaa gcttttgtta aattttcaaa caaagttgac   3660
atgttatttt gagatttggt tcctgatttt gtatgaatat cattgcttgg tttgagttgg   3720
gtgtgaattc aaattcaaat attctttgtt tttcaattct gaactcaatt tctttttctc   3780
atgcatgtta tgcagaaatg atttttacta aataattttt gataaactat ttaaattaaa   3840
caattggatt aacaaattgt gaccatttat cataagcgtg ctaatataat aacttgtttt   3900
atgaacgatt agttaatcca ttaatattaa aatatatatt agtcagttag ctatgtgtaa   3960
catttgtcat gtttaaaaaa                                               3980
```

```
<210> SEQ ID NO 15
<211> LENGTH: 889
<212> TYPE: PRT
<213> ORGANISM: artificial
<220> FEATURE:
<223> OTHER INFORMATION: Poncirus trifoliata and Citrus grandis hybrid

<400> SEQUENCE: 15

Met Gly Asn Ile Leu Gln Ile Ala Ile Asp Gly Ala Val Phe Asn Arg
1               5                   10                  15

Cys Met Asp Cys Phe Leu Gly Lys Ala Ala Tyr Ile Arg Asn Leu Gln
            20                  25                  30

Glu Asn Val Val Ala Leu Glu Thr Glu Leu Gly Lys Leu Ile Glu Ala
        35                  40                  45

Lys Asn Asp Val Met Ala Arg Val Val Asn Thr Glu Arg Gln Pro Met
    50                  55                  60

Met Thr Arg Leu Asn Lys Val Gln Gly Trp Leu Ser Gly Val Asp Ala
65                  70                  75                  80

Val Lys Ala Glu Ala Asp Glu Leu Ile Arg His Gly Ser Gln Glu Ile
                85                  90                  95
```

-continued

```
Glu Lys Leu Cys Leu Gly Gly Tyr Cys Ser Lys Asn Trp Lys Ser Ser
            100                 105                 110

Tyr Lys Phe Gly Lys Gln Val Ala Lys Lys Leu Arg Asp Ala Gly Thr
        115                 120                 125

Leu Met Ala Glu Gly Val Phe Glu Val Val Ala Glu Arg Ala Pro Glu
    130                 135                 140

Ser Ala Ala Val Gly Met Gln Ser Arg Leu Glu Pro Val Trp Arg Cys
145                 150                 155                 160

Leu Val Glu Glu Pro Val Gly Ile Val Gly Leu Tyr Gly Met Gly Gly
                165                 170                 175

Val Gly Lys Thr Thr Leu Leu Thr His Leu Asn Asn Lys Phe Leu Gly
            180                 185                 190

Gln Arg Asp Phe His Phe Asp Phe Leu Ile Trp Val Val Val Ser Lys
        195                 200                 205

Asp Leu Gln Ile Glu Lys Ile Gln Glu Ile Ile Gly Lys Lys Val Gly
    210                 215                 220

Phe Phe Asn Asp Ser Trp Met Lys Lys Asn Leu Ala Glu Arg Ala Val
225                 230                 235                 240

Asp Ile Tyr Asn Val Leu Lys Glu Lys Lys Phe Val Leu Leu Leu Asp
                245                 250                 255

Asp Val Trp Gln Arg Val Asp Phe Ala Thr Val Gly Val Pro Ile Pro
            260                 265                 270

Pro Arg Asp Lys Ser Ala Ser Lys Val Val Phe Thr Thr Arg Ser Ala
        275                 280                 285

Glu Val Cys Val Trp Met Gly Ala His Lys Lys Phe Gly Val Gly Cys
    290                 295                 300

Leu Ser Ala Asn Asp Ala Trp Glu Leu Phe Arg Gln Asn Val Gly Glu
305                 310                 315                 320

Glu Thr Leu Thr Ser Asp His Asp Ile Ala Glu Leu Ala Gln Ile Val
                325                 330                 335

Ala Glu Glu Cys Gly Gly Leu Pro Leu Ala Leu Ile Thr Ile Gly Gln
            340                 345                 350

Ala Met Ala Tyr Lys Lys Thr Val Glu Glu Trp Arg His Ala Ile Glu
        355                 360                 365

Val Leu Arg Arg Ser Ala Ser Glu Phe Pro Gly Phe Asp Asn Val Leu
    370                 375                 380

Arg Val Phe Lys Phe Ser Tyr Asp Ser Leu Pro Asp Asp Thr Thr Arg
385                 390                 395                 400

Ser Cys Phe Leu Tyr Cys Cys Leu Tyr Pro Lys Asp Tyr Gly Ile Leu
                405                 410                 415

Lys Trp Asp Leu Ile Asp Cys Trp Ile Gly Glu Gly Phe Leu Glu Glu
            420                 425                 430

Ser Ala Arg Phe Val Ala Glu Asn Gln Gly Tyr Cys Ile Val Gly Thr
        435                 440                 445

Leu Val Asp Ala Cys Leu Leu Glu Glu Ile Glu Asp Asp Lys Val Lys
    450                 455                 460

Met His Asp Val Val Arg Tyr Met Ala Leu Trp Ile Val Cys Glu Ile
465                 470                 475                 480

Glu Glu Glu Lys Arg Asn Phe Leu Val Arg Ala Gly Ala Gly Leu Glu
                485                 490                 495

Gln Ala Pro Ala Val Lys Glu Trp Glu Asn Val Arg Arg Leu Ser Leu
            500                 505                 510

Met Gln Asn Asp Ile Lys Ile Leu Ser Glu Val Pro Thr Cys Pro Asp
```

-continued

```
        515                 520                 525

Leu His Thr Leu Phe Leu Ala Ser Asn Asn Asn Leu Gln Arg Ile Thr
    530                 535                 540

Asp Gly Phe Phe Lys Phe Met Pro Ser Leu Lys Val Leu Lys Met Ser
545                 550                 555                 560

His Cys Gly Asp Leu Lys Val Leu Lys Leu Pro Leu Gly Met Ser Met
                565                 570                 575

Leu Gly Ser Leu Glu Leu Leu Asp Ile Ser Gln Thr Ser Ile Gly Glu
            580                 585                 590

Leu Pro Glu Glu Leu Lys Leu Leu Val Asn Leu Lys Cys Leu Asn Leu
        595                 600                 605

Arg Trp Ala Thr Trp Leu Ser Lys Ile Pro Arg Gln Leu Ile Ser Asn
    610                 615                 620

Ser Ser Arg Leu His Val Leu Arg Met Phe Ala Thr Gly Cys Ser His
625                 630                 635                 640

Ser Glu Ala Ser Glu Asp Ser Val Leu Phe Gly Gly Gly Glu Val Leu
                645                 650                 655

Ile Gln Glu Leu Leu Gly Leu Lys Tyr Leu Glu Val Leu Glu Leu Thr
            660                 665                 670

Leu Arg Ser Ser His Ala Leu Gln Leu Phe Phe Ser Ser Asn Lys Leu
        675                 680                 685

Lys Ser Cys Ile Arg Ser Leu Leu Leu Asp Glu Val Arg Gly Thr Lys
    690                 695                 700

Ser Ile Ile Asp Ala Thr Ala Phe Ala Asp Leu Asn His Leu Asn Glu
705                 710                 715                 720

Leu Arg Ile Asp Ser Val Ala Glu Val Glu Glu Leu Lys Ile Asp Tyr
                725                 730                 735

Thr Glu Ile Val Arg Lys Arg Arg Glu Pro Phe Val Phe Gly Ser Leu
            740                 745                 750

His Arg Val Thr Leu Gly Gln Cys Leu Lys Leu Lys Asp Leu Thr Phe
        755                 760                 765

Leu Val Phe Ala Pro Asn Leu Lys Ser Leu Gln Leu Leu Asn Cys Arg
    770                 775                 780

Ala Met Glu Glu Ile Ile Ser Val Gly Lys Phe Ala Glu Val Pro Glu
785                 790                 795                 800

Val Met Gly His Ile Ser Pro Phe Glu Asn Leu Gln Arg Leu His Leu
                805                 810                 815

Phe Asp Leu Pro Arg Leu Lys Ser Ile Tyr Trp Lys Pro Leu Pro Phe
            820                 825                 830

Thr His Leu Lys Glu Met Arg Val His Gly Cys Asn Gln Leu Lys Lys
        835                 840                 845

Leu Pro Leu Asp Ser Asn Ser Ala Lys Phe Val Ile Arg Gly Glu Ala
    850                 855                 860

Glu Gly Trp Asn Arg Leu Gln Trp Glu Asp Asp Ala Thr Gln Ile Ala
865                 870                 875                 880

Phe Arg Ser Cys Phe Gln Pro Tyr Pro
                885
```

```
<210> SEQ ID NO 16
<211> LENGTH: 5313
<212> TYPE: DNA
<213> ORGANISM: artificial
<220> FEATURE:
<223> OTHER INFORMATION: Poncirus trifoliata and Citrus grandis
```

-continued

<400> SEQUENCE: 16

```
tctgttcatt ttgcaatatt ttgcagtatg gccttttata ccacatcgat gacaaatggc     60
ttccttgaaa ttgaaaggag tttttggtgt ggctttaaaa tctttctttc tagggaatct    120
ggacttttta taaggcctag taggtttctt ataaaaattt tccctatgtc caagaaaggg    180
tttcctatgg ctttttgact tgtaatgttt tttgtaaggt ctcgaagagc acttaccatt    240
acaatctttg gaagtggaag ctttggagac catgagaact tctcaaggtg aagctaatca    300
cctctaaata tttcaaacca agcagttcct ctactatgag ttcacccccca ccaaataaaa    360
tgctgtcttc tgatgctcta tcgaaggcac tatgactagc agcaaacatt ctcaggacat    420
gtaaccttga aagattagat attagttgac gcgggattgt agttaaactc catgtatatt    480
ccaaattcaa acacttgaga tttaccaatg cctttaactc tagtggcaac tcttctatgc    540
tggattttga caggtcaaga tgttgcagtg aaaccaactt tgaaatcccc tctggtaagt    600
tggttagact gctgtctgcc agatttagaa ctttgagaga gggcataaat cggaagaagt    660
cattgtggat cctaattaga tagctctgtt atggtgcaat ctaaatctct aggcattgaa    720
aagattcttc ttcacatgag ctaaaaaaga aataatagaa gggtttaaca gccaattaat    780
tccttttttta aaaaaaaaaa ttctagttta aaactctcac cattgttctt ttacttaaaa    840
aaaaaaagac aaaaaaaaaa acatttgtcg ctcacatgca aatagtactc aacactcaca    900
agtcactagt gaggccgtga gaattttttt agtccaaaat gtaacccata tatgcatgca    960
tgtgaatgtg ggtgaaaaat tggaaaaaca gacaaaacac ttttataaag aagtgctttt   1020
gaaacaataa tgcttagtgc tgaagccata aattaagtag aatgaattga cacggtttaa   1080
taagcaacaa aaagtaaaat acacaattga tagatatgca tgtgaatgtg gaagaaaatt   1140
gaataaccaa caaaacactt ttaaaggatg tggttttgag atagtgctta gtactgaaag   1200
tgatttaaag tcattaagta acaaaagtag ataccatata tcccaattgt tatggagcca   1260
caaacaaaag agtcgtatct accatttttt ttcttttttt actttatttt tgttaattat   1320
ttttggaaga ttttgtatta aattattgat tacaagatag ataaaagaaa ttatgtattt   1380
ggtaaggcgg ccggactgtc tgtgataatt tgggcgtcaa attaattatg attatgttcc   1440
ttaggagtta atctaattaa ggctttatct ttattttttgc atgctttcaa tctaggcatc   1500
attagcaatc cgtctctgaa tctcgcaatt ttttttttc aattgtaatg attataaact   1560
tatctgtgag ttctctcatt taaaaaaaat tagatccctt catcattctt aatttcatca   1620
atttatttga actctcattc tgaattgagt tgtaattttt tttcttctca gtattaggct   1680
cattagtgtc attttgatcc gactcatttt acacctttaa tcttcaattc tttatgtgtg   1740
cgtgcgtgca tataacaaaa ataattttca tatctctgtc atcgaccttt ttttatttaa   1800
aaaaaaaaaa acccaaggga ttagaaattc tcaaccctta ggaaaccaat attacaaggt   1860
tttaaatttc tttcagcata tagattatat acttcggcat aattaagtta aattgtcaac   1920
agtttaagct ttcaactgaa ggattacttt atattatttt taggctaatc aggataataa   1980
taaaatagtc ttatacgtga tggcaggcag caagcctgca actaatacaa ttaaattaca   2040
attattttaa aagaaataaa ttacatgttt gtaatcttat tataaattca acaaaattag   2100
attcaagtga gtttttaaag attctaaaaa aaatttacca tatgtatttt aataacagta   2160
tatggataag aattaatttc ttttccaaat tcaacccaat taatcaatta cattatatat   2220
atttatggaa accaaacgga tacaattttt tttttatcaa atattaataa atgaatcact   2280
gccaaaaaga aaatccaaga aattcatatg caataaagtt tttcttcggg agtcgtaagg   2340
```

-continued atttaagaat taaattaagg caaagctgtg atgtcaactc ttttcctttt tgcttttaat 2400
ttttatgata aagcgttcaa atataataaa gtggtaatta attagttagt gatggcggac 2460
aacacctaat acaatgataa ttaacaatta aattttatgt caaccaagtc atcttatttt 2520
tattgtaaac ctccctcata tttaaaccga ccaatttgta taaagtagtt tcttgatcaa 2580
atttggaaga acttttctac aaatcattga tactataaga catcataatt aactagtaat 2640
tgttttctaa aattaaaaag aaaaattgaa aatttcccat gtcaatttgc aaaactaatt 2700
tttttctttc ttttatttc ctaagttaag cctaagccta ggacggacct agcaataacc 2760
caatctactt ctgttaggtg agattaatta atctagaaac tcaatggatc ttaactatga 2820
aaccatgctt ttcacaagtt attcaatatg gtcttaaagc aacggaagaa attgaataga 2880
ttctttaagc aggattagta gttgatgagt tagagctaat taataaaatt tgtcattcaa 2940
atcagttggt agcattgatt caaagggagt tgcttgtagt taaactaaaa accagagaac 3000
ccatcttttc ccacaagtcg agttgccttg tttgaaattt ttattccaaa attttccaca 3060
aaaacagaag tagtgggggg gggtccctac acgttactct tttcccatag cgtgattgat 3120
ggcaatccat tttctctcca agaattaaca atccttcgct cacactcctt gatcacattt 3180
tttggtgtta acattgccat ttggccatgc aaacccccact tcaaactttt ctttctgctt 3240
tattcattct caagtttcaa caaccatatc ataaaatgga agatagaaaa atatatatat 3300
aaaaaaatta tttgattatg ttacttttat ttgattatgt tactattagt gagtaatgct 3360
actactatta taatgagccg tactaatatt aaaattattt gattgatcca caatttcaat 3420
attattcaaa taaaattata aaattacgtc gtatgtccag ttactcatca gtgaattaaa 3480
ttgtttcact gcactaaatc atttctgtat gtttttattt atttatttat ttattatgca 3540
catgcatccc atttaagact ctctcatccg taggggcgca aaaaaaatta tttattattt 3600
aaaaaaaaac catttcctct tttccttctt tatatatata tagacacaca tatctctcaa 3660
actttcaaca cgcatcacac attcatttca ttacacttca aagagtcatg gactggtttt 3720
catggctctc taaaactggc ttggagccaa ctctcgtgta tgaatacggc cttgcttttg 3780
cccacaatga gctagaagaa gaagacatag cttatttcaa ccatgagttt cttcaaagca 3840
tgggcatatc tatagccaag cacaggctag agatcctcaa gctggcaaga aaagaaaagg 3900
gagcagctgg tccaaggcct gtgtcaaggc tcatagttgc tatcaagaga acaaaaagat 3960
ctcttgctaa gtatttgagg acttgggttc gaagagaaga ttcatctaca gctcttgttg 4020
ttgtgcctaa taagcctagt tatggcacaa gatggagaag tgccatgttg aagaggaaca 4080
agaagttgat gctgcctaaa cccggaagac tgctcctcac cagtggaagg gtcaatagtt 4140
tttcaagccc tgtacttagt tatgatcata ataaggagga gaagatgaat ggttatgatc 4200
atcatgaaca tgatcatgat catcatgagg ttgcagatga tgatcggtat tggtcaacag 4260
gagttgaaga gatcagatgg gatacaatgt ttcagaactt gaaacccaca tgaaaggtca 4320
aattttttct tttcaatatg tcgttctgaa tttgatttta gattgtaatg gtgagagatg 4380
ggtttttggg gttcttccac cagattttta ttttttttatt aattttttac ttaatttata 4440
ggggtgtgtt aaagaagaag atcattgaat tgatctttta ctttagtggt gggtcaagat 4500
aaaaaggaag acttaggcag caagggtctg tttcggcaat caagctgtct ccacttagct 4560
tttgtatgct ataatctttt tttcttttta cctttgatag acaagaatgc actagtcctt 4620
agtgtctttt tgaaaagaat ttgtgttaca tatgtccaaa tacgtagcaa gaattgtatc 4680

-continued

```
tttatccgtt ttttgggttg aaaatactga aaatttgtac tggcagaaat attcagatat   4740

atttgttttg ggtgaatctt gactcttttg atggtgttgt cacttttatt gaagtgtaaa   4800

catatttaat attggatttt ggcagctgta ttttgaccaa aaatttaaaa aagcacaaat   4860

gggagcgtcc gcatatttta tatttatgaa cgacaaagaa atgtctgggt ttaaaaggtt   4920

ccatttactg agaattttta tattggtaaa tttctattac ttcatgttgc aataatattt   4980

acaacgtata caattagtac atgatccaaa gaatacattg aagtacgatc ctaatgcaaa   5040

ataagacgtc agaaagaaaa actgtaaatt ataaattcct cttggggaag gacgaagctc   5100

aattatatta tattgatcaa tagcatctaa ttcaggagag tgcacatgct cctgtttaaa   5160

gtacagcatc atgggatgtt ttaactatgt atccacaaaa tcttggccat tgtttcatag   5220

tactcattgg tcactgactc acccagataa tatgcaacaa catcatatat atagccaatg   5280

caagcggcaa tctgcttcct agagagcaaa aaa                                5313
```

<210> SEQ ID NO 17
<211> LENGTH: 201
<212> TYPE: PRT
<213> ORGANISM: artificial
<220> FEATURE:
<223> OTHER INFORMATION: Poncirus trifoliata and Citrus grandis hybrid

<400> SEQUENCE: 17

```
Met Asp Trp Phe Ser Trp Leu Ser Lys Thr Gly Leu Glu Pro Thr Leu
1               5                   10                  15

Val Tyr Glu Tyr Gly Leu Ala Phe Ala His Asn Glu Leu Glu Glu Glu
            20                  25                  30

Asp Ile Ala Tyr Phe Asn His Glu Phe Leu Gln Ser Met Gly Ile Ser
        35                  40                  45

Ile Ala Lys His Arg Leu Glu Ile Leu Lys Leu Ala Arg Lys Glu Lys
    50                  55                  60

Gly Ala Ala Gly Pro Arg Pro Val Ser Arg Leu Ile Val Ala Ile Lys
65                  70                  75                  80

Arg Thr Lys Arg Ser Leu Ala Lys Tyr Leu Arg Thr Trp Val Arg Arg
                85                  90                  95

Glu Asp Ser Ser Thr Ala Leu Val Val Val Pro Asn Lys Pro Ser Tyr
            100                 105                 110

Gly Thr Arg Trp Arg Ser Ala Met Leu Lys Arg Asn Lys Lys Leu Met
        115                 120                 125

Leu Pro Lys Pro Gly Arg Leu Leu Leu Thr Ser Gly Arg Val Asn Ser
    130                 135                 140

Phe Ser Ser Pro Val Leu Ser Tyr Asp His Asn Lys Glu Glu Lys Met
145                 150                 155                 160

Asn Gly Tyr Asp His His Glu His Asp His Asp His His Glu Val Ala
                165                 170                 175

Asp Asp Asp Arg Tyr Trp Ser Thr Gly Val Glu Glu Ile Arg Trp Asp
            180                 185                 190

Thr Met Phe Gln Asn Leu Lys Pro Thr
        195                 200
```

<210> SEQ ID NO 18
<211> LENGTH: 2105
<212> TYPE: DNA
<213> ORGANISM: artificial
<220> FEATURE:
<223> OTHER INFORMATION: Poncirus trifoliata and Citrus grandis -continued

<400> SEQUENCE: 18

```
gaaacaataa gtaatgataa taattttagg caaagtttca aaattatagc tcttaacatt     60
tctcaatatt tcttacattt ttctagaaca aaaataattg aatgaaaaaa attaatggtg    120
gacaaatcgg gtttcagttt ggttgttcgg tttcggcttg ggttacaacc catttgggtt    180
ggagaattca acccaatccg cgttcgaaac acaaaccaat ttggttcgaa tttcgggttg    240
gatcggattc aaaattcaag tcaagatttt ggtttggatt ctaattcggg tgacaacctc    300
ttccaaaatt taattcaatt tcaaaatgaa tcaatcccac ccaggcagcg cctaaaattc    360
caaaaccaaa caccagccca actccagatg caaaaatgaa agcaaaaatg acaccaaatg    420
acaacatata taatacatta atacccatca ccattaacac tcaatacaac aaaaatttca    480
atgttaagaa accgaatcag gaacaattac aactgtttga gggaaaaata ggaaaggcag    540
tgaagcgcca cgtgtcgacc aatggaatgg ttccagcaca atccgaggta ccccgcacga    600
tccgaggtgc ccggcgtgat ttgaggtacc ccgcagaatt agaggtatcc cacacaaata    660
aaggtacccc atataatatg aggtacccca tacaaataga ggtaccccat acaaataggg    720
gtaccccgcg taatagggt accccacgta actcgaggta cccggcaaag cggatgcaag    780
ataatcctcc gaaaatatcc gccatgagaa acgtctccat ctcttaaaag atattattcg    840
attttgtcag aattatgaat caagaacgtc gtaccaaaag ggggggacag ccgcctgcta    900
cctctgccaa aagtgaagga cactttccca aggacagtgg tccccagccg cctacccgac    960
agctactgca gaggtaccct ggaccactct ccagcgcgtg ccacgtttcc aaaagatggg   1020
atacgccgcg aacatgcaga taacggccca aaaaaaatta taaagaggta aaaggacgtt   1080
agccaaaaag ggtacgccac gtggcagctg aattactcca tatataaagg cgcctaggtt   1140
tcattctcca ggaggctctc actcaccaaa aacactcaca ctccaaaaaa gaggttttct   1200
tcaaccttaa accctaattt acagagggct agctagctct ctttgccaca aaagcttgag   1260
tttgctaact tgagcgtcgg agtgtgaacg ccggggtacc ccggcttcac ctctaacctc   1320
tatttcactg ttttgcaggt gtggaaccta tttcgaagga taccactctc agttctaaac   1380
ctttcaccat tgttaccact ctctctccct ttctcacctc ccccgaattt cagttacacc   1440
gcaccgcaca caacatacta gtgaggtacc ccatcttccc aaaaaatata aattcattgt   1500
tcaagattga ttttggattt tcttgcccca aaatctgttg aaaacaacaa ccatcgttac   1560
acaaaagaag attgaacagt ttcagtgcca gtaatgcctc ttacccatgc ccaaaagaag   1620
attgatttac aaacaaccat tcatacacca tttggaaccg catacataaa cttgtgcagc   1680
tgacgaccgt gaatgaagct ggaggcagtg acggcagcag actgagcaga cgcaaacgat   1740
tcaagattgg ctcaaggcga cagtagcttg aagtcttgaa tgaggaacca gatcgactca   1800
agggaggagg aagggctaga agctgcaagc ctgcgacgtc ggtgctctga acggaatcaa   1860
cagcggcagc ggcacatggg tatgtcatgt gtgagtgtct gtgctcactg ctacgtgctg   1920
gctgtgctgt tgtggagcgc aaatgtgaaa gcgcaaagaa gaggcattag ggatttgaag   1980
gaaaggaagc aacgtttgag catatgtgtg tgaatatata ggctaacccg attagatttc   2040
gtacgctaac ccgaaccgaa cccgaaatga ataatttttt aaacattatt tgaaatataa   2100
ataaa                                                               2105
```

<210> SEQ ID NO 19
<211> LENGTH: 204
<212> TYPE: PRT
<213> ORGANISM: artificial

-continued

```
<220> FEATURE:
<223> OTHER INFORMATION: Poncirus trifoliata and Citrus grandis

<400> SEQUENCE: 19

Met Val Asp Lys Ser Gly Phe Ser Leu Val Val Arg Phe Arg Leu Gly
1               5                   10                  15

Leu Gln Pro Ile Trp Val Gly Glu Phe Asn Pro Ile Arg Val Arg Asn
            20                  25                  30

Thr Asn Gln Phe Gly Ser Asn Phe Gly Leu Asp Arg Ile Gln Asn Ser
        35                  40                  45

Ser Gln Asp Phe Gly Leu Asp Ser Asn Ser Ala Pro Lys Ile Pro Lys
    50                  55                  60

Pro Asn Thr Ser Pro Thr Pro Asp Ala Lys Met Lys Ala Lys Met Thr
65                  70                  75                  80

Pro Asn Asp Asn Ile Tyr Asn Thr Leu Ile Pro Ile Thr Ile Asn Thr
                85                  90                  95

Gln Tyr Asn Lys Asn Phe Asn Val Lys Lys Pro Asn Gln Glu Gln Leu
            100                 105                 110

Gln Leu Phe Glu Gly Lys Ile Gly Lys Ala Val Lys Arg His Val Ser
        115                 120                 125

Thr Asn Gly Met Val Pro Ala Gln Ser Glu Val Pro Arg Thr Ile Arg
    130                 135                 140

Gly Ala Arg Arg Asp Leu Arg Ile Met Asn Gln Glu Arg Arg Thr Lys
145                 150                 155                 160

Arg Gly Gly Gln Pro Pro Ala Thr Ser Ala Lys Ser Glu Gly His Phe
                165                 170                 175

Pro Lys Asp Ser Gly Pro Gln Pro Pro Thr Arg Gln Leu Leu Gln Arg
            180                 185                 190

Cys Gly Thr Tyr Phe Glu Gly Tyr His Ser Gln Phe
        195                 200
```

PLANT GENES CONFERRING RESISTANCE TO *CITRUS TRISTEZA* VIRUS

CROSS REFERENCE TO RELATED APPLICATION

The present application claims the priority of U.S. provisional application No. 60/336,549 filed Nov. 15, 2001.

STATEMENT AS TO FEDERALLY SPONSORED RESEARCH

The invention was made with U.S. government support under grant numbers ARS 5907908045, CSREES 00343999371, CSREES/CF/NRI 96353003742, CSREES/S 99343998479, ARS SCA 56-6617-4-018, and ARS SCA 58-6618-0-202, all awarded by the United States Department of Agriculture. The U.S. government may have certain rights in the invention.

FIELD OF THE INVENTION

The invention relates generally to the fields of molecular biology, biochemistry, plant pathology, and agriculture. More particularly, the invention relates to proteins and polynucleotides associated with resistance to microbial plant pathogens.

BACKGROUND

Citrus tristeza virus (CTV) is the most important cosmopolitan viral pathogen of citrus. CTV is a member of the closterovirus group and it induces several serious disease syndromes in citrus. Lee and Bar-Joseph, Tristeza, In: L M Timmer, S M Garnsey, J H Graham, Compendium of Citrus Diseases, 2nd Edition, APS Press, St. Paul, Minn. (2000). Examples of these syndromes include 'quick decline' or death of citrus trees on sour orange rootstock, and 'stem pitting' of scion cultivars regardless of the rootstock used. These diseases severely impact the citrus industry worldwide.

Sour orange is a traditionally used rootstock in many citrus growing regions of the world because of its broad adaptability to a wide range of soil and environmental conditions, as well as its positive influence on the quality of the fruit produced by scion cultivars grafted to it. There are many historical examples of the demise and destruction of regional citrus industries based on the near-exclusive use of sour orange rootstock, following the introduction and spread of quick decline strains of the virus. In such cases, less desirable rootstock alternatives must be used to replant entire regions; if no such alternatives can be found because of severe soil or water quality limitations, then production is dramatically hindered or even abandoned. Stem pitting disease can attack all scions regardless of the rootstock used.

Some citrus and citrus-related plants show resistance to CTV. For example, some pummelo varieties have recently been found to be resistant to certain CTV strains (Garnsey et al., Differential susceptibility of pummelo and Swingle citrumelo to isolates of CTV. In: Da Graca Jv, Moreno P, Yokomi R K, Proc. 13th Conf. Int. Organiz. Citrus Virol. University of California Press, Riverside, Calif. p. 138–146, 1997). *Poncirus trifoliata* L. Raf. (a close relative of *Citrus*), however, is resistant to a wide diversity of CTV strains (Garnsey et al., Phytophylactica 19:187, 1987). This resistance is thought to be controlled by a single genetic element. Successful introgression of this resistance into rootstock cultivars has been accomplished via sexual hybridization, but the development of CTV-resistant yet commercially acceptable scion cultivars has been very difficult due to the coincident introgression of undesirable fruit characteristics from *Poncirus.*

A number of disease resistance (R) genes have been cloned from several other model plant species. The proteins encoded by these genes can be grouped into several classes based on structure: serine/threonine kinases, proteins with a nucleotide binding site and leucine-rich repeats (NBS-LRR), presumed extracellular LRR-containing proteins with or without a transmembrane domain, and serine/threonine receptor-like kinases. Baker et al., Science 276, 726 (1997); Staskawicz et al., Science 268, 661 (1995); and Wang et al., Plant Cell 10, 765 (1998). Presently, however, there are no reports that identify a gene which confers CTV-resistance in *Citrus.* Molecular cloning of such a gene would provide the means for developing CTV-resistant scion cultivars through genetic transformation. Because CTV is a serious threat to the citrus industry worldwide, the development of rootstock and scion cultivars that are resistant to a wide range of CTV strains would mitigate the impact of this pathogen on the citrus industry.

SUMMARY

The invention relates to nucleic acids and polypeptides identified from *Poncirus trifoliata,* a sexually compatible close relative of *Citrus.* These sequences, when present in a plant genome, result in the expression of resistance to CTV infection. Several methods of transforming citrus plants to produce citrus plants that are resistant to the broad genetic diversity of CTV strains are within the invention. Such methods include the introduction of resistance genes to commercially grown citrus scion and rootstock cultivars, as well as to assorted germplasm and breeding lines. Transformed CTV-resistant germplasm and breeding lines can be used in conventional breeding programs, likewise, to create new cultivars that carry and express the resistance genes.

Accordingly the invention features a purified nucleic acid isolatable from *Poncirus trifoliata* that has the ability to confer resistance to pathology caused by CTV infection in a plant cell when the nucleic acid is present in the cell. The nucleic acid can be a purified Rcan5 or Rcan6 gene, e.g., a nucleic acid including a nucleotide sequence that encodes a protein (a) that has at least 65% (e.g., at least 75%, 85%, 95%, or 100%) sequence identity to the amino acid sequence of SEQ ID NOs:13 or 15 and (b) has at least one functional activity of native RCAN5 or native RCAN6. The nucleotide sequence can be that of SEQ ID NOs:12 or 14, or one that defines a polynucleotide whose complement hybridizes under high stringency conditions to the nucleotide sequence of SEQ ID NOs:12 or 14.

The invention also features a vector, a cell, and a seed that includes a nucleic acid of the invention, e.g., one of the nucleic acids described above. The nucleic acid in the vector, cell, or seed can be operably linked to one or more expression control sequences.

In addition the invention features a purified RCAN5 or RCAN6 protein. The protein can include an amino acid sequence that (a) shares at least 80% sequence identity with SEQ ID NOs:13 or 15, or (b) includes the amino acid sequence SEQ ID NOs:13 or 15. Proteins of the invention can be fused to a heterologous polypeptide.

In another aspect the invention features a purified antibody that specifically binds to a protein of the invention, e.g., one described above. The antibody can further include a detectable label.

The invention further features a plant into which has been introduced a nucleic acid of the invention, e.g., a purified Rcan5 or Rcan6 gene. In certain variations, the plant is of the genus *Citrus* (e.g., a plant that produces sweet oranges, grapefruits, mandarins, tangerines, pumelos, lemons, limes or citrons). The plant of the invention can include a citrus scion and a rootstock cultivar (e.g., one from sour orange, rough lemon, mandarin and citrus). The rootstock cultivar can also be a citrus intrageneric hybrid (e.g., tangelos and tangors) or a citrus intergeneric hybrid. The plant can be a breeding line. It can also be a *Fortunella* species, including calamondin and kumquat. The nucleic acid in the plant can include a selectable marker such as an antibiotic resistance gene(s), a β-glucuronidase gene (GUS), or a nucleotide sequence encoding green fluorescent protein (GFP).

Another aspect of the invention is a method of imparting disease resistance in a plant, plant cell or plant seed. This method includes the steps of: (A) providing a plant, plant cell or plant seed; and (B) introducing into the plant, plant cell or plant seed a purified nucleic acid of the invention. Step (B) can include incorporating the purified nucleic acid into a suitable expression vector, transforming the plant, plant cell or plant seed with an *Agrobacterium* strain, microprojectile bombardment, and/or direct nucleic acid uptake by protoplasts.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991: and Lewin, Genes V, Oxford University Press: New York, 1994.

By the term "gene" is meant a nucleic acid molecule that codes for a particular protein, or in certain cases a functional or structural RNA molecule. For example, the Rcan5 gene encodes the RCAN5 protein and the Rcan6 gene encodes the RCAN6 protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "Rcan5 gene," "Rcan5 polynucleotide," "Rcan5 nucleic acid", or simply "Rcan5" is meant a native RCAN5 protein-encoding nucleic acid sequence (a native *Poncirus* Rcan5 cDNA, genomic sequences from which Rcan5 cDNA can be transcribed, for instance, SEQ ID NO: 12, and/or allelic variants and homologs of the foregoing. The terms encompass double-stranded DNA, single-stranded DNA, and RNA.

By the terms "Rcan6 gene," "Rcan6 polynucleotide," "Rcan6 nucleic acid", or simply "Rcan6" is meant a native RCAN6 protein-encoding nucleic acid sequence (a native *Poncirus* Rcan6 cDNA, genomic sequences from which Rcan6 cDNA can be transcribed, for instance, SEQ ID NO:14, and/or allelic variants and homologs of the foregoing. The terms encompass double-stranded DNA, single-stranded DNA, and RNA.

As used herein, "protein" or "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "RCAN5 protein" or "RCAN5 polypeptide," is meant an expression product of a Rcan5 gene such as the protein of SEQ ID NO:13; or a protein that shares at least 65% but preferably 75, 80, 85, 90, 95, 96, 97, 98, or 99% amino acid sequence identity with SEQ ID NO:13 and displays a functional activity of RCAN5 protein. A "functional activity" of a protein is any activity associated with the physiological function of the protein. For example, functional activities of RCAN5 protein include the ability to confer disease resistance to a citrus plant to CTV infection.

By the terms "RCAN6 protein" or "RCAN6 polypeptide," is meant an expression product of a Rcan 6 gene (such as the protein of SEQ ID NO:15; or a protein that shares at least 65% but preferably 75, 80, 85, 90, 95, 96, 97, 98, or 99% amino acid sequence identity with SEQ ID NO:15 and displays a functional activity of RCAN6 protein. A "functional activity" of a protein is any activity associated with the physiological function of the protein. For example, functional activities of RCAN6 protein include the ability to confer disease resistance in a citrus plant to CTV infection.

When referring to a nucleic acid molecule or polypeptide, the term "native" refers to a naturally-occurring (e.g., a "wild-type") nucleic acid or polypeptide. A "homolog" of a *Poncirus* Rcan5 gene is a gene sequence encoding a RCAN5 polypeptide isolated from a plant other than *Poncirus*. A "homolog" of a *Poncirus* Rcan6 gene is a gene sequence encoding a RCAN6 polypeptide isolated from a plant other than *Poncirus*. Similarly, "homologs" of native RCAN5 or RCAN6 polypeptides are expression products of a Rcan5 or Rcan6 homolog, respectively.

A "fragment" of an Rcan5 or Rcan6 nucleic acid is a portion of an Rcan5 or Rcan6 nucleic acid, respectively, that is less than full-length and comprises at least a minimum length capable of hybridizing specifically with a native Rcan5 or Rcan6 nucleic acid, respectively, under stringent hybridization conditions. The length of such a fragment is preferably at least 15 nucleotides, more preferably at least 20 nucleotides, and most preferably at least 30 nucleotides of a native Rcan5 or Rcan6 nucleic acid sequence. A "fragment" of an RCAN5 or RCAN6 polypeptide is a portion of a RCAN5 or RCAN6 polypeptide, respectively, that is less than full-length (e.g., a polypeptide consisting of 10, 20, 30, 40, 50, 75, 100, 150, 200, 250, 300, 350, 400, 450, 500, 550, 600, 650, 700, 800 or more amino acids of native RCAN5 or RCAN6, respectively), and preferably retains at least one functional activity of native RCAN5 or RCAN6 polypeptide, respectively.

When referring to hybridization of one nucleic acid to another, "low stringency conditions" means in 10% formamide, 5× Denhart's solution, 6×SSPE, 0.2% SDS at 42° C., followed by washing in 1×SSPE, 0.2% SDS, at 50° C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics. Examples of conservative amino acid substitutions are ser for ala, thr, or cys; lys for arg; gln for asn, his, or lys; his for asn; glu for asp or lys; asn for his or gln; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors."

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell or organism (e.g., a plant) also includes progeny of the cell or organism, including progeny produced from a breeding program employing such a "transgenic" cell or organism as a parent in a cross. For example, a plant transgenic for Rcan5 or Rcan6 is one in which a Rcan5 or a Rcan6 nucleic acid, respectively, has been introduced.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawing, in which:

DETAILED DESCRIPTION

Figure 1:
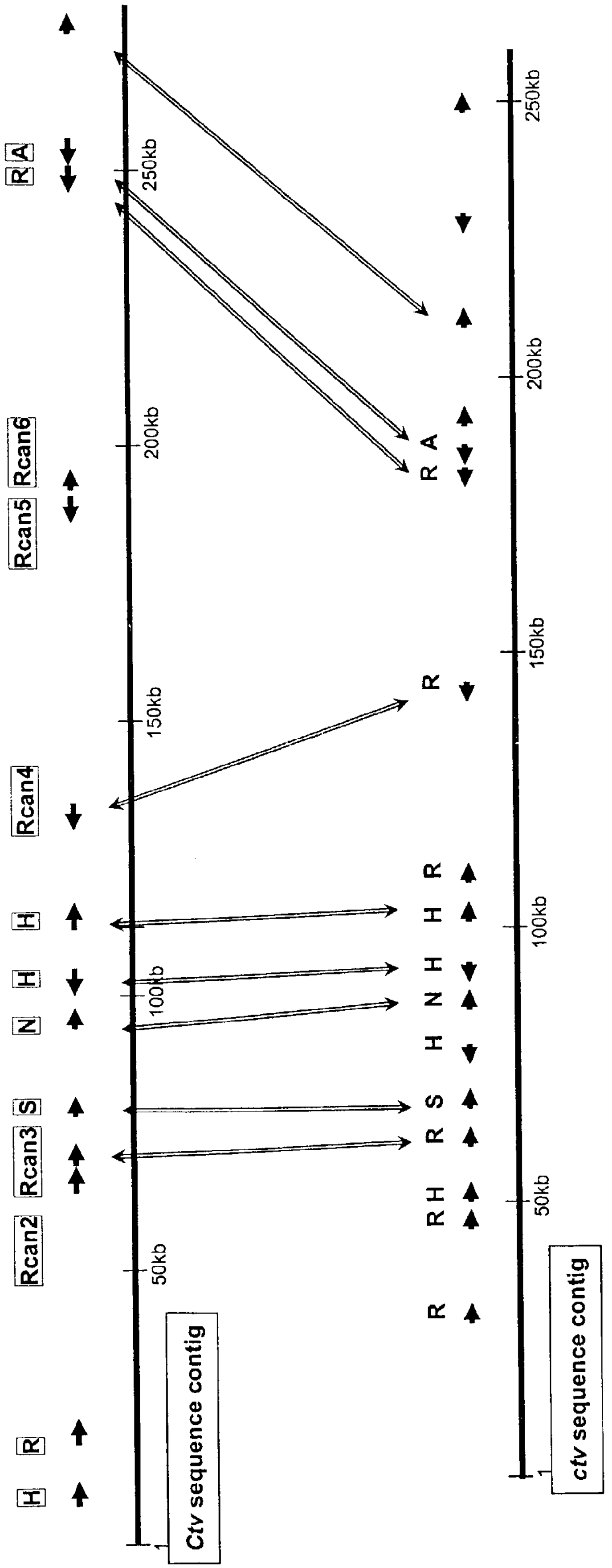
FIG. 1 is a comparison of gene content and gene order between the Ctv (resistance allele) and ctv (susceptibility allele) sequence contigs. The Ctv sequence contig is 277,831 base pairs (bp), and the ctv sequence contig is 252,672 bp. The predicted genes are described as H for hypothetical genes, N for nodulin-like genes, R for disease resistance genes, S for serine-rich protein genes, and A for amino-acid transporter gene. Several R genes are named as Rcan2, Rcan4, Rcan5, and Rcan6. Counterparts of Rcan5 and Rcan6 are not identified in the ctv sequence contig. The open reading frame (ORF) orientation of each gene is indicated by an arrow.

Nucleic acids conferring resistance to CTV infection in a plant have been cloned and sequenced. These resistance genes, known as Rcan5 and Rcan6, are single dominant genes that confer resistance to CTV. Two BAC (bacterial artificial chromosome) contigs derived from a CTV-resistant intergeneric hybrid (USDA 17-47) were constructed to clone genes that confer resistance to CTV infection. The BAC contigs consist of clone inserts from either the susceptibility allele region or the resistance allele region of the hybrid. To delineate genes that confer resistance to CTV, molecular markers were developed from BAC ends or full-length sequences, and mapped genetically in several backcross populations that together contain over one thousand individuals. BAC clone inserts from the susceptibility and resistance allele regions spanning approximately 100 kbp were sequenced. Several gene prediction programs (e.g., GenScan, Genemark, FGENESH, and Glimmer) were used to analyze the sequences within the 100 kb region to identify similar or identical sequences between the two allele regions. By this comparison, a conspicuous region of approximately 100 kb missing from the susceptible allele region was identified. Within this resistance allele region, Rcan5 and Rcan6, as well as two hypothetical genes, were found. In addition to being present in the resistance allele region yet not the susceptibility allele region, these genes are associated with disease resistance characteristics in plants that are hybrids of *Citrus* and *Poncirus*. The predicted peptides have been analyzed using software programs including BLAST.

The molecular cloning of these genes provides the means to develop CTV-resistant scion cultivars through genetic transformation. To introduce resistance genes into *Citrus* and *Citrus*-like plants, cloned resistance gene sequences are ligated into Ti plasmid vectors including promoter and enhancer regions, initiation and termination sequences, and genes for selectable markers such as antibiotic resistance, β-glucuronidase (GUS), green fluorescent protein (GFP), or other similar markers. Plasmid vector constructs are used to transform commonly used *Agrobacterium* strains, which are subsequently used to transform citrus plants with the inserted resistance gene sequences. Plasmid vector constructs may be introduced to citrus plants by other transformation techniques including microprojectile bombardment, direct DNA uptake by protoplasts, or other means. The resistance gene sequences can be cloned together into cosmid vectors, along with adjacent genomic sequences from *Poncirus,* or into other vectors capable of harboring and introducing large cloned DNA inserts (up to 150 kb) into plants, such as the BIBAC vectors. The resistance gene sequences are expected to be useful for creating virus resistant citrus plants of all commonly produced types of citrus fruits, including but not limited to sweet oranges, grapefruit, mandarins and tangerines, pummelos, lemons, limes, citrons, intrageneric hybrids such as tangelos and tangors, and citrus-type fruit such as calamondin and kumquat (*Fortunella* spp.). For example, resistance gene sequences can be introduced into commercially utilized rootstock cultivars, including but not limited to sour orange, rough lemon, various mandarins, and citrus intrageneric and intergeneric hybrids. Virus resistant trees, composed of modified scions and rootstocks, can then be used by citrus growers to counter CTV-induced disease challenges, and to avoid decreased productivity and/or tree death and replanting costs.

The invention encompasses compositions and methods relating to CTV resistance genes and methods of use. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1–3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods involving plant biology techniques are described herein and are described in detail in methodology treatises such as Methods In Plant Molecular Biology: A Laboratory Course Manual ed. Pal Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, Mass.). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

Nucleic Acids Encoding RCAN5 and RCAN6 Proteins

The invention provides purified nucleic acids (polynucleotides) that encode polypeptides having an amino acid sequence selected from the group consisting of SEQ ID NOs:13 and 15. Preferred nucleic acid molecules of the invention are the native Rcan5 and Rcan6 polynucleotides consisting of SEQ ID NO:13 and SEQ ID NO:15, respectively.

Nucleic acid molecules encoding polypeptides of the present invention can be obtained from *Poncirus* plants (e.g., *Poncirus trifoliata*).

Nucleic acid molecules of the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes a native RCAN5 or RCAN6 protein may be identical to a nucleotide sequence consisting of SEQ ID NO:12 and SEQ ID NO:14, respectively. It may also be a different coding sequence which, as a result of the redundancy or degeneracy of the genetic code, encodes the same polypeptide as a polynucleotide selected from the group consisting of SEQ ID NO. 12 and SEQ ID NO:14, respectively. Other nucleic acid molecules within the invention are variants of Rcan5 and Rcan6 such as those that encode fragments, analogs and derivatives of native RCAN5 and RCAN6 polypeptides, respectively. Such variants may be, e.g., a naturally occurring allelic variant of native Rcan5 or Rcan6, a homolog of native Rcan5 or Rcan6, or a non-naturally occurring variant of native Rcan5 or Rcan6. These variants have a nucleotide sequence that differs from native Rcan5 or Rcan6 in one or more bases. For example, the nucleotide sequence of such variants can feature a deletion, addition, or substitution of one or more nucleotides of a native Rcan5 or Rcan6. Nucleic acid insertions are preferably of about 1 to 10 contiguous nucleotides, and deletions are preferably of about 1 to 30 contiguous nucleotides.

In some applications, variant nucleic acid molecules encode polypeptides that substantially maintain a RCAN5 or RCAN6 protein functional activity. For other applications, variant nucleic acid molecules encode polypeptides that lack or feature a significant reduction in a CTV protein functional activity. Where it is desired to retain a functional activity of a native CTV protein, preferred variant nucleic acids feature silent or conservative nucleotide changes.

In other applications, variant RCAN5 and RCAN6 proteins displaying substantial changes in one or more functional activities of native RCAN5 and RCAN6 proteins, respectively, can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of native Rcan5 and Rcan6 within the invention are nucleic acids isolated from *Poncirus* that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Rcan5 and Rcan6, respectively, and encode polypeptides having at least one functional activity in common with a native RCAN5 or RCAN6 protein, respectively. Homologs of native Rcan5 and Rcan6 within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Rcan5 and Rcan6, respectively, and encode polypeptides having at least one functional activity in common with a native RCAN5 or RCAN6 protein, respectively. Naturally occurring allelic variants of Rcan5 and Rcan6 as well as homologs of Rcan5 and Rcan6 can be isolated by screening *Poncirus* species and non-*Poncirus* species, respectively, for a native RCAN5 or RCAN6 protein functional activity (e.g., ability to confer disease resistance) using a BAC library as described herein, other assays described herein, or other techniques known in the art. The nucleotide sequence of such homologs and allelic variants can be determined by conventional DNA sequencing methods. Alternatively, public or non-proprietary nucleic acid databases can be searched to identify other nucleic acid molecules having a high percent (e.g., 70, 80, 90% or more) sequence identity to native Rcan5 and Rcan6. Once identified, these sequences can be incorporated into expression constructs that can be used in various assays such as those described herein to screen for those molecules that encode proteins which share or lack one or more functional activities of native RCAN5 and RCAN6 polypeptides.

Non-naturally occurring Rcan5 and Rcan6 variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Rcan5 and Rcan6, respectively, and encode polypeptides having at least one functional activity in common with native Rcan5 and Rcan6 encoded polypeptides, respectively. Examples of non-naturally occurring Rcan5 and Rcan6 nucleic acids are those that encode a fragment of a RCAN5 and RCAN6 protein, respectively, those that hybridize to native Rcan5 and Rcan6, respectively, or a complement of native Rcan5 and Rcan6, respectively, under stringent conditions, those that share at least 65% sequence identity with native Rcan5 and Rcan6, respectively, or a complement of native Rcan5 and Rcan6, respectively, and those that encode a RCAN5 and RCAN6 polypeptide fusion protein, respectively.

Nucleic acids encoding fragments of RCAN5 and RCAN6 polypeptides within the invention are those that encode, e.g., 200, 250, 300, 350, 400, 450, 500, 550, 600, 650, 700, 750, 800 or more amino acid residues of a RCAN5 or RCAN6 polypeptide, respectively. Shorter oligonucleotides (e.g., those of 6, 12, 20, 30, 50, 100, 125, 150 or 200 base pairs in length) that encode or hybridize with nucleic acids that encode fragments of a RCAN5 or RCAN6 polypeptide, respectively, can be used as probes, primers, or antisense molecules. Longer polynucleotides (e.g., those of 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800 or 3900 base pairs) that encode or hybridize with nucleic acids that encode fragments of a RCAN5 or RCAN6 polypeptide, respectively, can be used in place of a native RCAN5 or RCAN6 polypeptide, respectively, in applications where it is desired to modulate a functional activity of a native RCAN5 or RCAN6 polypeptide, respectively. Nucleic acids encoding fragments of a RCAN5 or RCAN6 polypeptide can be made by enzymatic digestion (e.g., using a restriction enzyme) or chemical degradation of full length Rcan5 or Rcan6, respectively, or variants of Rcan5 or Rcan6, respectively.

Nucleic acids that hybridize under stringent conditions to a nucleic acid selected from the group consisting of SEQ ID NOs:12 and 14, or the complement of a sequence selected from the group consisting of SEQ ID NOs:12 and 14 are also within the invention. For example, such nucleic acids can be those that hybridize to a sequence selected from the group consisting of SEQ ID NOs:12 and 14 or the complement of a sequence selected from the group consisting of SEQ ID NOs:12 and 14 under low stringency conditions, moderate stringency conditions, or high stringency conditions are within the invention. Preferred such nucleic acids are those having a nucleotide sequence that is the complement of all or a portion of a sequence selected from the group consisting of SEQ ID NOs:12 and 14. Other variants of Rcan5 and Rcan6 within the invention are polynucleotides that share at least 65% (e.g., 65, 70, 75, 80, 85, 90, 91, 92, 93, 94, 95, 96, 97, 98, and 99%) sequence identity to a sequence selected from the group consisting of SEQ ID NOs:12 and 14, respectively, or the complement of a sequence selected from the group consisting of SEQ ID NOs:12 and 14, respectively. Nucleic acids that hybridize under stringent conditions to or share at least 65% sequence identity with a sequence selected from the group consisting of SEQ ID NOs:12 and 14 or the complement of a sequence selected from the group consisting of SEQ ID NOs:12 and 14 can be obtained by techniques known in the art such as by making mutations in native Rcan5 and Rcan6, respectively, by isolation from an organism expressing such a nucleic acid (e.g., a *Poncirus* plant expressing a variant of native Rcan5 or Rcan6), or a non-*Poncirus* plant expressing a homolog of native Rcan5 or Rcan6, respectively.

Nucleic acid molecules encoding RCAN5 and RCAN6 polypeptide fusion proteins are also within the invention. Such nucleic acids can be made by preparing a construct (e.g., an expression vector) that expresses a RCAN5 or RCAN6 polypeptide fusion protein, respectively, when introduced into a suitable host. For example, such a construct can be made by ligating a first polynucleotide encoding a RCAN5 or RCAN6 polypeptide fused in frame with a second polynucleotide encoding another protein such that expression of the construct in a suitable expression system yields a fusion protein.

Using the nucleotide sequences of native Rcan5 and Rcan6 and the amino acid sequences of RCAN5 and RCAN6 polypeptides disclosed herein, those skilled in the art can create nucleic acid molecules that have minor variations in their nucleotide sequences, by, for example, standard nucleic acid mutagenesis techniques or by chemical synthesis. Variant Rcan5 and Rcan6 nucleic acid molecules can be expressed to produce variant RCAN5 and RCAN6 polypeptides, respectively.

Antisense, Ribozyme, Triplex, and RNA Interference Techniques

Another aspect of the invention relates to the use of purified antisense nucleic acids to inhibit expression of Rcan5 and Rcan6. Antisense nucleic acid molecules within the invention are those that specifically hybridize (e.g. bind) under cellular conditions to cellular mRNA and/or genomic DNA encoding a RCAN5 or RCAN6 protein in a manner that inhibits expression of the RCAN5 or RCAN6 protein, respectively, e.g., by inhibiting transcription and/or translation. The binding may be by conventional base pair complementarity, or, for example, in the case of binding to DNA duplexes, through specific interactions in the major groove of the double helix. As non-limiting examples, antisense oligonucleotides may be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region.

Antisense constructs can be delivered, for example, as an expression plasmid which, when transcribed in the cell, produces RNA which is complementary to at least a unique portion of the cellular mRNA which encodes a RCAN5 or RCAN6 protein. Alternatively, the antisense construct can take the form of an oligonucleotide probe generated ex vivo which, when introduced into a Rcan5 or Rcan6 expressing cell, causes inhibition of Rcan5 or Rcan6 expression, respectively, by hybridizing with an mRNA and/or genomic sequences coding for RCAN5 or RCAN6 protein, respectively. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense methods have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of an RCAN5 or RCAN6 protein-encoding nucleotide sequence, are preferred.

Antisense approaches involve the design of oligonucleotides (either DNA or RNA or PNA) that are complementary to Rcan5 and Rcan6 mRNA. The antisense oligonucleotides will bind to Rcan5 or Rcan6 mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. Wagner, R. (1994) Nature 372:333. Therefore, oligonucleotides complementary to either the 5' or 3' untranslated, non-coding regions of a Rcan5 or Rcan6 gene could be used in an antisense approach to inhibit translation of endogenous Rcan5 or Rcan6 mRNA, respectively. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of Rcan5 or Rcan6 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, β-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Antisense oligonucleotides of the invention may also comprise at least one modified sugar moiety selected from the group including but not limited to arabinose, 2-fluoroarabinose, xylulose, and hexose; and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other. Gautier et al., Nucl. Acids Res. 15:6625–6641, 1987. Such an oligonucleotide can be a 2'-0-methylribonucleotide (Inoue et al., Nucl. Acids Res. 15:6131–6148, 1987), or a chimeric RNA-DNA analogue. Inoue et al., FEBS Lett. 215:327–330, 1987.

Oligonucleotides of the invention may be synthesized by standard methods known in the art, e.g by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. U.S.A. 85:7448–7451, 1988), etc.

The antisense molecules should be delivered into cells that express Rcan5 or Rcan6 in vivo. A number of methods have been developed for delivering antisense DNA or RNA into cells. For instance, antisense molecules can be introduced directly into the tissue site using bombardment-based methodology (see, e.g., Christou P (1997) Plant Mol Biol 35: 197) or by *Agrobacterium*-mediated transformation (see, e.g., Hiei et al., Plant Mol Biol 35: 205, 1997). Alternatively, modified antisense molecules, designed to target the desired cells (e.g., antisense linked to peptides or antibodies that specifically bind receptors or antigens expressed on the target cell surface) can be used.

However, because it is often difficult to achieve intracellular concentrations of the antisense sufficient to suppress translation on endogenous mRNAs, a preferred approach utilizes a recombinant DNA construct in which the antisense oligonucleotide is placed under the control of a strong promoter. The use of such a construct to transfect target cells will result in the transcription of sufficient amounts of single stranded RNAs that will form complementary base pairs with the endogenous transcripts specific for the peptides and proteins of interest of the current invention and thereby prevent translation of the respective mRNAs. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in plant cells. Expression of the sequence encoding the antisense RNA can be by any promoter known in the art to act in plant, preferably citrus, *P. trifiolata*, or *P. trfiolata* and citrus hybrid cells. Such promoters can be inducible or constitutive. Such promoters include, but are not limited to: the SV40 early promoter region (Bernoist and Chambon, Nature 290:304–310, 1981), the promoter contained in the 3' long terminal repeat of Rous sarcoma virus (Yamamoto et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982), Figwort Mosaic Virus promoter (Maiti et al., Transgenic Res. 6:143–156, 1997; and Sanger et al., Plant Mol. Biol. 14:433–443, 1990), etc. Any type of plasmid, cosmid, BAC, YAC or viral vector can be used to prepare the recombinant DNA construct which can be introduced directly into the tissue or cell derivation site; e.g., the tissue/cell type. Alternatively, viral vectors can be used which selectively infect the desired tissue or cell type; (e.g., viruses which infect cells of tissue/cell type), in which case administration may be accomplished by another route (e.g., systemically). The use of such a construct to transform the plant cell will result in the transcription of sufficient amounts of single stranded RNAs that will form complementary base pairs with the endogenous Rcan5 or Rcan6 transcripts and thereby prevent translation of Rcan5 or Rcan6 mRNA, respectively.

Ribozyme molecules designed to catalytically cleave Rcan5 and Rcan6 mRNA transcripts can also be used to prevent translation of Rcan5 and Rcan6 mRNA, respectively, and expression of RCAN5 and RCAN6, respectively (See, e.g., PCT Publication No. WO 90/11364, published Oct. 4, 1990; Sarver et al., Science 247:1222–1225, 1990; and U.S. Pat. No. 5,093,246). While ribozymes that cleave mRNA at site specific recognition sequences can be used to destroy Rcan5 and Rcan6 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591, 1988. There are hundreds of potential hammerhead ribozyme cleavage sites within the nucleotide sequences of native Rcan5 and Rcan6. Preferably the ribozyme is engineered so that the cleavage recognition site is located near the 5' end of Rcan5 and Rcan6 mRNA; i.e., to increase efficiency and minimize the intracellular accumulation of non-functional mRNA transcripts. Ribozymes within the invention can be delivered to a cell using a vector as described below.

The ribozymes of the present invention also include RNA endoribonucleases (e.g., "Cech-type ribozymes") such as the one which occurs naturally in *Tetrahymena Thermophila* (known as the IVS, or L-19 IVS RNA) and which has been extensively described by Thomas Cech and collaborators (Zaug et al., Science, 224:574–578; Zaug and Cech, 1984, Science, 231:470–475, 1986; Zaug et al., Nature, 324: 429–433, 1986; published International Patent Application No. WO 88/04300 by University Patents Inc.; Been and Cech, Cell, 47:207–216, 1986). The Cech-type ribozymes act as endoribonucleases by catalyzing the cleavage of large RNA molecules by a mechanism involving guanosine transfer. The sequence specificity approaches that of DNA restriction endonucleases. These ribozymes can be synthesized to cut at a variety of tetranucleotide sequences specific for the peptides and proteins of the present invention.

Endogenous Rcan5 and Rcan6 gene expression can also be reduced by inactivating or "knocking out" the Rcan5 and Rcan6 genes, respectively, or their promoters using targeted homologous recombination. See, for example, Kempin et al., Nature 389: 802, 1997; Smithies et al., Nature 317: 230–234, 1985; Thomas and Capecchi, Cell 51:503–512, 1987; and Thompson et al., Cell 5:313–321, 1989. For example, a mutant, non-functional Rcan5 or Rcan6 variant (or a completely unrelated DNA sequence) flanked by DNA homologous to the endogenous Rcan5 or Rcan6 genes, respectively, (either the coding regions or regulatory regions of the Rcan5 or Rcan6 genes) can be used, with or without a selectable marker and/or a negative selectable marker, to transfect cells that express RCAN5 or RCAN6, respectively, in vivo.

Alternatively, endogenous Rcan5 and Rcan6 gene expression might be reduced by targeting deoxyribonucleotide sequences complementary to the regulatory regions of the Rcan5 and Rcan6 genes, respectively, (i.e., the Rcan5 or Rcan6 promoter and/or enhancers) to form triple helical structures that prevent transcription of the Rcan5 or Rcan6 genes, respectively, in target cells. (See generally, Helene, C.

Anticancer Drug Des. 6(6):569–84, 1991; Helene, C., et al., Ann. N.Y. Acad. Sci. 660:27–36, 1992; and Maher, L. J. Bioassays 14(12):807–15, 1992).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Another technique that may be employed to modulate expression of Rcan5 and Rcan6 is RNA interference (RNAi). Chuang and Meyerowicz, Proc. Nat'l Acad. Sci. USA, 97:4985, 2000; Brantl S, Biochim. Biophys. Acta 1575(1–3):15–25, 2002; and Ueda R, J. Neurogenet. 15(3–4):193–204, 2001. In this technique, sequence-specific double-stranded RNA is introduced into a cell in order to generate a nonheritable, epigenetic knockout of gene function that phenocopies a null mutation in the targeted gene. By selecting appropriate sequences (e.g., those corresponding to nucleic acids encoding all or a portion of RCAN5 and RCAN6 polypeptides), expression of dsRNA can interfere with accumulation of endogenous mRNA encoding a target protein (e.g., RCAN5 and RCAN6).

In another method for modulating RCAN5 or RCAN6 protein function, nucleic acid molecules encoding dominant negative mutants of RCAN5 or RCAN6 proteins, respectively, are used to inhibit the function of native RCAN5 or RCAN6 proteins, respectively, by competing with native RCAN5 or RCAN6 protein, respectively.

Antisense RNA, DNA and PNA, ribozyme, and triple helix molecules of the invention may be prepared by any method known in the art for the synthesis of DNA, RNA and PNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Also included in the invention are methods for inhibiting Rcan5 and Rcan6 expression through sequence-specific silencing of homologous genes. Gene expression can be suppressed by synthetic small interfering RNAs and by small hairpin RNAs as described by McCaffrey et al., Nature, 418: 38–39, 2002.

Probes and Primers

The invention also includes oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to a native Rcan5 or Rcan6 sequence under high stringency conditions, and those that hybridize to Rcan5 or Rcan6 homologs, respectively, under at least moderately stringent conditions. Preferably, probes and primers according to the present invention have complete sequence identity with the native *Poncirus* Rcan5 or Rcan6 sequences, although probes differing from the *Poncirus* Rcan5 or Rcan6 sequences, respectively, and that retain the ability to hybridize to native Rcan5 or Rcan6 sequences, respectively, under stringent conditions may be designed by conventional methods. Primers and probes based on the native *Poncirus* Rcan5 and Rcan6 sequences disclosed herein can be used to confirm the disclosed Rcan5 and Rcan6 sequences, respectively, by conventional methods, e.g., by re-cloning and sequencing a *Poncirus* Rcan5 or Rcan6 cDNA, respectively.

Vectors for Expressing RCAN5 and RCAN6 Proteins

Natural or synthetic nucleic acids according to the present invention can be incorporated into recombinant nucleic acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, e.g., in Sambrook et al., supra, or Ausubel et al., supra.

Expression of Rcan5 and Rcan6 genes in plants is achieved by introducing into a plant a nucleic acid sequence containing a Rcan5 or Rcan6 gene encoding a RCAN5 or RCAN6 polypeptide, respectively. A number of vectors suitable for stable transformation of plant cells or for the establishment of transgenic plants are known. See, e.g., Pouwels et al., Cloning Vectors: A Laboratory Manual, 1985, Supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include (1) one or more cloned plant genes under the transcriptional control of 5' and 3' regulatory sequences and (2) a dominant selectable marker. Such plant expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

For expressing plant resistance genes according to the invention, useful promoters include those that are native to the resistance genes, as well as promoters that are not native to the resistance genes (e.g., derived from a plant genome other than *Poncirus*). For example, Rcan5 expression may be under the control of the native Rcan5 promoter. Similarly, expression of Rcan6 may be under the control of the native Rcan6 promoter. Enhancer sequences that are native to resistance genes of the invention may also be incorporated into expression vectors to enhance high level expression of these genes.

An example of a useful plant promoter that is derived from a plant other than *Poncirus* which could be used to express a plant resistance gene according to the invention is a caulimovirus promoter, e.g., the cauliflower mosaic virus (CaMV) 35S promoter. These promoters confer high levels of expression in most plant tissues, and are generally not dependent on the particular encoded proteins to be expressed. CaMV is a source for both the 35S and 19S promoters. In most tissues of transgenic plants, the CaMV 35S promoter is a strong promoter. See, e.g., Odel et al., Nature 313:810, (1985); Dekeyser et al., Plant Cell 2:591, (1990); Terada and Shimamoto, Mol. Gen. Genet. 220:389, (1990). The Figwort Mosaic Virus promoter is another example of a useful promoter (Sanger et al., Plant Mol. Biol. 14:433–443, 1990; and Maiti et al., Transgenic Res. 6:143–156, 1997. Other plant promoters that may be useful in the invention are known. See, e.g., An et al., Plant Physiol. 88:547, (1988), Fromm et al., Plant Cell 1:977, (1989); Callis et al., Plant Physiol. 88: 965, (1988); Kuhlemeier et al., Plant Cell 1: 471, (1989); Schaffner and Sheen, Plant Cell 3: 997, (1991); Simpson et al., EMBO J. 4: 2723, (1985); Marcotte et al., Plant Cell 1:969, (1989); Siebertz et al., Plant Cell 1: 961, (1989); Roshal et al., EMBO J. 6:1155, (1987); Schernthaner et al., EMBO J. 7: 1249, (1988); and Bustos et al., Plant Cell 1:839, (1989)).

Plant expression vectors may also include RNA processing signals such as introns, which have been shown to be important for efficient RNA synthesis and accumulation. Callis et al., Genes and Dev. 1: 1183, (1987). The location of the RNA splice sequences can influence the level of transgene expression in plants. In view of this fact, an intron may be positioned upstream or downstream of a Rcan5 or Rcan6 sequence in the transgene to modulate levels of gene expression.

Expression vectors within the invention may also include regulatory control regions which are generally present in the 3' regions of plant genes. See, e.g., Thornburg et al., Proc. Natl Acad. Sci USA 84: 744, (1987); An et al., Plant Cell 1: 115, (1989). For example, a 3' terminator region may be included in the expression vector to increase stability of the mRNA. For instance, 3' terminators derived from octopine or nopaline synthase genes could be used Plant expression vectors within the invention preferably contain a selectable marker gene used to identify the cells that have become transformed. Suitable selectable marker genes for plant systems include genes encoding enzymes that produce antibiotic resistance (e.g., those conferring resistance to hygromycin, kanamycin, bleomycin, G418, streptomycin or spectinomycin) or herbicide resistance (e.g., phosphinothricin acetyltransferase which confers resistance to the herbicide Basta® (Hoechst A G, Frankfurt, Germany). A useful strategy for selection of transformants for herbicide resistance is described in Vasil I. K., Cell Culture and Somatic Cell Genetics of Plants, Vol I, II, III Laboratory Procedures and Their Applications Academic Press, New York, 1984. Plant expression vectors may also contain a non-selectable marker gene to identify the cells that have been transformed. Examples of useful marker genes include those encoding green fluorescent protein (GFP) and β-glucoronidase (GUS).

Cells Transformed with Rcan5 and Rcan6

Upon construction of the plant expression vector, several standard methods are known for introduction of the recombinant genetic material into the host plant for the generation of a transgenic plant. Examples of such methods include (1) *Agrobacterium*-mediated transformation (*A. tumefaciens* or *A. rhizogenes*) (see, e.g., Lichtenstein and Fuller In: Genetic Engineering, vol 6, PWJ Rigby, ed, London, Academic Press, 1987; and Lichtenstein, C. P., and Draper, J,. In: DNA Cloning, Vol II, D. M. Glover, ed, Oxford, IRI Press, 1985), (2) the particle delivery system (see, e.g., Gordon-Kamm et al., Plant Cell 2:603, (1990); or BioRad Technical Bulletin 1687, supra), (3) microinjection protocols (see, e.g., Green et al., Plant Tissue and Cell Culture, Academic Press, New York, 1987), (4) polyethylene glycol (PEG) procedures (see, e.g., Draper et al., Plant Cell Physiol 23:451, (1982); or e.g., Zhang and Wu, Theor. Appl. Genet. 76:835, (1988)), (5) liposome-mediated DNA uptake (see, e.g., Freeman et al., Plant Cell Physiol 25: 1353, (1984)), (6) electroporation protocols (see, e.g., Gelvin et al supra; Dekeyser et al. supra; or Fromm et al Nature 319: 791, (1986)), and (7) the vortexing method (see, e.g., Kindle, K., Proc. Natl. Acad. Sci., USA 87:1228, (1990)).

*Agrobacterium*-mediated plant transformation is typically carried out in several phases. First, the plasmid of interest is grown in *E. coli* cells, then extracted and purified. The purified plasmid DNA is then transferred into electrocompetent *Agrobacterium* cells via electroporation. The resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, e.g., streptomycin, and another that will be expressed in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of *Agrobacterium*, delimit the region that will be transferred to the plant.

In another example, plant cells may be transformed by shooting into the cell tungsten microprojectiles on which cloned DNA is precipitated. In the Biolistic Apparatus (Bio-Rad, Hercules, Calif.) used for the shooting, a gunpowder charge (0.22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transgenic Plants

Transgenic plants within the invention can be made by regenerating plant cells transformed with a plant expression vector by standard plant tissue culture techniques. See, e.g., in Vasil supra; Green et al., supra; Weissbach and Weissbach, supra; Gelvin et al., supra; and Yu et al., Plant Cell, Tissue, and Organ Culture 71:147–155, 2002. For example, a vector carrying a selectable marker gene (e.g., kanamycin resistance), a cloned Rcan5 or Rcan6 gene under the control of its own promoter and terminator or, if desired, under the control of exogenous regulatory sequences such as the 35S CaMV promoter and the nopaline synthase terminator is transformed into *Agrobacterium.* A vector carrying both a cloned Rcan5 gene and an Rcan6 gene can also be transformed into *Agrobacterium.* Transformation of plant tissue with vector-containing *Agrobacterium* can be carried out as described in Yu et al. (Plant Cell, Tissue and Organ Culture 71:147–155, 2002). In one example of a transformation protocol, putative transformants are selected after a few weeks (e.g., 3 to 5 weeks) on plant tissue culture media containing kanamycin (e.g. 0–50 mg $l^{-1}$). Kanamycin-resistant shoots are then placed on plant tissue culture media without hormones for root initiation. Kanamycin-resistant plants are then selected for greenhouse growth. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra). Transgenic plants expressing the selectable marker are then screened for transmission of the transgene DNA by standard immunoblot and DNA and RNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). In situ hybridization according to standard protocols can be performed using transgene-specific nucleotide probes to localize sites of expression within transgenic tissue.

RCAN5 and RCAN6 Polypeptides

In another aspect, the present invention provides purified RCAN5 and RCAN6 polypeptides encoded by nucleic acids of the invention. A preferred form of a RCAN5 or RCAN6 polypeptide is a purified native RCAN5 or RCAN6 polypeptide, respectively, that has a deduced amino acid sequence of SEQ ID NO:13 or SEQ ID NO:15, respectively. Variants of native RCAN5 and RCAN6 polypeptides such as fragments, analogs and derivatives of native RCAN5 and RCAN6 polypeptides, respectively, are also within the invention. Such variants include, e.g., polypeptides encoded by naturally occurring allelic variants of native Rcan5 and Rcan6, polypeptides encoded by homologs of native Rcan5 and Rcan6, and polypeptides encoded by non-naturally occurring variants of native Rcan5 and Rcan6.

RCAN5 and RCAN6 polypeptide variants have peptide sequences that differ from native RCAN5 and RCAN6 polypeptides, respectively, in one or more amino acids. The peptide sequences of such variants can feature a deletion, addition, or substitution of one or more amino acids of a native RCAN5 or RCAN6 polypeptide. Amino acid insertions are preferably of about 1 to 4 contiguous amino acids, and deletions are preferably of about 1 to 10 contiguous amino acids. In some applications, variant RCAN5 and RCAN6 polypeptides substantially maintain a native RCAN5 and RCAN6 polypeptide, respectively, functional activity. For other applications, variant RCAN5 and RCAN6 polypeptides lack or feature a significant reduction in a RCAN5 and RCAN6 polypeptide, respectively, functional activity. Where it is desired to retain a functional activity of native RCAN5 and RCAN6 polypeptides, preferred RCAN5 and RCAN6 polypeptide variants can be made by expressing nucleic acid molecules within the invention that feature silent or conservative changes. Variant RCAN5 and RCAN6 polypeptides with substantial changes in functional activity can be made by expressing nucleic acid molecules within the invention that feature less than conservative changes.

Another aspect of the present invention concerns recombinant forms of the RCAN5 and RCAN6 proteins. Recombinant polypeptides preferred by the present invention, in addition to native RCAN5 and RCAN6 polypeptides, are encoded by nucleic acids that have at least 85% sequence identity (e.g., 85, 86, 87, 88, 89, 90, 91, 92, 93, 94, 95, 96, 97, 98, 99, 100%) with an amino acid sequence selected from the group consisting of SEQ ID NOs: 13 and 15, respectively. In a preferred embodiment, a RCAN5 or RCAN6 protein of the present invention is a *Poncirus* RCAN5 or RCAN6 protein, respectively. In a particularly preferred embodiment, a RCAN5 or RCAN6 protein has one or more functional activities of native RCAN5 or RCAN6 proteins, respectively.

RCAN5 and RCAN6 protein variants can be generated through various techniques known in the art. For example, RCAN5 and RCAN6 protein variants can be made by mutagenesis, such as by introducing discrete point mutation(s), or by truncation. Mutation can give rise to a RCAN5 or RCAN6 protein variant having substantially the same, or merely a subset of the biological activity of native RCAN5 or RCAN6 protein, respectively. Alternatively, antagonistic forms of the protein can be generated which are able to inhibit the function of the naturally occurring form of the protein. Whether a change in the amino acid sequence of a peptide results in a RCAN5 or RCAN6 protein variant having one or more functional activities of native RCAN5 or RCAN6 protein, respectively, can be readily determined by testing the variant for a native RCAN5 or RCAN6 protein functional activity in one or more of the assays described herein.

As another example, RCAN5 and RCAN6 protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential RCAN5 or RCAN6 protein sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223,409, 5,198,346, and 5,096,815).

Anti-RCAN5 and Anti-RCAN6 Antibodies

RCAN5 and RCAN6 polypeptides (or immunogenic fragments or analogs thereof) can be used to raise antibodies useful in the invention. Such polypeptides can be isolated as described herein. Fragments of RCAN5 and RCAN6 polypeptides can be prepared by digesting the native proteins with proteases or by synthesizing oligopeptides based on known amino acid sequence information. In general, RCAN5 and RCAN6 polypeptides can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with a RCAN5 or RCAN6 polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*. Antibodies can also be made in plants as described, for example, in U.S. Pat. No. 6,417,429

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, $F(ab')_2$ fragments, and molecules produced using a Fab expression library. Monoclonal antibodies, which are homogeneous populations of antibodies to a particular antigen, can be prepared using the RCAN5 and RCAN6 polypeptides described above and standard hybridoma technology. See e.g., Kohler et al., Nature 256:495, 1975; Kohler et al., Eur. J. Immunol. 6:511, 1976; Kohler et al., Eur. J. Immunol. 6:292, 1976; Hammerling et al., 1981, Monoclonal Antibodies and T Cell Hybridomas, Elsevier, N.Y.; Ausubel et al., supra. In particular, monoclonal antibodies can be obtained by any technique that provides for the production of antibody molecules by continuous cell lines in culture such as described in Kohler et al., Nature 256:495, 1975; and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al. (1983) Monoclonal Antibodies and Cancer Therapy, Alan R. Liss, Inc., pp. 77–96). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific RCAN5 or RCAN6 polypeptide recognition by Western blot or immunoprecipitation analysis by standard methods, for example, as described in Ausubel et al., supra. Antibodies that specifically recognize and bind to RCAN5 or RCAN6 polypeptides are useful in the invention. For example, such antibodies can be used in an immunoassay to monitor the level of RCAN5 or RCAN6 polypeptide produced by a plant (e.g., to determine the amount or subcellular location of RCAN5 or RCAN6 polypeptide).

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant RCAN5 or RCAN6 polypeptides or control proteins, such as glucocorticoid receptor, CAT, or luciferase.

The antibodies of the invention can be used, for example, in the detection of RCAN5 or RCAN6 polypeptides in a biological sample. Antibodies also can be used in a screening assay to measure the effect of a candidate compound on expression or localization of RCAN5 or RCAN6 polypeptides. Additionally, such antibodies can be used to interfere with the interaction of RCAN5 or RCAN6 polypeptides and other molecules that interact with RCAN5 or RCAN6 polypeptides.

Techniques described for the production of single chain antibodies (U.S. Pat. Nos. 4,946,778, 4,946,778, and 4,704,692) can be adapted to produce single chain antibodies against a RCAN5 or RCAN6 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., Science 246:1275, 1989) to allow rapid and easy identification of monoclonal Fab fragments with the desired specificity.

Detection of RCAN5 and RCAN6 or Nucleic Acid Molecules Encoding RCAN5 and RCAN6 Polypeptides The invention encompasses methods for detecting the presence of RCAN5 and RCAN6 proteins or Rcan5 and Rcan6 nucleic acids in a biological sample as well as methods for measuring the levels of RCAN5 and RCAN6 proteins or Rcan5 and Rcan6 nucleic acids in a biological sample. Such methods are useful for examining plant intracellular signaling pathways associated with disease resistance.

An exemplary method for detecting the presence or absence of RCAN5 or RCAN6 in a biological sample involves obtaining a biological sample from a test plant (or plant cell or plant seed) and contacting the biological sample with a compound or an agent capable of detecting a RCAN5 or RCAN6 polypeptide, respectively, or a nucleic acid encoding a RCAN5 or RCAN6 polypeptide, respectively (e.g., mRNA or genomic DNA). A preferred agent for detecting a nucleic acid encoding a RCAN5 or RCAN6 polypeptide is a labeled nucleic acid probe capable of hybridizing to the nucleic acid encoding the RCAN5 or RCAN6 polypeptide, respectively. The nucleic acid probe can be, for example, all or a portion of Rcan5 or Rcan6 (e.g., a nucleic acid molecule having the sequence of SEQ ID NOs:12 or 14, respectively) or all or a portion of a complement of Rcan5 or Rcan6. Similarly, the probe can also be all or a portion of a Rcan5 or Rcan6 variant, or all or a portion of a complement of a Rcan5 or Rcan6 variant, respectively. For instance, oligonucleotides at least 15, 30, 50, 100, 250, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 nucleotides in length that specifically hybridize under stringent conditions to native Rcan5 or Rcan6 or a complement of native Rcan5 or Rcan6 can be used as probes within the invention.

A preferred agent for detecting a RCAN5 or RCAN6 polypeptide is an antibody capable of binding to a RCAN5 or RCAN6 polypeptide, respectively, preferably an antibody with a detectable label. Such antibodies can be polyclonal, or more preferably, monoclonal. An intact antibody, or a fragment thereof (e.g., Fab or $F(ab')_2$) can be used.

The antibodies may be used in any known immunoassays that rely on the binding interaction between an antigenic determinant of a polypeptide of the invention, and the antibodies. Examples of such assays are radioimmunoassays, enzyme immunoassays (e.g. ELISA), immunofluorescence, immunoprecipitation, latex agglutination, hemagglutination, and histochemical tests.

Cytochemical techniques known in the art for localizing antigens using light and electron microscopy may be used to detect a polypeptide of the invention. Generally, an antibody of the invention may be labeled with a detectable substance and a polypeptide may be localized in tissues and cells based upon the presence of the detectable substance. Various methods of labeling polypeptides are known in the art and may be used. Examples of detectable substances include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, β-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

Where a radioactive label is used as a detectable substance, a polypeptide of the invention may be localized by radioautography. The results of radioautography may be quantitated by determining the density of particles in the radioautographs by various optical methods, or by counting the grains.

In another example, RCAN5 and RCAN6 polypeptides can be detected by two-dimensional polyacrylamide gel electrophoresis (2D gels) (O'Farrell, P. H. J. Biol. Chem. 250:4007–4021, 1975). In this technique, proteins are resolved on the basis of some physical property (e.g., isoelectric point) in a first dimension separation, and then by molecular weight in the second dimension. Many individual proteins from complex cell extracts can be resolved on 2D gels permitting the simultaneous analysis of hundreds or even thousands of gene products. Although 2D gels are currently a widely used separation tool, it is worth noting that reverse phase HPLC, capillary electrophoresis, isoelectric focusing and related hybrid techniques also provide powerful means of resolving complex protein mixtures and are included in the invention.

The nucleic acid molecules of the invention allow those skilled in the art to construct nucleotide probes for use in the detection of nucleic acid sequences of the invention in biological materials. Suitable probes include nucleic acid molecules based on nucleic acid sequences encoding at least 5 sequential amino acids from regions of the RCAN5 or RCAN6 polypeptides (SEQ ID Nos. 13 and 15, respectively), preferably they comprise 15 to 50 nucleotides, more preferably 15 to 40 nucleotides, most preferably 15–30 nucleotides. A nucleotide probe may be labeled with a detectable substance such as a radioactive label that provides for an adequate signal and has sufficient half-life such as $^{32}P$, $^{3}H$, $^{14}C$ or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes. The nucleic acid probes may be used to detect Rcan5 and Rcan6 genes, preferably in plant cells.

The probe may be used in hybridization techniques to detect a Rcan5 or Rcan6 gene. The technique generally involves contacting and incubating nucleic acids (e.g. recombinant DNA molecules, cloned genes) obtained from a sample from a plant or other cellular source with a probe of the present invention under conditions favorable for the specific annealing of the probes to complementary sequences in the nucleic acids. After incubation, the non-annealed nucleic acids are removed, and the presence of nucleic acids that have hybridized to the probe if any are detected.

Detection methods of the invention can be used to detect an mRNA encoding RCAN5 or RCAN6, a genomic DNA encoding RCAN5 or RCAN6, or a RCAN5 or RCAN6 poypeptide in a biological sample in vitro as well as in vivo.

For example, in vitro techniques for detection of mRNAs encoding RCAN5 or RCAN6 include Northern hybridizations and in situ hybridizations. In vitro techniques for detection of an RCAN5 or RCAN6 polypeptide include enzyme-linked immunosorbent assays (ELISAs), Western blots, immunoprecipitations and immunofluorescence. In vitro techniques for detection of genomic DNA encoding RCAN5 or RCAN6 include Southern hybridizations. Furthermore, in vivo techniques for detection of an RCAN5 or RCAN6 polypeptide include introducing into a plant or plant cell labeled anti-RCAN5 or anti-RCAN6 antibody, respectively. For example, the antibody can be labeled with a radioactive marker whose presence and location in a plant can be detected by standard imaging techniques.

The detection of nucleic acid molecules of the invention may involve the amplification of specific gene sequences using an amplification method (e.g. PCR), followed by the analysis of the amplified molecules using techniques known to those skilled in the art. Suitable primers can be routinely designed by one of skill in the art. For example, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 60° C. to 72° C.

Genomic DNA may be used in hybridization or amplification assays of biological samples to detect abnormalities involving Rcan5 or Rcan6 structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a Rcan5 or Rcan6 gene. The polymorphisms may be used to identify individuals in populations that are likely to carry mutations. If a polymorphism exhibits linkage disequalibrium with mutations in the Rcan5 or Rcan6 gene, it can also be used to screen for individuals in the general population likely to carry mutations. Polymorphisms which may be used include restriction fragment length polymorphisms (RFLPs), single-nucleotide polymorphisms (SNP), random amplified polymorphic DNA (RAPD) and simple sequence repeat polymorphisms (SSLPs).

A probe or primer of the invention may be used to directly identify RFLPs. A probe or primer of the invention can additionally be used to isolate genomic clones such as YACs, BACs, PACs, cosmids, phage or plasmids. The DNA in the clones can be screened for SSLPs, for example, using hybridization or sequencing procedures.

Hybridization and amplification techniques described herein may be used to assay qualitative and quantitative aspects of Rcan5 or Rcan6 expression. For example, RNA may be isolated from a cell type or tissue known to express Rcan5 or Rcan6 and tested utilizing the hybridization (e.g. Northern analyses) or PCR techniques referred to herein. The techniques may be used to detect differences in transcript size that may be due to normal or abnormal alternative splicing. The techniques may be used to detect quantitative differences between levels of fill length and/or alternatively spliced transcripts detected in normal individuals relative to those individuals exhibiting symptoms of a disease.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a phenotype (e.g., disease resistance), and to develop and monitor the activities of agents that modulate the phenotype.

The preparation, use, and analysis of microarrays are well known to a person skilled in the art. (See, for example, Brennan, T. M. et al., 1995, U.S. Pat. No. 5,474,796; Schena, et al., Proc. Natl. Acad. Sci. 93:10614–10619, 1996; Baldeschweiler et al., 1995, PCT Application WO95/251116; Shalon, D. et al., 1995, PCT application WO95/35505; Heller, R. A. et al., Proc. Natl. Acad. Sci. 94:2150–2155, 1997; and Heller, M. J. et al., 1997, U.S. Pat. No. 5,605, 662.).

Methods

The invention provides methods for producing RCAN5 and RCAN6 proteins. Such methods include transforming a cell with a nucleotide sequence that encodes an RCAN5 or RCAN6 protein (SEQ ID NOs:12 and 14, respectively), culturing the cell under conditions that allow expression of the RCAN5 or RCAN6 protein, and collecting the RCAN5 or RCAN6 protein from the cultured cell. For example, a host cell transfected with a nucleic acid vector directing expression of a nucleotide sequence encoding the subject polypeptides can be cultured under appropriate conditions to allow expression of the polypeptide to occur. The cells may be harvested, lysed, and the protein isolated. A recombinant Rcan5 or Rcan6 encoded polypeptide can be isolated from host cells using techniques known in the art for purifying proteins including ion-exchange chromatography, gel filtration chromatography, ultrafiltration, and electrophoresis. To transform a host cell with a nucleotide sequence that encodes RCAN5 or RCAN6 protein (SEQ ID NOs:12 and 14, respectively), any of a number of suitable transformation techniques may be employed. An example of a host cell that can be used for production of RCAN5 and RCAN6 proteins is a bacterial cell (e.g., *E. coli*).

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells (e.g., *E. coli*) containing the expression vector are grown in any of a number of suitable media (e.g., Luria Broth (LB)). The expression of the recombinant protein may be induced, e.g., by adding IPTG to the media or by altering the incubation temperature to a higher temperature, depending on the particular promoter construct employed. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

The invention also provides methods for imparting disease resistance to a plant, plant cell, or plant seed. Such methods include introducing into a plant, plant cell, or plant seed a purified nucleic acid encoding RCAN5 or RCAN6 (e.g., SEQ ID NOs:12 and 14, respectively) to create a transformed plant, plant cell, or plant seed. Introduction of the nucleic acid into the plant, plant cell, or plant seed produces a disease resistance phenotype (e.g., resistance to CTV) in the transformed plant, plant cell, or plant seed. A purified nucleic acid according to the invention may include a nucleotide sequence of SEQ ID NO:12 or SEQ ID NO:14 and a selectable marker. Suitable selectable markers include antibiotic resistance genes, β-glucuronidase gene (GUS), nucleotide sequence encoding green fluorescent protein (GFP), and other similar markers. To introduce a purified nucleic acid into a plant, plant cell, or plant seed, the purified nucleic acid may be incorporated into a suitable vector (e.g., Ti plasmid vector including promoter and enhancer regions and expression vectors). Suitable vectors include pCLD04541 (Chauhan et al., Mol. Genet. Genomics 267: 603–612, 2002), pGA482GG (An et al., EMBO J. 4:277–284, 1985), pYLTAC7 (Liu et al., PNAS 96:6535–6540, 1999), and the pCAMBIA series of vectors (CAMBIA, Black Mountain, Australia). The pCAMBIA vectors are a suite of modular DNA vectors useful for performing *Agrobacterium*-mediated and direct transformation experiments.

Plasmid vector constructs are used to transform commonly used *Agrobacterium* strains, which are subsequently used to transform a plant, plant cell, or plant seed with the inserted resistance gene sequences (e.g., SEQ ID NOs:12 and 14). Plasmid vector constructs may be introduced to plants, plant cells or plant seeds by other transformation techniques including microprojectile bombardment, direct DNA uptake by protoplasts, or other means. The resistance gene sequences can be cloned together into cosmid vectors, along with adjacent genomic sequences from *Poncirus*, or into other vectors capable of harboring and introducing large cloned DNA inserts (up to 150 kb) into plants, such as the BIBAC vectors. The resistance gene sequences are useful for creating virus-resistant plants of all commonly produced types of citrus fruits, including but not limited to sweet oranges, grapefruit, mandarins and tangerines, pummelos, lemons, limes, citrons, intrageneric hybrids such as tangelos and tangors, and citrus-type fruit such as calamondulin and kumquat (*Fortunella* spp.).

The present invention is further illustrated by the following specific examples. The examples are provided for illustration only and are not to be construed as limiting the scope or content of the invention in any way.

EXAMPLES

Example 1

Genetic Identification and Confirmation of Ctv, a Single Dominant Gene Conferring Resistance to CTV Infection Five segregating populations (families) were produced by crossing CTV resistant with susceptible materials. Individuals of each population were challenged with CTV virus by grafting buds onto virus-infected lemon rootstock, maintained under favorable environment conditions, and carefully evaluated for resistance phenotype. Plants that did not become infected with viruses as revealed by ELISA (enzyme-linked immunosorbent assay) after 6–12 months of constant challenges were considered virus resistant; those that were infected were considered susceptible. Phenotype data from all five evaluated populations over a period of 8 years showed a segregation ratio of 1:1 between resistant and susceptible individuals, thus indicating that a single dominant gene confers the resistance. This gene was designated as Ctv.

Example 2

Identification of Molecular Markers for Ctv

Based on the phenotype, plants were divided into resistant or susceptible groups. Genomic DNA was extracted from sub-samples of these groups and pooled according to the method of bulked segregant analysis (BSA; Michelmore et al., PNAS 88, p. 9828 [1991]), thus creating two DNA pools: resistance and susceptibility, respectively. These pools were used to screen the PCR products amplified with over 600 decamer primers (oligonucleotides). Those PCR products that were present in the resistance DNA pool, but absent in the susceptibility DNA pool, were genetically mapped further using the populations described above. The genetic distances and orders of these markers relative to Ctv were calculated based on their recombination frequencies and segregation in the populations.

Innovative uses have been made of some available techniques to identify markers more closely linked or co-segregating with disease resistance gene (R) loci. Current data suggest that plant resistance genes often fall into one of four or five classes: NBS-LRR (nucleotide-binding site—leucine rich repeats), LRR, protein kinase, kinase-LRR, etc. Structural domains are well conserved in the NBS-LRR class, which has enabled designing of degenerate PCR primers from the conserved amino acids in the structural domains, for rapid gain of access to some disease resistance gene loci. Examples have demonstrated that many of the PCR products amplified with the degenerate primers are linked to R genes, and even in some cases, the products are part of the targeted R genes.

The above-mentioned BSA strategy has been used to screen degenerate primers and PCR products for rapid identification of those that are linked or co-segregating with target R gene loci. In this use, each pair of degenerate primers and their products were screened in parallel with CTV resistant and susceptible parents, and two DNA pools—resistance and susceptibility that were derived from their progeny. This approach allowed the screening of several dozens of primer pairs and hundreds of PCR products and led to the finding of several PCR fragments that were present in the CTV-resistant parent and progeny DNA bulk, but absent in the susceptible parent and primers were designed, and their PCR products were mapped. Consequently, one fragment was found co-segregating with Ctv.

Example 3

Genetic Mapping of the Resistance Gene and Molecular Markers

A high-resolution genetic map is very critical for map-based gene cloning. Development of such a map has been very difficult in woody perennial plants like citrus and *Poncirus* due to the long life cycle, large tree sizes, great heterozygosity, and difficulty in resistance evaluation. To achieve this objective, a large population consisting of 678 individuals was generated by crossing CTV-resistant strain 17-47 and CTV-susceptible strain *Nakon pummelo*. All the individuals were analyzed for their genetic components at a number of marker loci that are located around Ctv. Those plants that contained recombination events among these marker loci were selected and thoroughly characterized for their resistance to CTV. The segregation ratio of 1:1 between CTV-resistant and susceptible individuals further confirmed the single dominant inheritance nature of Ctv. The recombinants from the population allowed separation of markers that were clustered previously in smaller populations and guided the chromosome walking toward the Ctv locus.

Example 4

Construction of Bacterial Artificial Chromosome (BAC) and Transformation-Competent Artificial Chromosome (TAC) Libraries Tender leaves were collected from mature trees of a CTV-resistant intergeneric hybrid (strain USDA 17-47) and used for BAC library construction. Nuclei of leaf cells were isolated and embedded in low melting point (LMP) agarose plugs (approximately 100 μl/plug). The nuclei were lysed to obtain megabase DNA, which was then subjected to partial digestion by a restriction enzyme, HindIII or BamHI. DNA fragments approximately 100–400 kb in size were recovered from CHEF gels and ligated to TAC cloning vector pYLTAC7. The ligation reactions were then used to transform *E. coli* strain DH101B. Recombinant bacterial clones containing DNA inserts from the CTV-resistant hybrid were picked and maintained. All together, two BAC libraries and one TAC library were produced and used in disease resistance gene cloning. They consisted of approximately 70,000 clones or DNA fragments that could represent more than 99% of the *Poncirus* and citrus genomes.

Example 5

Construction of a BAC Contig of the Resistance Gene Region

To develop a contiguous array of BAC or TAC clones that can represent the full Ctv gene region, chromosome landing was initiated at two marker loci that flanked Ctv and at another marker locus that co-segregated with Ctv. This was followed by repeated chromosome walking until the walks from the two sides met. Both techniques involve high-density colony screening of the 2 BAC and 1 TAC libraries. BAC and TAC clones were spotted onto nylon membrane filters using precision robotic arms and allowed to grow overnight on the filters. BAC DNA was released by alkaline lysis and fixed on the membranes in situ. The membrane sheets were hybridized with $^{32}P$-labeled DNA fragments of the molecular markers that were developed above to identify clones that came from the CTV-resistance gene region. This library screening was repeated until the whole resistance gene and its proximities were fully covered with different BAC clones.

Example 6

Physical and Genetic Mapping to Delineate the Ctv Locus

A BAC contig was constructed to clone Ctv, a single dominant gene as has been defined genetically, that confers resistance to CTV. The contig consists of 34 BAC clones and extends approximately 1000 kb. To delineate Ctv, molecular markers were developed from BAC ends or full-length sequences, and mapped genetically in several backcross populations that together contain over one thousand individuals. Current data indicate that the Ctv locus may be narrowed to a chromosomal region of approximately 150 kb.

Example 7

Sequencing and Sequence Analysis of BAC Inserts

The Ctv locus was mapped to a chromosomal region 150 kb in length. The chromosomal region that is most likely to contain the Ctv locus is represented by three BAC clones: BC7 (SEQ ID NO:2), HBC1, and TAC1 (SEQ ID NO:3). Sequencing of two of these clones has been completed; BC7 (SEQ ID NO:2) is 58 kb and TAC1 (SEQ ID NO:3) is 78 kb. The third clone (HBC1) carries a region of approximately 10 kb that is not represented by the two sequenced clones. Attempts were made to obtain sequences of two other BAC clones that are immediately adjacent to the 150 kb nucleic acid sequence. One clone is estimated to span approximately 120 kb (BC12, SEQ ID NO:1), and the other to span approximately 35 kb (BC6e).

Southern blotting indicated that these clones contain several copies of disease resistance gene-like sequences. Sequence analysis, gene identification and annotation have been conducted with all four clones, but primarily focused on BC7 and TAC1, as they seem to have full-length sequences. Several gene prediction programs (e.g., GenScan, Genemark, FGENESH, and Glimmer) have been used to analyze the sequences. The predicted peptides have been analyzed using software programs including BLAST.

Results from a GenScanW matrix analysis are as follows. For clone BC7, one peptide was found to be highly similar to the *Arabidopsis* RPS5 gene. This was named Ctv1.4 (DNA sequence is shown herein SEQ ID NO:10 and protein sequence is shown herein SEQ ID NO:11). For clone TAC1, two peptides were found to have complete structures and strong similarities to RPS5. These were named Ctv1.5 (DNA sequence is shown herein SEQ ID NO:12 and protein sequence is shown herein SEQ ID NO:13) and Ctv1.6 (DNA sequence is shown herein SEQ ID NO:14 and protein sequence is shown herein SEQ ID NO:15). For clone BC12, two peptides were found to have complete structures and strong similarities to RPS5. These were named Ctv1.1 (DNA sequence is shown herein SEQ ID NO:4 and protein sequence is shown herein SEQ ID NO:5) and Ctv1.3 (DNA sequence is shown herein SEQ ID NO:8 and protein sequence is shown herein SEQ ID NO:9). One peptide was found to have strong similarities to RPS5. This was named Ctv1.2 (DNA sequence is shown herein SEQ ID NO:6 and protein sequence is shown herein SEQ ID NO:7). One peptide was found to be similar to an *Arabidopsis* hypothetical protein containing a sterile alpha motif (SAM). The most abundant of the predicted peptides are retroelements, followed by five to seven copies of RPS5-like sequences.

Genetic evidence obtained so far indicates that the resistance to CTV in *Poncirus trifoliata* segregates as a single dominant locus. However, sequence analyses in other model plant species have repeatedly shown that disease resistance genes are present in clusters in plant genomes. The clustering of several copies of RPS5-like sequences seems in agreement with resistance gene's distribution features. Taking the genetic map location and molecular structure of these sequences into consideration, the RPS5-like sequences strongly indicate that one or more of them may be the best candidates for Ctv. As such, these candidates have been named Ctv1.1, Ctv1.2, Ctv1.3, Ctv1.4, Ctv1.5 and Ctv1.6. The conserved function domains found in RPS5 and many other *Arabidopsis* resistance genes are present and intact in these candidates, including a leucine zipper, nucleotide-binding site, and leucine-rich repeats. Additional sequences mapped to the BC12 and TAC1 clones were Ctv1.7 (SEQ ID NO:16) and Ctv1.8 (SEQ ID NO:18), respectively. The predicted amino acid sequences encoded by Ctv1.7 and Ctv1.8 are SEQ ID NO:17 and SEQ ID NO:19, respectively.

Example 8

Identification and Cloning of Two Resistance Genes, Rcan5 and Rcan6

To determine which of the above-described Ctv candidates is responsible for resistance to CTV infection in *Poncirus* plants, a BAC contig containing inserts from the susceptibility allele region was constructed (FIG. 1). BAC clone inserts from the susceptibility allele BAC contig were sequenced in the same manner as that described above for sequencing of the resistance allele region contig. Several gene prediction programs were used to identify sequences that were identical or similar between the susceptibility and resistance allele regions. By this comparison, a region of approximately 100 kb was defined that is absent from the susceptibility allele region but present in the resistance allele region. Rcan5 (SEQ ID NO:12, previously referred to as Ctv1.5) and Rcan6 (SEQ ID NO:14, previously referred to as Ctv1.6), as well as two hypothetical genes, are present within this 100 kb region unique to the resistance allele region. In addition, several transposable element sequences were found in this 100 kb region. The predicted amino acid sequences for RCAN5 and RCAN6 are SEQ ID NO:13 and SEQ ID NO:15, respectively.

Example 9

Transgenic Plants

The invention provides various transgenic plants. A transgenic plant can be made by transforming a plant cell with nucleic acids encoding RCAN5 or RCAN6 polypeptides using any suitable method, an example of which is described below. In addition to the example described below, other protocols for transforming citrus plants are well known in the art and may also be used.

Plant Materials

*Citrus* or *Citrus*-related plants seeds are freshly removed from fruits and air-dried. After the removal of seed coats, embryos are surface disinfected with 20% Clorox containing 0.01% Tween-20 for 10 min, and then rinsed four times in sterile distilled water. Sterilized embryos are placed individually with the micropylar end submerged in 25×150-mm culture tubes with 25 ml of RM medium consisting of ½ MS inorganic salts and vitamins (Murashige and Skoog, Physiol. Plant 15:473–479, 1962), 0.1 mg/l α-naphthaleneacetic acid (NAA), 500 mg/l charcoal, 3% sucrose, and 0.8% Phytagar (pH 5.7) and kept in darkness at 27° C. Three weeks later, epicotyl stems are harvested and cut into 1 cm segments. To test the effect of increasing the wound area, some epicotyl explants are cut longitudinally into two halves to yield two explants. Explants are submerged in 4 ml co-culture medium before inoculation.

All media described below, including those containing plant growth regulators, are sterilized by standard autoclaving procedures before use. During the culture, 15–20 explants are evenly distributed in 100×20-mm disposable Petri plates containing approximately 20 ml of medium. Cultures are kept at 25±2° C., with a 16-h photoperiod.

Inoculation, Co-culture, and Regeneration

A fresh single colony of disarmed *A. tumefaciens* strain EHA-101, harboring a vector plasmid such as pCLD04541, pCambia series vectors, BIBAC plasmids (or modifications thereof), pYLTAC7, or other suitable vector is cultured in 100 ml YEP medium overnight as described previously (Moore et al., Plant Cell Rep. 11:238–242, 1992). Bacteria cultures with a cell density less than 0.7 at $OD_{600}$ are pelleted at 4000 rpm for 10 min, resuspended in liquid co-culture medium, then diluted with co-culture medium to serials of $OD_{600}$ values (3.0, 2.0, 1.0, 0.8, 0.6 and 0.4). One ml diluted bacterial suspension is added to 4 ml medium with the explants and incubated at 25° C. for 10 min. When the effect of transformation conditions on regeneration efficiency is to be evaluated, bacteria are not added during inoculation, i.e., $OD_{600}$=0 and other conditions remain the same.

Explants are blotted dry with sterile filter paper following inoculation, and placed horizontally (with the longitudinally cut surface facing upwards if applicable) on solid co-culture medium in Petri dishes and kept in darkness for 2.5 days. The standard co-culture medium (CM1) consists of MS inorganic salts and vitamins (Murashige and Skoog, Physiol. Plant 15:473–479, 1962), 3 mg/l 6-benzyladenine (BA), 0.1 mg/l NAA, 3% sucrose, 200 μM acetosyringone and 0.8% Phytagar (Gibco-BRL) (pH 5.7). 2,4-dichlorophenoxyacetic acid (2,4-D) (0.45, 2.26, 4.52, 9.04 and 18.10 μM) is added to CM1 medium to examine its effect on regeneration and transformation efficiency from epicotyl explants. When the effect of 2,4-D in the co-culture medium is assessed, explants are submerged in 4 ml medium for 3 h before inoculation and then transferred to the same 2,4-D-containing medium. Following cocultivation, explants are transferred to regeneration medium (RM1), which consists of MS inorganic salts and vitamins (Murashige and Skoog, Physiol. Plant 15:473–479, 1962), 3 mg/l BA, 0.5 mg/l NAA, 400 mg/l cefotaxime, 100 mg/l kanamycin, 3% sucrose, and 0.8% Phytagar (pH 5.7). When the effect of only transformation methods on regeneration efficiency is to be evaluated, kanamycin is not included in the regeneration medium. Cultures on medium RM1 are maintained in darkness for 2 weeks, followed by transfer to a 16-h photoperiod (Peña et al., Plant Cell Rep, 16:731–737, 1997). After 5 weeks, the explants producing shoots are transferred to the SM1 medium until shoots reach 2 mm long for grafting or 1 cm long for rooting. SM1 medium consists of MS inorganic salts and vitamins (Murashige and Skoog, Physiol. Plant 15:473–479, 1962), 1 mg/l BA, 0.1 mg/l NAA, 3% sucrose, and 0.8% Phytagar (pH 5.7). The number (percentage) of explants producing shoots, total shoots produced, and average number of shoots produced per responding explant are scored. Regeneration frequency is defined as the total number of shoots produced/total number of explants evaluated× 100%. Duncan's multiple range test may be used to analyze statistical significance of differences among treatment mean values.

Evaluation of Transgenic Shoots and Plants

After regeneration, basal shoot ends are used for histochemical marker gene assay as described by Moore et al. (Plant Cell Rep. 11:238–242, 1992). After an overnight incubation at 37° C., the tissue is cleared of chlorophyll by submersion into ethanol:glacial acetic acid (3:1, v/v) for 1 h. The tissue that sectors or entirely stains the appropriate color for the marker gene used is recorded as transformed. The frequencies of marker gene+ shoots are recorded, and transformation frequency is calculated as the total number of marker gene+ shoots/total number of explants evaluated× 100%. Marker gene staining is also conducted on leaves, stems, roots, or whole plants after rooting or grafting. Molecular analyses are performed to verify the transformation events. Polymerase chain reaction (PCR) is used to amplify a fragment of the Ctv gene or appropriate marker gene. To test the possibility of bacterial contamination of the plant tissue, primers may be used to amplify a 650-bp fragment of the *Agrobacterium* chromosomal vir A gene (Bond and Roose, Plant Cell Rep. 18:229–234, 1998). Reaction components, concentrations and thermocycler conditions, as well as DNA extraction for Southern blot analysis are as described previously (Moore et al., Plant Cell Rep. 11:238–242, 1992; Gutiérrez-E et al., Plant Cell Rep. 16:745–753, 1997). Southern blot analysis is performed according to Sambrook et al. (Molecular Cloning: A Laboratory Manual, 2nd ed. Cold Spring Harbor Laboratory, Cold Spring Harbor, N.Y., 1989); 10 μg DNA is digested by HpaI, separated in a 0.8% agarose gel, and then blotted to nylon membranes (Hybond-N+, Amersham). Membranes are probed with a PCR-amplified marker gene fragment from the vector plasmid used in the transformation, which is labeled by a random priming reaction using $^{32}P$ and the Pharmacia Ready To Go™ labeling kit.

Regenerating Whole Plants

Whole plants are produced either by grafting in vitro or rooting by two-step culture. Grafting is carried out as described by Peña et al. (Plant Cell Rep. 14:616–619, 1995b), but the rootstocks used are the same cultivar as the scion. The basal rooting medium is RM2A, which consists of one-fourth strength MS inorganic salts and vitamins (Murashige and Skoog, Physiol. Plant 15:473–479, 1962), 2% sucrose, and 0.8% Phytagar. Rooting is achieved by two-step culture: first, shoots 1 cm or more in length are cultured on RM2A supplemented with 5 mg/l indole-3-butyric acid (IBA) and 0.5 mg/l NAA for 2 weeks and then transferred to RM2A for another 3 weeks. Kanamycin is added to the rooting medium of the second step to final concentrations of 0–50 mg/l for further selection of transformants. Rooting frequency and root length are determined after 4 weeks.

Example 10

Resistance to CTV Infection

Confirmation of resistance to CTV in Rcan5- and Rcan6-transgenic susceptible citrus plant materials essentially relies on inoculation of the transgenic plants, followed by ELISA testing for the presence or absence of replicating CTV in young tissues. Specifically, rootstock seedlings of rough lemon (*Citrus jambhiri*) are grown in an environmentally controlled greenhouse structure, to maintain temperatures most conducive for viral replication while still allowing for plant growth (e.g., 20–27° C.). Seedlings are pre-inoculated with bark patches, leaf pieces, or other materials taken from plants previously diagnosed as infected. The rootstock seedlings are allowed to grow, and young tissues are assayed by ELISA techniques to confirm successful inoculation with the virus. Buds or stem pieces from actively growing transgenic plants containing the resistance gene(s) are grafted to the CTV-infected rootstocks by standard plant propagation methods, and allowed to grow. Shoots of both the inoculated rootstock (positive control) and the putative resistant transgenic plants are grown for at least two growth flushes.

Transgenic susceptible citrus plant materials containing marker genes, but not Rcan5 and Rcan6 sequences, are treated in like manner to demonstrate that CTV resistance is not associated with the transformation vectors used, nor the process of transformation. Leaf and stem samples are collected and ELISA procedures are performed to determine the titer of CTV virus particles within the tissues; OD readings following ELISA incubation are obtained photometrically and compared with positive and negative controls, thus indicating whether there is viral replication occurring or not. ELISA tests on plant materials showing a negative reaction are repeated several times to confirm that CTV replication does not occur over time, thus demonstrating stable resistance. Further confirmation of resistance of the transgenic plant material is obtained by electron microscopy of viral preparations made from infected and resistant transgenic plant materials, to look for the presence of virus particles.

The nucleic acids of the invention may be used to confer resistance to a broad range of CTV strains in plants. To test plants for a broad spectrum resistance to CTV, a range of genetically distinct CTV strains (e.g., T36 and T3 from Florida, and other strains from the USDA's World CTV collection, Beltsville, Md.), are inoculated into rootstocks and tested for resistance as described above. In addition to this biochemical assay, CTV-induced symptoms such as stem-pitting, vein clearing, seedling yellows, or other visual symptoms are evaluated.

Other Embodiments

This description has been by way of example of how the compositions and methods of invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A purified nucleic acid isolarable from *Poncirus trifoliata*, the nucleic acid having the ability to confer resistance in a plant cell to pathology caused by CTV infection when present in the plant cell, wherein the nucleic acid encodes RCAN5.

2. The purified nucleic acid of claim 1, wherein the nucleic acid comprises a nucleotide sequence that encodes a protein (a) that comprises the amino acid sequence of SEQ ID NO:13 and (b) has at least one functional activity of native RCAN5.

3. The nucleic acid of claim 1, wherein the nucleic acid comprises the nucleotide sequence of SEQ ID NO:12.

4. The nucleic acid of claim 1, wherein the nucleotide sequence defines a polynucleotide whose complement hybridizes under high stringency conditions to the nucleotide sequence of SEQ ID NO:12.

5. A vector comprising the nucleic acid of claim 1.

6. The vector of claim 5, wherein said nucleic acid is operably linked to one or more expression control sequences.

7. A transgenic cell or seed comprising the nucleic acid of claim 1.

8. A plant into which has been introduced the nucleic acid of claim 1.

9. The plant of claim 8, wherein the plant is of the genus *Citrus*.

10. The plant of claim 9, wherein the plant is selected from the group consisting of sweet orange, grapefruit, mandarin, tangerines, pumelo, lemon, lime and citron.

11. The plant of claim 8, wherein the plant comprises citrus scion and a rootstock cultivar.

12. The plant of claim 8, wherein the plant comprises a rootstock cultivar selected from the group consisting of sour orange, rough lemon, mandarin and citrus.

13. The plant of claim 11, wherein the rootstock cultivar is a citrus intrageneric hybrid.

14. The plant of claim 12, wherein the rootstock cultivar is a citrus intergeneric hybrid.

15. The plant of claim 8, wherein the plant is an intrageneric hybrid.

16. The plant of claim 8, wherein the plant is a breeding line.

17. The plant of claim 8, wherein the plant is a *Fortunella* species.

18. The plant of claim 8, wherein the nucleic acid comprises a selectable marker.

19. The plant of claim 18, wherein the selectable marker is selected from the group consisting of antibiotic resistance gene(s), β-glucuronidase gene (GUS), and nucleotide sequence encoding green fluorescent protein (GFP).

20. A method of imparting disease resistance to a plant, plant cell or plant seed, the method comprising the steps of:

(A) providing a plant, plant cell or plant seed; and (B) introducing into the plant, plant cell or plant seed the purified nucleic acid of claim 1; thereby, imparting disease resistance to a plant, plant cell or plant seed.

21. The method of claim 20, wherein the purified nucleic acid further comprises a selectable marker.

22. The method of claim 21, wherein the selectable marker is selected from the group consisting of antibiotic resistance gene(s), beta-glucuronidase gene (GUS) and nucleotide sequence encoding GFP.

23. The method of claim 20, wherein the step (B) of introducing into the plant, plant cell or plant seed the purified nucleic acid comprises incorporating the purified nucleic acid into a suitable expression vector.

24. The method of claim 20, wherein the step (B) of introducing into the plant, plant cell or plant seed a purified nucleic acid comprises transforming the plant, plant cell or plant seed with an *Agrobacterium* strain.

25. The method of claim 20, wherein the step (B) of introducing into the plant, plant cell or plant seed a purified nucleic acid comprises microprojectile bombardment.

26. The method of claim 20, wherein the step (B) of introducing into the plant, plant cell or plant seed a purified nucleic acid comprises direct nucleic acid uptake by protoplasts.

* * * * *